United States Patent
Mortensen et al.

(10) Patent No.: US 7,981,893 B2
(45) Date of Patent: Jul. 19, 2011

(54) HETEROARYL COMPOUNDS, COMPOSITIONS THEREOF, AND METHODS OF TREATMENT THEREWITH

(75) Inventors: Deborah Sue Mortensen, San Diego, CA (US); Maria Mercedes Delgado Mederos, San Diego, CA (US); John Joseph Sapienza, Chula Vista, CA (US); Ronald J. Albers, San Diego, CA (US); Branden G. Lee, Vista, CA (US); Roy Leonard Harris, III, San Diego, CA (US); Graziella Isabel Shevlin, San Diego, CA (US); Dehua Huang, San Diego, CA (US); Kimberly Lyn Schwarz, San Diego, CA (US); Garrick K. Packard, San Diego, CA (US); Jason Simon Parnes, San Diego, CA (US); Patrick William Papa, Carlsbad, CA (US); Lida Radnia Tehrani, San Diego, CA (US); Sophie Perrin-Ninkovic, Carlsbad, CA (US); Jennifer R. Riggs, Cardiff, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 414 days.

(21) Appl. No.: 11/975,652

(22) Filed: Oct. 18, 2007

(65) Prior Publication Data

US 2009/0023724 A1    Jan. 22, 2009

Related U.S. Application Data

(60) Provisional application No. 60/853,166, filed on Oct. 19, 2006.

(51) Int. Cl.
*A61K 31/4985* (2006.01)
(52) U.S. Cl. ........................................ 514/249; 544/350
(58) Field of Classification Search ................... 544/350
See application file for complete search history.

(56) References Cited

U.S. PATENT DOCUMENTS

| | | | |
|---|---|---|---|
| 3,507,866 A | 4/1970 | Jones et al. |
| 3,567,725 A | 3/1971 | Grabowski et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,855,723 B2 | 2/2005 | McMahon et al. |
| 2003/0036652 A1 | 2/2003 | Bakthavatchalam et al. |
| 2003/0162968 A1 | 8/2003 | Ciriillo et al. |
| 2006/0004014 A1 | 1/2006 | Hoffmann et al. |
| 2006/0106022 A1 | 5/2006 | Liu et al. |
| 2006/0135511 A1* | 6/2006 | Burgey ........................ 514/221 |

FOREIGN PATENT DOCUMENTS

| | | |
|---|---|---|
| CA | 2 458 699 A1 | 3/2003 |
| DE | 262 026 | 11/1988 |
| EP | 0 385 850 | 9/1990 |
| JP | 63275582 | 5/1987 |
| JP | 200148882 | 2/2001 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/048152 | 6/2002 |
| WO | WO 03/032989 | 4/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |

(Continued)

OTHER PUBLICATIONS

Patani et al. "Bioisosterism: A Rational Approach in Drug Design", 1996, Chemical Reviews, 96, 3147-3176.*
Barlin, Gordon. "Purine analogs as amplifiers of phleomycin.VII. Some 1H-imidazo[4,5-b]pyrazines and related compound". 1982, Australian Journal of Chemistry, 35, 2299-306.(Abstract only).*
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.

(Continued)

*Primary Examiner* — James O Wilson
*Assistant Examiner* — Brian McDowell
(74) *Attorney, Agent, or Firm* — Jones Day

(57) ABSTRACT

Provided herein are Heteroaryl Compounds having the following structure:

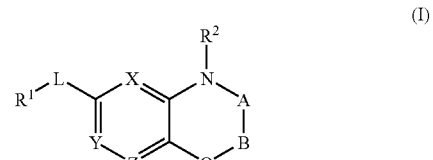

(I)

wherein $R^1$, $R^2$, L, X, Y, Z, Q, A and B are as defined herein, compositions comprising an effective amount of a Heteroaryl Compound and methods for treating or preventing cancer, inflammatory conditions, immunological conditions, metabolic conditions and conditions treatable or preventable by inhibition of a kinase pathway comprising administering an effective amount of a Heteroaryl Compound to a patient in need thereof.

10 Claims, No Drawings

FOREIGN PATENT DOCUMENTS

| WO | WO 2006/045828 | 5/2006 |
|---|---|---|
| WO | WO 2006/065703 | 6/2006 |
| WO | WO 2006/091737 | 8/2006 |
| WO | WO 2006/108103 | 10/2006 |
| WO | WO 2008/016669 | 2/2008 |
| WO | WO 2010/068483 | 6/2010 |

OTHER PUBLICATIONS

Killday et al., 2001, "Microxine, a new cdc2 kinase inhibitor from the Australian marine sponge Microxina species," J. of Natural Products, vol. 64(4):525-526.

Beresnev et al., 2000, "Interaction of 5-methoxy-1,2,4-traizines with uras as a new route to 6-azapurines," Medeleev Commu., vol. 2:58-59.

Bergman et al., 1963, "2-Phenylpurines, their chemical and enzumological reactivity," J. Chem Org. , pp. 3729-3735.

Chupakhin et al., 2001, "A simple one pot synthesis of condensed 1,2,4-triazines by using the tandem $A_N$-$S_N ipso$ and $S_N^H$—$S_N ipso$ reactions," J. of Heterocyclic Chemistry, vol. 38(4):901-907.

Cohen. P. 2001, "The role of protein phosphorylation in human health and diesease," eur. J. Biochem, vol. 268, pp. 5001-5010.

Cohen, P. 2002, "Protein kinases—The major drug targets of the twenty-first century?" Nature Reviews/Drug Discovery, vol. 1, pp. 309-315.

Crofts et al., 1997 "Metabolism of 2-amino-1-methyl-6-phenylimidazo[4,5-b]pyridine (PhIP) by human cytochrome P4501B1," Carcinogenesis, vol. 18(9):1793-1798.

DATABASE CAPLUS Online Chemical Abstracts Service, Columbus, Ohio, Database Accession No. 1951:49974 (XP-002472261) (1951).

DATABASE CAPLUS Online Chemical Abstracts Service, Columbus, Ohio, Database Accession No. 1978:433195 (XP-002472262) (1978).

DATABASE CAPLUS Online Chemical Abstracts Service, Columbus, Ohio, Database Accession No. 1966:26849 (XP-002472263) (1965).

Dornow et al., 1957, "Synthese von2-Oxy-imidazolo-(5',4':2,3)-pyridinen)," Arch Pharm. vol. 290, pp. 20-31 (w/English language abstract).

Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.

Fabbro et al., 2002, "Protein kinases as targets for anticancer agents: from inhibitors touseful drugs," Pharmacology & Therapeutics, vol. 93, pp. 79-98.

Farhadi et al.,2006, "The role of protien kinase C isoforms in modulating injury and repair of the intestinal barrier," J. Pharm. Exp. Ther. vol. 316, pp. 1-7.

Frandsen et al., 1992, "Reaction of the N2-acetoxy derivative of 2-amino-1-methyl-6-phenylimidazo[4,5,b] pyridine . . . ," Carcinogenesis, vol. 13(4):629-35.

Georgakis and Younes, 1978, "From rapa nui to rapamycin:targeting PI3K/Akt/mTOR for cancer therapy," Expert Rev. Anticancer Ther, vol. 6:131-140.

Irie et al., 2005, "Toward the development of new medicinal leads with selectivity for protein kinase C isozymes," The Chemical Record, vol. 5:185-195.

Itoh etal., 2004, "A novel practical synthesis of C-2-arylpurines," Advanced Synthesis & Catalysis, vol. 346:1859-1867.

Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.

Nagashima et al., 2004, "Solution-Phase parallel synthesis of an N-Alkylated dihydropteridinone library from fluorous amino acids," J of Comb. Chemistry, vol. 6, pp. 942-949.

Park et al., 2000, "A novel mechanism of TRAF signaling revealed by structural and functional analyses of the TRADD-TRAF2 interaction," Cell, vol. 101, pp. 777-787.

Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-54.

Sridhar et al., 2000, "Protein Kinasesas Therapeutic Targets," Pharm. Research, vol. 17(11):1345-53.

Yoneda et al., 1978, "Synthesis of imadazo[4,5-e]-as-triazine (6-Azapurine) Deriviatives," Chem & Pharm Bulletin, vol. 26(10):3154-60.

Yoneda etal., 1976, "A transformationof 7-azapteridines into 6-azapurines (Imidazo[4,5-e]- as—triazines)," Heterocycles, vol. 4(9):1503-8.

Barlin, 1982, "Purine Analogs as Amplifiers of Phleomycin. VII* Some 1H-Imidazo[4,5-b]pyrazines and Related Compounds," *Australian Journal of Chemistry* 35(11):2299-2306.

* cited by examiner

HETEROARYL COMPOUNDS, COMPOSITIONS THEREOF, AND METHODS OF TREATMENT THEREWITH

This application claims the benefit of U.S. provisional application No. 60/853,166, filed Oct. 19, 2006, which is incorporated by reference herein in its entirety.

1. FIELD

Provided herein are certain heteroaryl compounds, compositions comprising an effective amount of one or more such compounds and methods for treating or preventing cancer, inflammatory conditions, immunological conditions, metabolic conditions and conditions treatable or preventable by inhibition of a kinase pathway, comprising administering an effective amount of a heteroaryl compound to a patient in need thereof.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7): 777-787 (2000).

Protein kinases can be divided into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs).

Protein kinase C (PKC) is a family of serine/threonine kinases that play a pivotal role in cellular signal transduction. Irie et al., 2005, *The Chemical Record* 5:185-195. PKC isozymes are involved in tumor promotion, as well as other diverse biological events and, accordingly, are attractive targets for cancer therapy and other disorders. Id. One such PKC isozyme which is activated by tumor promoters is PKCθ. PKC isozymes are also expressed in epithelial cells of the gastrointestinal tract, especially the intestine. Farhadi et al., 2006, *J. Pharm. Exp. Ther.* 316:1-7. Accordingly, agents which modulate PCK activity are thought to be useful as therapeutics for gastrointestinal disorders such as cancer and inflammatory bowel disease.

mTOR (mammalian target of rapamycin), which is also called FRAP, RAFTI or SEPT), is a 2549-amino acid Ser/Thr protein kinase, which has been shown to be one of the most critical proteins in the PI3K/Akt pathway that regulates cell growth and proliferation. Georgakis and Younes, 2006, *Expert Rev. Anticancer Ther.* 6(1):131-140. Because PI3K and Akt are involved in the regulation of several cellular functions, there may be toxicities associated with inhibiting these kinases, making inhibition of mTOR the more promising approach. Id. Three mTOR inhibitors are currently in clinical trials for the treatment of cancer. These are CCI-779 (renal cancer, breast cancer, mantle cell lymphoma, glioblastoma multiforme and metastatic melanoma), RAD001 (refractory solid tumors, advanced hematologic tumors, GIST and advanced non-small cell lung cancer) and AP23573 (solid tumors, hematologic malignancy and sarcoma). Id. The preclinical success of these compounds demonstrates the usefulness of mTOR inhibitors in the treatment of cancer and the need for additional compounds with mTOR inhibitory activity.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

Citation or identification of any reference in Section 2 of this application is not to be construed as an admission that the reference is prior art to the present application.

3. SUMMARY

Provided herein are compounds having the following formula (I):

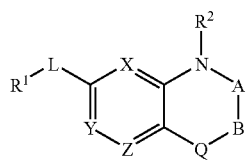

(I)

and pharmaceutically acceptable salts, polymorphs, clathrates, solvates, hydrates, stereoisomers and prodrugs thereof, wherein $R^1$, $R^2$, L, X, Y, Z, Q, A and B are as defined herein.

Compounds of formula (I), or pharmaceutically acceptable salts, clathrates, solvates, hydrates, stereoisomers or prodrugs thereof (each being referred to herein as "Heteroaryl Compounds"), are useful for treating or preventing cancer, inflammatory conditions, immunological conditions, metabolic conditions and conditions treatable or preventable by inhibition of a kinase pathway, in one embodiment, the PKCθ or mTOR pathway.

Further provided herein are compositions comprising an effective amount of a Heteroaryl Compound and compositions comprising an effective amount of a Heteroaryl Compound and a pharmaceutically acceptable carrier or vehicle. The compositions are useful for treating or preventing cancer, inflammatory conditions, immunological conditions, metabolic conditions and conditions treatable or preventable by inhibition of a kinase pathway, in one embodiment, the PKCθ or mTOR pathway.

Further provided herein are methods for treating or preventing cancer, inflammatory conditions, immunological conditions, metabolic conditions and conditions treatable or preventable by inhibition of a kinase pathway, in one embodiment, the PKCθ or mTOR pathway, comprising administering an effective amount of a Heteroaryl Compound to a patient in need of the treating or preventing.

The present embodiments can be understood more fully by reference to the detailed description and examples, which are intended to exemplify non-limiting embodiments.

4. DETAILED DESCRIPTION

4.1 Definitions

A "$C_{1-8}$alkyl" group is a saturated straight chain or branched non-cyclic hydrocarbon having from 1 to 8 carbon atoms. Representative —($C_{1-8}$alkyls) include -methyl, -ethyl, -n-propyl, -n-butyl, -n-pentyl, -n-hexyl, -n-heptyl and -n-octyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. A —($C_{1-8}$alkyl) group can be substituted or unsubstituted. For example, a $C_{1-8}$alkyl group can be substituted with phenyl to form a benzyl group.

A "$C_{2-8}$alkenyl" group is a straight chain or branched non-cyclic hydrocarbon having from 2 to 8 carbon atoms and including at least one carbon-carbon double bond. Representative straight chain and branched ($C_2$-$C_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "$C_{2-8}$alkynyl" group is a straight chain or branched non-cyclic hydrocarbon having from 2 to 8 carbon atoms and including at least one carbon-carbon triple bond. Representative straight chain and branched —($C_2$-$C_8$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, and the like. An alkynyl group can be unsubstituted or substituted.

The terms "halogen" and "halo" mean fluorine, chlorine, bromine and iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like. An aryl group can be substituted or unsubstituted.

A "heteroaryl" group is an aryl ring system having one to four heteroatoms (e.g., O, S or N) as ring atoms in a heteroaromatic ring system, wherein the remainder of the atoms are carbon atoms. Suitable heteroatoms include oxygen, sulfur and nitrogen. In certain embodiments, the heterocyclic ring system is monocyclic or bicyclic. Non-limiting examples include aromatic groups selected from the following:

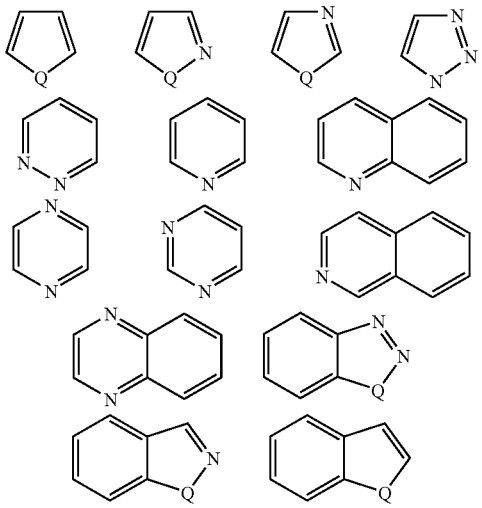

wherein Q is $CH_2$, CH=CH, O, S or NH. Further representative examples of heteroaryl groups include, but are not limited to, benzofuranyl, benzothienyl, indolyl, benzopyrazolyl, coumarinyl, furanyl, isothiazolyl, imidazolyl, isoxazolyl, thiazolyl, triazolyl, tetrazolyl, thiophenyl, pyrimidinyl, isoquinolinyl, quinolinyl, pyridinyl, pyrrolyl, pyrazolyl, 1H-indolyl, 1H-indazolyl, benzo[d]thiazolyl and pyrazinyl. Further representative examples of heteroaryl groups include those of the compounds disclosed herein. Heteroaryls can be bonded at any ring atom (i.e., at any carbon atom or heteroatom of the heteroaryl ring). A heteroaryl group can be substituted or unsubstituted. In one embodiment, the heteroaryl group is a $C_{3-10}$heteroaryl group.

A "cycloalkyl" group is a saturated or unsaturated non-aromatic carbocyclic ring. Representative cycloalkyl groups include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. A cycloalkyl group can be substituted or unsubstituted. In one embodiment, the cycloalkyl group is a $C_{3-8}$cycloalkyl group.

A "heterocycloalkyl" group is a non-aromatic cycloalkyl in which one to four of the ring carbon atoms are independently replaced with a heteroatom from the group consisting of O, S and N. Representative examples of a heterocycloalkyl group include, but are not limited to, morpholinyl, pyrrolidinyl, piperizinyl, (1,4)-dioxane, (1,3)-dioxolane, 4,5-dihydro-1H-imidazolyl. Heterocycloalkyls can also be bonded at any ring atom (i.e., at any carbon atom or heteroatom of the heterocyclic ring). A heterocycloalkyl group can be substituted or unsubstituted. In one embodiment, the heterocycloalkyl is a 3-7 membered heterocycloalkyl.

When the groups described herein are said to be "substituted or unsubstituted," when substituted, they may be substituted with one or more of any substituent. Examples of substituents are those found in the exemplary compounds and embodiments disclosed herein, as well as halo (e.g., chloro, iodo, bromo, or fluoro); $C_{1-8}$ alkyl; $C_{2-8}$ alkenyl; $C_{2-8}$ alkynyl; hydroxyl; $C_{1-8}$ alkoxyl; amino; nitro; thiol; thioether; imine; cyano; amido; phosphonato; phosphine; carboxyl; carbamoyl; carbamate; acetal; urea; thiocarbonyl; sulfonyl; sulfonamide; sulfinyl; ketone; aldehyde; ester; acetyl; acetoxy; oxygen (=O); haloalkyl (e.g., trifluoromethyl); substituted aminoacyl and aminoalkyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, furanyl, or thiazinyl); carbocyclic or heterocyclic, monocyclic or fused or non-fused polycyclic aryl (e.g., phenyl, naphthyl, pyrrolyl, indolyl, furanyl, thienyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothienyl, or benzofuranyl); amino (primary, secondary, or tertiary); —O-lower alkyl; —O-aryl; aryl; aryl-lower alkyl; $CO_2CH_3$; $CONH_2$; $OCH_2CONH_2$; $NH_2$; $N(C_{1-4}alkyl)_2$; $NHC(O)C_{1-4}alkyl$; $SO_2NH_2$; $SO_2C_{1-4}alkyl$; $OCHF_2$; $CF_3$; $OCF_3$; and such moieties may also be optionally substituted by a fused-ring structure or bridge, for example —OCH$_2$O— or —O-lower alkylene-O—. These substituents may optionally be further substituted with a substituent selected from such groups.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Heteroaryl Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sul fanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences,* 18$^{th}$ eds., Mack Publishing, Easton Pa. (1990) or *Remington: The Science and Practice of Pharmacy,* 19$^{th}$ eds., Mack Publishing, Easton Pa. (1995).

As used herein, the term "polymorph(s)" and related terms herein refer to solid forms of the Heteroaryl Compounds having different physical properties as a result of the order of the molecules in the crystal lattice. The differences in physical properties exhibited by solid forms affect pharmaceutical parameters such as storage stability, compressibility and density (important in formulation and product manufacturing), and dissolution rates (an important factor in determining bioavailability). Differences in stability can result from changes in chemical reactivity (e.g., differential oxidation, such that a dosage form discolors more rapidly when comprised of one solid form than when comprised of another solid form) or mechanical changes (e.g., tablets crumble on storage as a kinetically favored polymorph converts to thermodynamically more stable solid form) or both (e.g., tablets of one solid form are more susceptible to breakdown at high humidity). As a result of solubility/dissolution differences, in the extreme case, some solid form transitions may result in lack of potency or, at the other extreme, toxicity. In addition, the physical properties of the crystal may be important in processing, for example, one solid form might be more likely to form solvates or might be difficult to filter and wash free of impurities (i.e., particle shape and size distribution might be different between one solid form relative to the other).

As used herein and unless otherwise indicated, the term "clathrate" means a Heteroaryl Compound, or a salt thereof, in the form of a crystal lattice that contains spaces (e.g., channels) that have a guest molecule (e.g., a solvent or water) trapped within or a crystal lattice wherein a Heteroaryl Compound is a guest molecule.

As used herein and unless otherwise indicated, the term "hydrate" means a Heteroaryl Compound, or a salt thereof, that further includes a stoichiometric or non-stoichiometric amount of water bound by non-covalent intermolecular forces.

As used herein and unless otherwise indicated, the term "solvate" means a Heteroaryl Compound, or a salt thereof, that further includes a stoichiometric or non-stoichiometric amount of a solvent bound by non-covalent intermolecular forces.

As used herein and unless otherwise indicated, the term "prodrug" means a Heteroaryl Compound derivative that can hydrolyze, oxidize, or otherwise react under biological conditions (in vitro or in vivo) to provide an active compound, particularly a Heteroaryl Compound. Examples of prodrugs include, but are not limited to, derivatives and metabolites of a Heteroaryl Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed.

(Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a Heteroaryl Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Heteroaryl Compounds can have chiral centers and can occur as racemates, individual enantiomers or diastereomers, and mixtures thereof. All such isomeric forms are included within the embodiments disclosed herein, including mixtures thereof.

Various Heteroaryl Compounds contain one or more chiral centers, and can exist as racemic mixtures of enantiomers, mixtures of diastereomers or enantiomerically or optically pure compounds. The use of stereomerically pure forms of such Heteroaryl Compounds, as well as the use of mixtures of those forms are encompassed by the embodiments disclosed herein. For example, mixtures comprising equal or unequal amounts of the enantiomers of a particular Heteroaryl Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Heteroaryl Compounds can include E and Z isomers, or a mixture thereof, and cis and trans isomers or a mixture thereof. In certain embodiments, the Heteroaryl Compounds are isolated as either the E or Z isomer. In other embodiments, the Heteroaryl Compounds are a mixture of the E and Z isomers.

The term "effective amount" in connection with an Heteroaryl Compound can mean an amount capable of treating or preventing a disease disclosed herein, such as cancer, inflammatory conditions, immunological conditions, metabolic conditions or conditions treatable or preventable by inhibition of a kinase pathway, in one embodiment, the PKCθ or mTOR pathway.

The term "patient" includes an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

4.2 Heteroaryl Compounds

Provided herein are Heteroaryl Compounds having the following formula (I):

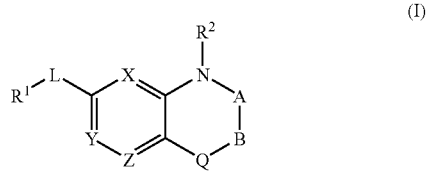

and pharmaceutically acceptable salts, polymorphs, clathrates, solvates, hydrates, stereoisomers, enantiomers and prodrugs thereof, wherein:

X, Y and Z are at each occurrence independently N or $CR^3$, wherein at least one of X, Y and Z is N and at least one of X, Y and Z is $CR^3$;

-A-B-Q- taken together form —$CHR^4C(O)NH$—, —$C(O)CHR^4NH$—, —$C(O)NH$—, —$CH_2C(O)O$—, —$C(O)CH_2O$—, —$C(O)O$— or $C(O)NR^3$;

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl;

$R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;

$R^3$ is H, substituted or unsubstituted $C_{1-8}$alkyl, substituted or unsubstituted aryl, substituted or unsubstituted heteroaryl, substituted or unsubstituted cycloalkyl, substituted or unsubstituted heterocycloalkyl, —$NHR^4$ or —$N(R^4)_2$; and $R^4$ is at each occurrence independently substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (I) are those wherein -A-B-Q- taken together form —$CH_2C(O)NH$—.

In another embodiment, the Heteroaryl Compounds of formula (I) are those wherein -A-B-Q- taken together form —$C(O)CH_2NH$—.

In another embodiment, the Heteroaryl Compounds of formula (I) are those wherein -A-B-Q- taken together form —$C(O)NH$—.

In another embodiment, the Heteroaryl Compounds of formula (I) are those wherein -A-B-Q- taken together form —$CH_2C(O)O$—.

In another embodiment, the Heteroaryl Compounds of formula (I) are those wherein -A-B-Q- taken together form —$C(O)CH_2O$—.

In another embodiment, the Heteroaryl Compounds of formula (I) are those wherein -A-B-Q- taken together form —$C(O)O$—.

In another embodiment, the Heteroaryl Compounds of formula (I) are those wherein -A-B-Q- taken together form —$C(O)NR^3$—.

In another embodiment, the Heteroaryl Compounds of formula (I) are those wherein Y is $CR^3$.

In another embodiment, the Heteroaryl Compounds of formula (I) are those wherein X and Z are N and Y is $CR^3$.

In another embodiment, the Heteroaryl Compounds of formula (I) are those wherein X and Z are N and Y is CH.

In another embodiment, the Heteroaryl Compounds of formula (I) are those wherein X and Z are CH and Y is N.

In another embodiment, the Heteroaryl Compounds of formula (I) are those wherein Y and Z are CH and X is N.

In another embodiment, the Heteroaryl Compounds of formula (I) are those wherein X and Y are CH and Z is N.

In another embodiment, the Heteroaryl Compounds of formula (I) are those wherein $R^1$ is substituted aryl, such as substituted phenyl.

In another embodiment, the Heteroaryl Compounds of formula (I) are those wherein $R^1$ is substituted or unsubstituted aryl, such as substituted or unsubstituted phenyl or substituted or unsubstituted naphthyl.

In another embodiment, the Heteroaryl Compounds of formula (I) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (I) are those wherein $R^1$ is H.

In another embodiment, the Heteroaryl Compounds of formula (I) are those wherein $R^2$ is substituted $C_{1-8}$alkyl.

In another embodiment, the Heteroaryl Compounds of formula (I) are those wherein $R^2$ is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (I) are those wherein $R^2$ is substituted or unsubstituted cycloalkyl or substituted or unsubstituted heterocycloalkyl.

In another embodiment, the Heteroaryl Compounds of formula (I) are those wherein $R^2$ is substituted or unsubstituted aryl, such as substituted or unsubstituted phenyl.

In another embodiment, the Heteroaryl Compounds of formula (I) are those wherein $R^2$ is H.

In another embodiment, the Heteroaryl Compounds of formula (I) are those wherein L is a direct bond.

In another embodiment, the Heteroaryl Compounds of formula (I) are those wherein -A-B-Q- taken together form —C(O)NH—, X and Z are N and Y is CH, $R^1$ is substituted or unsubstituted aryl or substituted or unsubstituted heteroaryl, L is a direct bond, and $R^2$ is substituted or unsubstituted $C_{1-8}$alkyl.

In another embodiment, the Heteroaryl Compounds of formula (I) are those wherein -A-B-Q- taken together form —C(O)NH—, X and Z are N and Y is CH, $R^1$ is substituted or unsubstituted aryl, L is a direct bond, and $R^2$ is substituted or unsubstituted $C_{1-8}$alkyl.

In another embodiment, the Heteroaryl Compounds of formula (I) are those wherein -A-B-Q- taken together form —C(O)NH—, X and Z are N and Y is CH, $R^1$ is substituted or unsubstituted aryl, and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (I) are those wherein -A-B-Q- taken together form —C(O)NH—, X and Z are N and Y is CH, $R^1$ is substituted or unsubstituted aryl, and $R^2$ is substituted or unsubstituted cycloalkyl, or substituted or unsubstituted heterocycloalkyl.

In another embodiment, the Heteroaryl Compounds of formula (I) are those wherein -A-B-Q- taken together form —C(O)NH—, X and Z are N and Y is CH, $R^1$ is substituted phenyl, L is a direct bond, and $R^2$ is substituted $C_{1-8}$alkyl.

In another embodiment, the Heteroaryl Compounds of formula (I) do not include compounds wherein X and Z are both N and Y is CH, -A-B-Q- is —C(O)NH—, L is a direct bond, $R^1$ is substituted or unsubstituted aryl or substituted or unsubstituted heteroaryl, and $R^2$ is $C_{1-8}$alkyl substituted with substituted or unsubstituted aryl or substituted or unsubstituted heteroaryl.

In another embodiment, the Heteroaryl Compounds of formula (I) do not include compounds wherein X and Z are both N and Y is CH, -A-B-Q- is —C(O)NH—, L is a direct bond, $R^1$ is phenyl, naphthyl, indanyl or biphenyl, each of which may be optionally substituted with one or more substituents independently selected from the group consisting substituted or unsubstituted $C_{1-8}$alkyl, substituted or unsubstituted $C_{2-8}$alkenyl, substituted or unsubstituted aryl, substituted or unsubstituted cycloalkyl or substituted or unsubstituted heterocycloalkyl.

In another embodiment, the Heteroaryl Compounds of formula (I) do not include compounds wherein X and Z are both N and Y is CH, -A-B-Q- is —C(O)NH—, L is a direct bond, $R^1$ is phenyl, naphthyl or biphenyl, each of which may be optionally substituted with one or more substituents each independently selected from the group consisting of $C_{1-4}$alkyl, amino, amino$C_{1-12}$alkyl, halogen, hydroxy, hydroxy$C_{1-4}$alkyl, $C_{1-4}$alkyloxy$C_{1-4}$alkyl, —$CF_3$, $C_{1-12}$alkoxy, aryloxy, aryl$C_{1-12}$alkoxy, —CN, —$OCF_3$, —$COR_g$, —$COOR_g$, —$CONR_gR_h$, —$NR_gCOR_h$, —$SO_2R_g$, —$SO_3R_g$ or —$SO_2NR_gR_h$, wherein each $R_g$ and $R_h$ are independently selected from the group consisting of hydrogen, $C_{1-4}$alkyl, $C_{3-6}$cycloalkyl, aryl, aryl$C_{1-6}$alkyl, heteroaryl or heteroaryl$C_{1-6}$alkyl; or A is a 5- to 6-membered monocyclic heteroaromatic ring having from one, two, three or four heteroatoms independently selected from the group consisting of N, O and S, that monocyclic heteroaromatic ring may be optionally substituted with one or more substituents each independently selected from the group consisting of $C_{1-6}$alkyl, amino, amino$C_{1-12}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —$CF_3$, —$OCF_3$, —$COR_i$, —$COOR_i$, —$CONR_iR_j$, —$NR_iCOR_j$, —$NR_iSO_2R_j$, —$SO_2R_i$, —$SO_3R_i$ or —$SO_2NR_iR_j$, wherein each $R_i$ and $R_j$ are independently selected from the group consisting of hydrogen, $C_{1-4}$ alkyl, $C_{3-6}$cycloalkyl, aryl, aryl$C_{1-6}$alkyl, heteroaryl or heteroaryl$C_{1-6}$alkyl; or A is a 8- to 10 membered bicyclic heteroaromatic ring from one, two, three or four heteroatoms selected from the group consisting of N, O and S, and may be optionally substituted with one, two or three substituents each independently selected from the group consisting of $C_{1-16}$alkyl, amino, amino$C_{1-12}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —$CF_3$, —$OCF_3$, —$COR_k$, —$COOR_k$, —$CONR_kR_l$, —$NR_kCOR_l$, —$NR_kSO_2R_l$, —$SO_2R_k$, —$SO_3R_k$ or —$SO_2NR_kR_l$, wherein each $R_k$ and $R_l$ are independently selected from the group consisting of hydrogen, $C_{1-4}$ alkyl, $C_{3-6}$ cycloalkyl, aryl, aryl$C_{1-6}$alkyl, heteroaryl or heteroaryl$C_{1-6}$alkyl, and $R^2$ is $C_{1-8}$alkyl substituted with substituted or unsubstituted aryl or substituted or unsubstituted heteroaryl.

In another embodiment, the Heteroaryl Compounds of formula (I) do not include compounds wherein X and Y are both N and Z is CH, -A-B-Q- is —C(O)NH—, L is a direct bond, $R^1$ is substituted or unsubstituted phenyl or substituted or unsubstituted heteroaryl, and $R^2$ is substituted or unsubstituted methyl, unsubstituted ethyl, unsubstituted propyl, or an acetamide.

In another embodiment, the Heteroaryl Compounds of formula (I) do not include compounds wherein X and Y are both N and Z is CH, -A-B-Q- is —C(O)NH—, L is a direct bond, $R^1$ is substituted or unsubstituted phenyl or substituted or unsubstituted heteroaryl, and $R^2$ is an acetamide.

In another embodiment, the Heteroaryl Compounds of formula (I) do not include compounds wherein X is N and Y and Z are both CH, -A-B-Q- is —C(O)NH—, L is a direct bond, $R^1$ is a (2,5'-Bi-1H-benzimidazole)-5-carboxamide, and $R^2$ is H.

In another embodiment, the Heteroaryl Compounds of formula (I) do not include compounds wherein one of X and Z is CH and the other is N, Y is CH, -A-B-Q- is —C(O)NH—, L is a direct bond, $R^1$ is unsubstituted pyridine, and $R^2$ is H, methyl or substituted ethyl.

In another embodiment, the Heteroaryl Compounds of formula (I) do not include compounds wherein X and Z are both N and Y is CH, -A-B-Q- is —C(O)NH—, $R^1$ is H, $C_{1-8}$alkyl, $C_{2-8}$alkenyl, aryl or cycloalkyl, and L is NH.

In another embodiment, the Heteroaryl Compounds of formula (I) do not include compounds wherein X and Z are both N and Y is CH, -A-B-Q- is —C(O)NR$^3$—, $R^2$ is H, substituted or unsubstituted $C_{1-8}$alkyl, substituted or unsubstituted phenyl, substituted or unsubstituted cycloalkyl, or substituted or unsubstituted heterocycloalkyl, and L is NH.

In another embodiment, the Heteroaryl Compounds of formula (I) do not include compounds wherein $R^1$ is a substituted or unsubstituted oxazolidinone.

In another embodiment, the Heteroaryl Compounds of formula (I) do not include one or more of the following compounds: 1,7-dihydro-2-phenyl-8H-Purin-8-one, 1,2-dihydro-3-phenyl-6H-Imidazo[4,5-e]-1,2,4-triazin-6-one, 1,3-dihydro-6-(4-pyridinyl)-2H-Imidazo[4,5-b]pyridin-2-one, 6-(1,3-benzodioxol-5-yl)-1,3-dihydro-1-[(1S)-1-phenylethyl]-2H-Imidazo[4,5-b]pyrazin-2-one, 3-[2,3-dihydro-2-oxo-3-(4-pyridinylmethyl)-1H-imidazo[4,5-b]pyrazin-5-yl]-Benzamide, 1-[2-(dimethylamino)ethyl]-1,3-dihydro-6-(3,4,5-trimethoxyphenyl)-2H-Imidazo[4,5-b]pyrazin-2-one, N-[5-(1,1-dimethylethyl)-2-methoxyphenyl]-N'-[4-(1,2,3,4-tetrahydro-2-oxopyrido[2,3-b]pyrazin-7-yl)-1-naphthalenyl]-Urea, N-[4-(2,3-dihydro-2-oxo-1H-imidazo[4,5-b]pyridin-6-yl)-1-naphthalenyl]-N'-[5-(1,1-dimethylethyl)-2-methoxyphenyl]-Urea, 1,3-dihydro-5-phenyl-2H-Imidazo[4,5-b]pyrazin-2-one, 1,3-dihydro-5-phenoxy-2H-Imidazo[4,5-b]pyridin-2-one, 1,3-dihydro-1-methyl-6-phenyl-2H-Imidazo[4,5-b]pyridin-2-one, 1,3-dihydro-5-(1H-imidazol-1-yl) 2H-Imidazo[4,5-b]pyridin-2-one, 6-(2,3-dihydro-2-oxo-1H-imidazo[4,5-b]pyridin-6-yl)-8-methyl-2(1H)-Quinolinone and 7,8-dihydro-8-oxo-2-phenyl-9H-purine-9-acetic acid.

In certain embodiments, the provisos set forth above with respect to the Heteroaryl Compounds of formula (I) also apply to Heteroaryl Compounds of formulas (II)-(VIII) as appropriate.

In a further embodiment, provided herein are Heteroaryl Compounds having the following formula (II):

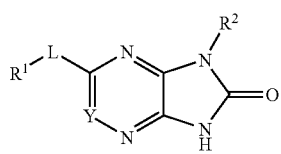

(II)

and pharmaceutically acceptable salts, polymorphs, clathrates, solvates, hydrates, stereoisomers, enantiomers and prodrugs thereof, wherein:

L is a direct bond, NH or O;

Y is N or CR$^3$;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl;

$R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl;

$R^3$ is H, substituted or unsubstituted $C_{1-8}$alkyl, substituted or unsubstituted aryl, substituted or unsubstituted heteroaryl, substituted or unsubstituted cycloalkyl, substituted or unsubstituted heterocycloalkyl, —NHR$^4$ or —N(R$^4$)$_2$; and $R^4$ is at each occurrence independently substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (II) are those wherein $R^1$ is substituted aryl, such as substituted phenyl.

In another embodiment, the Heteroaryl Compounds of formula (II) are those wherein $R^1$ is substituted or unsubstituted aryl, such as substituted or unsubstituted phenyl or substituted or unsubstituted naphthyl.

In another embodiment, the Heteroaryl Compounds of formula (II) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (II) are those wherein $R^1$ is H.

In another embodiment, the Heteroaryl Compounds of formula (II) are those wherein $R^2$ is substituted $C_{1-8}$alkyl.

In another embodiment, the Heteroaryl Compounds of formula (II) are those wherein $R^2$ is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (II) are those wherein $R^2$ is substituted or unsubstituted cycloalkyl or substituted or unsubstituted heterocycloalkyl.

In another embodiment, the Heteroaryl Compounds of formula (II) are those wherein $R^2$ is substituted or unsubstituted aryl, such as substituted or unsubstituted phenyl.

In another embodiment, the Heteroaryl Compounds of formula (II) are those wherein $R^2$ is H.

In another embodiment, the Heteroaryl Compounds of formula (II) are those wherein Y is CH.

In another embodiment, the Heteroaryl Compounds of formula (II) are those wherein L is a direct bond.

In another embodiment, the Heteroaryl Compounds of formula (II) are those wherein $R^1$ is substituted or unsubstituted aryl and $R^2$ is unsubstituted $C_{1-8}$alkyl.

In another embodiment, the Heteroaryl Compounds of formula (II) are those wherein $R^1$ is substituted or unsubstituted aryl and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (II) are those wherein R¹ is substituted or unsubstituted aryl and R² is substituted or unsubstituted cycloalkyl, or substituted or unsubstituted heterocycloalkyl.

In another embodiment, the Heteroaryl Compounds of formula (II) do not include compounds wherein Y is CH, L is a direct bond, R¹ is substituted or unsubstituted aryl or substituted or unsubstituted heteroaryl, and R² is $C_{1-8}$alkyl substituted with substituted or unsubstituted aryl or substituted or unsubstituted heteroaryl.

In a further embodiment, provided herein are Heteroaryl Compounds having the following formula (III):

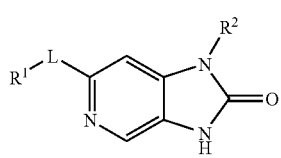

(III)

and pharmaceutically acceptable salts, polymorphs, clathrates, solvates, hydrates, stereoisomers, enantiomers and prodrugs thereof,
wherein:
L is a direct bond, NH or O;
R¹ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl; and
R² is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (III) are those wherein R¹ is substituted aryl, such as substituted phenyl.

In another embodiment, the Heteroaryl Compounds of formula (III) are those wherein R¹ is substituted or unsubstituted aryl, such as substituted or unsubstituted phenyl or substituted or unsubstituted naphthyl.

In another embodiment, the Heteroaryl Compounds of formula (III) are those wherein R¹ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (III) are those wherein R¹ is H.

In another embodiment, the Heteroaryl Compounds of formula (III) are those wherein R² is substituted $C_{1-8}$alkyl.

In another embodiment, the Heteroaryl Compounds of formula (III) are those wherein R² is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (III) are those wherein R² is substituted or unsubstituted cycloalkyl or substituted or unsubstituted heterocycloalkyl.

In another embodiment, the Heteroaryl Compounds of formula (III) are those wherein R² is substituted or unsubstituted aryl, such as substituted or unsubstituted phenyl.

In another embodiment, the Heteroaryl Compounds of formula (III) are those wherein R² is H.

In another embodiment, the Heteroaryl Compounds of formula (III) are those wherein L is a direct bond.

In another embodiment, the Heteroaryl Compounds of formula (III) are those wherein R¹ is substituted or unsubstituted aryl and R² is unsubstituted $C_{1-8}$alkyl.

In another embodiment, the Heteroaryl Compounds of formula (III) are those wherein R¹ is substituted or unsubstituted aryl and R² is $C_{1-8}$alkyl substituted with one or more substituents selected from alkoxy, amino, hydroxy, cycloalkyl, or heterocycloalkyl.

In another embodiment, the Heteroaryl Compounds of formula (III) are those wherein R¹ is substituted or unsubstituted aryl and R² is substituted or unsubstituted cycloalkyl, or substituted or unsubstituted heterocycloalkyl.

In a further embodiment, provided herein are Heteroaryl Compounds having the following formula (IV):

(IV)

and pharmaceutically acceptable salts, polymorphs, clathrates, solvates, hydrates, stereoisomers, enantiomers and prodrugs thereof,
wherein:
L is a direct bond, NH or O;
R¹ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl; and
R² is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (IV) are those wherein R¹ is substituted aryl, such as substituted phenyl.

In another embodiment, the Heteroaryl Compounds of formula (IV) are those wherein R¹ is substituted or unsubstituted aryl, such as substituted or unsubstituted phenyl or substituted or unsubstituted naphthyl.

In another embodiment, the Heteroaryl Compounds of formula (IV) are those wherein R¹ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (IV) are those wherein R¹ is H.

In another embodiment, the Heteroaryl Compounds of formula (IV) are those wherein R² is substituted $C_{1-8}$alkyl.

In another embodiment, the Heteroaryl Compounds of formula (IV) are those wherein R² is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (IV) are those wherein R² is substituted or unsubstituted cycloalkyl or substituted or unsubstituted heterocycloalkyl.

In another embodiment, the Heteroaryl Compounds of formula (IV) are those wherein $R^2$ is substituted or unsubstituted aryl, such as substituted or unsubstituted phenyl.

In another embodiment, the Heteroaryl Compounds of formula (IV) are those wherein $R^2$ is H.

In another embodiment, the Heteroaryl Compounds of formula (IV) are those wherein L is a direct bond.

In another embodiment, the Heteroaryl Compounds of formula (IV) are those wherein $R^1$ is substituted or unsubstituted aryl and $R^2$ is unsubstituted $C_{1-8}$alkyl.

In another embodiment, the Heteroaryl Compounds of formula (IV) are those wherein $R^1$ is substituted or unsubstituted aryl and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (IV) are those wherein $R^1$ is substituted or unsubstituted aryl and $R^2$ is substituted or unsubstituted cycloalkyl, or substituted or unsubstituted heterocycloalkyl.

In a further embodiment, provided herein are Heteroaryl Compounds having the following formula (V):

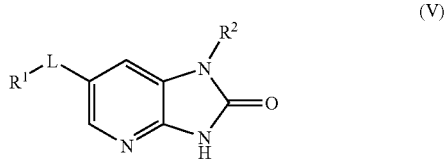

(V)

and pharmaceutically acceptable salts, polymorphs, clathrates, solvates, hydrates, stereoisomers, enantiomers and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (V) are those wherein $R^1$ is substituted aryl, such as substituted phenyl.

In another embodiment, the Heteroaryl Compounds of formula (V) are those wherein $R^1$ is substituted or unsubstituted aryl, such as substituted or unsubstituted phenyl or substituted or unsubstituted naphthyl.

In another embodiment, the Heteroaryl Compounds of formula (V) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (V) are those wherein $R^1$ is H.

In another embodiment, the Heteroaryl Compounds of formula (V) are those wherein $R^2$ is substituted $C_{1-8}$alkyl.

In another embodiment, the Heteroaryl Compounds of formula (V) are those wherein $R^2$ is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (V) are those wherein $R^2$ is substituted or unsubstituted cycloalkyl or substituted or unsubstituted heterocycloalkyl.

In another embodiment, the Heteroaryl Compounds of formula (V) are those wherein $R^2$ is substituted or unsubstituted aryl, such as substituted or unsubstituted phenyl.

In another embodiment, the Heteroaryl Compounds of formula (V) are those wherein $R^2$ is H.

In another embodiment, the Heteroaryl Compounds of formula (V) are those wherein L is a direct bond.

In another embodiment, the Heteroaryl Compounds of formula (V) are those wherein $R^1$ is substituted or unsubstituted aryl and $R^2$ is unsubstituted $C_{1-8}$alkyl.

In another embodiment, the Heteroaryl Compounds of formula (V) are those wherein $R^1$ is substituted or unsubstituted aryl and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (V) are those wherein $R^1$ is substituted or unsubstituted aryl and $R^2$ is substituted or unsubstituted cycloalkyl, or substituted or unsubstituted heterocycloalkyl.

In a further embodiment, provided herein are Heteroaryl Compounds having the following formula (VI):

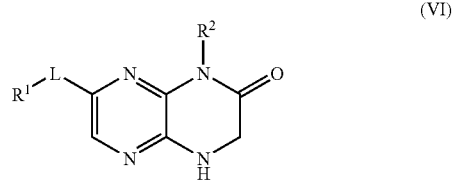

(VI)

and pharmaceutically acceptable salts, polymorphs, clathrates, solvates, hydrates, stereoisomers, enantiomers and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (VI) are those wherein $R^1$ is substituted aryl, such as substituted phenyl.

In another embodiment, the Heteroaryl Compounds of formula (VI) are those wherein $R^1$ is substituted or unsubstituted aryl, such as substituted or unsubstituted phenyl or substituted or unsubstituted naphthyl.

In another embodiment, the Heteroaryl Compounds of formula (VI) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (VI) are those wherein $R^1$ is H.

In another embodiment, the Heteroaryl Compounds of formula (VI) are those wherein $R^2$ is substituted $C_{1-8}$alkyl.

In another embodiment, the Heteroaryl Compounds of formula (VI) are those wherein $R^2$ is methyl or ethyl substituted with substituted or unsubstituted aryl, substituted unsubstituted heteroaryl, substituted or unsubstituted cycloalkyl, or substituted or unsubstituted heterocycloalkyl.

In another embodiment, the Heteroaryl Compounds of formula (VI) are those wherein $R^2$ is substituted or unsubstituted cycloalkyl or substituted or unsubstituted heterocycloalkyl.

In another embodiment, the Heteroaryl Compounds of formula (VI) are those wherein $R^2$ is substituted or unsubstituted aryl, such as substituted or unsubstituted phenyl.

In another embodiment, the Heteroaryl Compounds of formula (VI) are those wherein $R^2$ is H.

In another embodiment, the Heteroaryl Compounds of formula (VI) are those wherein L is a direct bond.

In another embodiment, the Heteroaryl Compounds of formula (VI) are those wherein $R^1$ is substituted or unsubstituted aryl and $R^2$ is unsubstituted $C_{1-8}$alkyl.

In another embodiment, the Heteroaryl Compounds of formula (VI) are those wherein $R^1$ is substituted or unsubstituted aryl and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (VI) are those wherein $R^1$ is substituted or unsubstituted aryl and $R^2$ is substituted or unsubstituted cycloalkyl, or substituted or unsubstituted heterocycloalkyl.

In a further embodiment, provided herein are Heteroaryl Compounds having the following formula (VII):

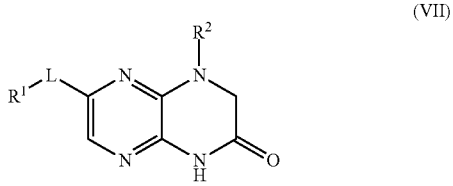

(VII)

and pharmaceutically acceptable salts, polymorphs, clathrates, solvates, hydrates, stereoisomers, enantiomers and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (VII) are those wherein $R^1$ is substituted aryl, such as substituted phenyl.

In another embodiment, the Heteroaryl Compounds of formula (VII) are those wherein $R^1$ is substituted or unsubstituted aryl, such as substituted or unsubstituted phenyl or substituted or unsubstituted naphthyl.

In another embodiment, the Heteroaryl Compounds of formula (VII) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (VII) are those wherein $R^1$ is H.

In another embodiment, the Heteroaryl Compounds of formula (VII) are those wherein $R^2$ is substituted $C_{1-8}$alkyl.

In another embodiment, the Heteroaryl Compounds of formula (VII) are those wherein $R^2$ is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (VII) are those wherein $R^2$ is substituted or unsubstituted cycloalkyl or substituted or unsubstituted heterocycloalkyl.

In another embodiment, the Heteroaryl Compounds of formula (VII) are those wherein $R^2$ is substituted or unsubstituted aryl, such as substituted or unsubstituted phenyl.

In another embodiment, the Heteroaryl Compounds of formula (VII) are those wherein $R^2$ is H.

In another embodiment, the Heteroaryl Compounds of formula (VII) are those wherein L is a direct bond.

In another embodiment, the Heteroaryl Compounds of formula (VII) are those wherein $R^1$ is substituted or unsubstituted aryl and $R^2$ is unsubstituted $C_{1-8}$alkyl.

In another embodiment, the Heteroaryl Compounds of formula (VII) are those wherein $R^1$ is substituted or unsubstituted aryl and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (VII) are those wherein $R^1$ is substituted or unsubstituted aryl and $R^2$ is substituted or unsubstituted cycloalkyl, or substituted or unsubstituted heterocycloalkyl.

In a further embodiment, provided herein are Heteroaryl Compounds having the following formula (VIII):

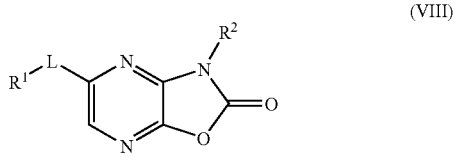

(VIII)

and pharmaceutically acceptable salts, polymorphs, clathrates, solvates, hydrates, stereoisomers, enantiomers and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocycloalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl.

In one embodiment, the Heteroaryl Compounds of formula (VIII) are those wherein $R^1$ is substituted aryl, such as substituted phenyl.

In another embodiment, the Heteroaryl Compounds of formula (VIII) are those wherein $R^1$ is substituted or unsubstituted aryl, such as substituted or unsubstituted phenyl or substituted or unsubstituted naphthyl.

In another embodiment, the Heteroaryl Compounds of formula (VIII) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the Heteroaryl Compounds of formula (VIII) are those wherein $R^1$ is H.

In another embodiment, the Heteroaryl Compounds of formula (VIII) are those wherein $R^2$ is substituted $C_{1-8}$alkyl.

In another embodiment, the Heteroaryl Compounds of formula (VIII) are those wherein $R^2$ is methyl or ethyl substituted with substituted or unsubstituted aryl, substituted or unsubstituted heteroaryl, substituted or unsubstituted cycloalkyl, or substituted or unsubstituted heterocycloalkyl.

In another embodiment, the Heteroaryl Compounds of formula (VIII) are those wherein $R^2$ is substituted or unsubstituted cycloalkyl or substituted or unsubstituted heterocycloalkyl.

In another embodiment, the Heteroaryl Compounds of formula (VIII) are those wherein $R^2$ is substituted or unsubstituted aryl, such as substituted or unsubstituted phenyl.

In another embodiment, the Heteroaryl Compounds of formula (VIII) are those wherein $R^2$ is H.

In another embodiment, the Heteroaryl Compounds of formula (VIII) are those wherein L is a direct bond.

In another embodiment, the Heteroaryl Compounds of formula (VIII) are those wherein $R^1$ is substituted or unsubstituted aryl and $R^2$ is unsubstituted $C_{1-8}$alkyl.

In another embodiment, the Heteroaryl Compounds of formula (VIII) are those wherein $R^1$ is substituted or unsubstituted aryl and $R^2$ is $C_{1-8}$alkyl substituted with one or more substituents selected from alkoxy, amino, hydroxy, cycloalkyl, or heterocycloalkyl.

In another embodiment, the Heteroaryl Compounds of formula (VIII) are those wherein $R^1$ is substituted or unsubstituted aryl and $R^2$ is substituted or unsubstituted cycloalkyl, or substituted or unsubstituted heterocycloalkyl.

Representative Heteroaryl Compounds are set forth in Table 1, below.

TABLE 1

| Compound | Compound |
|---|---|
| (S)-1-(1-hydroxy-3-methylbutan-2-yl)-6-phenyl-1H-imidazo[4,5-b]pyrazin-2(3H)-one 1 | 1-((tetrahydro-2H-pyran-4-yl)methyl)-6-(3,4,5-trimethoxyphenyl)-1H-imidazo[4,5-b]pyrazin-2(3H)-one 2 |
| (R)-6-(naphthalen-1-yl)-1-(1-phenylethyl)-1H-imidazo[4,5-b]pyrazin-2(3H)-one 3 | 1-(3-methoxybenzyl)-6-(4-(methylsulfonyl)phenyl)-1H-imidazo[4,5-b]pyrazin-2(3H)-one 4 |
| (S)-1-(1-phenylethyl)-6-(quinolin-5-yl)-1H-imidazo[4,5-b]pyrazin-2(3H)-one 5 | 6-(4-hydroxyphenyl)-1-((tetrahydro-2H-pyran-4-yl)methyl)-1H-imidazo[4,5-b]pyrazin-2(3H)-one 6 |
| (S)-6-(naphthalen-1-yl)-1-(1-phenylethyl)-1H-imidazo[4,5-b]pyrazin-2(3H)-one 7 | (S)-1-(1-hydroxy-3-methylbutan-2-yl)-6-(5-isopropyl-2-methoxyphenyl)-1H-imidazo[4,5-b]pyrazin-2(3H)-one 8 |
| (R)-1-(1-hydroxy-3-methylbutan-2-yl)-6-phenyl-1H-imidazo[4,5-b]pyrazin-2(3H)-one 9 | (R)-1-(1-phenylethyl)-6-(quinolin-5-yl)-1H-imidazo[4,5-b]pyrazin-2(3H)-one 10 |
| (S)-1-(1-hydroxy-3-methylbutan-2-yl)-6-(quinolin-5-yl)-1H-imidazo[4,5-b]pyrazin-2(3H)-one 11 | (R)-1-(1-hydroxy-3-methylbutan-2-yl)-6-(quinolin-5-yl)-1H-imidazo[4,5-b]pyrazin-2(3H)-one 12 |
| (R)-1-(1-hydroxy-3-methylbutan-2-yl)-6-(5-isopropyl-2-methoxyphenyl)-1H-imidazo[4,5-b]pyrazin-2(3H)-one 13 | 1-benzyl-6-(quinolin-5-yl)-1H-imidazo[4,5-b]pyrazin-2(3H)-one 14 |
| 1-(4-methoxybenzyl)-6-(quinolin-5-yl)-1H-imidazo[4,5-b]pyrazin-2(3H)-one 15 | (R)-1-(1-phenylethyl)-1H-imidazo[4,5-b]pyrazin-2(3H)-one 16 |
| (S)-1-(1-phenylethyl)-1H-imidazo[4,5-b]pyrazin-2(3H)-one 17 | 1-isopropyl-6-(5-isopropyl-2-methoxyphenyl)-1H-imidazo[4,5-b]pyrazin-2(3H)-one 18 |
| 1-cyclohexyl-6-(5-isopropyl-2-methoxyphenyl)-1H-imidazo[4,5-b]pyrazin-2(3H)-one 19 | 5-(quinolin-5-yl)-1H-imidazo[4,5-b]pyrazin-2(3H)-one 20 |
| 1-isobutyl-6-(5-isopropyl-2-methoxyphenyl)-1H-imidazo[4,5-b]pyrazin-2(3H)-one 21 | 1-(2-hydroxyethyl)-6-(5-isopropyl-2-methoxyphenyl)-1H-imidazo[4,5-b]pyrazin-2(3H)-one 22 |
| 6-(5-isopropyl-2-methoxyphenyl)-1-(tetrahydro-2H-pyran-4-yl)-1H-imidazo[4,5-b]pyrazin-2(3H)-one 23 | (R)-1-(1-phenylethyl)-6-(quinolin-5-yl)-1H-imidazo[4,5-c]pyridin-2(3H)-one 24 |
| (S)-1-(1-phenylethyl)-6-(quinolin-5-yl)-1H-imidazo[4,5-c]pyridin-2(3H)-one 25 | 3-(1-phenylethyl)-5-(quinolin-5-yl)-1H-imidazo[4,5-b]pyridin-2(3H)-one 26 |
| (R)-3-(1-phenylethyl)-5-(quinolin-5-yl)-1H-imidazo[4,5-b]pyridin-2(3H)-one 27 | (R)-6-(5-isopropyl-2-methoxyphenyl)-1-(3-methylbutan-2-yl)-1H-imidazo[4,5-b]pyrazin-2(3H)-one 28 |

TABLE 1-continued

| Compound | Compound |
|---|---|
| (S)-6-(5-isopropyl-2-methoxyphenyl)-1-(tetrahydrofuran-3-yl)-1H-imidazo[4,5-b]pyrazin-2(3H)-one<br>29 | (S)-6-(5-isopropyl-2-methoxyphenyl)-1-(3-methylbutan-2-yl)-1H-imidazo[4,5-b]pyrazin-2(3H)-one<br>30 |
| 1-cyclopentyl-6-(5-isopropyl-2-methoxyphenyl)-1H-imidazo[4,5-b]pyrazin-2(3H)-one<br>31 | (R)-6-(5-isopropyl-2-methoxyphenyl)-1-(tetrahydrofuran-3-yl)-1H-imidazo[4,5-b]pyrazin-2(3H)-one<br>32 |
| 1-(cyclopropylmethyl)-6-(5-isopropyl-2-methoxyphenyl)-1H-imidazo[4,5-b]pyrazin-2(3H)-one<br>33 | 1-(cyclopentylmethyl)-6-(5-isopropyl-2-methoxyphenyl)-1H-imidazo[4,5-b]pyrazin-2(3H)-one<br>34 |
| 1-(cyclohexylmethyl)-6-(5-isopropyl-2-methoxyphenyl)-1H-imidazo[4,5-b]pyrazin-2(3H)-one<br>35 | 6-(5-isopropyl-2-methoxyphenyl)-1-neopentyl-1H-imidazo[4,5-b]pyrazin-2(3H)-one<br>36 |
| 1-isopropyl-6-(3-isopropylphenyl)-1H-imidazo[4,5-b]pyrazin-2(3H)-one<br>37 | 1-isopropyl-6-(2-methoxyphenyl)-1H-imidazo[4,5-b]pyrazin-2(3H)-one<br>38 |
| (S)-3-(1-hydroxy-3-methylbutan-2-yl)-5-(5-isopropyl-2-methoxyphenyl)-1H-imidazo[4,5-b]pyridin-2(3H)-one<br>39 | (R)-1-(2-hydroxy-1-phenylethyl)-6-(quinolin-5-yl)-1H-imidazo[4,5-b]pyrazin-2(3H)-one<br>40 |
| (S)-1-(2-hydroxy-1-phenylethyl)-6-(quinolin-5-yl)-1H-imidazo[4,5-b]pyrazin-2(3H)-one<br>41 | 1-(1-phenylethyl)-6-(quinolin-5-yl)-1H-imidazo[4,5-b]pyrazin-2(3H)-one<br>42 |
| 1-benzhydryl-6-(quinolin-5-yl)-1H-imidazo[4,5-b]pyrazin-2(3H)-one<br>43 | (S)-1-(1-phenylpropyl)-6-(quinolin-5-yl)-1H-imidazo[4,5-b]pyrazin-2(3H)-one<br>44 |
| (R)-1-(1-phenylpropyl)-6-(quinolin-5-yl)-1H-imidazo[4,5-b]pyrazin-2(3H)-one<br>45 | 6-(5-isopropyl-2-methoxyphenyl)-1-(tetrahydro-2H-pyran-3-yl)-1H-imidazo[4,5-b]pyrazin-2(3H)-one<br>46 |
| 1-(3-methoxybenzyl)-6-(quinolin-5-yl)-1H-imidazo[4,5-b]pyrazin-2(3H)-one<br>47 | (R)-1-methyl-3-(1-phenylethyl)-5-(quinolin-5-yl)-1H-imidazo[4,5-b]pyrazin-2(3H)-one<br>48 |
| (S)-1-methyl-3-(1-phenylethyl)-5-(quinolin-5-yl)-1H-imidazo[4,5-b]pyrazin-2(3H)-one<br>49 | 1-(cyclopentylmethyl)-6-(quinolin-5-yl)-1H-imidazo[4,5-b]pyrazin-2(3H)-one<br>50 |
| 1-(1-(2-fluorophenyl)ethyl)-6-(quinolin-5-yl)-1H-imidazo[4,5-b]pyrazin-2(3H)-one<br>51 | 1-(1-(4-fluorophenyl)ethyl)-6-(quinolin-5-yl)-1H-imidazo[4,5-b]pyrazin-2(3H)-one<br>52 |
| 1-cyclopentyl-6-(quinolin-5-yl)-1H-imidazo[4,5-b]pyrazin-2(3H)-one<br>53 | 1-(1-(3-fluorophenyl)ethyl)-6-(quinolin-5-yl)-1H-imidazo[4,5-b]pyrazin-2(3H)-one<br>54 |
| 1-(1-(3-methoxyphenyl)ethyl)-6-(quinolin-5-yl)-1H-imidazo[4,5-b]pyrazin-2(3H)-one<br>55 | 1-(1-(4-methoxyphenyl)ethyl)-6-(quinolin-5-yl)-1H-imidazo[4,5-b]pyrazin-2(3H)-one<br>56 |
| 6-(quinolin-5-yl)-1-(tetrahydro-2H-pyran-4-yl)-1H-imidazo[4,5-b]pyrazin-2(3H)-one<br>57 | 6-(quinolin-5-yl)-1-(tetrahydro-2H-pyran-3-yl)-1H-imidazo[4,5-b]pyrazin-2(3H)-one<br>58 |
| 1-((1s,4s)-4-hydroxycyclohexyl)-6-(quinolin-5-yl)-1H-imidazo[4,5-b]pyrazin-2(3H)-one<br>59 | 1-((1r,4r)-4-hydroxycyclohexyl)-6-(quinolin-5-yl)-1H-imidazo[4,5-b]pyrazin-2(3H)-one<br>60 |
| 6-(isoquinolin-5-yl)-1-(1-phenylethyl)-1H-imidazo[4,5-b]pyrazin-2(3H)-one<br>61 | (R)-1-(1-phenylethyl)-6-(quinolin-5-yl)-1H-imidazo[4,5-b]pyridin-2(3H)-one<br>62 |
| 1-(1-phenylethyl)-6-(quinolin-5-yl)-1H-imidazo[4,5-b]pyridin-2(3H)-one<br>63 | 1-isopropyl-6-(quinolin-5-yl)-1H-imidazo[4,5-b]pyrazin-2(3H)-one<br>64 |
| 1-(1-(4-chlorophenyl)ethyl)-6-(quinolin-5-yl)-1H-imidazo[4,5-b]pyrazin-2(3H)-one<br>65 | 1-(1-(4-(methylsulfonyl)phenyl)ethyl)-6-(quinolin-5-yl)-1H-imidazo[4,5-b]pyrazin-2(3H)-one<br>66 |
| 1-(1-(pyridin-4-yl)ethyl)-6-(quinolin-5-yl)-1H-imidazo[4,5-b]pyrazin-2(3H)-one<br>67 | 5-methyl-1-((S)-1-phenylethyl)-6-(quinolin-5-yl)-1H-imidazo[4,5-b]pyrazin-2(3H)-one<br>68 |
| 5-methyl-1-((R)-1-phenylethyl)-6-(quinolin-5-yl)-1H-imidazo[4,5-b]pyrazin-2(3H)-one<br>69 | 1-(1-phenylethyl)-6-(quinolin-4-yl)-1H-imidazo[4,5-b]pyrazin-2(3H)-one<br>70 |

TABLE 1-continued

| Compound | Compound |
|---|---|
| 6-(3-fluorophenyl)-1-(1-phenylethyl)-1H-imidazo[4,5-b]pyrazin-2(3H)-one<br>71 | 6-(2-fluorophenyl)-1-(1-phenylethyl)-1H-imidazo[4,5-b]pyrazin-2(3H)-one<br>72 |
| 1-(1-phenylethyl)-6-(quinolin-6-yl)-1H-imidazo[4,5-b]pyrazin-2(3H)-one<br>73 | 1-(piperidin-4-ylmethyl)-6-(quinolin-5-yl)-1H-imidazo[4,5-b]pyrazin-2(3H)-one<br>74 |
| 1-(1-(pyridin-2-yl)ethyl)-6-(quinolin-5-yl)-1H-imidazo[4,5-b]pyrazin-2(3H)-one<br>75 | 1-(1-(pyridin-3-yl)ethyl)-6-(quinolin-5-yl)-1H-imidazo[4,5-b]pyrazin-2(3H)-one<br>76 |
| 1-((1s,4s)-4-(hydroxymethyl)cyclohexyl)-6-(quinolin-5-yl)-1H-imidazo[4,5-b]pyrazin-2(3H)-one<br>77 | N-(4-(2-oxo-3-(1-phenylethyl)-2,3-dihydro-1H-imidazo[4,5-b]pyrazin-5-yl)phenyl)methanesulfonamide<br>78 |
| 6-(3-(methylsulfonyl)phenyl)-1-(1-phenylethyl)-1H-imidazo[4,5-b]pyrazin-2(3H)-one<br>79 | 6-(3-aminophenyl)-1-(1-phenylethyl)-1H-imidazo[4,5-b]pyrazin-2(3H)-one<br>80 |
| 6-(3-(dimethylamino)phenyl)-1-(1-phenylethyl)-1H-imidazo[4,5-b]pyrazin-2(3H)-one<br>81 | 1-phenyl-6-(quinolin-5-yl)-1H-imidazo[4,5-b]pyrazin-2(3H)-one<br>82 |
| 1-(1-phenylethyl)-6-(4-(trifluoromethyl)phenyl)-1H-imidazo[4,5-b]pyrazin-2(3H)-one<br>83 | N-(3-(2-oxo-3-(1-phenylethyl)-2,3-dihydro-1H-imidazo[4,5-b]pyrazin-5-yl)phenyl)methanesulfonamide<br>84 |
| 6-(4-(methylsulfonyl)phenyl)-1-(1-phenylethyl)-1H-imidazo[4,5-b]pyrazin-2(3H)-one<br>85 | 3-(1-phenylethyl)-5-(quinolin-5-yl)oxazolo[5,4-b]pyrazin-2(3H)-one<br>86 |
| 1-cyclopentylmethyl)-6-(4-hydroxyphenyl)-1H-imidazo[4,5-b]pyrazin-2(3H)-one<br>87 | 6-(4-hydroxyphenyl)-1-isopropyl-1H-imidazo[4,5-b]pyrazin-2(3H)-one<br>88 |
| 6-(4-hydroxyphenyl)-1-isobutyl-1H-imidazo[4,5-b]pyrazin-2(3H)-one<br>89 | 6-(4-hydroxyphenyl)-1-((tetrahydro-2H-pyran-3-yl)methyl)-1H-imidazo[4,5-b]pyrazin-2(3H)-one<br>90 |
| 1-(cyclohexylmethyl)-6-(4-hydroxyphenyl)-1H-imidazo[4,5-b]pyrazin-2(3H)-one<br>91 | 5-(3-Hydroxyphenyl)-3-(2-methoxyphenyl)-1H-imidazo[4,5-b]pyridin-2(3H)-one<br>92 |
| 4-(3-(3-Methoxybenzyl)-2-oxo-2,3-dihydrooxazolo[5,4-b]pyrazin-5-yl)-N-methyl benzamide<br>93 | 1-Cyclopentyl-6-(4-hydroxyphenyl)-1H-imidazo[4,5-b]pyrazin-2(3H)-one<br>94 |
| 1-Cyclohexyl-6-(4-hydroxyphenyl)-1H-imidazo[4,5-b]pyrazin-2(3H)-one<br>95 | 4-(3-(Cyclohexylmethyl)-2-oxo-2,3-dihydro-1H-imidazo[4,5-b]pyrazin-5-yl)benzamide<br>96 |
| Methyl 4-(3-(cyclohexylmethyl)-2-oxo-2,3-dihydro-1H-imidazo[4,5-b]pyrazin-5-yl)benzoate<br>97 | 1-(Cyclohexylmethyl)-6-(pyridin-4-yl)-1H-imidazo[4,5-b]pyrazin-2(3H)-one<br>98 |
| 4-(3-(Cyclohexylmethyl)-2-oxo-2,3-dihydro-1H-imidazo[4,5-b]pyrazin-5-yl)-N-methylbenzamide<br>99 | 1-(Cyclohexylmethyl)-6-(4-(hydroxymethyl)phenyl)-1H-imidazo[4,5-b]pyrazin-2(3H)-one<br>100 |
| 1-(Cyclohexylmethyl)-6-(pyridin-3-yl)-1H-imidazo[4,5-b]pyrazin-2(3H)-one<br>101 | 3-(Cyclohexylmethyl)-2-oxo-2,3-dihydro-1H-imidazo[4,5-b]pyrazin-5-yl)benzonitrile<br>102 |
| 1-(Cyclohexylmethyl)-6-(1H-indol-5-yl)-1H-imidazo[4,5-b]pyrazin-2(3H)-one<br>103 | 4-(3-(Cyclohexylmethyl)-2-oxo-2,3-dihydro-1H-imidazo[4,5-b]pyrazin-5-yl)-N-isopropylbenzamide<br>104 |
| 1-(2-Hydroxyethyl)-6-(4-hydroxyphenyl)-1H-imidazo[4,5-b]pyrazin-2(3H)-one<br>105 | 1-(Cyclohexylmethyl)-6-(1H-indol-6-yl)-1H-imidazo[4,5-b]pyrazin-2(3H)-one<br>106 |
| 3-(3-(Cyclohexylmethyl)-2-oxo-2,3-dihydro-1H-imidazo[4,5-b]pyrazin-5-yl)benzamide<br>107 | 6-(4-(Aminomethyl)phenyl)-1-(cyclohexylmethyl)-1H-imidazo[4,5-b]pyrazin-2(3H)-one<br>108 |
| 6-(4-Hydroxyphenyl)-1-((1-methylpiperidin-4-yl)methyl)-1H-imidazo[4,5-b]pyrazin-2(3H)-one<br>109 | 4-(3-(Cyclohexylmethyl)-2-oxo-2,3-dihydro-1H-imidazo[4,5-b]pyrazin-5-yl)benzonitrile<br>110 |

TABLE 1-continued

| Compound | Compound |
|---|---|
| 1-((1s,4s)-4-Hydroxycyclohexyl)-6-(4-hydroxyphenyl)-1H-imidazo[4,5-b]pyrazin-2(3H)-one<br>111 | 1-(Cyclohexylmethyl)-6-(pyridin-2-yl)-1H-imidazo[4,5-b]pyrazin-2(3H)-one<br>112 |
| 4-(3-(Cyclohexylmethyl)-2-oxo-2,3-dihydro-1H-imidazo[4,5-b]pyrazin-5-yl)-N-ethylbenzamide<br>113 | 1-(Cyclohexylmethyl)-6-(4-(2-hydroxypropan-2-yl)phenyl)-1H-imidazo[4,5-b]pyrazin-2(3H)-one<br>114 |
| 1-(Cyclohexylmethyl)-6-(4-hydroxy-2-methylphenyl)-1H-imidazo[4,5-b]pyrazin-2(3H)-one<br>115 | 4-(3-(Cyclohexylmethyl)-2-oxo-2,3-dihydro-1H-imidazo[4,5-b]pyrazin-5-yl)benzoic acid<br>116 |
| 6-(4-Hydroxyphenyl)-1-(2-methoxyethyl)-1H-imidazo[4,5-b]pyrazin-2(3H)-one<br>117 | 6-(4-Hydroxyphenyl)-1-(3-methoxypropyl)-1H-imidazo[4,5-b]pyrazin-2(3H)-one<br>118 |
| 6-(4-Hydroxyphenyl)-4-(3-methoxybenzyl)-3,4-dihydropyrazino[2,3-b]pyrazin-2(1H)-one<br>119 | 6-(4-Hydroxyphenyl)-1-(2-(tetrahydro-2H-pyran-4-yl)ethyl)-1H-imidazo[4,5-b]pyrazin-2(3H)-one<br>120 |
| 6-(4-Hydroxyphenyl)-1-phenethyl-1H-imidazo[4,5-b]pyrazin-2(3H)-one<br>121 | 1-((1r,4r)-4-Hydroxycyclohexyl)-6-(4-hydroxyphenyl)-1H-imidazo[4,5-b]pyrazin-2(3H)-one<br>122 |
| 6-(4-(1H-1,2,4-Triazol-3-yl)phenyl)-1-(cyclohexylmethyl)-1H-imidazo[4,5-b]pyrazin-2(3H)-one<br>123 | 1-(Cyclohexylmethyl)-6-phenyl-1H-imidazo[4,5-b]pyrazin-2(3H)-one<br>124 |
| 1-(Cyclohexylmethyl)-6-(1H-pyrazol-5-yl)-1H-imidazo[4,5-b]pyrazin-2(3H)-one<br>125 | 1-(Cyclohexylmethyl)-6-(1H-pyrazol-4-yl)-1H-imidazo[4,5-b]pyrazin-2(3H)-one<br>126 |
| 1-(Cyclohexylmethyl)-6-(1-oxoisoindolin-5-yl)-1H-imidazo[4,5-b]pyrazin-2(3H)-one<br>127 | 6-(3-(1H-Tetrazol-5-yl)phenyl)-1-(cyclohexylmethyl)-1H-imidazo[4,5-b]pyrazin-2(3H)-one<br>128 |
| 1-(Cyclohexylmethyl)-6-(2-oxoindolin-5-yl)-1H-imidazo[4,5-b]pyrazin-2(3H)-one<br>129 | 1-(Cyclohexylmethyl)-6-(1H-indazol-5-yl)-1H-imidazo[4,5-b]pyrazin-2(3H)-one<br>130 |
| 1-(Cyclohexylmethyl)-6-(6-methoxypyridin-3-yl)-1H-imidazo[4,5-b]pyrazin-2(3H)-one<br>131 | 6-(4-Hydroxyphenyl)-1-(tetrahydro-2H-pyran-4-yl)-1H-imidazo[4,5-b]pyrazin-2(3H)-one<br>132 |
| 6-(4-Hydroxyphenyl)-1-(piperidin-4-ylmethyl)-1H-imidazo[4,5-b]pyrazin-2(3H)-one<br>133 | 1-(((1r,4r)-4-Aminocyclohexyl)methyl)-6-(4-hydroxyphenyl)-1H-imidazo[4,5-b]pyrazin-2(3H)-one<br>134 |
| 1-(Cyclohexylmethyl)-6-(6-hydroxypyridin-3-yl)-1H-imidazo[4,5-b]pyrazin-2(3H)-one<br>135 | 1-(Cyclohexylmethyl)-6-(2-methoxypyridin-4-yl)-1H-imidazo[4,5-b]pyrazin-2(3H)-one<br>136 |
| 4-(3-((1r,4r)-4-Hydroxycyclohexyl)-2-oxo-2,3-dihydro-1H-imidazo[4,5-b]pyrazin-5-yl)benzamide<br>137 | 2-(4-(3-(Cyclohexylmethyl)-2-oxo-2,3-dihydro-1H-imidazo[4,5-b]pyrazin-5-yl)phenyl) acetic acid<br>138 |
| 2-(4-(3-(Cyclohexylmethyl)-2-oxo-2,3-dihydro-1H-imidazo[4,5-b]pyrazin-5-yl)phenyl) acetamide<br>139 | 1-(Cyclohexylmethyl)-6-(2-oxoindolin-6-yl)-1H-imidazo[4,5-b]pyrazin-2(3H)-one<br>140 |
| 4-(3-(Cyclohexylmethyl)-2-oxo-2,3-dihydro-1H-imidazo[4,5-b]pyrazin-5-yl)-3-methyl benzoic acid<br>141 | N-Methyl-4-(2-oxo-3-((tetrahydro-2H-pyran-4-yl)methyl)-2,3-dihydro-1H-imidazo[4,5-b]pyrazin-5-yl)benzamide<br>142 |
| 4-(2-oxo-3-((Tetrahydro-2H-pyran-4-yl)methyl)-2,3-dihydro-1H-imidazo[4,5-b]pyrazin-5-yl)benzamide<br>143 | 7-(4-Hydroxyphenyl)-1-(3-methoxybenzyl)-3,4-dihydropyrazino[2,3-b]pyrazin-2(1H)-one<br>144 |
| 6-(4-(2-Hydroxypropan-2-yl)phenyl)-1-((tetrahydro-2H-pyran-4-yl)methyl)-1H-imidazo[4,5-b]pyrazin-2(3H)-one<br>145 | 6-(1H-Indol-5-yl)-1-((tetrahydro-2H-pyran-4-yl)methyl)-1H-imidazo[4,5-b]pyrazin-2(3H)-one<br>146 |
| 6-(4-(4H-1,2,4-Triazol-3-yl)phenyl)-1-((tetrahydro-2H-pyran-4-yl)methyl)-1H-imidazo [4,5-b]pyrazin-2(3H)-one<br>147 | 6-(1H-Benzo[d]imidazol-5-yl)-1-(cyclohexylmethyl)-1H-imidazo[4,5-b]pyrazin-2(3H)-one<br>148 |

TABLE 1-continued

| Compound | Compound |
|---|---|
| 4-(2-oxo-3-(2-(Tetrahydro-2H-pyran-4-yl)ethyl)-2,3-dihydro-1H-imidazo[4,5-b]pyrazin-5-yl)benzamide<br>149 | 6-(3-(2H-1,2,3-Triazol-4-yl)phenyl)-1-(cyclohexylmethyl)-1H-imidazo[4,5-b]pyrazin-2(3H)-one<br>150 |
| 6-(4-(1H-Imidazol-1-yl)phenyl)-1-(cyclohexylmethyl)-1H-imidazo[4,5-b]pyrazin-2(3H)-one<br>151 | 6-(4-(1H-1,2,4-Triazol-3-yl)phenyl)-1-((1r,4r)-4-hydroxycyclohexyl)-1H-imidazo[4,5-b]pyrazin-2(3H)-one<br>152 |
| 6-(4-(2H-tetrazol-5-yl)phenyl)-1-(cyclohexylmethyl)-1H-imidazo[4,5-b]pyrazin-2(3H)-one<br>153 | 1-(Cyclohexylmethyl)-6-(2-hydroxypyridin-4-yl)-1H-imidazo[4,5-b]pyrazin-2(3H)-one<br>154 |
| 6-(4-(1H-1,2,4-Triazol-3-yl)phenyl)-1-(2-(tetrahydro-2H-pyran-4-yl)ethyl)-1H-imidazo [4,5-b]pyrazin-2(3H)-one<br>155 | 6-(4-(1H-Imidazol-2-yl)phenyl)-1-(cyclohexylmethyl)-1H-imidazo[4,5-b]pyrazin-2(3H)-one<br>156 |
| 6-(4-(1H-1,2,3-Triazol-1-yl)phenyl)-1-(cyclohexylmethyl)-1H-imidazo[4,5-b]pyrazin-2(3H)-one<br>157 | 6-(4-(2-Hydroxypropan-2-yl)phenyl)-1-(2-(tetrahydro-2H-pyran-4-yl)ethyl)-1H-imidazo[4,5-b]pyrazin-2(3H)-one<br>158 |
| 1-(Cyclohexylmethyl)-6-(4-(5-methyl-1H-1,2,4-triazol-3-yl)phenyl)-1H-imidazo[4,5-b]pyrazin-2(3H)-one<br>159 | 6-(4-(1H-Pyrazol-3-yl)phenyl)-1-(cyclohexylmethyl)-1H-imidazo[4,5-b]pyrazin-2(3H)-one<br>160 |
| 6-(4-(1H-Pyrazol-4-yl)phenyl)-1-(cyclohexylmethyl)-1H-imidazo[4,5-b]pyrazin-2(3H)-one<br>161 | 6-(4-(5-(Aminomethyl)-1H-1,2,4-triazol-3-yl)phenyl)-1-(cyclohexylmethyl)-1H-imidazo[4,5-b]pyrazin-2(3H)-one hydrochloride<br>162 |
| 1-(Cyclohexylmethyl)-6-(4-(5-(trifluoromethyl)-1H-1,2,4-triazol-3-yl)phenyl)-1H-imidazo[4,5-b]pyrazin-2(3H)-one<br>163 | 6-(4-Hydroxyphenyl)-1-((1r,4r)-4-methoxycyclohexyl)-1H-imidazo[4,5-b]pyrazin-2(3H)-one<br>164 |
| 6-(4-Hydroxyphenyl)-1-((tetrahydrofuran-2-yl)methyl)-1H-imidazo[4,5-b]pyrazin-2(3H)-one<br>165 | 6-(3-(1H-1,2,4-Triazol-3-yl)phenyl)-1-(cyclohexylmethyl)-1H-imidazo[4,5-b]pyrazin-2(3H)-one<br>166 |
| 1-((1r,4r)-4-(Hydroxymethyl)cyclohexyl)-6-(4-hydroxyphenyl)-1H-imidazo[4,5-b]pyrazin-2(3H)-one<br>167 | 6-(4-Hydroxyphenyl)-1-((1s,4s)-4-methoxycyclohexyl)-1H-imidazo[4,5-b]pyrazin-2(3H)-one<br>168 |
| 6-(4-Hydroxyphenyl)-1-((1r,4r)-4-(methoxymethyl)cyclohexyl)-1H-imidazo[4,5-b]pyrazin-2(3H)-one<br>169 | 6-(1-Methyl-1H-pyrazol-4-yl)-1-((tetrahydro-2H-pyran-4-yl)methyl)-1H-imidazo[4,5-b]pyrazin-2(3H)-one<br>170 |
| 1-(((1r,4r)-4-Hydroxycyclohexyl)methyl)-6-(4-hydroxyphenyl)-1H-imidazo[4,5-b]pyrazin-2(3H)-one<br>171 | 6-(4-Hydroxyphenyl)-1-((tetrahydrofuran-3-yl)methyl)-1H-imidazo[4,5-b]pyrazin-2(3H)-one<br>172 |
| 1-(((1s,4s)-4-Hydroxycyclohexyl)methyl)-6-(4-hydroxyphenyl)-1H-imidazo[4,5-b]pyrazin-2(3H)-one<br>173 | 6-(1H-Benzo[d]imidazol-5-yl)-1-((tetrahydro-2H-pyran-4-yl)methyl)-1H-imidazo[4,5-b]pyrazin-2(3H)-one hydrochloride<br>174 |
| 6-(4-(5-(Morpholinomethyl)-1H-1,2,4-triazol-3-yl)phenyl)-1-((tetrahydro-2H-pyran-4-yl)methyl)-1H-imidazo[4,5-b]pyrazin-2(3H)-one<br>175 | 6-(4-Hydroxyphenyl)-1-(3-(2-oxopyrrolidin-1-yl)propyl)-1H-imidazo[4,5-b]pyrazin-2(3H)-one<br>176 |
| 6-(4-Hydroxyphenyl)-1-(2-morpholinoethyl)-1H-imidazo[4,5-b]pyrazin-2(3H)-one hydrochloride<br>177 | 1-(Cyclohexylmethyl)-6-(4-(oxazol-5-yl)phenyl)-1H-imidazo[4,5-b]pyrazin-2(3H)-one<br>178 |
| 6-(2-Methyl-1H-benzo[d]imidazol-5-yl)-1-((tetrahydro-2H-pyran-4-yl)methyl)-1H-imidazo[4,5-b]pyrazin-2(3H)-one hydrocholoride<br>179 | 6-(4-(5-(Methoxymethyl)-1H-1,2,4-triazol-3-yl)phenyl)-1-((tetrahydro-2H-pyran-4-yl)methyl)-1H-imidazo[4,5-b]pyrazin-2(3H)-one<br>180 |
| 1-((1s,4s)-4-(Hydroxymethyl)cyclohexyl)-6-(4-hydroxyphenyl)-1H-imidazo[4,5-b]pyrazin-2(3H)-one<br>181 | 6-(3-Methyl-1H-pyrazol-4-yl)-1-((tetrahydro-2H-pyran-4-yl)methyl)-1H-imidazo[4,5-b]pyrazin-2(3H)-one<br>182 |
| 6-(1H-Pyrazol-4-yl)-1-((tetrahydro-2H-pyran-4-yl)methyl)-1H-imidazo[4,5-b]pyrazin-2(3H)-one<br>183 | 6-(2-Amino-1H-benzo[d]imidazol-5-yl)-1-((tetrahydro-2H-pyran-4-yl)methyl)-1H-imidazo[4,5-b]pyrazin-2(3H)-one di hydrochloride<br>184 |

TABLE 1-continued

| Compound | Compound |
|---|---|
| 6-(4-(5-(2-Hydroxypropan-2-yl)-1H-1,2,4-triazol-3-yl)phenyl)-1-((tetrahydro-2H-pyran-4-yl)methyl)-1H-imidazo[4,5-b]pyrazin-2(3H)-one<br>185 | 6-(4-(5-Isopropyl-1H-1,2,4-triazol-3-yl)phenyl)-1-((tetrahydro-2H-pyran-4-yl)methyl)-1H-imidazo[4,5-b]pyrazin-2(3H)-one<br>186 |
| 4-(2-Methoxy-1-(2-morpholinoethyl)-1H-imidazo[4,5-b]pyrazin-6-yl)benzamide hydrochloride<br>187 | 4-(1-((1s,4s)-4-Hydroxycyclohexyl)-2-methoxy-1H-imidazo[4,5-b]pyrazin-6-yl)benzamide<br>188 |
| 6-(4-Hydroxyphenyl)-1-((1s,4s)-4-(methoxymethyl)cyclohexyl)-1H-imidazo[4,5-b]pyrazin-2(3H)-one<br>189 | 6-(3H-imidazo[4,5-b]pyridin-6-yl)-1-((tetrahydro-2H-pyran-4-yl)methyl)-1H-imidazo[4,5-b]pyrazin-2(3H)-one<br>190 |
| 1-(2-(2,2-Dimethyltetrahydro-2H-pyran-4-yl)ethyl)-6-(4-hydroxyphenyl)-1H-imidazo[4,5-b]pyrazin-2(3H)-one<br>191 | 6-(4-(1H-Pyrazol-1-yl)phenyl)-1-((tetrahydro-2H-pyran-4-yl)methyl)-1H-imidazo[4,5-b]pyrazin-2(3H)-one<br>192 |
| 6-(4-(4H-1,2,4-Triazol-3-yl)phenyl)-1-(2-morpholinoethyl)-1H-imidazo[4,5-b]pyrazin-2(3H)-one<br>193 | 6-(4-(1H-Benzo[d]imidazol-2-yl)phenyl)-1-((tetrahydro-2H-pyran-4-yl)methyl)-1H-imidazo[4,5-b]pyrazin-2(3H)-one<br>194 |
| 6-(4-(1H-Imidazol-2-yl)phenyl)-1-((tetrahydro-2H-pyran-4-yl)methyl)-1H-imidazo[4,5-b]pyrazin-2(3H)-one hydrochloride<br>195 | 6-(4-(5-(Hydroxymethyl)-1H-1,2,4-triazol-3-yl)phenyl)-1-((tetrahydro-2H-pyran-4-yl)methyl)-1H-imidazo[4,5-b]pyrazin-2(3H)-one<br>196 |
| 6-(4-(1H-Imidazol-5-yl)phenyl)-1-((tetrahydro-2H-pyran-4-yl)methyl)-1H-imidazo[4,5-b]pyrazin-2(3H)-one hydrochloride<br>197 | 6-(4-Hydroxyphenyl)-1-((5-oxopyrrolidin-2-yl)methyl)-1H-imidazo[4,5-b]pyrazin-2(3H)-one<br>198 |
| 6-(4-(4,5-Dimethyl-1H-imidazol-2-yl)phenyl)-1-((tetrahydro-2H-pyran-4-yl)methyl)-1H-imidazo[4,5-b]pyrazin-2(3H)-one<br>199 | 6-(4-(1H-1,2,4-Triazol-5-yl)phenyl)-1-(((1s,4s)-4-methoxycyclohexyl)methyl)-1H-imidazo[4,5-b]pyrazin-2(3H)-one<br>200 |
| 6-(4-(1H-1,2,4-Triazol-5-yl)phenyl)-1-(((1r,4r)-4-methoxycyclohexyl)methyl)-1H-imidazo[4,5-b]pyrazin-2(3H)-one<br>201 | 6-(6-(1H-1,2,4-Triazol-3-yl)pyridin-3-yl)-1-((tetrahydro-2H-pyran-4-yl)methyl)-1H-imidazo[4,5-b]pyrazin-2(3H)-one<br>202 |
| 6-(4-(1H-1,2,4-Triazol-3-yl)phenyl)-1-(2-(2-oxopyrrolidin-1-yl)ethyl)-1H-imidazo[4,5-b]pyrazin-2(3H)-one<br>203 | 6-(4-(5-((dimethylamino)methyl)-1H-1,2,4-triazol-3-yl)phenyl)-1-((tetrahydro-2H-pyran-4-yl)methyl)-1H-imidazo[4,5-b]pyrazin-2(3H)-one<br>204 |
| 6-(4-Hydroxyphenyl)-1-(pyrrolidin-2-ylmethyl)-1H-imidazo[4,5-b]pyrazin-2(3H)-one hydrochloride<br>205 | 6-(2-Aminobenzimidazol-5-yl)-1-(cyclohexylmethyl)-4-imidazolino[4,5-b]pyrazin-2-one di hydrochloride<br>206 |
| 6-(2-(Dimethylamino)-1H-benzo[d]imidazol-5-yl)-1-((tetrahydro-2H-pyran-4-yl) methyl)-1H-imidazo[4,5-b]pyrazin-2(3H)-one<br>207 | 6-(4-Hydroxyphenyl)-1-(piperidin-3-ylmethyl)-1H-imidazo[4,5-b]pyrazin-2(3H)-one<br>208 |
| 6-(4-(4H-1,2,4-triazol-3-yl)phenyl)-1-(2-(piperidin-1-yl)ethyl)-1H-imidazo[4,5-b]pyrazin-2(3H)-one hydrochloride<br>209 | 1-(Cyclohexylmethyl)-6-(2-(methylamino)pyrimidin-5-yl)-1H-imidazo[4,5-b]pyrazin-2(3H)-one<br>210 |
| 6-(3-methyl-4-(1H-1,2,4-triazol-3-yl)phenyl)-1-((tetrahydro-2H-pyran-4-yl)methyl)-1H-imidazo[4,5-b]pyrazin-2(3H)-one<br>211 | 1-(Cyclohexylmethyl)-6-(2-(2-methoxyethylamino)pyrimidin-5-yl)-1H-imidazo[4,5-b]pyrazin-2(3H)-one<br>212 |
| 6-(4-(5-((methylamino)methyl)-1H-1,2,4-triazol-3-yl)phenyl)-1-((tetrahydro-2H-pyran-4-yl)methyl)-1H-imidazo[4,5-b]pyrazin-2(3H)-one<br>213 | 6-(4-(5-Oxopyrrolidin-2-yl)phenyl)-1-(2-(tetrahydro-2H-pyran-4-yl)ethyl)-1H-imidazo[4,5-b]pyrazin-2(3H)-one<br>214 |
| 6-(4-(5-methyl-1H-1,2,4-triazol-3-yl)phenyl)-1-(2-(tetrahydro-2H-pyran-4-yl)ethyl)-1H-imidazo[4,5-b]pyrazin-2(3H)-one<br>215 | 6-(4-(1H-imidazol-2-yl)phenyl)-1-(2-(tetrahydro-2H-pyran-4-yl)ethyl)-1H-imidazo[4,5-b]pyrazin-2(3H)-one<br>216 |

TABLE 1-continued

| Compound | Compound |
|---|---|
| 6-(4-(4H-1,2,4-triazol-3-yl)phenyl)-1-(2-methyl-2-morpholinopropyl)-1H-imidazo[4,5-b]pyrazin-2(3H)-one<br>217 | 6-(4-(4H-1,2,4-Triazol-3-yl)phenyl)-1-(1-morpholinopropan-2-yl)-1H-imidazo[4,5-b]pyrazin-2(3H)-one<br>218 |
| 6-(4-(Pyrrolidin-2-yl)phenyl)-1-(2-(tetrahydro-2H-pyran-4-yl)ethyl)-1H-imidazo[4,5-b]pyrazin-2(3H)-one<br>219 | 6-(4-(5-(aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one<br>220 |
| 6-(5-(Hydroxymethyl)thiophen-2-yl)-1-((tetrahydro-2H-pyran-4-yl)methyl)-1H-imidazo[4,5-b]pyrazin-2(3H)-one<br>221 | (1r,4r)-4-(6-(4-Hydroxyphenyl)-2-oxo-2,3-dihydro-1H-imidazo[4,5-b]pyrazin-1-yl)cyclo-hexanecarboxamide<br>222 |
| (1s,4s)-4-(6-(4-Hydroxyphenyl)-2-oxo-2,3-dihydro-1H-imidazo[4,5-b]pyrazin-1-yl)cyclohexanecarboxamide<br>223 | 6-(4-(5-methyl-1H-1,2,4-triazol-3-yl)phenyl)-1-(2-morpholinoethyl)-1H-imidazo[4,5-b]pyrazin-2(3H)-one<br>224 |
| 6-(4-(5-Oxopyrrolidin-3-yl)phenyl)-1-(2-(tetrahydro-2H-pyran-4-yl)ethyl)-1H-imidazo[4,5-b]pyrazin-2(3H)-one<br>225 | 6-(4-(Pyrrolidin-3-yl)phenyl)-1-(2-(tetrahydro-2H-pyran-4-yl)ethyl)-1H-imidazo[4,5-b]pyrazin-2(3H)-one<br>226 |
| 6-(1H-benzo[d]imidazol-5-yl)-1-(2-(tetrahydro-2H-pyran-4-yl)ethyl)-1H-imidazo[4,5-b]pyrazin-2(3H)-one<br>227 | 6-(3-(Hydroxymethyl)thiophen-2-yl)-1-((tetrahydro-2H-pyran-4-yl)methyl)-1H-imidazo[4,5-b]pyrazin-2(3H)-one<br>228 |
| 6-(5-(2-Hydroxyethyl)thiophen-2-yl)-1-((tetrahydro-2H-pyran-4-yl)methyl)-1H-imidazo[4,5-b]pyrazin-2(3H)-one<br>229 | 1-(Cyclohexylmethyl)-6-(pyrimidin-5-yl)-1H-imidazo[4,5-b]pyrazin-2(3H)-one<br>230 |
| 6-(6-Fluoropyridin-3-yl)-1-((tetrahydro-2H-pyran-4-yl)methyl)-1H-imidazo[4,5-b]pyrazin-2(3H)-one<br>231 | 6-(6-Aminopyridin-3-yl)-1-((tetrahydro-2H-pyran-4-yl)methyl)-1H-imidazo[4,5-b]pyrazin-2(3H)-one<br>232 |
| 6-(4-(5-methyl-1H-imidazol-2-yl)phenyl)-1-((tetrahydro-2H-pyran-4-yl)methyl)-1H-imidazo[4,5-b]pyrazin-2(3H)-one<br>233 | 6-(4-(5-Methyl-1H-1,2,4-triazol-3-yl)phenyl)-1-(2-(2-oxopyrrolidin-1-yl)ethyl)-1H-imidazo[4,5-b]pyrazin-2(3H)-one<br>234 |
| 6-(6-(Methylamino)pyridin-3-yl)-1-((tetrahydro-2H-pyran-4-yl)methyl)-1H-imidazo[4,5-b]pyrazin-2(3H)-one<br>235 | 6-(2-aminopyrimidin-5-yl)-1-(cyclohexylmethyl)-1H-imidazo[4,5-b]pyrazin-2(3H)-one<br>236 |
| 6-(4-(2-hydroxypropan-2-yl)phenyl)-1-(((1r,4r)-4-methoxycyclohexyl)methyl)-1H-imidazo[4,5-b]pyrazin-2(3H)-one<br>237 | 6-(4-hydroxyphenyl)-1-((1-methylpiperidin-3-yl)methyl)-1H-imidazo[4,5-b]pyrazin-2(3H)-one<br>238 |
| 6-(2-methyl-4-(1H-1,2,4-triazol-3-yl)phenyl)-1-(2-(tetrahydro-2H-pyran-4-yl)ethyl)-1H-imidazo[4,5-b]pyrazin-2(3H)-one<br>239 | 1-(cyclohexylmethyl)-6-(6-(2-hydroxypropan-2-yl)pyridin-3-yl)-1H-imidazo[4,5-b]pyrazin-2(3H)-one<br>240 |
| 6-(4-(hydroxymethyl)thiophen-2-yl)-1-((tetrahydro-2H-pyran-4-yl)methyl)-1H-imidazo[4,5-b]pyrazin-2(3H)-one<br>241 | 6-(1H-benzo[d]imidazol-6-yl)-1-(((1r,4r)-4-methoxycyclohexyl)methyl)-1H-imidazo[4,5-b]pyrazin-2(3H)-one<br>242 |
| 6-(4-(4,5-dimethyl-1H-imidazol-2-yl)phenyl)-1-(2-morpholinoethyl)-1H-imidazo[4,5-b]pyrazin-2(3H)-one<br>243 | 6-(6-(2-hydroxypropan-2-yl)pyridin-3-yl)-1-((tetrahydro-2H-pyran-4-yl)methyl)-1H-imidazo[4,5-b]pyrazin-2(3H)-one<br>244 |
| 6-(6-(2-hydroxypropan-2-yl)pyridin-3-yl)-1-(2-(tetrahydro-2H-pyran-4-yl)ethyl)-1H-imidazo[4,5-b]pyrazin-2(3H)-one<br>245 | 6-(4-(4H-1,2,4-triazol-3-yl)phenyl)-1-(2-morpholino-2-oxoethyl)-1H-imidazo[4,5-b]pyrazin-2(3H)-one<br>246 |
| 6-(4-(4H-1,2,4-triazol-3-yl)phenyl)-3-(cyclohexylmethyl)-3,4-dihydropyrazino[2,3-b]pyrazin-2(1H)-one<br>247 | 6-(4-(1H-1,2,4-triazol-3-yl)phenyl)-1-(2-(tetrahydro-2H-pyran-4-yl)ethyl)-1H-imidazo[4,5-b]pyridin-2(3H)-one<br>248 |
| (R)-6-(4-(1H-1,2,4-triazol-3-yl)phenyl)-1-(1-phenylethyl)-1H-imidazo[4,5-b]pyrazin-2(3H)-one<br>249 | (S)-6-(4-(1H-1,2,4-triazol-3-yl)phenyl)-1-(1-phenylethyl)-1H-imidazo[4,5-b]pyrazin-2(3H)-one<br>250 |
| (1r,4r)-4-(6-(4-(2-hydroxypropan-2-yl)phenyl)-2-oxo-2,3-dihydro-1H-imidazo[4,5-b]pyrazin-1-yl)cyclohexanecarboxamide<br>251 | 6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one<br>252 |

TABLE 1-continued

| Compound | Compound |
|---|---|
| 6-(4-(1H-imidazol-2-yl)phenyl)-1-(2-(tetrahydro-2H-pyran-4-yl)ethyl)-1H-imidazo[4,5-b]pyrazin-2(3H)-one 253 | 6-(4-(5-(Aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one 254 |
| 6-(1H-benzo[d]imidazol-5-yl)-1-(2-(tetrahydro-2H-pyran-4-yl)ethyl)-1H-imidazo[4,5-b]pyrazin-2(3H)-one 255 | 6-(2-Aminopyrimidin-5-yl)-1-(cyclohexylmethyl)-1H-imidazo[4,5-b]pyrazin-2(3H)-one 256 |
| 6-(4-Hydroxyphenyl)-1-((1-methylpiperidin-2-yl)methyl)-1H-imidazo[4,5-b]pyrazin-2(3H)-one hydrochloride 257 | 6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one 258 |
| 1-(Cyclohexylmethyl)-6-(6-(2-hydroxypropan-2-yl)pyridin-3-yl)-1H-imidazo[4,5-b]pyrazin-2(3H)-one 259 | 6-(6-(2-Hydroxypropan-2-yl)pyridin-3-yl)-1-((tetrahydro-2H-pyran-4-yl)methyl)-1H-imidazo[4,5-b]pyrazin-2(3H)-one 260 |
| 6-(6-(2-Hydroxypropan-2-yl)pyridin-3-yl)-1-(2-(tetrahydro-2H-pyran-4-yl)ethyl)-1H-imidazo[4,5-b]pyrazin-2(3H)-one 261 | 6-(4-(4H-1,2,4-Triazol-3-yl)phenyl)-1-(2-morpholino-2-oxoethyl)-1H-imidazo[4,5-b]pyrazin-2(3H)-one 262 |
| (R)-6-(4-(4H-1,2,4-Triazol-3-yl)phenyl)-3-(cyclohexylmethyl)-3,4-dihydropyrazino[2,3-b]pyrazin-2(1H)-one 263 | (R)-6-(4-(1H-1,2,4-Triazol-3-yl)phenyl)-1-(1-phenylethyl)-1H-imidazo[4,5-B]pyrazin-2(3H)-one 264 |
| (S)-6-(4-(4H-1,2,4-Triazol-3-yl)phenyl)-1-(1-phenylethyl)-1H-imidazo[4,5-b]pyrazin-2(3H)-one 265 | (1r,4r)-4-(6-(4-(2-Hydroxypropan-2-yl)phenyl)-2-oxo-2,3-dihydro-1H-imidazo[4,5-b]pyrazin-1-yl)cyclohexanecarboxamide 266 |
| 6-(4-(5-Methyl-1H-1,2,4-triazol-3-yl)phenyl)-1-(2-(tetrahydro-2H-pyran-4-yl)ethyl)-1H-imidazo[4,5-b]pyrazin-2(3H)-one 267 | |

4.3 Methods for Making Heteroaryl Compounds

The Heteroaryl Compounds can be made by one skilled in the art using conventional organic syntheses and commercially available materials. By way of example and not limitation, a Heteroaryl Compound can be prepared as outlined in Schemes 1-12 shown below, as well as in the examples set forth in Section 5.1. It should be noted that one skilled in the art can modify the procedures set forth in the illustrative schemes and examples to arrive at the desired product.

Scheme 1:

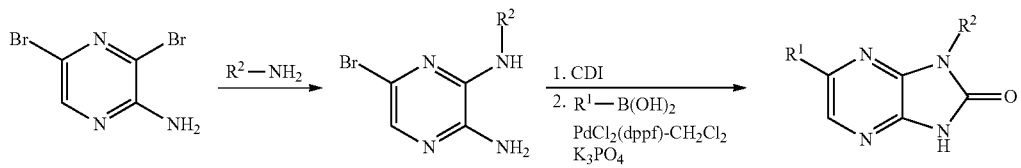

Scheme 2:

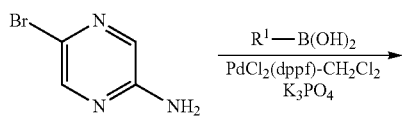

35
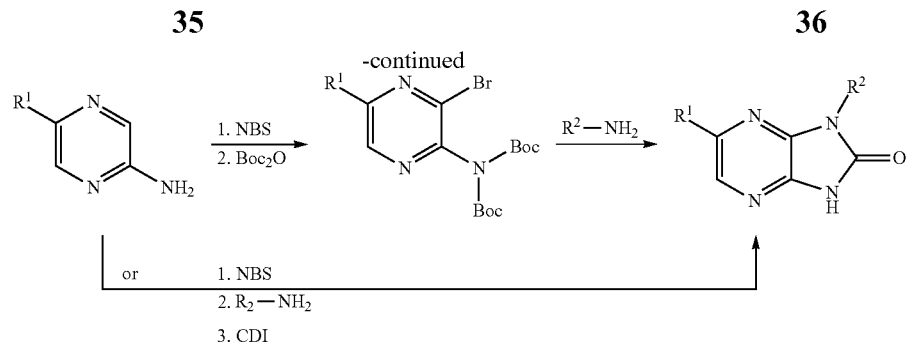
36
Scheme 3:
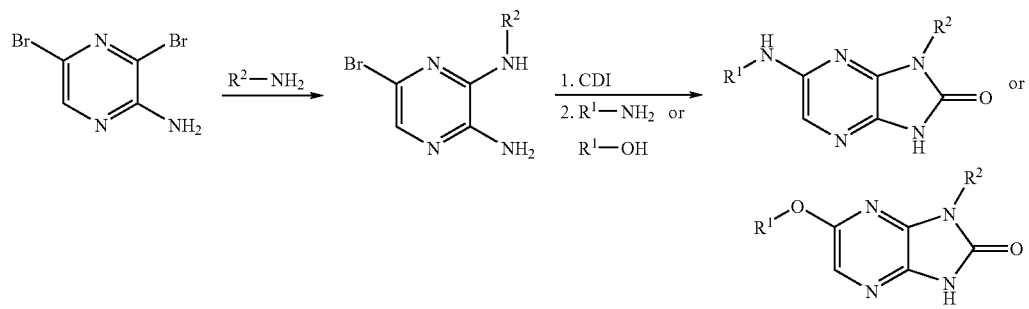
Scheme 4:
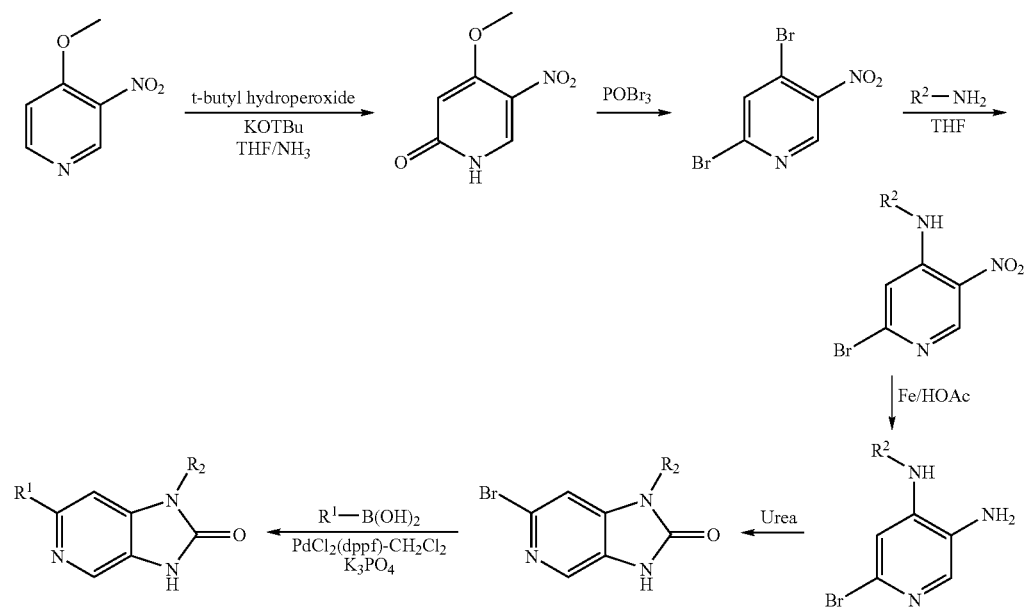
Scheme 5:
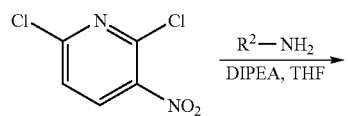
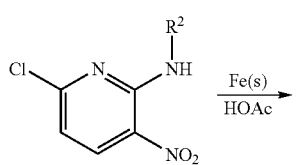

37
-continued
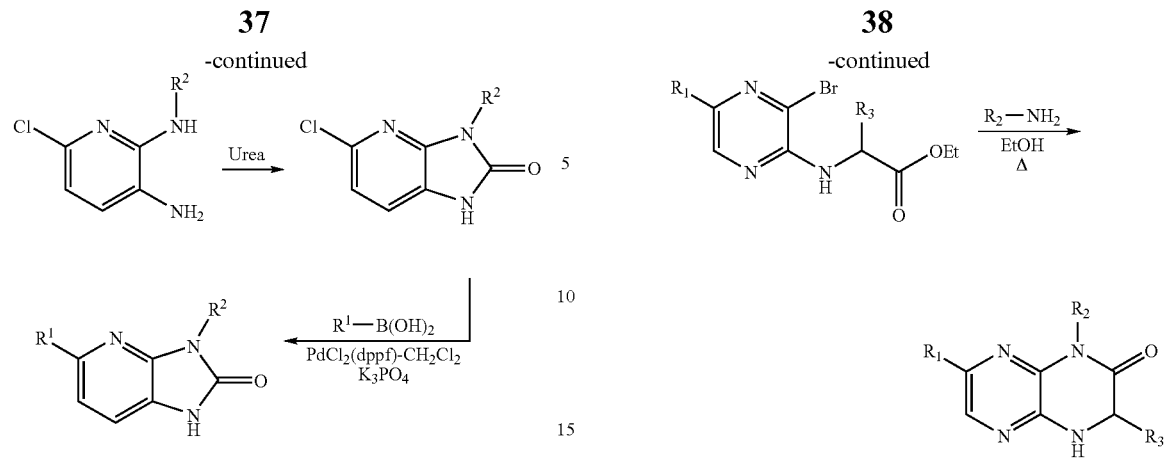
38
-continued
Scheme 6:
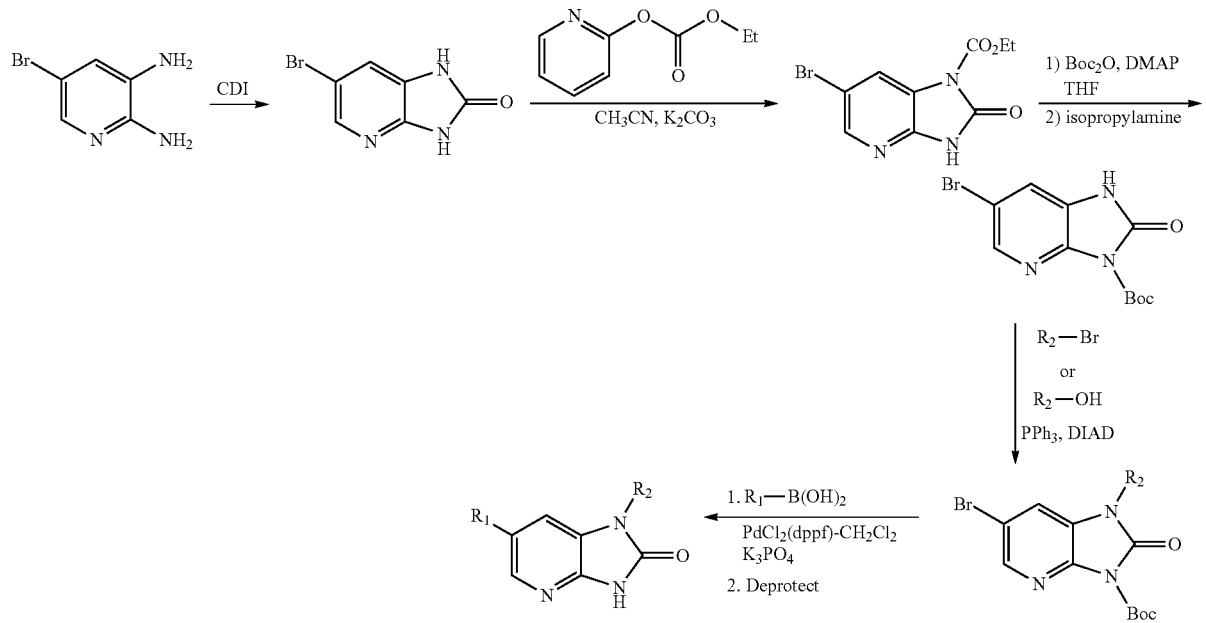
Scheme 7:
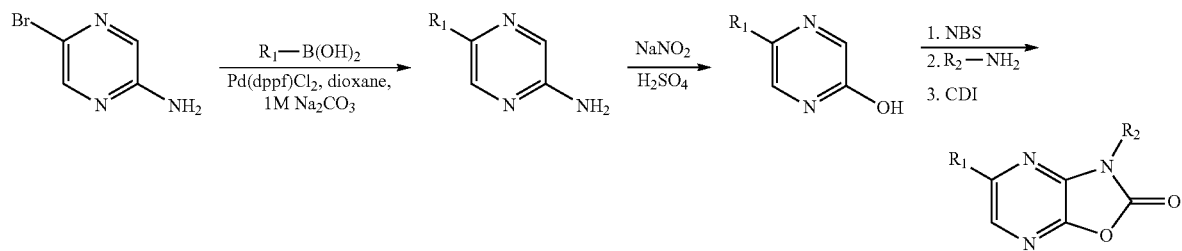
Scheme 8:
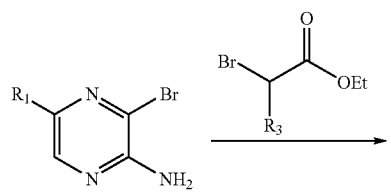
Scheme 9:
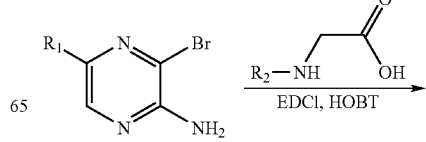

-continued

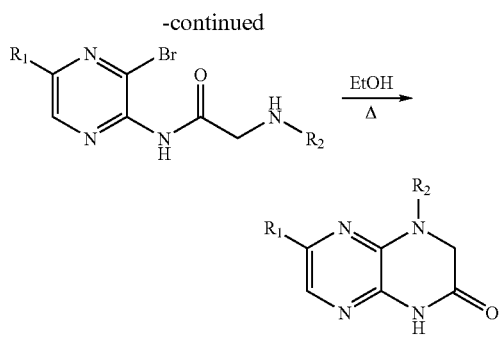

Scheme 10:

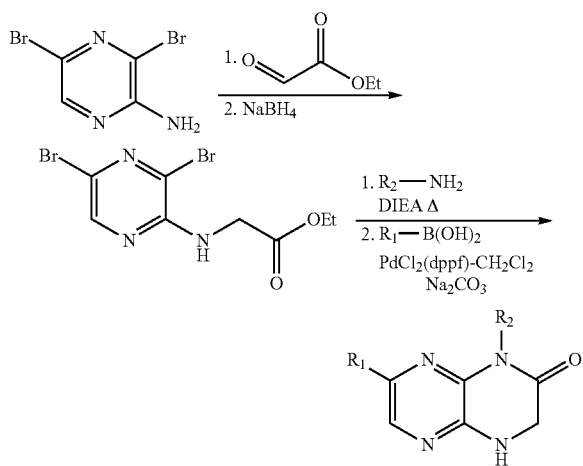

Scheme 11:

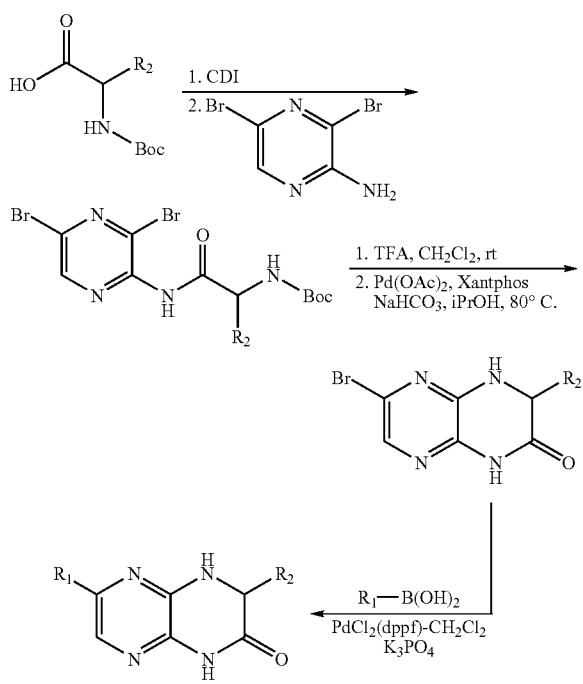

Scheme 12:

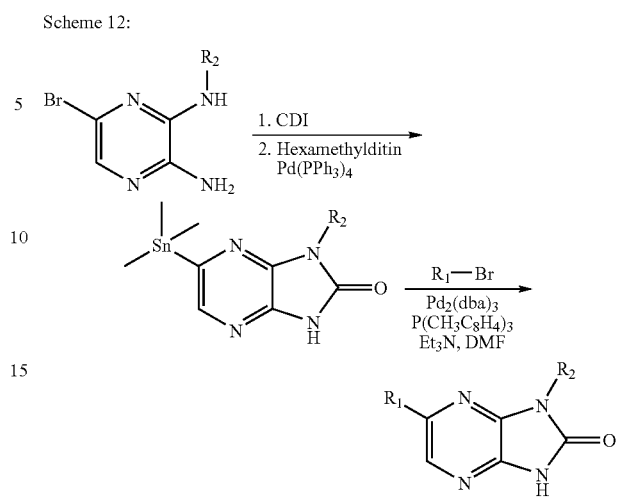

Pharmaceutically acceptable salts of the Heteroaryl Compounds can be formed by conventional and known techniques, such as by reacting a Heteroaryl Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Heteroaryl Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

4.4 Methods of Use

Heteroaryl Compounds described herein have utility as pharmaceuticals to treat or prevent disease in animals or humans. Further, Heteroaryl Compounds described herein are active against kinases (e.g., protein kinases), including those involved in cancer, inflammatory conditions, immunological conditions, neurodegenerative diseases, cardiovascular diseases and metabolic conditions. Without being limited by theory, it is thought the Heteroaryl Compounds are effective for treating and preventing cancer, inflammatory conditions, immunological conditions, neurodegenerative diseases, cardiovascular diseases, and metabolic conditions due to their ability to modulate (e.g., inhibit) kinases which are involved in the etiology of these conditions. Accordingly, provided herein are many uses of the Heteroaryl Compounds, including the treatment or prevention of those diseases set forth below. The methods provided herein comprise the administration of an effective amount of one or more Heteroaryl Compounds to a patient in need thereof.

Representative immunological conditions that Heteroaryl Compounds are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Grave's disease and diabetes (e.g., Type I diabetes).

Representative inflammatory conditions that Heteroaryl Compounds are useful for treating or preventing include, but are not limited to, psoriasis, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, diabetes (e.g., Type I diabetes and Type II diabetes) and obesity.

Representative cardiovascular diseases that Heteroaryl Compounds are useful for treating or preventing include, but are not limited to, restenosis, stroke, myocardial infarction or ischemic damage to the heart, lung, gut, kidney, liver, pancreas, spleen or brain.

Representative metabolic conditions that Heteroaryl Compounds are useful for treating or preventing include, but are not limited to, obesity and diabetes (e.g., Type II diabetes).

Representative neurodegenerative diseases that Heteroaryl Compounds are useful for treating or preventing include, but are not limited to, Huntington's disease, Alzheimer's disease and HIV-associated encephalitis.

In a particular embodiment, provided herein are methods for the treatment or prevention of insulin resistance. In certain embodiments, provided herein are methods for the treatment or prevention of insulin resistance that leads to diabetes (e.g., Type II diabetes).

In another embodiment, provided herein are methods for the treatment or prevention of syndrome X or metabolic syndrome.

In another embodiment, provide herein are methods for the treatment or prevention of diabetes.

In another embodiment, provide herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, prediabetes (e.g., impaired glucose metabolism), cystic fibrosis related diabetes, hemochromatosis and ketosis-resistant diabetes.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

Representative cancers that Heteroaryl Compounds are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. Heteroaryl Compounds are also useful for treating or preventing solid tumors and blood born tumors.

Particular cancers within the scope of the methods provided herein include those associated with PKCθ, mTOR, Syk and Tyk2 kinases and mutants or isoforms thereof. Other cancers within the scope of the methods provided herein include those associated with the pathways of the following kinases: IKK1, PKA, Akt, PKC (all isoforms), Aurora, Abl, c-Raf, PI3K (all isoforms), ATM, ATX, DNA-PK, and Yes.

More particularly, cancers and related disorders that can be treated or prevented by methods and compositions provided herein include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia and chronic myelomonocytic leukemia (CMML), chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions provided herein are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions disclosed herein. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, kidney or uterus. In other specific embodiments, sarcoma, melanoma, or leukemia is treated or prevented.

In a particular embodiment, the methods and compositions provided herein are also useful for treating, preventing or managing various types of lymphomas (i.e., a heterogenous group of neoplasms arising in the reticuloendothelial and lymphatic systems), such as Non-Hodgkin's lymphoma (NHL) (i.e., a malignant monoclonal proliferation of lymphoid cells in sites of the immune system, including lymph nodes, bone marrow, spleen, liver and gastrointestinal tract). NHLs that the Heteroaryl Compounds are useful for treating or preventing include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma).

In another embodiment, the methods and compositions provided herein are also useful for administration to patients in need of a bone marrow transplant to treat a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., patients suffering from hematologic disorders, congenital immunodeficiencies, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In another embodiment, provided herein are methods for the treatment of myeloproliferative disorders or myelodysplastic syndromes, comprising administering to a patient in need thereof an effective amount of a Heteroaryl Compound or a composition thereof. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibroerythroleukemia; or agnogenic myeloid metaplasia.

In another embodiment, provided herein are methods for the treatment of cancer or tumors resistant to other kinase inhibitors such as imatinib mesylate (STI-571 or Gleevec™) treatment, comprising administering to a patient in need thereof an effective amount of a Heteroaryl Compound or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a patient in need thereof an effective amount of a Heteroaryl Compound or a composition thereof.

In a particular embodiment, provided herein are methods for the treatment or prevention of a disease or disorder associated with the inhibition of PKCθ or mTOR. Particular diseases which are treatable or preventable by inhibiting PKCθ or mTOR include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

In a specific embodiment, provided herein are methods for treating or preventing leukemia (i.e., malignant neoplasms of the blood-forming tissues) including, but not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

The various types of the cancers are described in U.S. provisional application No. 60/380,842, filed May 17, 2002, the entireties of which are incorporated herein by reference (see, e.g., Section 2.2. Types of Cancers). Specific cancers include, but are not limited to, leukemias such as chronic lymphocytic leukemia, chronic myelocytic leukemia, acute lymphoblastic leukemia, acute myelogenous leukemia, and acute myeloblastic leukemia; advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In one embodiment, the cancer is primary or metastatic. In another embodiment, the cancer is relapsed, refractory or resistance to chemotherapy or radiation; in particular, refractory to thalidomide.

Further provide herein are methods for treating patients who have been previously treated for cancer, but are non-responsive to standard therapies, as well as those who have not previously been treated. Also provided herein are methods for treating patients regardless of patient's age, although some cancers are more common in certain age groups. Still further provided herein are methods for treating patients who have undergone surgery in an attempt to treat the cancer at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In another embodiment, provided herein are methods for the treatment or prevention of a disease or disorder (e.g., a cancer or tumor) associated with the inhibition of IKK1, PKA, Akt, PKC (all isoforms), Aurora, Abl, c-Raf, PI3K (all isoforms), ATM, ATX, DNA-PK, Syk, PI3K or Yes.

In a particular embodiment, provide herein are methods for the treatment or prevention of a disease or disorder associated with the inhibition of mTOR including, but not limited to, tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (neurofibromin 1), AMPK (AMP-dependent protein kinase STK11, serine/threonine kinase 11), and LKB1. Without being limited by theory, it is thought that genetic defects associated with these proteins results in hyperactivation of the mTOR pathway. Particular diseases which are treatable or preventable through inhibition of the mTOR pathway include, but are not limited to, Cowden's disease, Cowden syndrome, Cowden-like syndrome, Bannayan-Zonana syndrome, Bannayan-Riley-Ruvalcaba syndrome, Lhermitte-Duclos disease, Endometrial carcinoma, Prostate carcinoma and Malignant melanoma, Tuberous sclerosis complex, Lymphangioleiomyomatosis, Neurofibromatosis 1, Familial hypertrophic cardiomyopathy, Peutz-jeghers syndrome, Renal Cell Carcinoma and polycystic kidney disease.

In a particular embodiment, provided herein are methods for the treatment or prevention of a disease or disorder associated with the modulation, for example inhibition, of a kinase, including, but are not limited to, tyrosine-protein kinase (SYK), tyrosine-protein kinase (ZAP-70), protein tyrosine kinase 2 beta (PYK2), focal adhesion kinase 1 (FAK), B lymphocyte kinase (BLK), hemopoietic cell kinase (HCK), v-yes-1 Yamaguchi sarcoma viral related oncogene homolog (LYN), T cell-specific protein-tyrosine kinase (LCK), proto-oncogene tyrosine-protein kinase (YES), proto-oncogene tyrosine-protein kinase (SRC), proto-oncogene tyrosine-protein kinase (FYN), proto-oncogene tyrosine-protein kinase (FGR), proto-oncogene tyrosine-protein kinase (FER), proto-oncogene tyrosine-protein kinase (FES), C-SRC kinase, protein-tyrosine kinase (CYL), tyrosine protein kinase (CSK), megakaryocyte-associated tyrosine-protein kinase (CTK), tyrosine-protein kinase receptor (EPH), Ephrin type-A receptor 1, Ephrin type-A receptor 4 (EPHA4), Ephrin type-B receptor 3 (EPHB3), Ephrin type-A receptor 8 (EPHA8), neurotrophic tyrosine kinase receptor, type 1 (NTRK1), protein-tyrosine kinase (PTK2), syk-related tyrosine kinase (SRK), protein tyrosine kinase (CTK), tyro3 protein tyrosine kinase (TYRO3), bruton agammaglobulinemia tyrosine kinase (BTK), leukocyte tyrosine kinase (LTK), protein-tyrosine kinase (SYK), protein-tyrosine kinase (STY), tek tyrosine kinase (TEK), elk-related tyrosine kinase (ERK), tyrosine kinase with immunoglobulin and egf factor homology domains (TIE), protein tyrosine kinase (TKF), neurotrophic tyrosine kinase, receptor, type 3 (NTRK3), mixed-lineage protein kinase-3 (MLK3), protein kinase, mitogen-activated 4 (PRKM4), protein kinase, mitogen-activated 1 (PRKM1), protein tyrosine kinase (PTK7), protein tyrosine kinase (EEK), minibrain (drosophila) homolog (MNBH), bone marrow kinase, x-linked (BMX), eph-like tyrosine kinase 1 (ETK1), macrophage stimulating 1 receptor (MST1R), btk-associated protein, 135 kd, lymphocyte-specific protein tyrosine kinase (LCK), fibroblast growth factor receptor-2 (FGFR2), protein tyrosine kinase-3 (TYK3), protein tyrosine kinase (TXK), tec protein tyrosine kinase (TEC), protein tyrosine kinase-2 (TYK2), eph-related receptor tyrosine kinase ligand 1 (EPLG1), t-cell tyrosine kinase (EMT), eph tyrosine kinase 1 (EPHT1), zona pellucida receptor tyrosine kinase, 95 kd (ZRK), protein kinase, mitogen-activated, kinase 1 (PRKMK1), eph tyrosine kinase 3 (EPHT3), growth arrest-specific gene-6 (GAS6), kinase insert domain receptor (KDR), axl receptor tyrosine kinase (AXL), fibroblast growth factor receptor-1 (FGFR1), v-erb-b2 avian erythroblastic leukemia viral oncogene homolog 2 (ERBB2), fms-like tyrosine kinase-3 (FLT3), neuroepithelial tyrosine kinase (NEP), neurotrophic tyrosine kinase receptor-related 3 (NTRKR3), eph-related receptor tyrosine kinase ligand 5 (EPLG5), neurotrophic tyrosine kinase, receptor, type 2 (NTRK2), receptor-like tyrosine kinase (RYK), tyrosine kinase, b-lymphocyte specific (BLK), eph tyrosine kinase 2 (EPHT2), eph-related receptor tyrosine kinase ligand 2 (EPLG2), glycogen storage disease VIII, eph-related receptor tyrosine kinase ligand 7 (EPLG7), janus kinase 1 (JAK1), fms-related tyrosine kinase-1 (FLT1), protein kinase, camp-dependent, regulatory, type I, alpha (PRKAR1A), wee-1 tyrosine kinase (WEE1), eph-like tyrosine kinase 2 (ETK2), receptor tyrosine kinase musk, insulin receptor (INSR), janus kinase 3 (JAK3), fms-related tyrosine kinase-3 ligand protein kinase c, beta 1 (PRKCB1), tyrosine kinase-type cell surface receptor (HER3), janus kinase 2 (JAK2), lim domain kinase 1 (LIMK1), dual specificity phosphatase 1 (DUSP1), hemopoietic cell kinase (HCK), tyrosine 3-monooxygenase/tryptophan 5-monooxygenase activation protein, eta polypeptide (YWHAH), ret proto-oncogene (RET), tyrosine 3-monooxygenase/tryptophan 5-monooxygenase activation protein, zeta polypeptide (YWHAZ), tyrosine 3-monooxygenase/tryptophan 5-monooxygenase activation protein, beta polypeptide (YWHAB), hepatoma transmembrane kinase (HTK), map kinase kinase 6, phosphatidylinositol 3-kinase, catalytic, alpha polypeptide (PIK3CA), cyclin-dependent kinase inhibitor 3 (CDKN3), diacylglycerol kinase, delta, 130 kd, protein-tyrosine phosphatase, nonreceptor type, 13 (PTPN13), abelson murine leukemia viral oncogene homolog 1 (ABL1), diacylglycerol kinase, alpha (DAGK1), focal adhesion kinase 2, epithelial discoidin domain receptor 1 (EDDR1), anaplastic lymphoma kinase (ALK), phosphatidylinositol 3-kinase, catalytic, gamma polypeptide (PIK3CG), phosphatidylinositol 3-kinase regulatory subunit, (PIK3R1), eph homology kinase-1 (EHK1), v-kit hardy-zuckerman 4 feline sarcoma viral oncogene homolog (KIT), fibroblast growth factor receptor-3 (FGFR3), vascular endothelial growth factor c (VEGFC), epidermal growth factor receptor (EGFR), oncogene (TRK), growth factor receptor-bound protein-7 (GRB7), ras p21 protein activator (RASA2), met proto-onco gene (MET), src-like adapter (SLA), vascular endothelial growth factor (VEGF), vascular endothelial growth factor receptor (VEGFR), nerve growth factor receptor (NGFR), platelet derived growth factor receptor (PDGFR), platelet derived growth factor receptor beta (PDGFRB), dual-specificity tyrosine-(Y)-phosphorylation regulated kinase 2 (DYRK2), dual-specificity tyrosine-(Y)-phosphorylation regulated kinase 3 (DYRK3), dual-specificity tyrosine-(Y)-phosphorylation regulated kinase 4 (DYRK4), dual-specificity tyrosine-(Y)-phosphorylation regulated kinase 1A (DYRK1A), dual-specificity tyrosine-(Y)-phosphorylation regulated kinase 1B (DYRK1B), CDC-like kinase 1 (CLK1), protein tyrosine kinase STY, CDC-like kinase 4 (CLK4), CDC-like kinase 2 (CLK2) or CDC-like kinase 3 (CLK3).

In another embodiment, provided herein are methods for the treatment or prevention of a disease or disorder associated with the modulation, for example inhibition, of serine/threonine kinases or related molecules, including, but not limited to, Akt/protine kinase B, protein kinase A (PKA), CK2, cyclin-dependent kinase 7 (CDK7), rac serine/threonine protein kinase, serine-threonine protein kinase n (PKN), serine/threonine protein kinase 2 (STK2), zipper protein kinase (ZPK), protein-tyrosine kinase (STY), bruton agammaglobulinemia tyrosine kinase (BTK), mkn28 kinase, protein kinase, x-linked (PRKX), elk-related tyrosine kinase (ERK), ribosomal protein s6 kinase, 90 kd, polypeptide 3 (RPS6KA3), glycogen storage disease VIII, death-associated protein kinase 1 (DAPK1), pctaire protein kinase 1 (PCTK1), protein kinase, interferon-inducible double-stranded ma (PRKR), activin a receptor, type II-like kinase 1 (ACVRLK1), protein kinase, camp-dependent, catalytic, alpha (PRKACA), protein kinase, y-linked (PRKY), G protein-coupled receptor kinase 2 (GPRK21), protein kinase c, theta form (PRKCQ), lim domain kinase 1 (LIMK1), phosphoglycerate kinase 1 PGK1), lim domain kinase 2 (LIMK2), c-jun kinase, activin a receptor, type II-like kinase 2 (ACVRLK2), janus kinase 1 (JAK1), elk1 motif kinase (EMK1), male germ cell-associated kinase (MAK), casein kinase 2, alpha-prime subunit (CSNK2A2), casein kinase 2, beta polypeptide (CSNK2B), casein kinase 2, alpha 1 polypeptide (CSNK2A1), ret proto-oncogene (RET), hematopoietic progenitor kinase 1, conserved helix-loop-helix ubiquitous kinase (CHUK), casein kinase 1, delta (CSNK1D), casein kinase 1, epsilon (CSNK1E), v-akt murine thymoma viral oncogene homolog 1 (AKT1), tumor protein p53 (TP53), protein phosphatase 1, regulatory (inhibitor) subunit 2 (PPP1R2), oncogene pim-1 (PIM1), transforming growth factor-beta receptor, type II (TGFBR2), transforming growth factor-beta receptor, type I (TGFBR1), v-raf murine sarcoma viral oncogene homolog b1 (BRAF), bone morphogenetic receptor type II (BMPR2), v-raf murine sarcoma 3611 viral oncogene homolog 1 (ARAF1), v-raf murine sarcoma 3611 viral oncogene homolog 2 (ARAF2), protein kinase C (PKC), v-kit hardy-zuckerman 4 feline sarcoma viral oncogene homolog (KIT) or c-KIT receptor (KITR).

In another embodiment, provided herein are methods for the treatment or prevention of a disease or disorder associated with the modulation, for example inhibition, of a MAP kinase, including, but not limited to, mitogen-activated protein kinase 3 (MAPK3), p44erk1, p44mapk, mitogen-activated protein kinase 3 (MAP kinase 3; p44), ERK1, PRKM3, P44ERK1, P44MAPK, mitogen-activated protein kinase 1 (MAPK1), mitogen-activated protein kinase kinase 1

(MEK1), MAP2K1 protein tyrosine kinase ERK2, mitogen-activated protein kinase 2, extracellular signal-regulated kinase 2, protein tyrosine kinase ERK2, mitogen-activated protein kinase 2, extracellular signal-regulated kinase 2, ERK, p38, p40, p41, ERK2, ERT1, MAPK2, PRKM1, PRKM2, P42MAPK, p41mapk, mitogen-activated protein kinase 7 (MAPK7), BMK1 kinase, extracellular-signal-regulated kinase 5, BMK1, ERK4, ERK5, PRKM7, nemo-like kinase (NLK), likely ortholog of mouse nemo like kinase, mitogen-activated protein kinase 8 (MAPK8), protein kinase JNK1, JNK1 beta protein kinase, JNK1 alpha protein kinase, c-Jun N-terminal kinase 1, stress-activated protein kinase JNK1, JNK, JNK1, PRKM8, SAPK1, JNK1A2, JNK21B1/2, mitogen-activated protein kinase 10 (MAPK10), c-Jun kinase 3, JNK3 alpha protein kinase, c-Jun N-terminal kinase 3, stress activated protein kinase JNK3, stress activated protein kinase beta, mitogen-activated protein kinase 9 (MAPK9), MAP kinase 9, c-Jun kinase 2, c-Jun N-terminal kinase 2, stress-activated protein kinase JNK2, JNK2, JNK2A, JNK2B, PRKM9, JNK-55, JNK2BETA, p54aSAPK, JNK2ALPHA, mitogen-activated protein kinase 14 (MAPK14), p38 MAP kinase, MAP kinase Mxi2, Csaids binding protein, MAX-interacting protein 2, stress-activated protein kinase 2A, p38 mitogen activated protein kinase, cytokine suppressive anti-inflammatory drug binding protein, RK, p38, EXIP, Mxi2, CSBP1, CSBP2, CSPB1, PRKM14, PRKM15, SAPK2A, p38ALPHA, mitogen-activated protein kinase 11 (MAPK11), stress-activated protein kinase-2, stress-activated protein kinase-2b, mitogen-activated protein kinase p38-2, mitogen-activated protein kinase p38beta, P38B, SAPK2, p38-2, PRKM11, SAPK2B, p38Beta, P38BETA2, mitogen-activated protein kinase 13 (MAPK13), stress-activated protein kinase 4, mitogen-activated protein kinase p38 delta, SAPK4, PRKM13, p38delta, mitogen-activated protein kinase 12 (MAPK12), p38gamma, stress-activated protein kinase 3, mitogen-activated protein kinase 3, ERK3, ERK6, SAPK3, PRKM12, SAPK-3, P38GAMMA, mitogen-activated protein kinase 6 (MAPK6), MAP kinase isoform p97, mitogen-activated 5 protein kinase, mitogen-activated 6 protein kinase, extracellular signal-regulated kinase 3, extracellular signal-regulated kinase, p97, ERK3, PRKM6, p97MAPK, mitogen-activated protein kinase 4 (MAPK4), Erk3-related protein kinase, mitogen-activated 4 protein kinase (MAP kinase 4; p63), PRKM4, p63MAPK, ERK3-RELATED or Extracellular signal-regulated kinase 8 (ERK7).

A Heteroaryl Compound can be combined with other pharmacologically active compounds ("second active agents") in methods and compositions described herein. It is believed that certain combinations may work synergistically in the treatment of particular types diseases or disorders, and conditions and symptoms associated with such diseases or disorders. A Heteroaryl Compound can also work to alleviate adverse effects associated with certain second active agents, and vice versa.

One or more second active ingredients or agents can be used in the methods and compositions described herein. Second active agents can be large molecules (e.g., proteins) or small molecules (e.g., synthetic inorganic, organometallic, or organic molecules).

Examples of large molecule second active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with a Heteroaryl Compound vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium;

taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminlevulinic acid, amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycini SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), bortezomib, statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Similarly, examples of specific second agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483,213, 10/411,656, 10/693,794, 10/699,154, and 10/981,189; and U.S. provisional application Nos. 60/554,923, 60/565,172, 60/626,975, 60/630,599, 60/631,870, and 60/533,862.

Examples of additional second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of additional second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2ÿ, pentoxifylline, tin etiopurpurin, motexafin lutetium, 9-fluoro-11,21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of additional second active agents include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of additional second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of additional second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of additional second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of additional second active agents include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-ÿ), antibodies (e.g., anti-CD40 and IgM), oligonucleotides containing unmethylated CpG motifs, and vaccines (e.g., viral and tumor peptide vaccines).

Examples of additional second active agents include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of additional second active agents include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a Heteroaryl Compound and a second active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for Heteroaryl Compounds is oral. Preferred routes of administration for the second active agents or ingredients of the invention are known to those of ordinary skill in the art. See, e.g., *Physicians' Desk Reference,* 1755-1760 (56th ed., 2002).

In one embodiment, the second active agent is administered intravenously or subcutaneously. In another embodiment, the second active agent is administered intravenously or subcutaneously once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of a Heteroaryl Compound and any optional additional active agents concurrently administered to the patient.

Further provided herein are methods of reducing, treating and/or preventing adverse or undesired effects associated with conventional therapy including, but not limited to, surgery, chemotherapy, radiation therapy, hormonal therapy, biological therapy and immunotherapy. Heteroaryl Compounds and other active ingredients can be administered to a patient prior to, during, or after the occurrence of the adverse effect associated with conventional therapy.

4.5 Pharmaceutical Compositions and Routes of Administration

The Heteroaryl Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Heteroaryl Compound in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a Heteroaryl Compound to be administered to a patient is rather widely variable and can be subject to the judgment of a health-care practitioner. In general, the Heteroaryl Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the Heteroaryl Compound administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Heteroaryl Compound to a patient in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Heteroaryl Compound to a patient in need thereof. In a particular embodiment, the methods disclosed herein comprise the administration of 400 mg/day, 600 mg/day or 800 mg/day of a Heteroaryl Compound to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Heteroaryl Compound.

In a particular embodiment, provided herein are unit dosage formulation comprising about 100 mg or 400 mg of a Heteroaryl Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Heteroaryl Compound.

A Heteroaryl Compound can be administered once, twice, three, four or more times daily. In a particular embodiment, doses of 600 mg or less are administered as a once daily dose and doses of more than 600 mg are administered twice daily in an amount equal to one half of the total daily dose.

A Heteroaryl Compound can be administered orally for reasons of convenience. In one embodiment, when administered orally, a Heteroaryl Compound is administered with a meal and water. In another embodiment, the Heteroaryl Compound is dispersed in water or juice (e.g., apple juice or orange juice) and administered orally as a suspension.

The Heteroaryl Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Heteroaryl Compound without an additional carrier, excipient or vehicle.

In another embodiment, provided herein are compositions comprising an effective amount of a Heteroaryl Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Heteroaryl Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Heteroaryl Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Heteroaryl Compound can be delayed or prolonged by proper formulation. For example, a slowly soluble pellet of the Heteroaryl Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Heteroaryl Compound in oily or emulsified vehicles that allow it to disperse slowly in the serum.

5. EXAMPLES

The following Examples are presented by way of illustration, not limitation.

5.1 Synthetic Examples

General Procedure A. To a thick-well borosilicate glass vial (5-10 mL) was added 2-amino-3,5-dibromo-pyrazine, desired amine, and diisopropylethylamine, in n-butanol. The reaction vial was sealed and placed in the microwave reactor and irradiated at 220° C. for 3600 s. The solution was condensed under reduced pressure, dissolved in ethyl acetate, washed with brine, partitioned, extracted with ethyl acetate (2×), organics were pooled, dried over sodium sulfate, filtered, and condensed to yield the crude product.

General Procedure B. Substrate (1 equiv) and boronic acid (1.2 equiv) were dissolved in DMF (15 mL). Nitrogen was bubbled through the solution for 2 min. An appropriate base in water (5 mL) and Pd catalyst (0.1 equiv) were added. The solution was then heated to 85-95° C. under nitrogen. Upon consumption of the starting material, the solution was condensed under reduced pressure. The resulting material was diluted with ethyl acetate and filtered through celite or flushed through a Bakerbond SPE SiOH disposable extraction column. The filtrate was condensed under reduced pressure to afford the crude product.

General Procedure B. Bromide, desired boronic acid, Pd catalyst, aqueous base (1M), and dioxane were heated together in a Biotage Emrys Optimizer microwave reactor at 150° C. for 20 min. The reaction was extracted with ethyl acetate and water. The organic layer was dried over magnesium sulfate, and then concentrated.

General Procedure B2. Substrate (1 equiv) and boronic acid (1.2 equiv) were dissolved in DMF (10 mL). Nitrogen was bubbled through the solution for 2 min. An appropriate base in water (5 mL) and Pd catalyst (0.1 equiv) were added. The solution was then heated together in a Biotage Emrys Optimizer microwave reactor at 120° C. for 15 min. Upon consumption of the starting material, the solution was condensed under reduced pressure. The resulting material was diluted with ethyl acetate and filtered through celite. The filtrate was condensed under reduced pressure to afford the crude product.

General Procedure B3. Substrate (1 equiv) and boronic acid (1.2 equiv) were dissolved in DMF (10 mL). Nitrogen was bubbled through the solution for 2 min. Sodium carbonate (1M) (5 mL), acetonitrile (5 mL) and dichlorobis(triphenylphosphine)palladium(II) (0.05 equiv). The solution was then heated together in a Biotage Emrys Optimizer microwave reactor at 120° C. for 15 min. Upon consumption of the starting material, the solution was condensed under reduced pressure. The resulting material was diluted with ethyl acetate and filtered through celite. The filtrate was condensed under reduced pressure to afford the crude product.

General Procedure C. Bromide, desired boronic acid (or boronic ester) and dichloro[1,1'-bis(diphenylphosphino)ferrocene]palladium (II) dichloromethane were combined in DMF. Potassium phosphate was dissolved in water and added to the reaction mixture and allowed to stir at 100° C. for 16 h. The reaction solution was condensed under reduced pressure and diluted with 10% methanol in ethyl acetate and flushed through a Bakerbond SPE SiOH disposable extraction column. The filtrate was condensed under reduced pressure to afford the crude product.

General Procedure D1. To a thick-well borosilicate glass vial (5-10 mL) was added substrate and 1,1'-carbonyldiimidazole, in THF. The reaction vial was sealed and placed in the microwave reactor and irradiated at 180° C. for 3600 s. The reaction solution was condensed under reduced pressure to afford the crude product.

General Procedure D2. To a thick-well borosilicate glass vial (5-10 mL) was added substrate, urea and dimethylformamide. The reaction vial was sealed and placed in the microwave reactor and irradiated at 220° C. for 2700 s. The solution was condensed under reduced pressure to afford the crude product.

General Procedure E. A solution of N-bis-boc-3-bromo-5-(5-isopropyl-2-methoxy-phenyl)-pyrazin-2-ylamine (see Example 5.C) and the desired amine in ethanol (4 mL) was heated in a Biotage Emrys Optimizer microwave reactor at 150° C. for 4 h.

General Procedure E1. A solution of N-bis-boc-3-bromo-5-(quinoline-5-yl)-pyrazin-2-ylamine (See Example 26.E) and the desired amine (or the amine salt and triethylamine) in ethanol was heated in a Emrys microwave reactor at 150° C. for 4 h. The product was isolated by reverse-phase semi-preparatory HPLC (5-70% acetonitrile+0.1% TFA in $H_2O$+0.1% TFA, over 30 min). Fractions containing clean product were passed through a Phenomenex Strata-X-C solid phase extraction column to remove TFA. The product was released from the column using 2M ammonia in methanol. The solution was concentrated under reduced pressure and dried under vacuum to give product as a white solid.

General Procedure F. Substrate (1 equiv) and triethyl amine (20 equiv) were dissolved in methanol (3.0 mL) in a sealed tube and stirred for 5 min. Hydrazide (4.0 equiv) was added and the reaction is heated to 100° C. for 18 h. Upon consumption of the starting material, the solution was condensed under reduced pressure to afford the crude product.

5.1.1 Example 1

SYNTHESIS OF 1-(4-METHOXYBENZYL)-6-(QUINOLIN-5-YL)-1H-IMIDAZO[4,5-B]PYRAZIN-2(3H)-ONE

A. 6-Bromo-$N^2$-(4-methoxybenzyl)pyrazine-2,3-diamine. 2-Amino-3,5-dibrompyrazine (3.0 g, 11.95 mmol) and 4-methoxybenzylamine (2.13 g, 15.53 mmol) were reacted according to General Procedure A and purified via Biotage silica gel chromatography (30-100% ethyl acetate in hexanes) to afford the title compound (1.75 g, 47% yield). MS (ESI) m/z 311.2 [M+1]$^+$.

B. (3-Amino-6-(5-quinolyl)pyrazin-2-yl][(4-methoxyphenyl)methyl]amine. 6-Bromo-$N^2$-(4-methoxybenzyl) pyrazine-2,3-diamine (0.928 g, 3.00 mmol), quinoline-5-boronic acid (0.675 g, 3.9 mmol), tetrakis(triphenylphosphine) palladium (0.306 g, 0.265 mmol), potassium carbonate (1.10 g, 7.95 mmol), water (7 ml) and dimethylformamide (35 mL) were reacted according to General Procedure B. The crude material was purified via Biotage silica gel chromatography (0-10% methanol in dichloromethane) followed by triturating with water/methanol to afford the title compound (0.165 g, 15% yield). MS (ESI) m/z 358.3 [M+1]$^+$.

C. 1-(4-Methoxybenzyl)-6-(quinolin-5-yl)-1H-imidazo[4,5-b]pyrazin-2(3H)-one. (3-Amino-6-(5-quinolyl)pyrazin-2-yl)[(4-methoxyphenyl)methyl]amine (0.200 g, 0.560 mmol) and urea (0.67 g, 1.12 mmol) were reacted according to General Procedure D2. The solution was condensed under reduced pressure and triturated with water/methanol to afford the title compound (0.180 g, 84% yield). $^1$H NMR (300 MHz, $CD_3OD$) δ 8.88 (m, 1H), 8.47 (d, 1H), 8.19 (s, 1H), 8.12 (d, 2H), 7.86 (m, 1H), 7.56 (d, 1H), 7.46 (m, 1H), 7.38 (d, 2H), 6.91 (d, 2H), 5.07 (s, 2H), 3.78 (s, 3H); MS (ESI) m/z 384.4 [M+1]$^+$.

5.1.2 Example 2

SYNTHESIS OF (R)-1-(1-PHENYLETHYL)-1H-IMIDAZO[4,5-B]PYRAZIN-2(3H)-ONE

A. (R)-6-Bromo-$N^2$-(1-phenylethyl)pyrazine-2,3-diamine. The title compound was prepared using (R)-α-methylbenzylamine (2.28 mL, 17.93 mmol), 2-amino-3,5-dibromo-pyrazine (3.00 g, 11.96 mmol), and n-BuOH (30 mL) as described in General Procedure A. The crude compound was purified via silica gel chromatography (20%-30% EtOAc in hexanes). Clean fractions were combined and condensed, and subsequently triturated from methanol with water while sonicating to afford 1.92 g (6.54 mmol, 55%) of (R)-6-bromo-$N^2$-(1-phenylethyl)pyrazine-2,3-diamine. MS (ESI) m/z 294.0 [M+1]$^+$.

B. (R)—$N^2$-(1-Phenylethyl)pyrazine-2,3-diamine. The title compound was prepared by dissolving (R)-6-bromo-$N^2$-(1-phenylethyl)pyrazine-2,3-diamine (1.00 g, 3.37 mmol) in neat formic acid (15 mL), and adding 10% Pd/C (0.34 mmol). This solution was purged with hydrogen gas at 1 atm., and stirred for 4 hours at room temperature. Upon completion, the reaction was filtered through celite and concentrated. The crude material was purified using silica gel chromatography (0-10% methanol in dichloromethane). Clean fractions were combined and condensed to afford 0.65 g (3.03 mmol, 90%) of (R)—N2-(1-phenylethyl)pyrazine-2,3-diamine. MS (ESI) m/z 215.4 [M+1]$^+$.

C. (R)-1-(1-Phenylethyl)-1H-imidazo[4,5-b]pyrazin-2 (3H)-one. The title compound was prepared using (R)—$N^2$-(1-phenylethyl)pyrazine-2,3-diamine (0.65 g, 3.03 mmol), 1,1'-carbonyldiimidazole (0.62 g, 3.79 mmol), and tetrahydrofuran (10 mL) as described in General Procedure D1. Upon cooling to room temperature the volatiles were removed under reduced pressure. The crude oil was purified using silica gel chromatography (10-70% EtOAc in hexanes). Clean fractions were combined and condensed to afford 0.10 g (0.42 mmol, 40%) of (R)-1-(1-phenylethyl)-1H-imidazo[4,5-b]pyrazin-2(3H)-one. $^1$H NMR (400 MHz, DMSO-$d_6$) δ

12.08 (s, 1H), 7.89 (s, 1H), 7.43 (d, 2H), 7.33 (t, 2H), 7.26 (t, 1H), 5.67 (dd, 1H), 1.94 (d, 3H); MS (ESI) m/z 241.3 [M+1]+.

5.1.3 Example 3

SYNTHESIS OF (S)-1-(1-PHENYLETHYL)-1H-IMIDAZO[4,5-B]PYRAZIN-2(3H)-ONE

A. (S)-6-Bromo-N2-(1-phenylethyl)pyrazine-2,3-diamine. The title compound was prepared using (S)-α-methylbenzylamine (2.28 mL, 17.93 mmol), 2-amino-3,5-dibromo-pyrazine (3.00 g, 11.96 mmol), and n-BuOH (30 mL) as described in General Procedure A. The crude molecule was purified via silica gel chromatography (20-30% EtOAc in hexanes). Clean fractions were combined and condensed, and subsequently triturated from methanol with water while sonicating to afford 1.52 g (5.18 mmol, 43%) of (S)-6-bromo-N2-(1-phenylethyl)pyrazine-2,3-diamine. MS (ESI) m/z 294.0 [M+1]+.

B. (S)—$N^2$-(1-Phenylethyl)pyrazine-2,3-diamine. The title compound was prepared by dissolving (S)-6-bromo-$N^2$-(1-phenylethyl)pyrazine-2,3-diamine (1.00 g, 3.37 mmol) in neat formic acid (15 mL), and adding 10% Pd/C (0.34 mmol). This solution was purged with hydrogen gas at 1 atm., and stirred for 4 hours at room temperature. Upon completion, the reaction was filtered through celite and concentrated. The crude material was purified using silica gel chromatography (0-10% methanol in dichloromethane). Clean fractions were combined and condensed to afford 0.47 g (2.19 mmol, 65%) of (S)—$N^2$-(1-phenylethyl)pyrazine-2,3-diamine. MS (ESI) m/z 215.4 [M+1]+.

C. (S)-1-(1-Phenylethyl)-1H-imidazo[4,5-b]pyrazin-2(3H)-one. The title compound was prepared using (S)—$N^2$-(1-phenylethyl)pyrazine-2,3-diamine (0.40 g, 1.87 mmol), 1,1'-carbonyldiimidazole (0.38 g, 2.33 mmol), and tetrahydrofuran (7 mL) as described in General Procedure D1. Upon cooling to room temperature the volatiles were removed under reduced pressure. The crude oil was purified using silica gel chromatography (10-70% EtOAc in hexanes). Clean fractions were combined and condensed to afford 0.18 g (0.74 mmol, 40%) of (S)-1-(1'-phenylethyl)-1H-imidazo[4,5-b]pyrazin-2(3H)-one. $^1$H NMR (400 MHz, DMSO-$d_6$) δ 12.08 (s, 1H), 7.89 (s, 1H), 7.43 (d, 2H), 7.33 (t, 2H), 7.26 (t, 1H), 5.67 (dd, 1H), 1.94 (d, 3H); MS (ESI) m/z 241.3 [M+1]+.

5.1.4 Example 4

SYNTHESIS OF 5-(QUINOLIN-5-YL)-1H-IMIDAZO[4,5-B]PYRAZIN-2(3H)-ONE

A. 5-(5-Quinolyl)pyrazine-2,3-diamine. (3-Amino-6-(5-quinolyl)pyrazin-2-yl)[(4-methoxy phenyl)methyl]amine (see Example 1.B) (0.210 g, 0.588 mmol) was dissolved in trifluoroacetic acid/dichloromethane (2 mL:2 mL) with PS-thiophenol as a scavenger. The solution was heated to 70° C. in a sealed tube for two hours and then concentrated under reduced pressure and diluted with methanol. The methanol/product solution was filtered through a Phenomenex Strata-X-C solid phase extraction column to remove TFA. Additional water was added to the eluted compound to induce precipitation. The precipitate was filtered and dried under vacuum to afford the title compound (0.080 g, 57% yield). MS (ESI) m/z 238.1 [M+1]+.

B. 5-(Quinolin-5-yl)-1H-imidazo[4,5-b]pyrazin-2(3H)-one. 5-(5-Quinolyl)pyrazine-2,3-diamine (0.080 g, 0.337 mmol) and urea (0.061 g, 1.01 mmol) were reacted as described in General Procedure D2. Water was added portionwise to the reaction vessel to assist precipitation of the product. The resultant precipitate was filtered and dried under vacuum to afford the title compound (0.055 g, 62% yield). $^1$H NMR (400 MHz, DMSO-$d_6$) δ 11.89 (bs, 2H), 8.94 (d, 1H), 8.56 (d, 1H), 8.14 (s, 1H), 8.10 (d, 1H), 7.84 (t, 1H), 7.72 (d, 1H), 7.54 (dd, 1H). MS (ESI) m/z 264.2 [M+1]+.

5.1.5 Example 5

SYNTHESIS OF 1-(2-HYDROXYETHYL)-6-(5-ISOPROPYL-2-METHOXY-PHENYL)-1,3-DIHYDRO-IMIDAZO [4,5-B]PYRAZIN-2-ONE

A. 5-(5-Isopropyl-2-methoxyphenyl)-pyrazin-2-ylamine. 5-Bromopyrazin-2-amine (5.7 g, 33 mmol), 5-isopropyl-2-methoxybenzeneboronic acid (6.4 g, 33 mmol), tetrakis (triphenylphosphine)palladium(0) (1.9 g, 1.6 mmol) and sodium carbonate (99 mL, 99 mmol), and dioxane (300 mL) were heated together at 90° C. for 16 hours. The reaction was extracted with ethyl acetate and water. The organic layer was dried over magnesium sulfate, and then concentrated. The residue was purified via Biotage silica gel chromatography (0-60% ethyl acetate in hexanes) to give an oil (4.1 g, 51% yield). $^1$H NMR (300 MHz, CD$_3$OD) δ 8.36 (d, J=1.2, 1H), 8.00 (d, J=1.2, 1H), 7.46 (d, J=2.4, 1H), 7.20 (dd, J=8.1, 2.1, 1H), 7.00 (d, J=8.1, 1H), 3.83 (s, 3H), 2.86-2.93 (m, 1H), 1.25 (d, J=6.9, 6H); MS (ESI) m/z 244.4 [M+1]+.

B. 3-Bromo-5-(5-isopropyl-2-methoxyphenyl)-pyrazin-2-ylamine. 5-(5-Isopropyl-2-methoxyphenyl)-pyrazin-2-ylamine (4.1 g, 16.8 mmol) was dissolved in DMSO (20 mL) and stirred over a water bath. N-Bromosuccinimide (3.6 g, 20.2 mmol) was added and the reaction was stirred at room temperature for 16 hours. The reaction was extracted with ethyl acetate and water. An emulsion solid was filtered off. The organic layer was dried over magnesium sulfate, filtered, and then concentrated. The residue was purified via Biotage silica gel chromatography (0-60% ethyl acetate in hexanes) to give a tan colored solid (4 g, 74% yield). $^1$H NMR (400 MHz, DMSO-$d_6$) δ 8.47 (s, 1H), 7.48 (d, J=2.3, 1H), 7.22 (dd, J=8.6, 2.3, 1H), 7.05 (d, J=8.6, 1H), 6.78 (s, 2H), 3.82 (s, 3H), 2.86-2.93 (m, 1H), 1.20 (d, J=6.8, 6H); MS (ESI) m/z 322.0, 324.1 [M+1]+.

C. N-bis-Boc-3-Bromo-5-(5-isopropyl-2-methoxy-phenyl)-pyrazin-2-ylamine. 3-Bromo-5-(5-isopropyl-2-methoxy-phenyl)-pyrazin-2-ylamine (1 g, 3.1 mmol), di-t-butyl dicarbonate (1.6 g, 8 mmol), 4-dimethylaminopyridine (38 mg, 0.3 mmol), and acetonitrile (15 mL) were heated to 50° C. for 30 minutes. The reaction was concentrated and the residue was purified via Biotage silica gel chromatography (0-40% ethyl acetate in hexanes) to give a yellow oil (1.6 g, 99% yield). $^1$H NMR (300 MHz, DMSO-$d_6$) δ 9.09 (s, 1H), 7.65 (d, J=2.4, 1H), 7.42 (dd, J=9.0, 2.7, 1H), 7.18 (d, J=8.1 Hz, 1H), 3.87 (s, 3H), 2.86-2.93 (m, 1H), 1.40 (s, 18H), 1.22 (d, J=6.8, 6H). MS (ESI) m/z 424.5 [M+1]+.

D. 1-(2-Hydroxyethyl)-6-(5-isopropyl-2-methoxy-phenyl)-1,3-dihydro-imidazo[4,5-b]pyrazin-2-one. N-Bis-Boc-3-bromo-5-(5-isopropyl-2-methoxy-phenyl)-pyrazin-2-ylamine (150 mg, 0.29 mmol), 2-hydroxyethylamine (0.177 mL, 2.9 mmol), and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (20 mg, 21% yield). $^1$H NMR (400 MHz, DMSO-$d_6$) δ 11.90 (s, 1H), 8.28 (s, 1H), 7.50 (d, J=2.3, 1H), 7.21 (dd, J=8.5, 2.4, 1H), 7.02 (d, J=8.4, 1H), 4.81 (t, J=6.0, 1H), 3.87 (t, J=6.0, 2H), 3.76 (s, 3H), 3.70 (q, J=5.9, 2H), 2.85 (s, 1H), 1.16 (d, J=6.8, 6H); MS (ESI) m/z 329.3 [M+1]$^+$.

5.1.6 Example 6

SYNTHESIS OF 1-((R)-1,2-DIMETHYL-PROPYL)-6-(5-ISOPROPYL-2-METHOXY-PHENYL)-1,3-DIHYDRO-IMIDAZO[4,5-B]PYRAZIN-2-ONE

A. 1-((R)-1,2-Dimethyl-propyl)-6-(5-isopropyl-2-methoxy-phenyl)-1,3-dihydro-imidazo[4,5-b]pyrazin-2-one. N-Bis-Boc-3-bromo-5-(5-isopropyl-2-methoxy-phenyl)-pyrazin-2-yl amine (see Example 5.C) (150 mg, 0.29 mmol) and (R)-1,2-dimethyl-propylamine (0.336 mL, 2.9 mmol), and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (36 mg, 35% yield). $^1$H NMR (400 MHz, DMSO-d$_6$) δ 11.96 (s, 1H), 8.37 (s, 1H), 7.58 (d, J=2.3, 1H), 7.26 (dd, J=8.7, 2.2, 1H), 7.08 (d, J=8.4, 1H), 4.11 (dq, J=9.6, 6.9, 1H), 3.82 (s, 3H), 2.86-2.94 (m, 1H), 2.39-2.47 (m, 1H), 1.55 (d, J=6.8, 3H), 1.22 (d, J=7.0, 6H), 1.02 (d, J=6.8, 3H), 0.77 (d, J=6.6, 3H); MS (ESI) m/z 355.4 [M+1]$^+$.

5.1.7 Example 7

SYNTHESIS OF 6-(5-ISOPROPYL-2-METHOXY-PHENYL)-1-(S)-TETRAHYDRO-FURAN-3-YL-1,3-DIHYDRO-IMIDAZO[4,5-B]PYRAZIN-2-ONE

A. 6-(5-Isopropyl-2-methoxy-phenyl)-1-(S)-tetrahydro-furan-3-yl-1,3-dihydro-imidazo[4,5-b]pyrazin-2-one. N-Bis-Boc-3-bromo-5-(5-isopropyl-2-methoxy-phenyl)-pyrazin-2-ylamine (see Example 5.C) (150 mg, 0.29 mmol), (S)-3-aminotetrahydrofuran tosylate salt (0.75 g, 2.9 mmol), triethylamine (1 mL), and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (44 mg, 43% yield). $^1$H NMR (400 MHz, DMSO-d$_6$) δ 11.92 (s, 1H), 8.37 (s, 1H), 7.61 (d, J=2.5, 1H), 7.20 (dd, J=8.7, 2.2, 1H), 7.02 (d, J=8.6, 1H), 3.85-3.97 (m, 3H), 3.78 (s, 3H), 2.85 (dt, J=13.7, 6.9, 1H), 2.46-2.52 (m, 1H), 2.20-2.28 (m, 1H), 1.17 (d, J=7.0, 6H); MS (ESI) m/z 355.5 [M+1]$^+$.

5.1.8 Example 8

SYNTHESIS OF 1-((S)-1,2-DIMETHYL-PROPYL)-6-(5-ISOPROPYL-2-METHOXY-PHENYL)-1,3-DIHYDRO-IMIDAZO[4,5-B]PYRAZIN-2-ONE

A. 1-((S)-1,2-Dimethyl-propyl)-6-(5-isopropyl-2-methoxy-phenyl)-1,3-dihydro-imidazo[4,5-b]pyrazin-2-one. N-Bis-Boc-3-bromo-5-(5-isopropyl-2-methoxy-phenyl)-pyrazin-2-ylamine (see Example 5.C) (150 mg, 0.29 mmol), (S)-1,2-dimethyl-propylamine (0.336 mL, 2.9 mmol) and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (56 mg, 55% yield). $^1$H NMR (400 MHz, DMSO-d$_6$) δ 11.97 (s, 1H), 8.37 (s, 1H), 7.58 (d, J=2.3, 1H), 7.26 (dd, J=8.6, 2.5, 1H), 7.08 (d, J=8.6, 1H), 4.10 (dq, J=9.5, 7.0, 1H), 3.82 (s, 3H), 2.87-2.94 (m, 1H), 2.43 (m, 1H), 1.55 (d, J=7.0, 3H), 1.22 (d, J=6.8, 6H), 1.02 (d, J=6.6, 3H), 0.77 (d, J=6.6, 3H). MS (ESI) m/z 355.4 [M+1]$^+$.

5.1.9 Example 9

SYNTHESIS OF 6-(5-ISOPROPYL-2-METHOXY-PHENYL)-1-(R)-TETRAHYDRO-FURAN-3-YL-1,3-DIHYDRO-IMIDAZO[4,5-B]PYRAZIN-2-ONE

A. 6-(5-Isopropyl-2-methoxy-phenyl)-1-(R)-tetrahydro-furan-3-yl-1,3-dihydro-imidazo[4,5-b]pyrazin-2-one. N-Bis-Boc-3-bromo-5-(5-isopropyl-2-methoxy-phenyl)-pyrazin-2-yl amine (see Example 5.C) (150 mg, 0.29 mmol), (R)-3-aminotetrahydrofuran tosylate (0.75 g, 2.9 mmol), triethylamine (1 mL) and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (31 mg, 30% yield). $^1$H NMR (400 MHz, DMSO-d$_6$) δ 11.96 (s, 1H), 8.37 (s, 1H), 7.61 (d, J=2.5, 1H), 7.19 (dd, J=8.9, 2.4, 1H), 7.02 (d, J=8.6, 1H), 4.96-5.03 (m, 1H), 4.16 (q, J=7.5, 1H), 3.85-3.97 (m, 3H), 3.78 (s, 3H), 2.82-2.89 (m, 1H), 2.46-2.50 (m, 1H), 2.20-2.28 (m, 1H), 1.17 (d, J=6.8, 6H); MS (ESI) m/z 355.5 [M+1]$^+$.

5.1.10 Example 10

SYNTHESIS OF 1-CYCLOPENTYLMETHYL-6-(5-ISOPROPYL-2-METHOXY-PHENYL)-1,3-DIHYDRO-IMIDAZO[4,5-B]PYRAZIN-2-ONE

A. 1-Cyclopentylmethyl-6-(5-isopropyl-2-methoxy-phenyl)-1,3-dihydro-imidazo[4,5-b]pyrazin-2-one. N-Bis-Boc-3-bromo-5-(5-isopropyl-2-methoxy-phenyl)-pyrazin-2-ylamine (see Example 5.C) (150 mg, 0.29 mmol), cyclopentylmethylamine (0.287 mL, 2.9 mmol) and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (77 mg, 75% yield). $^1$H NMR (300 MHz, DMSO-d$_6$) δ 11.98 (s, 1H), 8.36 (s, 1H), 7.60 (d, J=2.5, 1H), 7.26 (dd, J=8.7, 2.6, 1H), 7.08 (d, J=8.5, 1H), 3.82 (s, 3H), 3.78 (d, J=7.4, 2H), 2.45 (d, J=7.1, 1H), 1.58-1.70 (m, 4H), 1.53 (d, J=9.3, 2H), 1.38 (d, J=4.4, 2H), 1.22 (d, J=6.9, 6H); MS (ESI) m/z 367.5 [M+1]$^+$.

5.1.11 Example 11

SYNTHESIS OF 1-CYCLOHEXYLMETHYL-6-(5-ISOPROPYL-2-METHOXY-PHENYL)-1,3-DIHYDRO-IMIDAZO[4,5-B]PYRAZIN-2-ONE

A. 1-Cyclohexylmethyl-6-(5-isopropyl-2-methoxy-phenyl)-1,3-dihydro-imidazo[4,5-b]pyrazin-2-one. N-Bis-Boc-3-bromo-5-(5-isopropyl-2-methoxy-phenyl)-pyrazin-2-ylamine (see Example 5.C) (150 mg, 0.29 mmol), cyclohexylmethylamine (0.287 mL, 2.9 mmol) and ethanol (4 mL) were heated according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (76 mg, 74% yield). ¹H NMR (300 MHz, DMSO-d₆) δ 11.97 (s, 1H), 8.35 (s, 1H), 7.60 (d, J=2.5, 1H), 7.26 (dd, J=8.7, 2.6, 1H), 7.08 (d, J=8.5, 1H), 3.82 (s, 3H), 3.71 (d, J=7.4, 2H), 2.90 (d, J=7.1, 1H), 1.90 (m, 1H), 1.5-1.7 (m, 5H), 1.0-1.3 (m, 11H); MS (ESI) m/z 381.3 [M+1]⁺.

5.1.12 Example 12

SYNTHESIS OF 1-(2,2-DIMETHYL-PROPYL)-6-(5-ISOPROPYL-2-METHOXY-PHENYL)-1,3-DI-HYDRO-IMIDAZO[4,5-B]PYRAZIN-2-ONE

A. 1-(2,2-Dimethyl-propyl)-6-(5-isopropyl-2-methoxy-phenyl)-1,3-dihydro-imidazo[4,5-b]pyrazin-2-one. N-Bis-Boc-3-bromo-5-(5-isopropyl-2-methoxy-phenyl)-pyrazin-2-ylamine (see Example 5.C) (150 mg, 0.29 mmol), 2,2-dimethyl-propylamine (0.341 mL, 2.9 mmol) and ethanol (4 mL) were heated according to General Procedure E. The product was purified using reverse-phase semi-preparatory HPLC (5-70% acetonitrile+0.1% TFA in H₂O+0.1% TFA, over 30 min). Product fractions were concentrated and then triturated with 50% methanol in H₂O to give a white solid (69 mg, 67% yield). ¹H NMR (400 MHz, DMSO-d₆) δ 11.96 (s, 1H), 8.34 (s, 1H), 7.58 (d, J=2.5, 1H), 7.19 (dd, J=8.8, 2.3, 1H), 7.01 (d, J=8.4, 1H), 3.76 (s, 3H), 3.61 (s, 2H), 1.15 (d, J=7.0, 6H), 0.96 (s, 9H); MS (ESI) m/z 355.4 [M+1]⁺.

5.1.13 Example 13

SYNTHESIS OF 1-ISOPROPYL-6-(3-ISOPRO-PYL-PHENYL)-1,3-DIHYDRO-IMIDAZO[4,5-B]PYRAZIN-2-ONE

A. 5-Bromo-3-isopropyl-pyrazine-2,3-diamine. 2-Amino-3,5-dibromo-pyrazine (0.9 g, 3.5 mmol) and isopropylamine (1 g, 18 mmol) were heated together to 150° C. for 16 hours. The intermediate was purified via Biotage silica gel chromatography (0-60% ethyl acetate in hexanes) to give a dark colored oil (0.56 g, 69% yield). MS (ESI) m/z 233.1 [M+1]⁺.

B. 6-Bromo-1-isopropyl-1,3-dihydro-imidazo[4,5-b]pyrazin-2-one. 5-Bromo-3-isopropyl-pyrazine-2,3-diamine was added with 1,1'-carbonyldiimidazole (0.86 g, 5.3 mmol) and DMSO (3 mL) and then heated in a Emrys microwave reactor at 150° C. for 1 h. The reaction was extracted with ethyl acetate and water. The organic layer was dried over magnesium sulfate and then filtered. The filtrate was concentrated and then purified via Biotage silica gel chromatography (0-100% ethyl acetate in hexanes) to give a white solid (370 mg, 60% yield). ¹H NMR (400 MHz, DMSO-d₆) δ 12.1 (s, 1H), 8.01 (s, 1H), 4.55 (q, J=6.8, 1H), 1.46 (d, J=6.8, 6H); MS (ESI) m/z 259.1 [M+1]⁺.

C. 1-Isopropyl-6-(3-isopropyl-phenyl)-1,3-dihydro-imidazo[4,5-b]pyrazin-2-one. 6-Bromo-1-isopropyl-1,3-dihydro-imidazo[4,5-b]pyrazin-2-one (65 mg, 0.4 mmol), 3-isopropyl phenylboronic acid (0.92 mg, 0.4 mmol), tetrakis-(triphenylphosphine)palladium(0) (42 mg, 0.036 mmol) and sodium carbonate (2.1 mL, 1M, 2.1 mmol), and dioxane (6 mL) were reacted according to General Procedure B2. The product was purified using reverse-phase semi-preparatory HPLC (5-70% acetonitrile+0.1% TFA in H₂O+0.1% TFA, over 30 min). Product fractions were concentrated and then triturated with 50% methanol in H₂O to give a white solid (24 mg, 23% yield). ¹H NMR (300 MHz, DMSO-d₆) δ 11.96 (s, 1H), 8.47 (s, 1H), 7.78 (s, 1H), 7.81 (d, J=6.8, 1H), 7.40 (t, J=7.7, 1H), 7.28 (d, J=7.5, 1H), 4.66 (q, J=6.9, 1H), 2.98 (q, J=6.9, 1H), 1.55 (d, J=6.9, 6H), 1.25 (d, J=6.9, 6H); MS (ESI) m/z 297.3 [M+1]⁺.

5.1.14 Example 14

SYNTHESIS OF (R)-1-(2-HYDROXY-1-PHENYL-ETHYL)-6-(QUINOLIN-5-YL)-1H-IMIDAZO[4,5-B]PYRAZIN-2(3H)-ONE

A. (R)-2-(3-Amino-6-bromopyrazin-2-ylamino)-2-phenylethanol. 2-Amino-3,5-dibromo pyrazine (1.0 g, 3.98 mmol) and (R)-(−)-2-phenylglycinol (1.09 g, 7.96 mmol) were reacted according to General Procedure A and purified via Biotage silica gel chromatography (40-100% ethyl acetate/hexanes, 25M column) to afford the title compound (0.700 g, 57% yield). MS (ESI) m/z 309.2 [M+1]⁺, 311.2[M+2]⁺.

B. (R)-2-(3-Amino-6-(quinolin-5-yl)pyrazin-2-ylamino)-2-phenylethanol. (R)-2-(3-Amino-6-bromopyrazin-2-ylamino)-2-phenylethanol (0.700 g, 2.26 mmol), quinoline-5-boronic acid (0.431 g, 2.48 mmol), tetrakis(triphenylphosphine)-palladium (0.287 g, 0.226 mmol), potassium carbonate (1.24 g, 9.04 mmol), water (8 mL) and dimethylformamide (35 mL) were reacted according to General Procedure B. The crude material was purified via Biotage silica gel chromatography (40-100% ethyl acetate/hexanes, 40S column) to afford the title compound (0.546 g, 67% yield). MS (ESI) m/z 358.3 [M+1]⁺.

C. (R)-1-(2-Hydroxy-1-phenylethyl)-6-(quinolin-5-yl)-1H-imidazo[4,5-b]pyrazin-2(3H)-one. (R)-2-(3-Amino-6-(quinolin-5-yl)pyrazin-2-ylamino)-2-phenylethanol (0.546 g, 1.53 mmol) and urea (0.183 g, 3.05 mmol) were reacted according to General Procedure D2. The solution was condensed under reduced pressure and triturated with water/methanol to afford the title compound (0.150 g, 26% yield). ¹H NMR (300 MHz, CD₃OD) δ 8.94 (s, 1H), 8.56 (d, 1H), 8.27 (s, 1H), 8.14 (d, 1H), 7.85 (m, 2H), 7.51 (t, 3H), 7.39 (m, 3H), 5.65 (m, 1H), 4.76 (t, 1H), 4.14 (s, 3H); MS (ESI) m/z 384.3 [M+1]⁺.

5.1.15 Example 15

SYNTHESIS OF (S)-1-(2-HYDROXY-1-PHENYL-ETHYL)-6-(QUINOLIN-5-YL)-1H-IMIDAZO[4,5-B]PYRAZIN-2(3H)-ONE

A. (S)-2-(3-Amino-6-bromopyrazin-2-ylamino)-2-phenylethanol. 2-Amino-3,5-dibromo pyrazine (1.0 g, 3.98 mmol) and (S)-(+)-2-phenylglycinol (1.09 g, 7.96 mmol) were reacted according to General Procedure A and purified via Biotage silica gel chromatography (40-100% ethyl acetate/hexanes, 25M column) to afford the title compound (0.882 g, 72% yield). MS (ESI) m/z 309.2 [M+1]+0.311.2 [M+2]⁺.

B. (S)-2-(3-Amino-6-(quinolin-5-yl)pyrazin-2-ylamino)-2-phenylethanol. (S)-2-(3-Amino-6-bromopyrazin-2-ylamino)-2-phenylethanol (0.882 g, 2.26 mmol), quinoline-5-boronic acid (0.544 g, 2.48 mmol) tetrakis(triphenylphosphine)-palladium (0.331 g, 0.287 mmol), potassium carbonate (1.25 g, 9.08 mmol), water (8 mL) and dimethylformamide (30 mL) were reacted according to General Procedure B. The crude material was purified via Biotage silica gel chromatography (0-10% methanol/dichloromethane, 40S column) to afford the title compound (0.524 g, 51% yield). MS (ESI) m/z 358.3 [M+1]⁺.

C. (S)-1-(2-Hydroxy-1-phenylethyl)-6-(quinolin-5-yl)-1H-imidazo[4,5-b]pyrazin-2(3H)-one. (S)-2-(3-Amino-6-(quinolin-5-yl)pyrazin-2-ylamino)-2-phenylethanol (0.524 g, 1.46 mmol) and urea (0.176 g, 2.93 mmol) were reacted according to General Procedure D2. The solution was condensed under reduced pressure and triturated with water/methanol to afford the title compound (0.103 g, 18% yield). $^1$H NMR (300 MHz, CD$_3$OD) δ 8.95 (m, 1H), 8.56 (d, 1H), 8.28 (s, 1H), 8.16 (d, 1H), 7.86 (m, 2H), 7.51 (t, 3H), 7.39 (m, 3H), 5.67 (m, 1H), 4.76 (t, 1H), 4.12 (m, 2H); MS (ESI) m/z 384.4 [M+1]$^+$.

5.1.16 Example 16

SYNTHESIS OF 1-(DIPHENYLMETHYL)-6-(5-QUINOLYL)-4-IMIDAZOLINO[4,5-B]PYRAZIN-2-ONE

A. (3-Amino-6-bromopyrazin-2-yl)(diphenylmethyl)amine. 2-Amino-3,5-dibromopyrazine (1.0 g, 3.98 mmol) and aminodiphenylmethane (1.82 g, 10.0 mmol) were reacted according to General Procedure A and purified via Biotage silica gel chromatography (5-70% ethyl acetate in hexanes, 25M column) to afford the title compound (1.00 g, 71% yield). MS (ESI) m/z 355.3 [M+1]$^+$0.357.3 [M+2]$^+$.

B. (3-Amino-6-(5-quinolyl)pyrazin-2-yl)(diphenylmethyl)amine. (3-Amino-6-bromopyrazin-2-yl)(diphenylmethyl)amine (1.0 g, 2.82 mmol), quinoline-5-boronic acid (0.537 g, 3.1 mmol), tetrakis(triphenylphosphine)palladium (0.325 g, 0.282 mmol), potassium carbonate (1.55 g, 11.28 mmol), water (8 mL) and dimethylformamide (35 mL) were reacted according to General Procedure B. The crude was purified via Biotage silica gel chromatography (10-100% ethyl acetate/hexanes, 40S column) to afford the title compound (0.539 g, 47% yield). MS (ESI) m/z 404.6 [M+1]$^+$.

C. 1-(Diphenylmethyl)-6-(5-quinolyl)-4-imidazolino[4,5-b]pyrazin-2-one. (3-Amino-6-(5-quinolyl)pyrazin-2-yl)(diphenylmethyl)amine (0.539 g, 1.33 mmol) and urea (0.160 g, 2.67 mmol) were reacted according to General Procedure D2. The solution was condensed under reduced pressure and triturated with methanol:ethyl acetate (1:1) to afford the title compound (0.195 g, 34% yield). $^1$H NMR (300 MHz, CD$_3$OD) δ 8.84 (m, 1H), 8.22 (s, 1H), 8.09 (m, 2H), 7.82 (t, 1H), 7.70 (d, 1H), 6.96 (s, 1H), 4.25 (m, 1H); MS (ESI) m/z 430.3 [M+1]$^+$.

5.1.17 Example 17

SYNTHESIS OF (S)-1-(1-PHENYLPROPYL)-6-(QUINOLIN-5-YL)-1H-IMIDAZO[4,5-B]PYRAZIN-2(3H)-ONE

A. (S)-6-bromo-N$^2$-(1-phenylpropyl)pyrazine-2,3-diamine. 2-Amino-3,5-dibrompyrazine (1.0 g, 3.98 mmol) and (S)-(−)-α-ethylbenzylamine (2.15 g, 15.93 mmol) were reacted according to General Procedure A and purified via Biotage silica gel chromatography (10-80% ethyl acetate/hexanes, 25S column) to afford the title compound (0.560 g, 47% yield). MS (ESI) m/z 307.4 [M+1]$^+$, 309.4[M+2]$^+$.

B. (S)—N$^2$-(1-phenylpropyl)-6-(quinolin-5-yl)pyrazine-2,3-diamine. (S)-6-Bromo-N$^2$-(1-phenylpropyl)pyrazine-2,3-diamine (0.560 g, 1.83 mmol), quinoline-5-boronic acid (0.348 g, 2.01 mmol), tetrakis(triphenylphosphine)palladium (0.211 g, 0.183 mmol), potassium carbonate (1.01 g, 7.32 mmol), water (8 mL) and dimethylformamide (30 mL) were reacted according to General Procedure B. The crude was purified via Biotage silica gel chromatography (0-10% methanol/dichloromethane, 40S column) to afford the title compound (0.500 g, 77% yield). MS (ESI) m/z 356.3 [M+1]$^+$.

C. (S)-1-(1-Phenylpropyl)-6-(quinolin-5-yl)-1H-imidazo[4,5-b]pyrazin-2(3H)-one. (S)—N$^2$-(1-Phenylpropyl)-6-(quinolin-5-yl)pyrazine-2,3-diamine (0.500 g, 1.40 mmol) and urea (0.170 g, 2.81 mmol) were reacted according to General Procedure D2. The solution was condensed under reduced pressure and triturated with water/methanol to afford the title compound (0.195 g, 36% yield). $^1$H NMR (300 MHz, CD$_3$OD) δ 8.89 (d, 1H), 8.44 (d, 1H), 8.20 (s, 1H), 8.12 (d, 1H), 7.87 (t, 1H), 7.76 (d, 1H), 7.51 (m, 3H), 7.34 (m, 2H), 5.50 (dd, 1H), 0.981 (t, 3H), 2.39 (m, 2H); MS (ESI) m/z 382.5 [M+1]$^+$.

5.1.18 Example 18

SYNTHESIS OF (R)-1-(1-PHENYLPROPYL)-6-(QUINOLIN-5-YL)-1H-IMIDAZO[4,5-b]PYRAZIN-2(3H)-ONE

A. (R)-6-bromo-N$^2$-(1-phenylpropyl)pyrazine-2,3-diamine. 2-Amino-3,5-dibrompyrazine (1.0 g, 3.98 mmol) and (R)-(+)-α-ethylbenzylamine (2.15 g, 15.93 mmol) were reacted according to General Procedure A and purified via Biotage silica gel chromatography (10-80% ethyl acetate/hexanes, 25S column) to afford the title compound (0.440 g, 36% yield). MS (ESI) m/z 307.4 [M+1]$^+$0.309.4 [M+2]$^+$.

B. (R)—N$^2$-(1-phenylpropyl)-6-(quinolin-5-yl)pyrazine-2,3-diamine. (R)-6-Bromo-N$^2$-(1-phenylpropyl)pyrazine-2,3-diamine (0.440 g, 1.43 mmol), quinoline-5-boronic acid (0.273 g, 1.58 mmol), tetrakis(triphenylphosphine)palladium (0.165 g, 0.143 mmol), potassium carbonate (0.789 g, 5.72 mmol), water (8 mL) and dimethylformamide (30 mL) were reacted according to General Procedure B. The crude was purified via Biotage silica gel chromatography (0-10% methanol/dichloromethane, 40S column) to afford the title compound (0.476 g, 93% yield). MS (ESI) m/z 356.4 [M+1]$^+$.

C. (R)-1-(1-Phenylpropyl)-6-(quinolin-5-yl)-1H-imidazo[4,5-b]pyrazin-2(3H)-one. (R)—N$^2$-(1-Phenylpropyl)-6-(quinolin-5-yl)pyrazine-2,3-diamine (0.476 g, 1.34 mmol) and urea (0.160 g, 2.68 mmol) were reacted according to General Procedure D2. The solution was condensed under reduced pressure and triturated with water/methanol to afford the title compound (0.105 g, 20% yield). $^1$H NMR (300 MHz, CD$_3$OD) δ 8.89 (d, 1H), 8.44 (d, 1H), 8.20 (s, 1H), 8.12 (d, 1H), 7.87 (t, 1H), 7.76 (d, 1H), 7.51 (m, 3H), 7.34 (m, 2H), 5.50 (dd, 1H), 0.981 (t, 3H), 2.39 (m, 2H); MS (ESI) m/z 382 [M+1]$^+$.

5.1.19 Example 19

SYNTHESIS OF 6-(5-ISOPROPYL-2-METHOXYPHENYL)-1-(TETRAHYDRO-2H-PYRAN-3-YL)-1H-IMIDAZO[4,5-B]PYRAZIN-2(3H)-ONE

A. 6-(5-Isopropyl-2-methoxyphenyl)-1-(tetrahydro-2H-pyran-3-yl)-1H-imidazo[4,5-b]pyrazin-2(3H)-one. N-Bis-Boc-3-Bromo-5-(5-isopropyl-2-methoxy-phenyl)-pyrazin-2-ylamine (see Example 5.C) (150 mg, 0.29 mmol), tetrahydro-pyran-3-ylamine hydrochloride (0.395 g, 2.9 mmol) and triethylamine (1 mL) were reacted according to General Procedure E. The product was purified using reverse-phase semi-preparatory HPLC (5-70% acetonitrile+0.1% TFA in H$_2$O+0.1% TFA, over 30 min). Product fractions were concentrated and then triturated with 50% methanol in H$_2$O to give a white solid (53 mg, 50% yield). $^1$H NMR (300 MHz, DMSO-d$_6$) δ 12.04 (s, 1H), 8.40 (s, 1H), 7.65 (d, J=2.5, 1H), 7.27 (dd, J=8.4, 2.3, 1H), 7.09 (d, J=8.5, 1H), 4.30-4.41 (m, 1H), 4.05 (t, J=10.7, 1H), 3.86-3.95 (m, 2H), 3.83 (s, 3H), 2.93 (dd, J=13.8, 6.8, 1H), 1.23 (d, J=6.9, 6H), 2.60 (dd, J=12.1, 5.2, 1H), 1.93-2.02 (m, 1H), 1.77 (s, 2H); MS (ESI) m/z 369.0 [M+1]$^+$.

5.1.20 Example 20

SYNTHESIS OF (S)-1-METHYL-3-(1-PHENYL-ETHYL)-5-(QUINOLIN-5-YL)-1H-IMIDAZO[4,5-B]PYRAZIN-2(3H)-ONE

A. (S)-6-Bromo-1-(1-phenylethyl)-1H-imidazo[4,5-b]pyrazin-2(3H)-one. The title compound was prepared using (S)-6-bromo-$N^2$-(1-phenylethyl)pyrazine-2,3-diamine (See Example 3.A) (0.50 g, 1.71 mmol), 1,1'-carbonyldiimidazole (0.35 g, 2.13 mmol), and tetrahydrofuran (7 mL) as described in General Procedure D1. The crude material was dissolved in methanol (5 mL), and the product was triturated with $H_2O$ while sonicating. The resulting precipitate was filtered and dried in a vacuum oven overnight to afford 0.34 g (1.07 mmol, 62%) of (S)-6-bromo-1-(1-phenylethyl)-1H-imidazo[4,5-b]pyrazin-2(3H)-one. MS (ESI) m/z 319.4 $[M+1]^+$.

B. (S)-5-Bromo-1-methyl-3-(1-phenylethyl)-1H-imidazo[4,5-b]pyrazin-2(3H)-one. To a solution of (S)-6-bromo-1-(1-phenylethyl)-1H-imidazo[4,5-b]pyrazin-2(3H)-one (0.300 g, 0.943 mmol) in dimethylformamide (3 mL) was added cesium carbonate (excess) followed by dimethylsulfate (0.130 g, 1.03 mmol). The solution was heated to 55° C. in a screw capped tube. After one hour, the solution was filtered to remove cesium carbonate salts. The filtrate was condensed under reduced pressure and the crude product purified via Biotage silica gel chromatography (5-50% ethyl acetate/hexanes) to afford the title compound (0.306 g, 83% yield). $^1$H NMR (300 MHz, DMSO-$d_6$) δ 7.99 (s, 1H), 7.57 (d, 2H), 7.32 (m, 3H), 5.77 (q, 1H), 3.42 (s, 3H), 2.04 (d, 3H); $^{13}$C NMR (75 MHz, CHCl$_3$) δ 52.6 (C=O); MS (ESI) m/z 333.3 $[M+1]^+$, 335.3 $[M+2]^+$.

C. (S)-1-Methyl-3-(1-phenylethyl)-5-(quinolin-5-yl)-1H-imidazo[4,5-b]pyrazin-2(3H)-one. (S)-5-Bromo-1-methyl-3-(1-phenylethyl)-1H-imidazo[4,5-b]pyrazin-2(3H)-one (0.276 g, 0.831 mmol), quinoline-5-boronic acid (0.158 g, 0.914 mmol), tetrakis(triphenylphosphine)palladium (0.096 g, 0.083 mmol), potassium carbonate (0.458 g, 3.32 mmol), water (8 mL) and dimethylformamide (30 mL were reacted according General Procedure B and purified via preparative HPLC (5-70% acetonitrile/water, 60 mL/min.) to afford the title compound (0.130 g, 43% yield). $^1$H NMR (300 MHz, CD$_3$OD) δ 8.86 (d, 1H), 8.36 (d, 1H), 8.23 (s, 1H), 8.10 (d, 1H), 7.85 (t, 1H), 7.74 (d, 1H), 7.51 (d, 2H), 7.41 (m, 1H), 7.33 (m, 3H), 5.85 (q, 1H), 3.53 (s, 3H), 2.01 (d, 3H); MS (ESI) m/z 382.4 $[M+1]^+$.

5.1.21 Example 21

SYNTHESIS OF (R)-1-METHYL-3-(1-PHENYL-ETHYL)-5-(QUINOLIN-5-YL)-1H-IMIDAZO[4,5-B]PYRAZIN-2(3H)-ONE

A. (R)-5-Bromo-1-methyl-3-(1-phenylethyl)-1H-imidazo[4,5-b]pyrazin-2(3H)-one. To a solution of (R)-6-bromo-1-(1-phenylethyl)-1H-imidazo[4,5-b]pyrazin-2(3H)-one (0.360 g, 1.13 mmol) in dimethylformamide (3 mL) was added cesium carbonate (excess) followed by dimethylsulfate (0.150 g, 1.13 mmol). The solution was heated to 55° C. in a screw capped tube. After one hour, the solution was filtered to remove cesium carbonate salts. The filtrate was condensed under reduced pressure and the crude product purified via Biotage silica gel chromatography (5-50% ethyl acetate/hexanes) to afford the title compound (0.306 g, 83% yield). $^1$H NMR (300 MHz, DMSO-$d_6$) δ 7.99 (s, 1H), 7.57 (d, 2H), 7.32 (m, 3H), 5.77 (q, 1H), 3.42 (s, 3H), 2.04 (d, 3H); $^{13}$C NMR (75 MHz, CHCl$_3$) δ 52.6 (C=O); MS (ESI) m/z 333.3 $[M+1]^+$, 335.3 $[M+2]^+$.

B. (R)-1-Methyl-3-(1-phenylethyl)-5-(quinolin-5-yl)-1H-imidazo[4,5-b]pyrazin-2(3H)-one. (R)-5-Bromo-1-methyl-3-(1-phenylethyl)-1H-imidazo[4,5-b]pyrazin-2(3H)-one (0.283 g, 0.849 mmol), quinoline-5-boronic acid (0.161 g, 0.933 mmol), tetrakis(triphenyl phosphine)palladium (0.161 g, 0.933 mmol), potassium carbonate (0.468 g, 3.39 mmol), water (8 mL) and dimethylformamide (30 mL) were reacted according to General Procedure B and purified via preparative HPLC (5-70% acetonitrile/water, 60 mL/min.) to afford the title compound (0.137 g, 42% yield). $^1$H NMR (300 MHz, CD$_3$OD) δ 8.86 (d, 1H), 8.36 (d, 1H), 8.24 (s, 1H), 8.10 (d, 1H), 7.85 (t, 1H), 7.75 (d, 1H), 7.51 (d, 2H), 7.41 (m, 1H), 7.34 (m, 3H), 5.85 (q, 1H), 3.53 (s, 3H), 2.01 (d, 3H); MS (ESI) m/z 382.4 $[M+1]^+$.

5.1.22 Example 22

SYNTHESIS OF 1-CYCLOPENTYLMETHYL-6-QUINOLIN-5-YL-1,3-DIHYDRO-IMIDAZO[4,5-B]PYRAZIN-2-ONE

A. Quinolin-5-yl trifluoromethanesulfonate. Quinolin-5-ol (5 g, 34 mmol) was dissolved in pyridine (5.6 mL, 69 mmol) and dichloromethane (100 mL). The solution was cooled in an ice-bath while trifluoromethanesulfonic anhydride (7 mL, 41 mmol) was added via syringe. The reaction was stirred for 30 minutes and then quenched with water. The reaction was extracted with saturated sodium bicarbonate, water, and brine. The organic layer was dried over magnesium sulfate and then concentrated. The resulting residue was purified via Biotage silica gel chromatography (0-60% ethyl acetate in hexanes) to give the product as a yellow oil (9.5 g, 100% yield). $^1$H NMR (400 MHz, DMSO-$d_6$) δ 9.10 (dd, J=4.4, 1.6, 1H), 8.42 (dt, J=8.4, 1.2, 1H), 8.21 (dt, J=8.8, 0.8, 1H), 7.93 (dd, J=8.0, 1H), 7.82 (m, 2H); MS (ESI) m/z 278.0 $[M+1]^+$.

B. 5-(4,4,5,5-Tetramethyl-1,3,2-dioxaborolan-2-yl)quinoline. Quinolin-5-yl trifluoromethane sulfonate (9.5 g, 34 mmol), bis(pinacolato)diboron (18.2 g, 51 mmol), dichloro[1,1'-bis(diphenyl phosphino)ferrocene]palladium(II) dichloromethane (753 mg, 1 mmol), triethylamine (14 mL, 102 mmol), and dioxane (100 mL) were heated to reflux under nitrogen for 16 hours. The reaction was concentrated and the resulting residue was purified via Biotage silica gel chromatography (0-60% ethyl acetate in hexanes) to give the product as a yellow oil (7.0 g, 80% yield). $^1$H NMR (300 MHz, DMSO-$d_6$) δ 9.00 (d, J=9.3, 1H), 8.93 (dd, J=4.1, 1.9, 1H), 8.15 (d, J=8.2, 1H), 8.06 (dd, J=6.9, 1.4, 1H), 7.78 (dd, J=8.5, 6.9, 1H), 7.61 (dd, J=8.5, 4.1, 1H), 1.39 (s, 12H); MS (ESI) m/z 256.4 $[M+1]^+$.

C. 5-(Quinolin-5-yl)pyrazin-2-amine. A solution 5-(4,4,5,5-tetramethyl-1,3,2-dioxaborolan-2-yl)quinoline (5.5 g, 21 mmol), 5-bromopyrazin-2-amine (3.8 g, 21 mmol), tetrakis(triphenyl phosphine)palladium(0) (1.2 g, 1 mmol) and sodium carbonate (63 mL, 1M, 63 mmol), in dioxane (240 mL) was heated to reflux for 16 hours under nitrogen. The reaction was cooled and extracted with EtOAc and water. An emulsion that formed during the extraction was filtered and then dried to give a reddish solid (3.2 g, 67% yield). $^1$H NMR (300 MHz, DMSO-$d_6$) δ 8.93 (dd, J=4.1, 1.6, 1H), 8.60 (d, J=8.5, 1H), 8.24 (d, J=1.4, 1H), 8.03-8.08 (m, 2H), 7.85 (m, 1H); MS (ESI) m/z 223.2 $[M+1]^+$.

D. 3-Bromo-5-(quinolin-5-yl)pyrazin-2-amine. A solution of 5-(quinolin-5-yl)pyrazin-2-amine (1.1 g, 5 mmol) and N-bromosuccinimide (882 mg, 5 mmol) in DMF (50 mL) was stirred at room temperature for 16 hours. The reaction was diluted with water (300 mL) and then filtered through celite. The filtrate was adjusted to pH 8 with saturated sodium bicarbonate (100 mL) and then diluted with EtOAc (100 mL). The mixture was stirred for 2 hours and the solid precipitate that formed was filtered, rinsed with EtOAc, and then dried under vacuum to give an orange solid (300 mg, 20% yield). $^1$H NMR (400 MHz, DMSO-$d_6$) δ 8.94 (d, J=3.2, 1H), 8.56 (d, J=8.4, 1H), 8.33 (s, 1H), 7.83 (d, J=7.2, 1H), 7.73 (d, J=6.8, 1H), 7.57 (dd, J=8.8, 4.0, 1H), 6.98 (s, 2H); MS (ESI) m/z 301.4 [M+1]$^+$.

E. N-Bis-Boc-3-bromo-5-(quinoline-5-yl)-pyrazin-2-ylamine. 3-Bromo-5-(quinolin-5-yl)pyrazin-2-amine (1.5 g, 5.0 mmol), di-t-butyl dicarbonate (2.7 g, 12.5 mmol), 4-dimethylaminopyridine (61 mg, 0.5 mmol), and acetonitrile (15 mL) were heated to 50° C. for 30 minutes. The reaction was concentrated and the resulting residue was purified via Biotage silica gel chromatography (0-100% ethyl acetate in hexanes) to give a yellow solid (2.4 g, 96% yield). $^1$H NMR (300 MHz, DMSO-$d_6$) δ 9.08 (s, 1H), 9.02 (dd, J=4.1, 1.4, 1H), 8.49 (d, J=8.5, 1H), 8.25 (d, J=8.0, 1H), 7.91-8.02 (m, 2H), 7.68 (dd, J=8.7, 4.3, 1H), 1.43 (s, 18H); MS (ESI) m/z 501.3 [M+1]$^+$.

F. 1-Cyclopentylmethyl-6-quinolin-5-yl-1,3-dihydro-imidazo[4,5-b]pyrazin-2-one. A solution of N-bis-boc-3-bromo-5-(quinoline-5-yl)-pyrazin-2-ylamine (150 mg, 0.29 mmol), cyclopentylmethylamine hydrochloride (268 mg, 2 mmol), and triethylamine in ethanol (4 mL) was reacted and purified according to General Procedure E2 to give 25 mg (36% yield) of white solid. $^1$H NMR (300 MHz, DMSO-$d_6$) δ 8.96 (dd, J=4.1, 1.6, 1H), 8.54-8.61 (m, 2H), 8.12 (d, J=8.2, 1H), 7.77-7.90 (m, 2H), 7.47-7.59 (m, 2H), 3.11-3.19 (m, 2H), 1.98-2.12 (m, 1H), 1.67-1.77 (m, 2H), 1.49-1.65 (m, 4H), 1.15-1.30 (m, 2H); MS (ESI) m/z 346.4 [M+1]$^+$.

5.1.23 Example 23

SYNTHESIS OF 1-[1-(2-FLUORO-PHENYL)-ETHYL]-6-QUINOLIN-5-YL-1,3-DIHYDRO-IMIDAZO[4,5-B]PYRAZIN-2-ONE

A. 1-[1-(2-Fluoro-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (see Example 22.E) (150 mg, 0.29 mmol) and 1-(2-fluoro-phenyl)-ethylamine (278 mg, 2 mmol) in ethanol (4 mL) was reacted and purified according to General Procedure E2 to give 55 mg (36% yield) of white solid. $^1$H NMR (300 MHz, DMSO-$d_6$) δ 12.27 (s, 1H), 8.94 (dd, J=4.1, 1.6, 1H), 8.33 (d, J=8.0, 1H), 8.22 (s, 1H), 8.10 (d, J=8.2, 1H), 7.81-7.91 (m, 1H), 7.72-7.78 (m, 1H), 7.60-7.69 (m, 1H), 7.37-7.49 (m, 2H), 7.17-7.26 (m, 2H), 5.94 (q, J=7.1, 1H), 1.90 (d, J=7.1, 3H); MS (ESI) m/z 386.0 [M+1]$^+$.

5.1.24 Example 24

SYNTHESIS OF 1-[1-(4-FLUORO-PHENYL)-ETHYL]-6-QUINOLIN-5-YL-1,3-DIHYDRO-IMIDAZO[4,5-B]PYRAZIN-2-ONE

A. 1-[1-(4-Fluoro-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-(4-fluoro-phenyl)-ethylamine (278 mg, 2 mmol) in ethanol (4 mL) was reacted and purified according to General Procedure E2 to give 75 mg (49% yield) of white solid. $^1$H NMR (300 MHz, DMSO-$d_6$) δ 12.29 (s, 1H), 8.91-9.01 (m, 1H), 8.32 (d, J=8.5, 1H), 8.22 (s, 1H), 8.10 (d, J=8.2, 1H), 7.80-7.91 (m, 1H), 7.72-7.79 (m, 1H), 7.41-7.53 (m, 3H), 7.19 (t, J=8.9, 2H), 5.72 (q, J=7.2, 1H), 1.91 (d, J=7.1, 3H); MS (ESI) m/z 385.9 [M+1]$^+$.

5.1.25 Example 25

SYNTHESIS OF 1-[1-(3-FLUORO-PHENYL)-ETHYL]-6-QUINOLIN-5-YL-1,3-DIHYDRO-IMIDAZO[4,5-B]PYRAZIN-2-ONE

A. 1-[1-(3-Fluoro-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-(3-fluoro-phenyl)-ethylamine (278 mg, 2 mmol) in ethanol (4 mL) was reacted and purified according to General Procedure E2 to give 53 mg (69% yield) of white solid. $^1$H NMR (400 MHz, DMSO-$d_6$) δ 8.93 (dd, J=4.1, 1.6, 1H), 8.31-8.34 (m, 1H), 8.22 (s, 1H), 8.10 (d, J=8.4, 1H), 7.82-7.86 (m, 1H), 7.75 (dd, J=7.1, 1.3, 1H), 7.39-7.44 (m, 2H), 7.23-7.31 (m, 2H), 7.13-7.19 (m, 1H), 5.73 (q, J=7.4, 1H), 1.91 (d, J=7.2, 3H); MS (ESI) m/z 386.1 [M+1]$^+$.

5.1.26 Example 26

SYNTHESIS OF 1-[1-(3-METHOXY-PHENYL)-ETHYL]-6-QUINOLIN-5-YL-1,3-DIHYDRO-IMIDAZO [4,5-B]PYRAZIN-2-ONE

A. 1-[1-(3-Methoxy-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-(3-methoxyphenyl)-ethylamine (278 mg, 2 mmol) in ethanol (4 mL) was reacted and purified according to General Procedure E2 to give 44 mg (38% yield) of white solid. $^1$H NMR (400 MHz, DMSO-$d_6$) δ 8.93 (dd, J=4.1, 1.8, 1H), 8.35-8.38 (m, 1H), 8.22 (s, 1H), 8.10 (d, J=8.4, 1H), 7.82-7.86 (m, 1H), 7.76 (dd, J=7.1, 1.3, 1H), 7.42 (dd, J=8.6, 4.1, 1H), 7.26-7.31 (m, 1H), 6.97-7.00 (m, 2H), 6.87-6.91 (m, 1H), 5.67 (q, J=7.3, 1H), 3.68 (s, 3H), 1.92 (d, J=7.2, 3H); MS (ESI) m/z 398.4 [M+1]$^+$.

5.1.27 Example 27

SYNTHESIS OF 1-[1-(4-METHOXY-PHENYL)-ETHYL]-6-QUINOLIN-5-YL-1,3-DIHYDRO-IMIDAZO[4,5-B]PYRAZIN-2-ONE

A. 1-[1-(4-Methoxy-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-(4-methoxyphenyl)-ethylamine (278 mg, 2 mmol) in ethanol (4 mL) was reacted and purified according to General Procedure E2 to give 44 mg (38% yield) of white solid. $^1$H NMR (400 MHz, DMSO-$d_6$) δ 12.24 (s, 1H), 8.94 (dd, J=4.1, 1.8, 1H), 8.33-8.36 (m, 1H), 8.21 (s, 1H), 8.10 (d, J=8.4, 1H), 7.85 (dd, J=8.4, 7.2, 1H), 7.75 (dd, J=7.2, 1.2, 1H), 7.44 (dd, J=8.6, 4.1, 1H), 7.35-7.38 (m, 2H), 6.90-6.94 (m, 2H), 5.67 (q, J=7.2, 1H), 3.74 (s, 3H), 1.91 (d, J=7.2, 3H); MS (ESI) m/z 397.9 [M+1]$^+$.

5.1.28 Example 28

SYNTHESIS OF 6-QUINOLIN-5-YL-1-(TET-RAHYDRO-PYRAN-3-YL)-1,3-DIHYDRO-IMI-DAZO[4,5-B]PYRAZIN-2-ONE

A. 6-Quinolin-5-yl-1-(tetrahydro-pyran-3-yl)-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol), tetrahydro-pyran-3-ylamine hydrochloride (278 mg, 2 mmol), and triethylamine (1 mL) in ethanol (4 mL) was reacted and purified according to General Procedure E2 to give 21 mg (21% yield) of white solid. $^1$H NMR (400 MHz, DMSO-$d_6$) δ 12.22 (s, 1H), 8.96 (dd, J=4.1, 1.8, 1H), 8.61 (d, J=8.0, 1H), 8.22 (s, 1H), 8.12 (d, J=8.4, 1H), 7.87 (dd, J=8.4, 7.0, 1H), 7.78 (dd, J=7.1, 1.3, 1H), 7.58 (dd, J=8.6, 4.1, 1H), 4.31-4.39 (m, 1H), 3.89-3.99 (m, 2H), 3.82 (dd, J=11.0, 4.0, 1H), 3.21 (td, J=11.6, 2.8, 1H), 2.54 (d, J=4.7, 1H), 1.99 (d, J=12.1, 1H), 1.63-1.75 (m, 2H); MS (ESI) m/z 348.4 [M+1]$^+$.

5.1.29 Example 29

SYNTHESIS OF 1-((1s,4s)-4-HYDROXYCYCLO-HEXYL)-6-(QUINOLIN-5-YL)-1H-IMIDAZO[4,5-B]PYRAZIN-2(3H)-ONE

A. 1-((1s,4s)-4-Hydroxycyclohexyl)-6-(quinolin-5-yl)-1H-imidazo[4,5-b]pyrazin-2(3H)-one. A solution of N-bis-boc-3-bromo-5-(quinoline-5-yl)-pyrazin-2-ylamine (See Example 22.E) (150 mg, 0.29 mmol), (1s,4s)-4-aminocyclohexanol hydrochloride (278 mg, 2 mmol), and triethylamine (1 mL) in ethanol (4 mL) was reacted and purified according to General Procedure E2 to give 50 mg (35% yield) of white solid. $^1$H NMR (400 MHz, DMSO-$d_6$) δ 12.16 (s, 1H), 8.96 (dd, J=4.1, 1.8, 1H), 8.58-8.62 (m, 1H), 8.20 (s, 1H), 8.12 (d, J=8.4, 1H), 7.85-7.89 (m, 1H), 7.78 (dd, J=7.2, 1.2, 1H), 7.57 (dd, J=8.8, 4.1, 1H), 4.62 (d, J=4.5, 1H), 4.21 (tt, J=12.3, 4.3, 1H), 3.33-3.39 (m, 1H), 2.27-2.38 (m, 2H), 1.91 (d, J=10.9, 2H), 1.81 (d, J=11.7, 2H), 1.24-1.34 (m, 2H); MS (ESI) m/z 362.0 [M+1]$^+$.

5.1.30 Example 30

SYNTHESIS OF 1-((1r,4r)-4-HYDROXYCYCLO-HEXYL)-6-(QUINOLIN-5-YL)-1H-IMIDAZO[4,5-B]PYRAZIN-2(3H)-ONE

A. 1-((1r,4r)-4-Hydroxycyclohexyl)-6-(quinolin-5-yl)-1H-imidazo[4,5-b]pyrazin-2(3H)-one. A solution of N-bis-boc-3-bromo-5-(quinoline-5-yl)-pyrazin-2-ylamine (See Example 22.E) (150 mg, 0.29 mmol), (1r,4r)-4-aminocyclohexanol hydrochloride (278 mg, 2 mmol), and triethylamine (1 mL) in ethanol (4 mL) was reacted and purified according to General Procedure E2 to give 55 mg (38% yield) of white solid. $^1$H NMR (400 MHz, DMSO-$d_6$) δ 12.13 (s, 1H), 8.95 (dd, J=4.2, 1.7, 1H), 8.66 (dd, J=8.8, 1.3, 1H), 8.19 (s, 1H), 8.12 (d, J=8.4, 1H), 7.84-7.88 (m, 1H), 7.77-7.80 (m, 1H), 7.55 (dd, J=8.8, 4.1, 1H), 4.18-4.28 (m, 2H), 3.83 (s, 1H), 2.64-2.75 (m, 2H), 1.76 (d, J=12.3, 2H), 1.47-1.58 (m, 4H); MS (ESI) m/z 362.4 [M+1]$^+$.

5.1.31 Example 31

SYNTHESIS OF 6-(5-ISOQUINOLYL)-1-(PHE-NYLETHYL)-4-IMIDAZOLINO[4,5-B]PYRAZIN-2-ONE

A. 6-Bromo-N$^2$-(1-phenylethyl)pyrazine-2,3-diamine. α-Methylbenzylamine (1.3 mL, 10.21 mmol) was added to 2-amino-3,5-dibromo-pyrazine (2.00 g, 7.97 mmol) in n-BuOH (10 mL) and the resulting mixture was heated at 220° C. for 4500 s in the Emrys Optimizer microwave reactor. The reaction mixture was condensed to a brown oil. Purification using silica gel flash column chromatography (10-80% EtOAc in hexanes) provided 1.65 g (5.62 mmol, 71%) of 6-bromo-N$^2$-(1-phenylethyl)pyrazine-2,3-diamine. MS (ESI) m/z 293.0 [M+1]$^+$.

B. 6-Bromo-1-(1-phenylethyl)-1H-imidazo[4,5-b]pyrazin-2(3H)-one. 1,1'-Carbonyldi-imidazole (1.14 g, 7.04 mmol) was added to 6-bromo-N$^2$-(1-phenylethyl)pyrazine-2,3-diamine (1.65 g, 5.63 mmol) and dissolved in THF (15 mL). The resulting mixture was heated for 3600 s at 180° C. in the Emrys Optimizer microwave reactor. Reaction was condensed to a brown oil. The crude oil was taken up in a minimal amount of methanol, and while sonicating, water was added to induce precipitation. The resulting solid was collected by filtration and dried in a vacuum oven overnight to yield 1.54 g (4.83 mmol, 86%) of the title compound. MS (ESI) m/z 319.1 [M+1]$^+$.

C. 6-(5-Isoquinolyl)-1-(phenylethyl)-4-imidazolino[4,5-b]pyrazin-2-one. A solution of 6-bromo-1-(1-phenylethyl)-1H-imidazo[4,5-b]pyrazin-2(3H)-one (0.5 g, 1.567 mmol), isoquinoline-5-boronic acid (0.4 g, 2.35 mmol), potassium phosphate (1.6 g, 7.8 mmol) and [1,1'-bis(diphenylphosphino)ferrocene]dichloropalladium (II) methylene chloride complex (0.13 g, 0.16 mmol) in dimethylformamide (10 mL) was heated at 130° C. for 1 hour in Emrys Optimizer microwave reactor. The reaction mixture was filtered through Celite and solvent was removed under reduced pressure. The crude material was purified by column chromatography (SiO$_2$, 20-100% ethyl acetate in hexanes). The resulting material was further purified using column chromatography (SiO$_2$, 2% methanol in methylene chloride). Clean fraction were combined, solvent removed under reduced pressure and the resulting solid was sonicated in the presence of acetonitrile. The resulting precipitate was filtered and dried under high vacuum to afford the title compound, 99.9% pure, (33.7 mg, 6%). $^1$H NMR (400 MHz, CD$_3$OD) δ 9.29 (s, 1H), 8.32 (d, J=6.2, 1H), 8.18 (overlapping signals, 2H), 7.93 (dd, J=7.1, 1.2 1H), 7.82 (d, J=6.1, 1H), 7.78 (dd, J=8.2, 7.2, 1H), 7.51 (d, J=6.6, 2H), 7.34 (m, 3H), 5.83 (q, J=7.22, 1H), 2.03 (d, J=7.22, 3H); MS (ESI) m/z 368.1 [M+1]$^+$.

5.1.32 Example 32

SYNTHESIS OF 1-[1-(4-CHLORO-PHENYL)-ETHYL]-6-QUINOLIN-5-YL-1,3-DIHYDRO-IMI-DAZO[4,5-B]PYRAZIN-2-ONE

A. 1-[1-(4-Chloro-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-(4-chlorophenyl)-ethylamine (278 mg, 2 mmol) in ethanol (4 mL) was reacted and purified according to General Procedure E2 to give 49 mg (42% yield) of white solid. $^1$H NMR (400 MHz, DMSO-$d_6$) δ 12.29 (s, 1H), 8.94 (dd, J=4.1, 1.8, 1H), 8.29 (dd, J=9.2, 1.2, 1H), 8.22 (s, 1H), 8.10 (d, J=8.2, 1H), 7.84 (dd, J=8.4, 7.2, 1H), 7.75 (dd, J=7.1, 1.3, 1H), 7.40-7.46 (m, 5H), 5.68-5.74 (m, 1H), 1.90 (d, J=7.2, 3H); MS (ESI) m/z 402.3 [M+1]$^+$.

5.1.33 Example 33

SYNTHESIS OF 1-[1-(4-METHANESULFONYL-PHENYL)-ETHYL]-6-QUINOLIN-5-YL-1,3-DI-HYDRO-IMIDAZO[4,5-B]PYRAZIN-2-ONE

A. 1-[1-(4-Methanesulfonyl-phenyl)-ethyl]-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-(4-methanesulfonyl-phenyl)-ethylamine (400 mg, 2 mmol) in ethanol (4 mL) was reacted and purified according to General Procedure E2 to give 33 mg (37% yield) of white solid. $^1$H NMR (400 MHz, DMSO-d$_6$) d 12.31 (s, 1H), 8.88 (dd, J=4.1, 1.6, 1H), 8.26-8.29 (m, 1H), 8.21 (s, 1H), 8.06 (d, J=8.4, 1H), 7.89 (dt, J=8.6, 2.0, 2H), 7.78-7.83 (m, 1H), 7.71 (dd, J=7.1, 1.3, 1H), 7.66 (d, J=8.4, 2H), 7.40 (dd, J=8.6, 4.1, 1H), 5.78 (q, J=7.3, 1H), 3.18 (s, 3H), 1.92 (d, J=7.2, 3H); MS (ESI) m/z 446.4 [M+1]$^+$.

5.1.34 Example 34

SYNTHESIS OF 1-(1-PYRIDIN-4-YL-ETHYL)-6-QUINOLIN-5-YL-1,3-DIHYDRO-IMIDAZO[4,5-B]PYRAZIN-2-ONE

A. 1-(1-Pyridin-4-yl-ethyl)-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and 1-pyridin-4-yl-ethylamine (250 mg, 2 mmol) in ethanol (4 mL) was reacted and purified according to General Procedure E2 to give 15 mg (20% yield) of white solid. $^1$H NMR (400 MHz, DMSO-d$_6$) δ 12.30 (s, 1H), 8.87 (d, J=3.9, 1H), 8.52 (d, J=6.1, 2H), 8.20 (s, 1H), 8.18 (s, 1H), 8.05 (d, J=8.4, 1H), 7.79 (t, J=7.7, 1H), 7.70 (d, J=7.0, 1H), 7.37 (d, J=6.1, 2H), 7.33 (dd, J=8.7, 4.2, 1H), 5.69 (d, J=7.2, 1H), 1.86 (d, J=7.2, 3H); MS (ESI) m/z 369.4 [M+1]$^+$.

5.1.35 Example 35

SYNTHESIS OF 5-METHYL-1-((S)-1-PHENYL-ETHYL)-6-(QUINOLIN-5-YL)-1H-IMIDAZO[4,5-B]PYRAZIN-2(3H)-ONE

A. 6-Methylpyrazine-2-ylamine. To a solution containing 6-chloro-2-pyrazineamine (5.0 g, 38.75 mmol) in 1,4-dioxane (70 mL) was added [1,3-bis(diphenylphosphino]Ni(II)Cl$_2$ (2.10 g, 38.76 mmol), followed by drop-wise addition of dimethylzinc in toluene (38.75 mL, 2.0 M, 77.50 mmol), over 15 min. The solution was allowed stir at 105° C. for 16 hours. The solution was then condensed under reduced pressure, diluted with ethyl acetate and filtered through celite to remove the nickel salts. The resultant slurry was purified via Biotage silica gel chromatography (0-8% methanol in dichloromethane) to afford the title compound as an orange solid (1.18 g, 28% yield). MS (ESI) m/z 110.3 [M+1]$^+$.

B. 3,5-Dibromo-6-methylpyrazine-2-ylamine. 6-Methylpyrazine-2-ylamine (1.18 g, 10.82 mmol) and pyridine (1.79 g, 22.72 mmol) were combined in chloroform (100 mL) at ambient temperature. Bromine (3.63 g, 22.72 mmol) in chloroform (5 mL) was then added drop-wise over 5 minutes. Upon consumption of the starting material, as indicated by TLC, the reaction solution was transferred to a separatory funnel and the organic layer washed twice with water. The organics were dried over magnesium sulfate, filtered and solvent removed under reduced pressure to afford the title compound (2.70 g, 95% yield). MS (ESI) m/z 268.0[M+2]$^+$.

C. (S)-6-Bromo-5-methyl-N$^2$-(1-phenylethyl)pyrazine-2,3-diamine. 3,5-Dibromo-6-methylpyrazine-2-ylamine (1.45 g, 5.45 mmol) and (S)-(−)-α-methylbenzylamine (1.65 g, 13.62 mmol) were reacted according to General Procedure A and purified via Biotage silica gel chromatography (5-75% ethyl acetate in hexanes, 40M column) to afford the title compound (0.975 g, 65% yield). MS (ESI) m/z 309.4[M+2]$^+$.

D. 5-Methyl-N$^2$—((S)-1-phenylethyl)-6-(quinolin-5-yl)pyrazine-2,3-diamine. A solution of (S)-6-bromo-5-methyl-N$^2$-(1-phenylethyl)pyrazine-2,3-diamine (0.975 g, 3.19 mmol), quinoline-5-boronic acid (0.606 g, 3.50 mmol), tetrakis(triphenylphosphine)palladium (0.368 g, 0.319 mmol), and potassium carbonate (1.76 g, 12.76 mmol) in water (8 mL) and dimethylformamide (30 mL) was reacted according to General Procedure B and purified via Biotage silica gel chromatography (0-10% methanol in dichloromethane, 40M column). The resultant solid was triturated with water/methanol to afford the title compound (0.200 g, 18% yield). MS (ESI) m/z 356.5 [M+1]$^+$.

E. 5-Methyl-1-((S)-1-phenylethyl)-6-(quinolin-5-yl)-1H-imidazo[4,5-b]pyrazin-2(3H)-one. 5-Methyl-N$^2$—((S)-1-phenylethyl)-6-(quinolin-5-yl)pyrazine-2,3-diamine (0.200 g, 0.563 mmol) and urea (0.067 g, 1.12 mmol) were reacted according to General Procedure D2 and purified via Biotage silica gel chromatography (0-10% methanol in dichloromethane, 25M column) to afford the title compound (0.063 g, 30% yield). $^1$H NMR (300 MHz, DMSO-d$_6$) δ 12.10 (bs, 1H), 8.92 (dd, 1H), 8.10 (d, 2H), 7.84 (m, 2H), 7.62 (d, 1H), 7.41 (m, 1H), 7.30 (m, 6H), 5.63 (q, 1H), 3.32 (s, 2H), 1.85 (d, 3H); MS (ESI) m/z 382.5 [M+1]$^+$.

5.1.36 Example 36

SYNTHESIS OF 5-METHYL-1-((R)-1-PHENYL-ETHYL)-6-(QUINOLIN-5-YL)-1H-IMIDAZO[4,5-B]PYRAZIN-2(3H)-ONE

A. (R)-6-Bromo-5-methyl-N$^2$-(1-phenylethyl)pyrazine-2,3-diamine. 3,5-Dibromo-6-methylpyrazine-2-ylamine (See Example 35.B) (0.900 g, 3.38 mmol) and (R)-(+)-αα-methylbenzylamine (1.63 g, 13.52 mmol) were reacted according to General Procedure A and purified via Biotage silica gel chromatography (5-80% ethyl acetate in hexanes, 40S column) to afford the title compound (0.534 g, 52% yield). MS (ESI) m/z 309.4[M+2]$^+$.

B. 5-Methyl-N$^2$—((R)-1-phenylethyl)-6-(quinolin-5-yl)pyrazine-2,3-diamine. (R)-6-Bromo-5-methyl-N$^2$-(1-phenylethyl)pyrazine-2,3-diamine (0.534 g, 1.74 mmol), quinoline-5-boronic acid (0.331 g, 1.91 mmol), tetrakis(triphenylphosphine) palladium (0.20 g, 0.175 mmol), and potassium carbonate (0.96 g, 6.96 mmol) in water (4 mL) and dimethylformamide (15 mL) was reacted according to General Procedure B and purified via Biotage silica gel chromatography (0-10% methanol in dichloromethane, 40M column) and the resultant solid triturated with water/methanol to afford the title compound (0.42 g, 67% yield). MS (ESI) m/z 356.4 [M+1]$^+$.

C. 5-Methyl-1-((R)-1-phenylethyl)-6-(quinolin-5-yl)-1H-imidazo[4,5-b]pyrazin-2(3H)-one. 5-Methyl-N$^2$—((R)-1-phenylethyl)-6-(quinolin-5-yl)pyrazine-2,3-diamine (0.418 g, 1.11 mmol) and urea (0.141 g, 2.35 mmol) were reacted according to General Procedure D2. The solution was condensed under reduced pressure and diluted with methanol and triturated with water while sonicating. The resultant precipitate was filtered and dried to afford the title compound (0.142 g, 32% yield). $^1$H NMR (300 MHz, DMSO) δ 12.10 (bs, 1H), 8.92 (dd, 1H), 8.10 (d, 2H), 7.84 (m, 2H), 7.62 (d, 1H), 7.41 (m, 1H), 7.30 (m, 6H), 5.63 (q, 1H), 3.32 (s, 2H), 1.85 (d, 3H). MS (ESI) m/z 382.5 [M+1]$^+$.

5.1.37 Example 37

SYNTHESIS OF 1-(1-PHENYLETHYL)-6-(QUINOLIN-4-YL)-1H-IMIDAZO[4,5-B]PYRAZIN-2(3H)-ONE

A. 1-(1-Phenylethyl)-6-(quinolin-4-yl)-1H-imidazo[4,5-b]pyrazin-2(3H)-one. The title compound was prepared using 6-bromo-1-(1-phenylethyl)-1H-imidazo[4,5-b]pyrazin-2 (3H)-one (see Example 31.B) (0.50 g, 1.57 mmol), 4-quinoline boronic acid (0.27 g, 1.89 mmol), potassium carbonate (1.00 g, 4.71 mmol), tetrakis(triphenylphosphine) palladium (0) (0.13 g, 0.16 mmol), dimethylformamide (7 mL), and water (4 mL) as described in General Procedure B. The crude material was purified using silica gel chromatography (20-70% EtOAc in hexanes). Clean fractions were combined and condensed to afford 0.1 g (0.27 mmol, 17%) of 1-(1-phenylethyl)-6-(quinolin-4-yl)-H-imidazo[4,5-b]pyrazin-2(3H)-one. $^1$H NMR (300 MHz, CD$_3$OD) δ 8.91 (d, 1H), 8.27 (s, 1H), 8.09 (m, 2H), 7.81 (m, 1H), 7.63 (d, 2H), 7.53 (m, 2H), 7.34 (m, 2H), 5.83 (m, 1H), 2.03 (d, 3H); MS (ESI) m/z 368.4 [M+1]$^+$; mp 252-254° C.

5.1.38 Example 38

SYNTHESIS OF 6-(2-FLUOROPHENYL)-1-(1-PHENYLETHYL)-1H-IMIDAZO[4,5-B]PYRAZIN-2(3H)-ONE

A. 6-(2-Fluorophenyl)-1-(1-phenylethyl)-1H-imidazo[4,5-b]pyrazin-2(3H)-one. A solution of 6-bromo-1-(1-phenylethyl)-1H-imidazo[4,5-b]pyrazin-2(3H)-one (See Example 31.B) (0.125 g, 0.393 mmol), 2-fluorophenyl boronic acid (0.065 g, 0.470 mmol), dichloro[1,1'-bis(diphenylphosphino)ferrocene]palladium(II) dichloromethane adduct (0.032 g, 0.039 mmol) and potassium phosphate (0.333 g, 1.57 mmol) in water (0.6 ml) and dimethylformamide (2 ml) was reacted according General Procedure C and purified via preparative HPLC (10-100% acetonitrile/water, 60 mL/min) to afford the title compound (0.050 g, 38% yield). $^1$H NMR (300 MHz, DMSO-d$_6$) δ 12.10 (s, 1H), 8.35 (s, 1H), 7.85 (t, 1H), 7.45 (t, 3H), 7.37 (m, 3H), 7.30 (m, 1H), 5.77 (q, 1H), 2.00 (d, 3H). MS (ESI) m/z 335.1 [M+1]$^+$.

5.1.39 Example 39

SYNTHESIS OF 1-(1-PHENYLETHYL)-6-(QUINOLIN-6-YL)-1H-IMIDAZO[4,5-B]PYRAZIN-2(3H)-ONE

A. 4,4,5,5-Tetramethyl-2-(6-quinolyl)-1,3,2-dioxaborolane. To a suspension of 6-bromo quinoline (0.9 g, 4.35 mmol), bis(pinacolato)diboron (8.85 g, 34.8 mmol) and potassium acetate (2.56 g, 5.22 mmol) in DMF (50 mL) was added [1,1'-bis(diphenylphosphino)ferrocene]dichloro-palladium (II) dichloromethane adduct (355 mg, 0.435 mmol) and the reaction mixture was heated in the Emrys Optimizer microwave reactor at 100° C. for 30 minutes. The reaction mixture was filtered through Celite and the solvent was removed under reduced pressure. The crude material was purified by column chromatography (SiO$_2$, 20-50% ethyl acetate in hexanes) to yield the title compound (1.1 g, 99% yield). MS (ESI) m/z 256.5 [M+1]$^+$.

B. 1-(1-Phenylethyl)-6-(quinolin-6-yl)-1H-imidazo[4,5-b]pyrazin-2(3H)-one. A solution of 6-bromo-1-(1-phenylethyl)-1H-imidazo[4,5-b]pyrazin-2(3H)-one (See Example 35.B) (0.5 g, 1.567 mmol), 4,4,5,5-tetramethyl-2-(6-quinolyl)-1,3,2-dioxaborolane (0.6 g, 2.35 mmol), potassium phosphate (1.6 g, 7.8 mmol) and [1,1'-bis(diphenylphosphino)ferrocene]dichloropalladium (II) dichloromethane adduct (0.13 g, 0.16 mmol) in 10:1 DMF:water (10 mL) was heated at 130° C. for 1 hour in the Emrys Optimizer microwave reactor. The reaction mixture was filtered through Celite and solvent was removed under reduced pressure. The crude material was purified using column chromatography (SiO$_2$, 1:1 nHexane:ethyl acetate). Further purification using column chromatography (SiO$_2$, 2% methanol in methylene chloride) followed by passing through a C18 column using acetonitrile as eluent, afforded the title compound, 98.9% pure, (3 mg, 0.5%). $^1$H NMR (400 MHz, CD$_3$OD) δ 8.84 (dd, J=4.3, 1.6, 1H), 8.61 (s, 1H), 8.53 (d, J=1.9, 1H), 8.46 (d, J=7.2, 1H), 8.41 (dd, J=8.9, 2.2, 1H), 8.11 (d, J=8.8, 1H), 7.59 (overlapping signals, 3H), 7.35 (t, J=7.7, 2H), 7.28 (t, J=7.2, 1H), 5.87 (q, J=7.4, 1H), 2.03 (d, J=7.4, 3H); MS (ESI) m/z 368.3 [M+1]$^+$.

5.1.40 Example 40

SYNTHESIS OF 1-PIPERIDIN-4-YLMETHYL-6-QUINOLIN-5-YL-1,3-DIHYDRO-IMIDAZO[4,5-B]PYRAZIN-2-ONE

A. 1-Piperidin-4-ylmethyl-6-quinolin-5-yl-1,3-dihydro-imidazo[4,5-b]pyrazin-2-one. A solution of N-bis-boc-3-bromo-5-(quinoline-5-yl)-pyrazin-2-ylamine (See Example 22.E) (150 mg, 0.29 mmol) and tert-butyl 4-(aminomethyl)piperidine-1-carboxylate (400 mg, 2 mmol) in ethanol (4 mL) was reacted and purified according to General Procedure E2. The reaction was triturated with 1:1 DMSO:methanol to give 19 mg (26% yield) of white solid. $^1$H NMR (400 MHz, DMSO-d$_6$) δ 8.94 (dd, J=4.1, 1.8, 1H), 8.59-8.61 (m, 1H), 8.10 (s, 1H), 8.08 (d, J=7.2, 1H), 7.82-7.86 (m, 1H), 7.73 (dd, J=7.2, 1.2, 1H), 7.51 (dd, J=8.8, 4.1, 1H), 3.68 (d, J=6.8, 1H), 2.96-3.04 (m, 2H), 1.94-2.04 (m, 1H), 1.56-1.64 (m, 2H), 1.12-1.24 (m, 2H); MS (ESI) m/z 405.5 [M+1]$^+$.

5.1.41 Example 41

SYNTHESIS OF 1-(1-(PYRIDIN-2-YL)ETHYL)-6-(QUINOLIN-5-YL)-1H-IMIDAZO[4,5-B]PYRAZIN-2(3H)-ONE

A. 1-(Pyridin-2-yl)ethanamine. 2-Acetylpyridine (0.5 g, 4.1 mmol), potassium carbonate (1.7 g, 12.3 mmol), hydroxylamine hydrochloride (342 mg, 5 mmol), and methanol (10 mL) were stirred together at room temperature for 16 hours, then the reaction mixture was filtered. To the filtrate was added with zinc dust (1.3 g, 21 mmol) and ammonium chloride (1.1 g, 21 mmol). The resulting suspension was stirred at room temperature for 24 hours. The reaction was diluted with water (10 mL) and then filtered. The filtrate was concentrated and dried to give 300 mg (60% yield) of white solid. $^1$H NMR (300 MHz, DMSO-d$_6$) δ 8.47 (d, J=4.9, 1H), 7.73 (td, J=7.7, 1.9, 1H), 7.45 (d, J=7.7, 1H), 7.20 (ddd, J=7.5, 4.9, 1.1, 1H), 3.98 (q, J=6.0, 1H), 1.27 (d, J=6.6, 3H); MS (ESI) m/z 123.6 [M+1]$^+$.

B. 1-(1-(Pyridin-2-yl)ethyl)-6-(quinolin-5-yl)-1H-imidazo[4,5-b]pyrazin-2(3H)-one. A solution of N-bis-boc-3-bromo-5-(quinolin-5-yl)-pyrazin-2-ylamine (See Example 22.E) (150 mg, 0.29 mmol) and 1-(pyridin-2-yl)ethanamine (250 mg, 2 mmol) in ethanol (4 mL) was reacted and purified according to General Procedure E2 to give 53 mg (48% yield) of white solid. $^1$H NMR (400 MHz, DMSO-d$_6$) δ 12.27 (s, 1H), 8.88 (dd, J=4.1, 1.6, 1H), 8.50-8.52 (m, 1H), 8.21 (s, 1H), 8.16 (d, J=8.4, 1H), 8.06 (d, J=8.4, 1H), 7.79-7.84 (m, 2H), 7.71-7.73 (d, J=7.5, 1H), 7.48 (d, J=8.5, 1H), 7.30-7.36 (m, 2H), 5.72-5.77 (dd, J=9.0, 1H), 1.94 (d, J=9.0, 3H); MS (ESI) m/z 369.5 [M+1]$^+$.

5.1.42 Example 42

SYNTHESIS OF 1-(1-(PYRIDIN-3-YL)ETHYL)-6-(QUINOLIN-5-YL)-1H-IMIDAZO[4,5-B]PYRAZIN-2(3H)-ONE

A. 1-(Pyridin-3-yl)ethanamine. 3-Acetylpyridine (0.5 g, 4.1 mmol), potassium carbonate (1.7 g, 12.3 mmol), hydroxylamine hydrochloride (342 mg, 5 mmol), and methanol (10 mL) were stirred together at room temperature for 16 hours, then the reaction mixture was filtered. To the filtrate was added with zinc dust (1.3 g, 21 mmol) and ammonium chloride (1.1 g, 21 mmol). The solution was stirred at room temperature for 24 hours. The reaction was added with water (10 mL) and then filtered. The filtrate was concentrated and dried to give 300 mg (60% yield) of white solid. $^1$H NMR (300 MHz, DMSO-d$_6$) δ 8.52 (d, J=4.9, 1H), 8.32 (td, J=7.7, 1.9, 1H), 7.68 (d, J=7.7, 1H), 7.28 (ddd, J=7.5, 4.9, 1.1, 1H), 4.6 (q, J=6.0, 1H), 1.25 (d, J=6.6, 3H); MS (ESI) m/z 123.4 [M+1]$^+$.

B. 1-(1-(Pyridin-3-yl)ethyl)-6-(quinolin-5-yl)-1H-imidazo[4,5-b]pyrazin-2(3H)-one. A solution of N-bis-boc-3-bromo-5-(quinoline-5-yl)-pyrazin-2-ylamine (See Example 22.E) (150 mg, 0.29 mmol) and 1-(pyridin-3-yl)ethanamine (250 mg, 2 mmol) in ethanol (4 mL) was reacted and purified according to General Procedure E2 to give 15 mg (14% yield) of white solid. $^1$H NMR (400 MHz, DMSO-d$_6$) δ 12.29 (s, 1H), 8.93 (m, 1H), 8.60 (d, J=2.0, 1H), 8.52-8.54 (d, J=6.0, 1H), 8.30 (d, J=10.0, 1H), 8.22 (s, 1H), 8.09 (d, J=10.5, 1H), 7.82-7.86 (m, 2H), 7.73 (d, J=8.5, 1H), 7.38-7.46 (m, 2H), 5.75-5.81 (dd, J=9.0, 1H), 1.94 (d, J=9.5, 3H); MS (ESI) m/z 369.5 [M+1]$^+$.

5.1.43 Example 43

SYNTHESIS OF 1-((1s,4s)-4-(HYDROXYM-ETHYL)CYCLOHEXYL)-6-(QUINOLIN-5-YL)-1H-IMIDAZO[4,5-B]PYRAZIN-2(3H)-ONE

A. ((1s,4s)-4-Aminocyclohexyl)methanol. ((1s,4s)-4-(Dibenzylamino) cyclohexyl)methanol (2 g, 6.5 mmol) was added with methanol (50 mL) and 10% Pd/C (100 mg). The reaction mixture was shaken in a Parr hydrogenator with hydrogen gas (40 psi) for 16 hours. The reaction was filtered through celite and then concentrated to an oil. $^1$H NMR (300 MHz, DMSO-d$_6$) δ 4.49 (s, 1H), 3.25 (s, 2H), 2.81 (s, 1H), 1.38 (m, 8H); MS (ESI) m/z 130.3 [M+1]$^+$.

B. 1-((1s,4s)-4-(Hydroxymethyl)cyclohexyl)-6-(quinolin-5-yl)-1H-imidazo[4,5-b]pyrazin-2(3H)-one. A solution of N-bis-boc-3-bromo-5-(quinoline-5-yl)-pyrazin-2-ylamine (See Example 22.E) (150 mg, 0.29 mmol) and ((1s,4s)-4-aminocyclohexyl)methanol (250 mg, 2 mmol) in ethanol (4 mL) was reacted and purified according to General Procedure E2 to give 40 mg (36% yield) of white solid. $^1$H NMR (400 MHz, DMSO-d$_6$) δ 12.14 (s, 1H), 8.96 (dd, J=4.2, 1.7, 1H), 8.69 (d, J=8.0, 1H), 8.22 (s, 1H), 8.21 (d, J=8.4, 1H), 7.84-7.88 (m, 1H), 7.78-7.80 (m, 1H), 7.58 (dd, J=8.8, 4.1, 1H), 8.06 (t, J=5.6, 1H), 4.24 (dt, J=8.0, 4.4, 1H), 3.50-3.41 (m, 2H), 3.16 (d, J=5.2, 1H), 2.31-2.48 (m, 2H), 1.79-1.85 (m, 2H), 1.71 (br s, 1H), 1.45-1.62 (m, 4H); MS (ESI) m/z 376.4 [M+1]$^+$.

5.1.44 Example 44

SYNTHESIS OF 6-(3-(METHYLSULFONYL) PHENYL)-1-(1-PHENYLETHYL)-1H-IMIDAZO [4,5-B]PYRAZIN-2(3H)-ONE

A. 6-(3-(Methylsulfonyl)phenyl)-1-(1-phenylethyl)-1H-imidazo[4,5-b]pyrazin-2(3H)-one. A solution of 6-bromo-1-(1-phenylethyl)-1H-imidazo[4,5-b]pyrazin-2(3H)-one (See Example 31.B) (0.13 g, 0.40 mmol), (3-methylsulfonyl-phenyl)boronic acid (0.094 g, 0.47 mmol), dichloro[1,1'-bis (diphenyl phosphino)ferrocene]palladium (II) dichloromethane adduct (0.032 g, 0.039 mmol), and potassium phosphate (0.333 g, 1.57 mmol), dissolved in water (0.6 mL) in DMF (4 mL) was reacted according to General Procedure C and purified via preparative HPLC (10-100% acetonitrile/water, 60 mL/min.) to afford the title compound (0.038 g, 0.1 mmol, 24% yield). $^1$H NMR (400 MHz, DMSO-d$_6$) δ 12.23 (s, 1H), 8.62 (s, 1H), 8.52 (s, 1H), 8.37 (d, 1H), 7.97 (d, 1H), 7.79 (t, 1H), 7.57 (d, 2H), 7.38 (2, t), 7.29 (m, 1H), 5.75 (m, 1H), 3.29 (d, 3H), 2.00 (d, 3H); MS (ESI) m/z 395.4 [M+1]$^+$.

5.1.45 Example 45

SYNTHESIS OF 3-(1-PHENYL-ETHYL)-5-QUINOLIN-5-YL-3H-OXAZOLO[4,5-B] PYRAZIN-2-ONE

A. 5-(Quinolin-5-yl)pyrazin-2-amine. Quinolin-5-ylboronic acid (2.0 g, 11.5 mmol), 5-bromopyrazin-2-amine (2.0 g, 11.5 mmol)), dichloro[1,1'-bis(diphenylphosphino)ferrocene]palladium(II) dichloromethane adduct (252 mg, 0.34 mmol), 1M sodium carbonate (35 mL, 35 mmol), and dioxane (120 mL) were heated together to 100° C. for 2 hours under nitrogen. The reaction was concentrated to a paste, and then triturated with water. The residue was filtered and rinsed with water to give a dark tan solid, (2.2 g, 90% yield). $^1$H NMR (400 MHz, DMSO-d$_6$) δ 8.93 (dd, J=4.1, 1.8, 1H), 8.60 (d, J=7.8, 1H), 8.24 (d, J=1.6, 1H), 8.05 (m, 2H), 7.81 (m, 1H), 7.69 (d, J=5.9, 1H), 7.53 (dd, J=8.6, 4.3, 1H), 6.69 (s, 2H); MS (ESI) m/z 223.3 [M+1]$^+$.

B. 5-Quinolin-5-yl-1H-pyrazin-2-one. 5-(Quinolin-5-yl) pyrazin-2-amine (2.2 g, 10 mmol) and sodium nitrite (1.4 g, 20 mmol) were added together and cooled with an ice-bath. Concentrated sulfuric acid (6 mL) was added to the mixture. The reaction was slowly heated to 50° C. in a water bath for 30 minutes. The reaction mixture was poured into crushed ice (50 g) and the pH adjusted to 7 with 1M NaOH. The resulting solid was filtered, rinsed with water, and then dried to give a tan colored solid, (1.4 g, 65% yield). $^1$H NMR (400 MHz, DMSO-d$_6$) δ 8.93 (dd, J=4.3, 1.6, 1H), 8.53 (d, J=8.6, 1H), 8.19 (s, 1H), 8.06 (d, J=8.6, 1H), 7.81 (m, 2H), 7.69 (d, J=6.2, 1H), 7.54 (dd, J=8.6, 3.9, 1H); MS (ESI) m/z 224.4 [M+1]$^+$.

C. 3-Bromo-5-quinolin-5-yl-1H-pyrazin-2-one. 5-Quinolin-5-yl-1H-pyrazin-2-one (600 mg, 2.6 mmol), N-bromosuccinimide (480 mg, 2.6 mmol), and DMF (7 mL) was stirred at room temperature in the dark for 3 hours. The reaction was concentrated under reduced pressure and then triturated with water. The mixture was filtered, rinsed with water, and then dried to give a tan color solid, (380 mg, 47% yield). $^1$H NMR (400 MHz, DMSO-d$_6$) δ 8.88 (dd, J=4.1, 1.8, 1H), 8.69 (d, J=8.6, 1H), 7.92 (m, 2H), 7.74 (dd, J=8.4, 7.2, 1H), 7.58 (dd, J=7.0, 1.2, 1H), 7.52 (dd, J=8.6, 4.3, 1H); MS (ESI) m/z 304.0 [M+1]$^+$.

D. 3-(1-Phenyl-ethylamino)-5-quinolin-5-yl-1H-pyrazin-2-one. 3-Bromo-5-quinolin-5-yl-1H-pyrazin-2-one (0.82 g, 2.7 mmol), 1-phenylethanamine (394 mg, 3.3 mmol), and diisopropylethylamine (2 mL) were heated together to 130° C. for 16 hours. The reaction was triturated with water and EtOAc to give a solid. The mixture was filtered and dried to give a dark brown solid, (0.74 g, 80% yield). $^1$H NMR (400 MHz, DMSO-d$_6$) δ 11.94 (s, 1H), 8.83 (s, 1H), 8.29 (d, J=9.0, 1H), 7.95 (d, J=8.6, 1H), 7.70 (t, J=7.6, 1H), 7.60 (d, J=7.4, 1H), 7.55 (d, J=7.0, 1H), 7.36 (d, J=3.9, 3H), 7.28 (dd, J=7.8, 3.5, 1H), 7.18 (dd, J=8.2, 3.9, 1H), 6.86 (s, 1H), 5.03 (m, 1H), 1.50 (d, J=6.6, 3H); MS (ESI) m/z 343.1 [M+1]$^+$.

E. 3-(1-Phenyl-ethyl)-5-quinolin-5-yl-3H-oxazolo[4,5-b] pyrazin-2-one. 3-(1-Phenyl-ethylamino)-5-quinolin-5-yl-1H-pyrazin-2-one (50 mg, 0.15 mmol), 1,1'-carbonyldiimidazole (470 mg, 1.5 mmol), and dioxane (5 mL) were heated together in a pressure tube to 150° C. for 20 hours. The reaction was filtered through celite, rinsed with EtOAc, and then concentrated. The residue was purified via Biotage silica gel chromatography (0-100% ethyl acetate in hexanes). The product factions were concentrated and then triturated with ether to give a white solid, (28 mg, 52% yield). $^1$H NMR (400 MHz, CD$_3$OD) δ 9.73 (dd, J=4.1, 1.8, 1H), 9.11 (s, 1H), 9.09 (d, J=8.2, 1H), 8.93 (d, J=8.6, 1H), 8.66 (m, 1H), 8.58 (dd, J=7.2, 1.4, 1H), 8.31 (m, 2H), 8.26 (dd, J=8.6, 4.3, 1H), 8.17 (m, 2H), 6.43 (q, J=7.0, 1H), 2.71 (d, J=7.0, 3H); MS (ESI) m/z 369.4 [M+1]$^+$.

5.1.46 Example 46

SYNTHESIS OF 6-(4-HYDROXYPHENYL)-1-ISOPROPYL-1H-IMIDAZO[4,5-B]PYRAZIN-2(3H)-ONE

A. (4-Bromophenoxy)triisopropylsilane. 4-Bromophenol (5.5 g, 32 mmol), imidazole (5.4 g, 80 mmol), and dichloromethane (200 mL) were stirred under nitrogen. Triisopropylsilyl chloride (8.1 mL, 38 mmol) was added and the reaction was stirred at room temperature for 3 h. The reaction was extracted with water, 1M sodium hydroxide, and brine. The organic layer was dried over magnesium sulfate, filtered and concentrated to give a colorless oil (10 g, 100% yield). $^1$H NMR (400 MHz, DMSO-d$_6$) δ 7.42 (d, J=9.0, 2H), 6.83 (d, J=9.0, 2H), 1.23 (dq, J=14.7, 7.3, 3H), 1.05 (d, J=7.4, 18H).

B. Triisopropyl(4-(4,4,5,5-tetramethyl-1,3,2-dioxaborolan-2-yl)phenoxy)silane. (4-Bromophenoxy)triisopropylsilane (10 g, 32 mmol), bis(pinacolato)diboron (8.1 g, 32 mmol), potassium acetate (9.4 g, 96 mmol), and dioxane (200 mL) were added together and degassed under vacuum. Dichloro[1,1'-bis(diphenylphosphino)ferrocene]palladium (II) dichloromethane adduct (0.7 g, 0.96 mmol) was added and the reaction was heated to 100° C. under nitrogen for 20 h. Upon cooling to room temperature, the reaction was filtered through celite and rinsed with ethyl acetate. The filtrate was concentrated and the resulting material was purified using Biotage silica gel chromatography (0-20% ethyl acetate in hexanes) to give a colorless oil (10.1 g, 84% yield). $^1$H NMR (400 MHz, DMSO-d$_6$) δ 7.58 (d, J=8.6, 2H), 6.87 (d, J=8.6, 2H), 1.27 (s, 15H), 1.05 (d, J=7.4, 18H).

C. 5-(4-(Triisopropylsilyloxy)phenyl)pyrazin-2-amine. Triisopropyl(4-(4,4,5,5-tetramethyl-1,3,2-dioxaborolan-2-yl)phenoxy)silane (1.1 g, 2.9 mmol), 5-bromopyrazin-2-amine (507 mg, 2.9 mmol), dichloro[1,1'-bis(diphenylphosphino)ferrocene]palladium(II) dichloromethane adduct (64 mg, 0.087 mmol), 1M sodium carbonate (8.7 mL, 8.7 mmol), and dioxane (10 mL) were heated in a Biotage Emrys Optimizer microwave reactor at 120° C. for 10 min. The reaction was extracted with water and ethyl acetate. The organic layer was dried over magnesium sulfate, filtered and concentrated. The resulting residue was purified using Biotage silica gel chromatography (0-100% ethyl acetate in hexanes) to give a tan solid (0.8 g, 80% yield). $^1$H NMR (400 MHz, DMSO-d$_6$) δ 8.42 (s, 1H), 7.92 (s, 1H), 7.80 (d, J=8.6, 2H), 6.90 (d, J=8.6, 2H), 6.45 (s, 2H), 1.26 (q, J=7.4, 7.2, 3H), 1.08 (d, J=7.4, 18H); MS (ESI) m/z 344.4 [M+1]$^+$.

D. 3-Bromo-5-(4-(triisopropylsilyloxy)phenyl)pyrazin-2-amine. 5-(4-(Triisopropylsilyloxy)phenyl)pyrazin-2-amine (1.6 g, 4.7 mmol), N-bromosuccinimide (830 mg, 4.7 mmol), and dimethylformamide (10 mL) were stirred together at room temperature for 1 h. The reaction was extracted with water and ethyl acetate. The organic layer was dried over magnesium sulfate, filtered and concentrated. The residue was purified using Biotage silica gel chromatography (0-100% ethyl acetate in hexanes) to give a dark solid (1.1 g, 56% yield). $^1$H NMR (400 MHz, DMSO-d$_6$) δ 8.51 (s, 1H), 7.78 (d, J=8.6, 2H), 6.93 (d, J=9.0, 2H), 6.75 (s, 2H), 1.21-1.31 (m, 3H), 1.08 (d, J=7.0, 18H); MS (ESI) m/z 422.4 [M+1]$^+$.

E. 3-Bromo-N,N-bis-boc-5-(4-(triisopropylsilyloxy)phenyl)pyrazin-2-amine. 3-Bromo-5-(4-(triisopropylsilyloxy)phenyl)pyrazin-2-amine (1.1 g, 2.6 mmol), di-t-butyl dicarbonate (2.8 g, 13 mmol), 4-dimethylaminopyridine (32 mg, 0.26 mmol), and acetonitrile (30 mL) were heated together to 50° C. for 2 h. The reaction was concentrated and then purified using Biotage silica gel chromatography (0-20% ethyl acetate in hexanes) to give a dark oil (1.6 g, 99% yield). $^1$H NMR (400 MHz, DMSO-d$_6$) δ 9.29 (s, 1H), 8.22 (d, J=8.6, 2H), 7.42 (d, J=8.6, 2H), 1.38 (s, 18H), 1.20-1.30 (m, 3H), 1.04 (d, J=7.4, 18H).

F. 4-(6-Bromo-5-(N,N-bis-boc-amino)pyrazin-2-yl)phenol. 3-Bromo-N,N-bis-boc-5-(4-(triisopropylsilyloxy)phenyl)pyrazin-2-amine (1.6 g, 2.6 mmol) was dissolved in tetrahydrofuran (20 mL) and tetrabutylammonium fluoride (0.68 g, 2.6 mmol) was added. Upon consumption of starting material (monitored by TLC), the reaction was extracted with water and ethyl acetate. The organic layer was dried over magnesium sulfate, filtered and concentrated. The resulting residue was purified using Biotage silica gel chromatography (0-50% ethyl acetate in hexanes) to give a white solid (1.1 g, 92% yield). $^1$H NMR (400 MHz, DMSO-d$_6$) δ 9.13 (s, 1H), 8.02 (d, J=8.6, 2H), 6.93 (d, J=8.6, 2H), 1.38 (s, 18H).

G. 6-(4-Hydroxyphenyl)-1-isopropyl-1H-imidazo[4,5-b]pyrazin-2(3H)-one. 4-(6-Bromo-5-(N,N-bis-boc-amino)pyrazin-2-yl)phenol (150 mg, 0.32 mmol), isopropylamine (0.272 mL, 3.2 mmol), and ethanol (2 mL) were heated in a Biotage Emrys Optimizer microwave reactor at 150° C. for 3 h. The reaction was concentrated and then triturated with water and ether. The solid was filtered and then purified by reverse-phase semi-preparatory HPLC (5-70% acetonitrile+0.1% TFA in H$_2$O+0.1% TFA, over 30 min). Product fractions were concentrated and then triturated with ether to give a white solid (14 mg, 16% yield). $^1$H NMR (400 MHz, DMSO-d$_6$) δ 11.88 (s, 1H), 9.69 (s, 1H), 8.35 (s, 1H), 7.83-7.88 (m, 2H), 6.85-6.89 (m, 2H), 4.60-4.69 (m, 1H), 1.55 (d, J=6.6, 6H); MS (ESI) m/z 271.3 [M+1]$^+$; mp 323-324° C.

5.1.47 Example 47

SYNTHESIS OF 1-(CYCLOPENTYLMETHYL)-6-(4-HYDROXYPHENYL)-1H-IMIDAZO[4,5-B]PYRAZIN-2(3H)-ONE

A. 1-(Cyclopentylmethyl)-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (150 mg, 0.32 mmol), cyclopropylmethylamine hydrochloride (438 mg, 3.2 mmol), triethylamine (0.5 mL), and ethanol (2 mL) were heated in a Biotage Emrys Optimizer microwave reactor at 150° C. for 3 h. The reaction was concentrated and then triturated with water and ether. The solid was filtered and then purified by reverse-phase semi-preparatory HPLC (5-70% acetonitrile+0.1% TFA in H$_2$O+0.1% TFA, over 30 min). Product fractions were concentrated and then triturated with ether to give a white solid (25 mg, 25% yield). $^1$H NMR (400 MHz, DMSO-d$_6$) δ 11.91 (s, 1H), 9.67 (s, 1H), 8.35 (s, 1H), 7.84 (s, 2H), 6.86 (s, 2H), 3.79 (s, 2H), 1.65 (s, 5H), 1.52 (s, 2H), 1.34 (s, 2H); MS (ESI) m/z 311.3 [M+1]$^+$; mp 296-297° C.

5.1.48 Example 48

SYNTHESIS OF 6-(4-HYDROXYPHENYL)-1-ISOBUTYL-1H-IMIDAZO[4,5-B]PYRAZIN-2(3H)-ONE

A. 6-(4-Hydroxyphenyl)-1-isobutyl-1H-imidazo[4,5-b]pyrazin-2(3H)-one. 4-(6-Bromo-5-(N,N-bis-boc-amino)pyrazin-2-yl)phenol (see Example 46.F) (150 mg, 0.32 mmol), 2-methylpropan-1-amine (0.317 mL, 3.2 mmol), and ethanol (2 mL) were heated in a Biotage Emrys Optimizer microwave reactor at 150° C. for 3 h. The reaction was concentrated and then triturated with water and ether. The solid was filtered and then purified by reverse-phase semi-preparatory HPLC (5-70% acetonitrile+0.1% TFA in $H_2O$+0.1% TFA, over 30 min). Product fractions were concentrated and then triturated with ether to give a white solid (21 mg, 23% yield). $^1$H NMR (400 MHz, DMSO-$d_6$) δ 11.92 (s, 1H), 9.69 (s, 1H), 8.36 (s, 1H), 7.83-7.86 (m, 2H), 6.84-6.88 (m, 2H), 3.68 (d, J=7.4, 2H), 2.24 (dt, J=13.7, 6.8, 1H), 0.92 (d, J=6.6, 6H); MS (ESI) m/z 285.5 [M+1]$^+$; mp 290-291° C.

5.1.49 Example 49

SYNTHESIS OF 6-(4-HYDROXYPHENYL)-1-((TETRAHYDRO-2H-PYRAN-3-YL)METHYL)-1H-IMIDAZO[4,5-B]PYRAZIN-2(3H)-ONE

A. 6-(4-Hydroxyphenyl)-1-((tetrahydro-2H-pyran-3-yl)methyl)-1H-imidazo[4,5-b]pyrazin-2(3H)-one. 4-(6-Bromo-5-(N,N-bis-boc-amino)pyrazin-2-yl)phenol (see Example 46.F) (150 mg, 0.32 mmol), (tetrahydro-2H-pyran-3-yl)methanamine (368 mg, 3.2 mmol), and ethanol (2 mL) were heated in a Biotage Emrys Optimizer microwave reactor at 150° C. for 3 h. The reaction was concentrated and then triturated with water and ether. The solid was filtered and then purified by reverse-phase semi-preparatory HPLC (5-70% acetonitrile+0.1% TFA in $H_2O$+0.1% TFA, over 30 min). Product fractions were concentrated and then triturated with ether to give a white solid (25 mg, 24% yield). $^1$H NMR (400 MHz, DMSO-$d_6$) δ 11.94 (s, 1H), 9.70 (s, 1H), 8.36 (s, 1H), 7.85 (d, J=8.6, 2H), 6.87 (d, J=8.6, 2H), 3.73-3.82 (m, 3H), 3.69 (ddd, J=11.1, 3.7, 3.5, 1H), 3.35-3.40 (m, 1H), 3.25 (dd, J=11.3, 9.0, 1H), 2.10-2.18 (m, 1H), 1.74 (s, 1H), 1.63 (d, J=3.9, 1H), 1.39-1.49 (m, 1H), 1.26-1.35 (m, 1H); MS (ESI) m/z 327.5 [M+1]$^+$; mp 271-272° C.

5.1.50 Example 50

SYNTHESIS OF 1-(CYCLOHEXYLMETHYL)-6-(4-HYDROXYPHENYL)-1H-IMIDAZO[4,5-B]PYRAZIN-2(3H)-ONE

A. 1-(Cyclohexylmethyl)-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (226 mg, 0.48 mmol), cyclohexylmethanamine (629 mg, 4.8 mmol), and ethanol (2 mL) were heated in a Biotage Emrys Optimizer microwave reactor at 150° C. for 3 h. The reaction was concentrated and then triturated with water and ether. The solid was filtered and then purified by reverse-phase semi-preparatory HPLC (5-70% acetonitrile+0.1% TFA in $H_2O$+0.1% TFA, over 30 min). Product fractions were concentrated and then triturated with ether to give a white solid (45 mg, 29% yield). $^1$H NMR (400 MHz, DMSO-$d_6$) δ 11.92 (s, 1H), 9.69 (s, 1H), 8.35 (s, 1H), 7.84 (d, J=8.6, 2H), 6.87 (d, J=8.6, 2H), 3.71 (d, J=7.4, 2H), 1.89 (s, 1H), 1.58-1.69 (m, 6H), 1.17 (t, J=8.4, 3H), 0.98-1.08 (m, 2H); MS (ESI) m/z 325.4 [M+1]$^+$; mp 302-303° C.

5.1.51 Example 51

5-(3-HYDROXYPHENYL)-3-(2-METHOXYPHENYL)-1H-IMIDAZO[4,5-B]PYRIDIN-2(3H)-ONE

A. 6-Chloro-N-(2-methoxyphenyl)-3-nitropyridin-2-amine. 2,6-Dichloro-3-nitropyridine (3.0 g, 15.54 mmol) was dissolved in tetrahydrofuran (50 mL) and cooled to −78° C. A solution of o-anisidine (1.91 g, 15.54 mmol) and diisopropylamine (2.10 g, 16.31 mmol) in tetrahydrofuran (5 mL) was added dropwise. The mixture was stirred at ambient temperature for 16 h. The solution was condensed under reduced pressure and partitioned between water and ethyl acetate (3×), organics were pooled and dried over magnesium sulfate, filtered and solvent removed under reduced pressure to give the crude product. The solid was triturated with ethyl acetate/hexanes and the resultant precipitate filtered to afford the title compound (3.53 g, 81%). MS (ESI) m/z 280.1 [M+1]$^+$.

B. 3-(6-(2-Methoxyphenylamino)-5-nitropyridin-2-yl)phenol. 6-Chloro-N-(2-methoxy-phenyl)-3-nitropyridin-2-amine (2.03 g, 7.27 mmol), 3-hydroxyphenylboronic acid (1.50 g, 10.90 mmol), palladium (II) acetate (0.489 g, 0.727 mmol), 1,1'-(bis(di-tertbutyl)phosphine)ferrocene (0.344 g, 0.727 mmol) and potassium phosphate (4.62 g, 21.81 mmol) were combined in dioxane and heated to 98° C. under nitrogen conditions for 16 h. Upon consumption of starting material (monitored by TLC), the reaction mixture was filtered through celite. The filtrate was condensed under reduced pressure to afford the crude product. The crude material was purified using Biotage silica gel chromatography (10-40% ethyl acetate in hexanes) to afford the title compound (1.48 g, 59%). MS (ESI) m/z 338.4 [M+1]$^+$.

C. 3-(5-Amino-6-(2-methoxyphenylamino)pyridin-2-yl)phenol. 3-(6-(2-Methoxyphenyl-amino)-5-nitropyridin-2-yl)phenol (1.48 g, 4.39 mmol) was dissolved in glacial acetic acid (120 mL). Iron powder (0.489 g, 8.78 mmol) was then added and the solution heated to 80° C. The reaction was monitored via thin layer chromatography for starting material consumption. After 2 h, the solution was cooled and filtered through celite and condensed under reduced pressure. The resultant oil was partitioned between sodium bicarbonate solution and ethyl acetate (3×). The organics were combined, dried over magnesium sulfate, filtered and solvent removed under reduced pressure to afford the title compound (1.15 g, 85%). MS (ESI) m/z 308.4 [M+1]$^+$.

D. 5-(3-Hydroxyphenyl)-3-(2-methoxyphenyl)-1H-imidazo[4,5-b]pyridin-2(3H)-one. 3-(5-Amino-6-(2-methoxyphenylamino)pyridin-2-yl)phenol (1.08 g, 3.51 mmol) and urea (0.528 g, 8.79 mmol) were reacted according to General Procedure C. The crude product was purified via reverse-phase preparative HPLC (5-65% acetonitrile+0.1% TFA in $H_2O$+0.1% TFA, over 39 min) to afford the title compound (0.056 g, 5%). $^1$H NMR (400 MHz, DMSO-$d_6$) δ 11.28 (s, 1H), 9.43 (s, 1H), 7.51 (t, J=8.1, 2H), 7.42 (t, J=8.1, 2H), 7.23 (m, 3H), 7.12 (m, 2H), 6.70 (d, J=7.80, 1H), 3.73 (s, 3H); MS (ESI) m/z 334.0 [M+1]$^+$; mp 240-242° C.

5.1.52 Example 52

SYNTHESIS OF 4-(3-(3-METHOXYBENZYL)-2-OXO-2,3-DIHYDROOXAZOLO[5,4-B]PYRAZIN-5-YL)-N-METHYLBENZAMIDE

A. Methyl 4-(5-aminopyrazin-2-yl)benzoate. 4-(Methoxycarbonyl)phenylboronic acid (1.8 g, 9.7 mmol), 5-bromopyrazin-2-amine (1.8 g, 9.7 mmol), dichloro[1,1'-bis(diphenylphosphino) ferrocene]palladium(II) dichloromethane adduct (213 mg, 0.29 mmol), 1M sodium carbonate (29 mL, 29 mmol), and dioxane (100 mL) were heated together to 100° C. for 16 h under nitrogen. The reaction was filtered through celite and then added with water and ethyl acetate to give a solid. The solid was filtered and dried to give a black solid (1.1 g, 50% yield). $^1$H NMR (400 MHz, DMSO-$d_6$) δ 8.63 (s, 1H), 8.07 (s, 2H), 7.99 (s, 3H), 6.78 (s, 2H), 3.86 (s, 3H); MS (ESI) m/z 230.4 [M+1]$^+$.

B. 4-(5-Hydroxypyrazin-2-yl)benzoic acid. Methyl 4-(5-aminopyrazin-2-yl)benzoate (1.1 g, 4.8 mmol) and sodium nitrite (6.6 g, 9.6 mmol) were combined and cooled with an ice-bath. Concentrated sulfuric acid (6 mL) was added to the mixture. The reaction was slowly heated to 50° C. in a water bath for 30 min. The reaction was mixture was poured into crushed ice (50 g) and the aqueous mixture was adjusted to pH 7 with 1M sodium hydroxide. The resulting solid was filtered, rinsed with water, and then dried to give a the product as a tan solid (0.4 g, 36% yield). $^1$H NMR (400 MHz, DMSO-$d_6$) δ 8.20 (s, 1H), 8.14 (s, 1H), 8.05 (d, J=8.2, 2H), 7.87 (d, J=7.8, 2H); MS (ESI) m/z 217.1 [M+1]$^+$.

C. 4-(5-Hydroxypyrazin-2-yl)-N-methylbenzamide. 4-(5-Hydroxypyrazin-2-yl)benzoic acid (0.4 g, 1.8 mmol), methylamine hydrochloride (149 mg, 2.2 mmol), O-(benzotriazol-1-yl)-N,N,N'N'-tetramethyluronium hexafluorophosphate (824 mg, 2.2 mmol), triethylamine (0.8 mL, 1 mmol), and dimethylformamide (20 ml) were stirred together at room temperature for 16 h. The reaction was purified by reverse-phase semi-preparatory HPLC (5-70% acetonitrile+0.1% TFA in H$_2$O+0.1% TFA, over 30 min). Product fractions were concentrated to give a tan solid (250 mg, 59% yield). $^1$H NMR (400 MHz, DMSO-$d_6$) δ 8.46 (q, J=4.4, 1H), 8.17 (s, 1H), 8.13 (m, 1H), 7.93-7.99 (m, 2H), 7.86-7.91 (m, 2H), 2.79 (d, J=4.7, 3H); MS (ESI) m/z 230.4 [M+1]$^+$.

D. 4-(6-Bromo-5-hydroxypyrazin-2-yl)-N-methylbenzamide. A solution of 4-(5-hydroxypyrazin-2-yl)-N-methylbenzamide (250 mg, 1.1 mmol) and N-bromosuccinimide (233 mg, 1.3 mmol) in DMF (4 mL) was stirred at room temperature in the dark for 30 min. The reaction was purified by reverse-phase semi-preparatory HPLC (5-70% acetonitrile+0.1% TFA in H$_2$O+0.1% TFA, over 30 min). Product fractions were concentrated to give a tan solid (195 mg, 58% yield). $^1$H NMR (400 MHz, DMSO-$d_6$) δ 8.49 (s, 1H), 8.23 (s, 1H), 7.90 (s, 4H), 2.79 (d, J=3.9, 3H); MS (ESI) m/z 308.1 [M+1]$^+$.

E. 4-(5-Hydroxy-6-(3-methoxybenzylamino)pyrazin-2-yl)-N-methylbenzamide. 4-(6-Bromo-5-hydroxypyrazin-2-yl)-N-methylbenzamide (195 mg, 0.63 mmol), 3-methoxybenzylamine (130 mg, 0.95 mmol), diisopropylethylamine (2 mL), and dimethylsulfoxide (1 mL) were heated together to 130° C. for 16 h. The reaction was triturated with water and ethyl acetate to give a solid. The mixture was filtered and dried to give a dark brown solid (101 mg, 44% yield). $^1$H NMR (400 MHz, DMSO-$d_6$) δ 8.40 (s, 1H), 7.88 (d, J=7.8, 3H), 7.78-7.84 (m, 2H), 7.31 (s, 1H), 7.22 (t, J=7.6, 1H), 6.97-7.03 (m, 2H), 6.78 (d, J=7.8, 1H), 4.56 (s, 2H), 3.71 (s, 3H), 2.77-2.81 (m, 3H); MS (ESI) m/z 365.3 [M+1]$^+$.

F. 4-(3-(3-Methoxybenzyl)-2-oxo-2,3-dihydrooxazolo[5,4-b]pyrazin-5-yl)-N-methyl benzamide. 4-(5-Hydroxy-6-(3-methoxybenzylamino)pyrazin-2-yl)-N-methylbenzamide (100 mg, 0.27 mmol), 1,1'-carbonyldiimidazole (445 mg, 2.7 mmol), and dioxane (2 mL) were heated together in a sealed tube to 150° C. for 16 h. The reaction was purified by reverse-phase semi-preparatory HPLC (5-70% acetonitrile+0.1% TFA in H$_2$O+0.1% TFA, over 30 min). Product fractions were concentrated to give a white solid (27 mg, 25% yield). $^1$H NMR (400 MHz, DMSO-$d_6$) δ 8.71 (s, 1H), 8.51-8.59 (m, 1H), 8.15 (d, J=8.5, 2H), 7.95 (d, J=8.5, 2H), 7.26-7.33 (m, 1H), 7.04-7.12 (m, 2H), 6.89 (dd, J=7.8, 2.9, 1H), 5.07 (s, 2H), 3.74 (s, 3H), 2.81 (d, J=4.4, 3H); MS (ESI) m/z 391.0 [M+1]$^+$; mp 168-169° C.

5.1.53 Example 53

SYNTHESIS OF 1-CYCLOPENTYL-6-(4-HYDROXYPHENYL)-1H-IMIDAZO[4,5-B]PYRAZIN-2(3H)-ONE

A. 1-Cyclopentyl-6-(4-hydroxyphenyl)-1H-imidazo[4,5-b]pyrazin-2(3H)-one. 4-(6-Bromo-5-(N,N-bis-Boc-amino)pyrazin-2-yl)phenol (see Example 46.F) (200 mg, 0.43 mmol), cyclopentylamine (365 mg, 4.3 mmol), and ethanol (2 mL) were heated in a Biotage Emrys Optimizer microwave reactor at 150° C. for 4 h. The reaction was concentrated and then purified using Biotage silica gel chromatography (0-10% methanol in ethyl acetate) to give a white solid (46 mg, 36% yield). $^1$H NMR (300 MHz, DMSO-$d_6$) δ 9.70 (s, 1H), 8.35 (s, 1H), 7.84 (d, J=8.8, 2H), 6.86 (d, J=8.5, 2H), 4.75-4.86 (m, 1H), 2.14-2.28 (m, 2H), 1.90-2.04 (m, 4H), 1.60-1.73 (m, 2H); MS (ESI) m/z 297.3 [M+1]$^+$; mp 299-301° C.

5.1.54 Example 54

SYNTHESIS OF 1-CYCLOHEXYL-6-(4-HYDROXYPHENYL)-1H-IMIDAZO[4,5-B]PYRAZIN-2(3H)-ONE

A. 1-Cyclohexyl-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (200 mg, 0.43 mmol), cyclohexylamine (425 mg, 4.3 mmol), and ethanol (2 mL) were heated in a Biotage Emrys Optimizer microwave reactor at 150° C. for 4 h. The reaction was concentrated and then purified using Biotage silica gel chromatography (0-10% methanol in ethyl acetate) to give a white solid, (50 mg, 37% yield). $^1$H NMR (300 MHz, DMSO-$d_6$) δ 11.90 (s, 1H), 9.70 (s, 1H), 8.35 (s, 1H), 7.85 (d, J=8.5, 2H), 6.87 (d, J=8.5, 2H), 4.24 (t, J=11.9, 1H), 2.25-2.39 (m, 2H), 1.76-1.90 (m, 6H), 1.30-1.43 (m, 2H); MS (ESI) m/z 311.5 [M+1]$^+$; mp 318-320° C.

5.1.55 Example 55

SYNTHESIS OF 4-(3-(CYCLOHEXYLMETHYL)-2-OXO-2,3-DIHYDRO-1H-IMIDAZO[4,5-B]PYRAZIN-5-YL)BENZAMIDE

A. 6-Bromo-N-(cyclohexylmethyl)pyrazine-2,3-diamine. 3,5-Dibromopyrazin-2-amine (5.0 g, 19.92 mmol) and cyclohexylmethanamine (3.25 mL, 24.90 mmol) were dissolved in n-butanol (120 mL). Diisopropylethylamine (8.34 mL, 47.88 mmol) was added to the mixture and the stirred reaction was heated at 130° C. for 2 d. Upon complete consumption of starting material (monitored by LCMS), reaction was allowed to cool to room temperature and the volatiles were removed under reduced pressure. The semi-solid oil was dissolved in ethyl acetate and triturated from hexanes while sonicating. The precipitate was filtered to afford the title compound (4.85 g, 86%). MS (ESI) m/z 285.0 [M]$^+$, 287.2 [M+2]$^+$ B. 6-Bromo-1-(cyclohexylmethyl)-1H-imidazo[4,5-b]pyrazin-2(3H)-one. 6-Bromo-N$^2$-(cyclohexylmethyl)pyrazine-2,3-diamine. (4.85 g, 17.01 mmol) was dissolved in THF (50 mL), 1,1'-carbonyldiimidazole (3.45 g, 21.26 mmol) was added, and the reaction solution was divided into 4 different vials. Each fraction was heated in a Biotage Emrys Optimizer microwave reactor at 120° C. for 30 min. The reacted fractions were combined and condensed under reduced pressure. The crude material was dissolved in minimal DMF and precipitated with deionized water while sonicating. The filtered product was dried in a vacuum oven at 60° C. over night to afford the title compound (4.72 g, 89%). MS (ESI) m/z 311.3 [M]$^+$, 313.5 [M+2]$^+$ C. 4-(3-(Cyclohexylmethyl)-2-oxo-2,3-dihydro-1H-imidazo[4,5-b]pyrazin-5-yl)benzamide. 6-Bromo-1-(cyclohexylmethyl)-1H-imidazo[4,5-b]pyrazin-2(3H)-one (200 mg, 0.64 mmol), (4-aminocarbonylphenyl)boronic acid (128 mg, 0.77 mmol), dichloro[1,1'-bis(diphenylphosphino)ferrocene]palladium (II) dichloromethane (53 mg, 0.06 mmol) and potassium phosphate (550 mg, 2.58 mmol) in DMF (15 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The desired product was collected by vacuum filtration, washed with water and dried under high vacuum to provide the title compound (35 mg, 15% yield) as a white fluffy powder. $^1$H NMR (300 MHz, DMSO-d$_6$) δ 12.18 (s, 1H), 8.66 (s, 1H), 8.19 (d, J=8.7, 2H), 8.06 (d, J=8.7, 2H), 7.51 (s, 2H), 3.82 (d, J=8.7, 2H), 1.98 (m, 1H), 1.76 (m, 5H), 1.26 (m, 5H); MS (ESI) m/z 352.2 [M+1]$^+$; mp 293-295° C.

5.1.56 Example 56

SYNTHESIS OF METHYL 4-(3-(CYCLOHEXYLMETHYL)-2-OXO-2,3-DIHYDRO-1H-IMIDAZO[4,5-B]PYRAZIN-5-YL)BENZOATE

A. Methyl 4-(3-(cyclohexylmethyl)-2-oxo-2,3-dihydro-1H-imidazo[4,5-b]pyrazin-5-yl)benzoate. 6-Bromo-1-(cyclohexylmethyl)-1H-imidazo[4,5-b]pyrazin-2(3H)-one (See Example 55.B) (1.0 g, 3.22 mmol), (4-methoxycarbonylphenyl)boronic acid (0.77 g, 3.87 mmol), dichloro[1,1'-bis(diphenylphosphino)ferrocene]palladium (II) dichloromethane (263 mg, 0.32 mmol) and potassium phosphate (2.73 g, 12.88 mmol) in DMF (30 mL) and water (4 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The desired product was collected by vacuum filtration, washed with water and dried under high vacuum to provide the title compound (360 mg, 31% yield) as a white fluffy powder. $^1$H NMR (300 MHz, DMSO-d$_6$) δ 12.23 (s, 1H), 8.69 (s, 1H), 8.27 (d, J=8.7, 2H), 8.15 (d, J=8.7, 2H), 3.83 (d, J=6.9, 2H), 1.99 (m, 1H), 1.76 (m, 5H), 1.26 (m, 5H); MS (ESI) m/z 367.2 [M+1]$^+$; mp 253-255° C.

5.1.57 Example 57

SYNTHESIS OF 1-(CYCLOHEXYLMETHYL)-6-(PYRIDIN-4-YL)-1H-IMIDAZO[4,5-B]PYRAZIN-2(3H)-ONE

A. 1-(Cyclohexylmethyl)-6-(pyridin-4-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.250 g, 0.80 mmol), pyridine-4-boronic acid (0.118 g, 0.96 mmol), and [1,1'-bis(diphenylphosphino) ferrocene]dichloropalladium(II) complex with dichloromethane (1:1) (0.065 g, 0.08 mmol), potassium phosphate (0.678 g, 3.2 mmol), water (2 ml) and dimethylformamide (10 mL) were reacted according to General Procedure B. The solution was condensed under reduced pressure and purified using Biotage silica gel chromatography (0-10% methanol in dichloromethane). Fractions containing product were concentrated and recrystallized from methanol to give (0.057 g, 23% yield). $^1$H NMR (300 MHz, CD$_3$OD) δ 8.62 (m, 3H), 8.08 (m, 2H), 3.87 (d, J=7.5, 2H), 2.01 (m, 1H), 1.75 (m, 5H), 1.28 (m, 6H); MS (ESI) m/z 310.4 [M+1]$^+$; mp 267-269° C.

5.1.58 Example 58

SYNTHESIS OF 4-(3-(CYCLOHEXYLMETHYL)-2-OXO-2,3-DIHYDRO-1H-IMIDAZO[4,5-B]PYRAZIN-5-YL)-N-METHYLBENZAMIDE

A. 4-(3-(Cyclohexylmethyl)-2-oxo-2,3-dihydro-1H-imidazo[4,5-b]pyrazin-5-yl)-N-methylbenzamide. 6-Bromo-1-(cyclohexylmethyl)-1H-imidazo[4,5-b]pyrazin-2(3H)-one (See Example 55.B) (200 mg, 0.64 mmol), [4-(N-methylamino-carbonyl)phenyl]boronic acid (139 mg, 0.77 mmol), dichloro[1,1'-bis(diphenylphosphino) ferrocene]palladium (II) dichloromethane (53 mg, 0.06 mmol) and potassium phosphate (550 mg, 2.58 mmol) in DMF (15 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The desired product was collected by vacuum filtration, washed with water and dried under high vacuum to provide the desired product (85 mg, 36% yield). $^1$H NMR (300 MHz, DMSO-d$_6$) δ 12.18 (s, 1H), 8.65 (s, 1H), 8.58 (s, 1H), 8.19 (d, J=8.4, 2H), 8.02 (d, J=8.4, 2H), 3.83 (d, J=6.9, 2H), 2.89 (s, 3H), 2.00 (m, 1H), 1.76 (m, 5H), 1.26 (m, 5H); MS (ESI) m/z 366.3 [M+1]$^+$; mp 273-275° C.

5.1.59 Example 59

SYNTHESIS OF 1-(CYCLOHEXYLMETHYL)-6-(4-(HYDROXYMETHYL)PHENYL)-1H-IMIDAZO[4,5-B]PYRAZIN-2(3H)-ONE

A. 1-(Cyclohexylmethyl)-6-(4-(hydroxymethyl)phenyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (200 mg, 0.64 mmol), 4-(hydroxymethyl)phenyl boronic acid (118 mg, 0.77 mmol), dichloro[1,1'-bis(diphenylphosphino)ferrocene]palladium (II) dichloromethane (53 mg, 0.06 mmol) and potassium phosphate (550 mg, 2.58 mmol) in DMF (15 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The resulting solid was collected by vacuum filtration, washed with water and dried under high vacuum to provide the desired product (66 mg, 30% yield). $^1$H NMR (300 MHz, DMSO-d$_6$) δ 12.01 (s, 1H), 8.47 (s, 1H), 7.97 (d, J=8.4, 2H), 7.42 (d, J=8.4, 2H), 5.22 (t, J=5.6, 1H), 4.53 (d, J=8.4, 2H), 3.73 (J=5.6, 2H), 1.90 (m, 1H), 1.67 (m, 5H), 1.17 (m, 5H); MS (ESI) m/z 339.1 [M+1]$^+$; mp 275-277° C.

5.1.60 Example 60

SYNTHESIS OF 1-(CYCLOHEXYLMETHYL)-6-(PYRIDIN-3-YL)-1H-IMIDAZO[4,5-B]PYRAZIN-2(3H)-ONE

A. 1-(Cyclohexylmethyl)-6-(pyridin-3-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.250 g, 0.80 mmol) and pyridine-3-boronic acid (0.098 g, 0.80 mmol), dichlorobis(triphenylphosphine)palladium(II) (0.028 g, 0.004 mmol), sodium carbonate (4.5 mL, 1M in water) and acetonitrile (4.5 mL) were reacted according to General Procedure B3. The solution was condensed under reduced pressure and the product was purified by reverse-phase semi-preparatory HPLC (5-70% acetonitrile+0.1% TFA in H$_2$O+0.1% TFA, over 30 min). Fractions containing clean product were neutralized with potassium carbonate and extracted with ethyl acetate, dried over magnesium sulfate, filtered, concentrated under reduced pressure and dried under vacuum to give (0.069 g, 28% yield). $^1$H NMR (300 MHz, CD$_3$OD) δ 9.15 (d, J=2.1, 1H), 8.54 (m, 1H), 8.47 (m, 2H), 7.55 (m, 2H), 3.85 (d, J=7.2, 2H), 2.03 (m, 1H), 1.74 (m, 5H) 1.27 (m, 5H); MS (ESI) m/z 310.4 [M+1]$^+$; mp 205° C.

5.1.61 Example 61

SYNTHESIS OF 3-(3-(CYCLOHEXYLMETHYL)-2-OXO-2,3-DIHYDRO-1H-IMIDAZO[4,5-B]PYRAZIN-5-YL)BENZONITRILE

A. 3-(3-(Cyclohexylmethyl)-2-oxo-2,3-dihydro-1H-imidazo[4,5-b]pyrazin-5-yl)benzonitrile. 6-Bromo-1-(cyclohexylmethyl)-1H-imidazo[4,5-b]pyrazin-2(3H)-one (See Example 55.B) (1.0 g, 3.22 mmol), 3-cyanophenylboronic acid (0.57 g, 3.87 mmol), dichloro[1,1'-bis(diphenylphosphino)ferrocene]palladium (II) dichloromethane (263 mg, 0.32 mmol) and potassium phosphate (2.73 g, 12.88 mmol) in DMF (30 mL) and water (4 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The resulting solid was collected by vacuum filtration, washed with water and dried under high vacuum to provide the desired product (164 mg, 16% yield). $^1$H NMR (300 MHz, DMSO-d$_6$) δ 12.23 (s, 1H), 8.71 (s, 1H), 8.53 (s, 1H), 8.46 (d, J=7.8, 1H), 7.95 (d, J=7.2, 1H), 7.78 (d, J=7.2, 2H), 3.82 (d, J=8.4, 2H), 1.98 (m, 1H), 1.76 (m, 5H), 1.26 (m, 5H); MS (ESI) m/z 334.2 [M+1]$^+$; mp 228-230° C.

5.1.62 Example 62

SYNTHESIS OF 1-(CYCLOHEXYLMETHYL)-6-(1H-INDOL-5-YL)-1H-IMIDAZO[4,5-B]PYRAZIN-2(3H)-ONE

A. 1-(Cyclohexylmethyl)-6-(1H-indol-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.250 g, 0.80 mmol), indole-5-boronic acid (0.155 g, 0.96 mmol), tetrakis(triphenylphosphine)palladium(0) (0.092 g, 0.08 mmol), sodium bicarbonate (0.268 g, 3.2 mmol), water (2 ml) and ethylene glycol dimethyl ether (10 mL) were reacted according to General Procedure B2. The product precipitated out of reaction and was filtered and dried to give (0.048 g, 17% yield). $^1$H NMR (300 MHz, DMSO-d$_6$) δ 11.9 (s, 1H), 11.2 (s, 1H), 8.44 (s, 1H), 8.19 (s, 1H), 7.79 (dd, J=1.5, 8.4, 2H), 7.50 (d, J=8.4, 1H), 7.40 (m, 1H), 6.52 (s, 1H), 3.76 (d, J=6.9, 1H), 1.93 (m, 1H), 1.69 (m, 5H), 1.18 (m, 5H); MS (ESI) m/z 348.4 [M+1]$^+$; mp 343-346° C.

5.1.63 Example 63

SYNTHESIS OF 4-(3-(CYCLOHEXYLMETHYL)-2-OXO-2,3-DIHYDRO-1H-IMIDAZO[4,5-B]PYRAZIN-5-YL)-N-ISOPROPYLBENZAMIDE

A. 4-(3-(Cyclohexylmethyl)-2-oxo-2,3-dihydro-1H-imidazo[4,5-b]pyrazin-5-yl)benzoic acid. A solution of methyl 4-(3-(cyclohexylmethyl)-2-oxo-2,3-dihydro-1H-imidazo[4,5-b]pyrazin-5-yl)benzoate (See Example 56.A) (350 mg, 0.95 mmol) in 1N lithium hydroxide (4.5 mL) and tetrahydrofuran (4.5 mL) was allowed to stir at rt for 19 h. Upon completion of the reaction, the volatiles were removed under reduced pressure. The residue was treated with 1N hydrochloric acid and sonicated. The resulting precipitate was collected by vacuum filtration, and dried under high vacuum to afford the title compound (300 mg, 90% yield) as a tan solid. MS (ESI) m/z 353.3 [M+1]$^+$.

B. 4-(3-(Cyclohexylmethyl)-2-oxo-2,3-dihydro-1H-imidazo[4,5-b]pyrazin-5-yl)-N-isopropylbenzamide. 4-(3-(Cyclohexylmethyl)-2-oxo-2,3-dihydro-1H-imidazo[4,5-b]pyrazin-5-yl)benzoic acid (150 mg, 0.42 mmol), diisopropylethylamine (47 μL, 0.55 mmol) and benzotriazol-1-yloxy-tris(dimethylamino)-phosphonium hexafluorophosphate (243 mg, 0.55 mmol) in DMF (3 mL) were allowed to stir at rt for 19 h. The crude product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The resulting solid was collected by vacuum filtration, washed with water and dried under high vacuum to provide the desired product (42 mg, 25% yield) as a tan solid. $^1$H NMR (300 MHz, DMSO-d$_6$) δ 12.18 (s, 1H), 8.66 (s, 1H), 8.35 (d, J=7.5, 1H), 8.20 (d, J=8.4, 2H), 8.03 (d, J=8.4, 2H), 4.20 (m, 1H), 3.83 (d, J=8.9, 1H), 2.01 (m, 1H), 1.76 (m, 5H), 1.25 (d, J=9.0, 6H), 1.16 (m, 5H); MS (ESI) m/z 394.2 [M+1]$^+$; mp 264-268° C.

5.1.64 Example 64

SYNTHESIS OF 1-(2-HYDROXYETHYL)-6-(4-HYDROXYPHENYL)-1H-IMIDAZO[4,5-B]PYRAZIN-2(3H)-ONE

A. 1-(2-Hydroxyethyl)-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (200 mg, 0.43 mmol), ethanolamine (262 mg, 4.3 mmol), and ethanol (2 mL) were heated in a Biotage Emrys Optimizer microwave reactor at 150° C. for 4 h. The reaction was concentrated and then triturated with 10% methanol in water to give a white solid (50 mg, 42% yield). $^1$H NMR (300 MHz, DMSO-d$_6$) δ 9.68 (s, 1H), 8.35 (s, 1H), 7.85 (d, J=8.8, 2H), 6.86 (d, J=8.8, 2H), 4.88 (t, J=5.9, 1H), 3.93 (t, J=5.8, 4H), 3.76 (q, J=6.1, 4H); MS (ESI) m/z 273.3 [M+1]$^+$; mp 308-310° C.

5.1.65 Example 65

SYNTHESIS OF 1-(CYCLOHEXYLMETHYL)-6-(1H-INDOL-6-YL)-1H-IMIDAZO[4,5-B]PYRAZIN-2(3H)-ONE

A. 1-(Cyclohexylmethyl)-6-(1H-indol-6-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.250 g, 0.80 mmol), indole-6-boronic acid (0.155 g, 0.96 mmol), tetrakis (triphenylphosphine)palladium(0) (0.092 g, 0.08 mmol), sodium bicarbonate (0.268 g, 3.2 mmol), water (2 ml) and ethylene glycol dimethyl ether (10 mL) were reacted according to General Procedure B2. The product precipitated out of the reaction and was filtered and dried to give (0.088 g, 32% yield). $^1$H NMR (300 MHz, CD$_3$OD) δ 11.94 (s, 1H), 11.27 (s, 1H), 8.46 (s, 1H), 8.06 (s, 1H), 7.68 (dd, J=15.0, 8.4, 2H), 7.42 (m, 1H) 6.46 (s, 1H) 3.76 (d, J=7.2, 1H) 1.93 (m, 1H) 1.69 (m, 5H) 1.18 (m, 5H); MS (ESI) m/z 348.4 [M+1]$^+$; mp 359-363° C.

5.1.66 Example 66

SYNTHESIS OF 3-(3-(CYCLOHEXYLMETHYL)-2-OXO-2,3-DIHYDRO-1H-IMIDAZO[4,5-B]PYRAZIN-5-YL)BENZAMIDE

A. 3-(3-(Cyclohexylmethyl)-2-oxo-2,3-dihydro-1H-imidazo[4,5-b]pyrazin-5-yl)benzamide. 6-Bromo-1-(cyclohexylmethyl)-1H-imidazo[4,5-b]pyrazin-2(3H)-one (See Example 55.B) (500 mg, 1.6 mmol), 3-aminocarbonylphenyl boronic acid (318 mg, 1.93 mmol), dichloro[1,1'-bis(diphenylphosphino)ferrocene]palladium (II) dichloromethane (131 mg, 0.16 mmol) and potassium phosphate (1.35 g, 6.4 mmol) in DMF (30 mL) and water (4 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The desired product was collected by vacuum filtration, washed with water and dried under high vacuum to provide the desired product (272 mg, 48% yield) as a tan solid. $^1$H NMR (300 MHz, DMSO-d$_6$) δ 12.06 (s, 1H), 8.55 (s, 1H), 8.47 (s, 1H), 8.16 (d, J=8.4, 1H), 8.09 (s, 1H), 7.89 (d, J=7.4, 1H), 7.58 (t, J=8.0, 1H), 7.45 (s, 1H), 3.74 (d, J=7.2, 2H), 1.91 (m, 1H), 1.67 (m, 5H), 1.17 (m, 5H); MS (ESI) m/z 352.2 [M+1]$^+$.

5.1.67 Example 67

SYNTHESIS OF 6-(4-(AMINOMETHYL)PHENYL)-1-(CYCLOHEXYLMETHYL)-1H-IMIDAZO[4,5-B]PYRAZIN-2(3H)-ONE

A. tert-Butyl 4-(3-(cyclohexylmethyl)-2-oxo-2,3-dihydro-1H-imidazo[4,5-b]pyrazin-5-yl)benzylcarbamate. 6-Bromo-1-(cyclohexylmethyl)-1H-imidazo[4,5-b]pyrazin-2(3H)-one (See Example 55.B) (200 mg, 0.64 mmol), [4-(N-boc-aminomethyl)phenyl]boronic acid (195 mg, 0.77 mmol), dichloro[1,1'-bis(diphenylphosphino)ferrocene]palladium (II) dichloromethane (53 mg, 0.06 mmol) and potassium phosphate (550 mg, 2.58 mmol) in DMF (15 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The desired product was collected by vacuum filtration, washed with water and dried under high vacuum to provide the title compound. The product was used directly in the next step without further purification or characterization. MS (ESI) m/z 438.1 [M+1]$^+$.

B. 6-(4-(Aminomethyl)phenyl)-1-(cyclohexylmethyl)-1H-imidazo[4,5-b]pyrazin-2(3H)-one. tert-Butyl 4-(3-(cyclohexylmethyl)-2-oxo-2,3-dihydro-1H-imidazo[4,5-b]pyrazin-5-yl)benzyl carbamate was treated with TFA (2 mL) in methylene chloride (2 mL) for 4 h at rt. The product was purified by reverse-phase semi-preparatory HPLC (30-100% acetonitrile+0.1% TFA in H$_2$O+0.1% TFA, over 30 min). The desired fractions were concentrated to approximately one third the original volume and treated with potassium carbonate (1.75 M). The desired product was collected by vacuum filtration, washed with water and dried under high vacuum to provide the desired product (42 mg, 19% yield over two steps) as a tan solid. $^1$H NMR (300 MHz, DMSO-d$_6$) δ 8.33 (s, 1H), 7.91 (d, J=8.0, 2H), 7.40 (d, J=8.4, 2H), 7.75 (s, 2H), 3.68 (d, J=7.2, 2H), 1.90 (m, 1H), 1.65 (m, 5H), 1.16 (m, 5H); MS (ESI) m/z 339.1 [M+1]$^+$.

5.1.68 Example 68

SYNTHESIS OF 6-(4-HYDROXYPHENYL)-1-((1-METHYLPIPERIDIN-4-YL)METHYL)-1H-IMIDAZO[4,5-B]PYRAZIN-2(3H)-ONE

A. tert-Butyl pyridin-4-ylmethylcarbamate. 4-(Aminomethyl)pyridine (1.08 g, 10 mmol) was added with 2-propanol (20 mL), di-tert-butyl dicarbonate (2.4 g, 11 mmol) was added and stirred at room temperature for 1 h. The reaction was concentrated to an oil and used without further purification. MS (ESI) m/z 209.3 [M+1]$^+$.

B. 4-((tert-Butoxycarbonylamino)methyl)-1-methylpyridinium iodide. tert-butyl pyridin-4-ylmethylcarbamate (2.08 g, 10 mmol) was added with acetonitrile (8 mL) followed with iodomethane (0.94 mL, 15 mmol). The reaction was heated in a Biotage Emrys Optimizer microwave reactor at 100° C. for 10 min. The reaction was concentrated to a purple residue and used without further purification. MS (ESI) m/z 223.4 [M+1]$^+$.

C. (1-Methylpiperidin-4-yl)methanamine hydrochloride. 4-((tert-Butoxycarbonylamino)-methyl)-1-methylpyridinium iodide (3.5 g, 10 mmol) was dissolved in methanol (200 mL) and platinum (IV) oxide (200 mg) was added. The reaction was shaken in a Parr hydrogenator under 40 psi of hydrogen for 20 h. The reaction was concentrated and then extracted with ethyl acetate and water. The organic layer was dried over magnesium sulfate, filtered and concentrated to an oil. The oil was treated with 4N hydrochloric acid in dioxane to give the amine. The reaction was concentrated and then triturated with 20% methanol in ethyl acetate to give a white solid (1.2 g, 75% yield over 3 steps). MS (ESI) m/z 128.9 [M+1]$^+$.

D. 6-(4-Hydroxyphenyl)-1-((1-methylpiperidin-4-yl)methyl)-1H-imidazo[4,5-b]pyrazin-2(3H)-one. 4-(6-Bromo-5-(N,N-bis-boc-amino)pyrazin-2-yl)phenol (see Example 46.F) (200 mg, 0.43 mmol), (1-methylpiperidin-4-yl)methanamine hydrochloride (262 mg, 4.3 mmol), triethylamine (1 mL) and ethanol (2 mL) were heated in a Biotage Emrys Optimizer microwave reactor at 150° C. for 4 h. The reaction was concentrated and then triturated with 10% methanol in water to give a white solid (50 mg, 37% yield). $^1$H NMR (400 MHz, DMSO-d$_6$) δ 9.69 (s, 1H), 8.34 (s, 1H), 7.84 (d, J=8.6, 2H), 6.87 (d, J=8.6, 2H), 3.74 (d, J=7.4, 2H), 2.72 (d, J=11.3, 2H), 2.11 (s, 3H), 1.74-1.85 (m, 3H), 1.58 (d, J=10.9, 2H), 1.22-1.33 (m, 2H); MS (ESI) m/z 340.1 [M+1]$^+$; mp 292-294° C.

5.1.69 Example 69

SYNTHESIS OF 4-(3-(CYCLOHEXYLMETHYL)-2-OXO-2,3-DIHYDRO-1H-IMIDAZO[4,5-B]PYRAZIN-5-YL)BENZONITRILE

A. 4-(3-(Cyclohexylmethyl)-2-oxo-2,3-dihydro-1H-imidazo[4,5-b]pyrazin-5-yl)benzonitrile. 6-Bromo-1-(cyclohexylmethyl)-1H-imidazo[4,5-b]pyrazin-2(3H)-one (See Example 55.B) (0.500 g, 1.61 mmol), 4-cyanophenyl-boronic acid (0.283 g, 1.93 mmol), bis(diphenylphosphino)ferrocene]dichloropalladium(II) complex with dichloromethane (1:1) (0.132 g, 0.161 mmol), potassium phosphate (1.37 g, 6.44 mmol), water (2 ml) and dimethylformamide (10 mL) were reacted according to General Procedure B. The solution was condensed under reduced pressure and the product was purified by reverse-phase semi-preparatory HPLC (5-70% acetonitrile+0.1% TFA in H$_2$O+0.1% TFA, over 30 min). Fractions containing clean product were neutralized with potassium carbonate and extracted with ethyl acetate, dried over magnesium sulfate, filtered, concentrated and dried under vacuum to give the product (0.144 g, 27% yield). $^1$H NMR (400 MHz, DMSO-d$_6$) δ 8.60 (s, 1H) 8.23 (d, J=7.2, 2H), 7.95 (d, J=8.0, 2H), 3.72 (d, J=7.2, 2H), 3.85 (d, J=7.2, 2H), 1.90 (m, 1H), 1.67 (m, 5H) 1.18 (m, 5H); MS (ESI) m/z 334.4 [M+1]$^+$; mp 255-257° C.

5.1.70 Example 70

SYNTHESIS OF 1-((1S,4S)-4-HYDROXYCYCLOHEXYL)-6-(4-HYDROXYPHENYL)-1H-IMIDAZO[4,5-B]PYRAZIN-2(3H)-ONE

A. 1-((1s,4s)-4-Hydroxycyclohexyl)-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (200 mg, 0.43 mmol), (1s,4s)-4-aminocyclohexanol hydrochloride (0.65 g, 4.3 mmol), triethylamine (1 mL), and ethanol (2 mL) were heated in a Biotage Emrys Optimizer microwave reactor at 150° C. for 4 h. The reaction was concentrated and then triturated with 10% methanol in water to give a white solid (50 mg, 37% yield). $^1$H NMR (400 MHz, DMSO-d$_6$) δ 11.88 (s, 1H), 9.69 (s, 1H), 8.35 (s, 1H), 7.88 (d, J=8.6, 2H), 6.83-6.87 (m, 2H), 4.46 (s, 1H), 4.23 (t, J=112.1, 1H), 3.90 (s, 1H), 2.74-2.84 (m, 2H), 1.82 (d, J=14.8, 2H), 1.54-1.61 (m, 2H), 1.49 (d, J=18.0, 2H); MS (ESI) m/z 327.1 [M+1]$^+$; mp 328-338° C.

5.1.71 Example 71

SYNTHESIS OF 1-(CYCLOHEXYLMETHYL)-6-(PYRIDIN-2-YL)-1H-IMIDAZO[4,5-B]PYRAZIN-2(3H)-ONE

A. 1-(Cyclohexylmethyl)-6-(pyridin-2-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.200 g, 0.643 mmol) 2-(trimethylstannyl)pyridine (0.101 g, 1.93 mmol), copper(I) iodide (0.008 g, 0.01 mmol), and dichlorobis(triphenylphosphine)palladium(II) were added to triethylamine (5 mL). The resulting solution was reacted in a Biotage Emrys Optimizer microwave reactor at 120° C. for 30 min. The solution was condensed under reduced pressure and the product was purified by reverse-phase semi-preparatory HPLC (5-70% acetonitrile+0.1% TFA in H$_2$O+0.1% TFA, over 30 min). Fractions containing clean product were neutralized with potassium carbonate, extracted with ethyl acetate, dried over magnesium sulfate, filtered, concentrated, and dried under vacuum to give (0.032 g, 16% yield). $^1$H NMR (400 MHz, DMSO-d$_6$) δ 8.85 (s, 1H), 8.60 (d, J=4, 1H), 8.29 (d, J=8.0, 1H), 7.94 (m, 1H), 7.40 (m, 1H), 3.87 (d, J=7.2, 2H), 2.02 (m, 1H), 1.74 (m, 5H), 1.28 (m, 5H); MS (ESI) m/z 334.4 [M+1]$^+$; mp 194-196° C.

5.1.72 Example 72

SYNTHESIS OF 4-(3-(CYCLOHEXYLMETHYL)-2-OXO-2,3-DIHYDRO-1H-IMIDAZO[4,5-B]PYRAZIN-5-YL)-N-ETHYLBENZAMIDE

A. 4-(3-(Cyclohexylmethyl)-2-oxo-2,3-dihydro-1H-imidazo[4,5-b]pyrazin-5-yl)-N-ethylbenzamide. 4-[3-(Cyclohexylmethyl)-2-oxo-4-imidazolino[4,5-e]pyrazin-5-yl]benzoic acid (See Example 63.A.) (150 mg, 0.42 mmol), ethylamine (2.0M in MeOH, 276 μL, 0.55 mmol) and benzotriazol-1-yloxy-tris(dimethylamino)-phosphonium hexafluorophosphate (243 mg, 0.55 mmol) in dimethylformamide (3 mL) were allowed to stir at rt for 19 h. The crude product was purified by reverse-phase semi-preparatory HPLC (30-100% acetonitrile+0.1% TFA in H$_2$O+0.1% TFA, over 30 min). The desired fractions were concentrated to approximately one third the original volume, treated with 1.75 M potassium carbonate. The desired product was collected by vacuum filtration, washed with water and dried under high vacuum to provide the title compound (8 mg, 5% yield) as a tan solid. $^1$H NMR (300 MHz, DMSO-d$_6$) δ 12.18 (s, 1H), 8.66 (s, 1H), 8.35 (d, J=7.5, 1H), 8.20 (d, J=8.4, 2H), 8.03 (d, J=8.4, 2H), 4.20 (m, 1H), 3.83 (d, J=8.9, 1H), 2.01 (m, 2H), 1.76 (m, 5H), 1.25 (m, 3H), 1.16 (m, 5H); MS (ESI) m/z 380.1 [M+1]$^+$.

5.1.73 Example 73

SYNTHESIS OF 1-(CYCLOHEXYLMETHYL)-6-(4-(2-HYDROXYPROPAN-2-YL)PHENYL)-1H-IMIDAZO[4,5-B]PYRAZIN-2(3H)-ONE

A. 1-(Cyclohexylmethyl)-6-(4-(2-hydroxypropan-2-yl)phenyl)-1H-imidazo[4,5-b]pyrazin-2(3H)-one. Methyl 4-(3-(cyclohexylmethyl)-2-oxo-2,3-dihydro-1H-imidazo[4,5-b]pyrazin-5-yl)benzoate (See Example 56.A) (0.075 g, 0.205 mmol) was dissolved in tetrahydrofuran (5 mL) and cooled to −78° C. Methylmagnesium bromide (1.4M in toluene/tetrahydrofuran, 0.410 mL, 0.410 mmol) was added and the reaction was stirred at −78° C. for 3 h. The reaction was not complete and additional methylmagnesium bromide (1.4M in toluene/tetrahydrofuran, 0.410 mL, 0.410 mmol) was added. After an additional 2 h, the reaction was quenched with water and extracted with methylene chloride. The product was purified using reverse-phase semi-preparatory HPLC (30-70% acetonitrile+0.1% TFA in H$_2$O+0.1% TFA, over 40 min). Fractions containing the desired material were combined and concentrated under reduced pressure. The residue was dissolved in hot DMSO and water was added to induce precipitation. The solid was filtered and washed with water and dried under vacuum to afford the title compound (0.055 g, 0.150 mmol, 73% yield). $^1$H NMR (400 MHz, DMSO-d$_6$) δ 12.01 (s, 1H), 8.45 (s, 1H), 7.93 (d, J=8.6, 2H), 7.57 (d, J=8.6, 2H), 4.95-5.14 (m, 1H), 3.73 (d, J=7.0, 2H), 1.84-1.96 (m, 1H), 1.54-1.72 (m, 5H), 1.45 (s, 6H), 1.12-1.22 (m, 3H), 0.98-1.09 (m, 2H); MS (ESI) m/z 367.3 [M+1]$^+$; mp 226-228° C.

5.1.74 Example 74

SYNTHESIS OF 1-(CYCLOHEXYLMETHYL)-6-(4-HYDROXY-2-METHYLPHENYL)-1H-IMIDAZO[4,5-B]PYRAZIN-2(3H)-ONE

A. 1-(Cyclohexylmethyl)-6-(4-hydroxy-2-methylphenyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.300 g, 0.96 mmol), 4-hydroxy-2-methylphenylboronic acid (0.175 g, 1.15 mmol), dichloro[1,1'-bis(diphenylphosphino)ferrocene]palladium (II) dichloromethane (78 mg, 0.096 mmol) and potassium phosphate (814 mg, 3.84 mmol) in DMF (20 mL) and water (4 mL) were reacted according to General Procedure B. The product was purified by reverse-phase preparatory HPLC (30-100% acetonitrile+0.1% TFA in H$_2$O+0.1% TFA, over 30 min). The desired fractions were concentrated and neutralized with sat. sodium bicarbonate The product was extracted with ethyl acetate and dried under high vacuum to provide the title compound (152 mg, 47% yield). $^1$H NMR (400 MHz, DMSO-d$_6$) δ 11.95 (s, 1H), 9.52 (s, 1H), 7.92 (s, 1H), 7.21 (d, J=8.2, 1H), 6.64-6.75 (m, 2H), 3.66 (d, J=7.4, 2H), 2.28 (s, 3H), 1.81-1.94 (m, 1H), 1.54-1.70 (m, 5H), 1.09-1.19 (m, 3H), 0.93-1.05 (m, 2H); MS (ESI) m/z 339.3 [M+1]$^+$; mp 212-214° C.

5.1.75 Example 75

SYNTHESIS OF 4-(3-(CYCLOHEXYLMETHYL)-2-OXO-2,3-DIHYDRO-1H-IMIDAZO[4,5-B]PYRAZIN-5-YL)BENZOIC ACID

A. 4-(3-(Cyclohexylmethyl)-2-oxo-2,3-dihydro-1H-imidazo[4,5-b]pyrazin-5-yl)benzoic acid. 6-Bromo-1-(cyclohexylmethyl)-1H-imidazo[4,5-b]pyrazin-2(3H)-one (See Example 55.B) (0.300 g, 0.96 mmol), 4-carboxyphenylboronic acid (0.192 g, 1.15 mmol), dichloro[1,1'-bis(diphenylphosphino)ferrocene]palladium (II) dichloromethane (79 mg, 0.096 mmol) and potassium phosphate (814 mg, 3.84 mmol) in DMF (20 mL) and water (4 mL) were reacted according to General Procedure B. The product was purified by reverse-phase preparatory HPLC (30-100% acetonitrile+0.1% TFA in H$_2$O+0.1% TFA, over 30 min). Fractions containing the desired material were combined and concentrated under reduced pressure. The residue was dissolved in hot DMSO and water was added to induce precipitation. The solid was filtered and washed with water and dried to afford the title compound (0.047 g, 14% yield). $^1$H NMR (400 MHz, DMSO-d$_6$) δ 8.58 (s, 1H), 8.14 (d, J=8.4, 2H), 8.03 (d, J=8.4, 2H), 3.74 (d, J=7.4, 2H), 1.86-1.97 (m, 1H), 1.54-1.72 (m, 6H), 1.13-1.23 (m, 4H), 0.99-1.10 (m, 2H); MS (ESI) m/z 353.3 [M+1]$^+$; mp >350° C.

5.1.76 Example 76

SYNTHESIS OF 6-(4-HYDROXYPHENYL)-1-(2-METHOXYETHYL)-1H-IMIDAZO[4,5-B]PYRAZIN-2(3H)-ONE

A. 6-(4-Hydroxyphenyl)-1-(2-methoxyethyl)-1H-imidazo[4,5-b]pyrazin-2(3H)-one. 4-(6-Bromo-5-(N,N-bis-boc-amino)pyrazin-2-yl)phenol (see Example 46.F) (200 mg, 0.4 mmol), 2-methoxyethylamine (0.27 g, 4 mmol), and N,N-dimethylformamide (4 mL) were heated in a Biotage Emrys Optimizer microwave reactor at 150° C. for 10 min. The reaction was extracted with water and ethyl acetate. The organic layer was concentrated and then purified by reverse-phase semi-preparatory HPLC (5-70% acetonitrile+0.1% TFA in H$_2$O+0.1% TFA, over 30 min). Product fractions were concentrated and then triturated with ether to give a white solid (35 mg, 29% yield). $^1$H NMR (400 MHz, DMSO-d$_6$) δ 11.95 (s, 1H), 9.70 (s, 1H), 8.37 (s, 1H), 7.85 (d, J=8.6, 2H), 6.86 (d, J=9.0, 2H), 4.04 (t, J=5.7, 2H), 3.73 (t, J=5.7, 2H), 3.26 (s, 3H); MS (ESI) m/z 287.5 [M+1]$^+$; mp 236-237° C.

5.1.77 Example 77

SYNTHESIS OF 6-(4-HYDROXYPHENYL)-1-(3-METHOXYPROPYL)-1H-IMIDAZO[4,5-B]PYRAZIN-2(3H)-ONE

A. 6-(4-Hydroxyphenyl)-1-(3-methoxypropyl)-1H-imidazo[4,5-b]pyrazin-2(3H)-one. 4-(6-Bromo-5-(N,N-bis-boc-amino)pyrazin-2-yl)phenol (see Example 46.F) (200 mg, 0.4 mmol), 3-methoxypropylamine (0.44 g, 4 mmol), and N-methylpyrrolidinone (4 mL) were heated in a Biotage Emrys Optimizer microwave reactor at 150° C. for 10 min. The reaction was extracted with water and ethyl acetate. The organic layer was concentrated and then purified by reverse-phase semi-preparatory HPLC (5-70% acetonitrile+0.1% TFA in H$_2$O+0.1% TFA, over 30 min). Product fractions were concentrated and then triturated with ether to give a white solid (83 mg, 66% yield). $^1$H NMR (400 MHz, DMSO-d$_6$) δ 11.90 (s, 1H), 9.69 (s, 1H), 8.35 (s, 1H), 7.86 (d, J=9.0, 2H), 6.86 (d, J=9.0, 2H), 3.93 (t, J=7.0, 2H), 3.39 (t, J=6.1, 2H), 3.19 (s, 3H), 1.95-2.02 (m, 2H); MS (ESI) m/z 301.5 [M+1]$^+$; mp 208-210° C.

5.1.78 Example 78

SYNTHESIS OF 6-(4-HYDROXYPHENYL)-4-(3-METHOXYBENZYL)-3,4-DIHYDROPYRAZINO[2,3-B]PYRAZIN-2(1H)-ONE

A. 6-Bromo-4-(3-methoxybenzyl)-3,4-dihydropyrazino[2,3-b]pyrazin-2(1H)-one. 3,5-Dibromopyrazin-2-amine (1.0 g, 4 mmol) was dissolved in acetonitrile (6 mL) and with bromoacetic anhydride (1.0 g, 4 mmol) was added. The reaction was heated to 50° C. for 16 h. 3-Methoxybenzylamine (1.6 g, 12 mmol) was added to the reaction and continued heating at 50° C. for 1 h. The reaction was diluted with water and ethyl acetate followed by filtering to give a tan solid (0.45 g, 32% yield). MS (ESI) m/z 350.9 [M+1]$^+$.

B. 6-(4-Hydroxyphenyl)-4-(3-methoxybenzyl)-3,4-dihydropyrazino[2,3-b]pyrazin-2(1H)-one. 4-Hydroxyphenylboronic acid (196 mg, 1.4 mmol), 6-bromo-4-(3-methoxybenzyl)-3,4-dihydropyrazino[2,3-b]pyrazin-2(1H)-one (450 mg, 1.3 mmol), dichloro[1,1'-bis(diphenylphosphino)ferrocene]palladium(II) dichloromethane adduct (28 mg, 0.04 mmol), 1M sodium carbonate (4 mL, 4 mmol), and dioxane (8 mL) were heated in a Biotage Emrys Optimizer microwave reactor at 120° C. for 10 min. The reaction was filtered through celite. The filtrate was adjusted to pH 7 with saturated ammonium chloride and then allowed to stand for 1 hr. The precipitated solid was filtered and then triturated in 10% dimethylsulfoxide and methanol to give a tan solid (102 mg, 21% yield). $^1$H NMR (400 MHz, DMSO-d$_6$) δ 11.23 (s, 1H), 9.65 (s, 1H), 7.96 (s, 1H), 7.82 (d, J=8.6, 2H), 7.26 (s, 1H), 7.00 (d, J=1.6, 2H), 6.78-6.87 (m, 3H), 4.79 (s, 2H), 4.06 (s, 2H), 3.71 (s, 3H); MS (ESI) m/z 363.3 [M+1]$^+$; mp 282-283° C.

5.1.79 Example 79

SYNTHESIS OF 6-(4-HYDROXYPHENYL)-1-(2-(TETRAHYDRO-2H-PYRAN-4-YL)ETHYL)-1H-IMIDAZO[4,5-B]PYRAZIN-2(3H)-ONE

A. 6-(4-Hydroxyphenyl)-1-(2-(tetrahydro-2H-pyran-4-yl) ethyl)-1H-imidazo[4,5-b]pyrazin-2(3H)-one. 4-(6-Bromo-5-(N,N-bis-boc-amino)pyrazin-2-yl)phenol (see Example 46.F) (100 mg, 0.2 mmol), 2-(tetrahydro-2H-pyran-4-yl) ethanamine (0.28 g, 2 mmol), and N-methylpyrrolidinone (2 mL) were heated in a Biotage Emrys Optimizer microwave reactor at 150° C. for 10 min. The reaction was extracted with water and ethyl acetate. The organic layer was concentrated and then purified by reverse-phase semi-preparatory HPLC (5-70% acetonitrile+0.1% TFA in H$_2$O+0.1% TFA, over 30 min). Product fractions were concentrated and then triturated with ether to give a white solid (45 mg, 62% yield). $^1$H NMR (400 MHz, DMSO-d$_6$) δ 11.92 (s, 1H), 9.70 (s, 1H), 8.37 (s, 1H), 7.84 (d, J=8.6, 2H), 6.86 (d, J=8.6, 2H), 3.91 (t, J=7.0, 2H), 3.79-3.85 (m, 2H), 3.21 (td, J=11.7, 2.0, 2H), 1.67-1.75 (m, 4H), 1.44-1.53 (m, 1H), 1.15-1.25 (m, 2H); MS (ESI) m/z 341.0 [M+1]$^+$; mp 276-277° C.

5.1.80 Example 80

SYNTHESIS OF 6-(4-HYDROXYPHENYL)-1-PHENETHYL-1H-IMIDAZO[4,5-B]PYRAZIN-2(3H)-ONE

A. 6-(4-Hydroxyphenyl)-1-phenethyl-1H-imidazo[4,5-b] pyrazin-2(3H)-one. 4-(6-Bromo-5-(N,N-bis-boc-amino) pyrazin-2-yl)phenol (see Example 46.F) (100 mg, 0.2 mmol), phenethylamine (0.26 g, 2 mmol), and N-methylpyrrolidinone (2 mL) were heated in a Biotage Emrys Optimizer microwave reactor at 150° C. for 10 min. The reaction was extracted with water and ethyl acetate. The organic layer was concentrated and then purified by reverse-phase semi-preparatory HPLC (5-70% acetonitrile+0.1% TFA in H$_2$O+0.1% TFA, over 30 min). Product fractions were concentrated and then triturated with ether to give a white solid (36 mg, 51% yield). $^1$H NMR (400 MHz, DMSO-d$_6$) δ 11.88 (s, 1H), 9.69 (s, 1H), 8.33 (s, 1H), 7.83 (d, J=9.0, 2H), 7.19-7.27 (m, 5H), 7.17 (d, J=7.0, 1H), 6.87 (d, J=9.0, 2H), 4.12 (t, J=7.2, 2H), 3.11 (t, J=7.2, 2H); MS (ESI) m/z 333.3 [M+1]$^+$, mp 283-284° C.

5.1.81 Example 81

SYNTHESIS OF 1-((1R,4R)-4-HYDROXYCYCLOHEXYL)-6-(4-HYDROXYPHENYL)-1H-IMIDAZO[4,5-B]PYRAZIN-2(3H)-ONE

A. 1-((1r,4r)-4-Hydroxycyclohexyl)-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (100 mg, 0.2 mmol), (1r,4r)-4-aminocyclohexanol hydrochloride (0.32 g, 2 mmol), triethylamine (0.5 mL), and N-methylpyrrolidinone (2 mL) were heated in a Biotage Emrys Optimizer microwave reactor at 150° C. for 10 min. The reaction was extracted with water and ethyl acetate. The organic layer was concentrated and then purified by reverse-phase semi-preparatory HPLC (5-70% acetonitrile+0.1% TFA in H$_2$O+0.1% TFA, over 30 min). Product fractions were concentrated and then triturated with ether to give a white solid (33 mg, 49% yield). $^1$H NMR (400 MHz, DMSO-d$_6$) δ 11.90 (s, 1H), 9.69 (s, 1H), 8.34 (s, 1H), 7.85 (d, J=8.6, 2H), 6.87 (d, J=8.6, 2H), 4.69 (d, J=4.3, 1H), 4.22 (t, J=12.3, 1H), 3.54 (d, J=4.7, 1H), 2.35-2.47 (m, 2H), 1.96 (d, J=11.3, 2H), 1.76 (d, J=11.7, 2H), 1.28-1.39 (m, 2H); MS (ESI) m/z 327.4 [M+1]$^+$; mp 348-350° C.

5.1.82 Example 82

SYNTHESIS OF 6-(4-(1H-1,2,4-TRIAZOL-3-YL) PHENYL)-1-(CYCLOHEXYLMETHYL)-1H-IMIDAZO[4,5-B]PYRAZIN-2(3H)-ONE

A. (E)-4-(3-(Cyclohexylmethyl)-2-oxo-2,3-dihydro-1H-imidazo[4,5-b]pyrazin-5-yl)-N-((dimethylamino)methylene)benzamide. 4-(3-(Cyclohexylmethyl)-2-oxo-2,3-dihydro-1H-imidazo[4,5-b]pyrazin-5-yl)benzamide (See Example 55.C) (0.456 g, 1.30 mmol) was added to dimethylformamide dimethylacetal (50 mL) and heated to 85° C. for 18 h. The product precipitated out of reaction and was filtered and dried to give (0.209 g, 40% yield). MS (ESI) m/z 407.5 [M+1]$^+$.

B. 6-(4-(1H-1,2,4-Triazol-3-yl)phenyl)-1-(cyclohexylmethyl)-1H-imidazo[4,5-b]pyrazin-2(3H)-one. Hydrazine (0.452 mL, 14.4 mmol) was added dropwise to a solution of (E)-4-(3-(cyclohexylmethyl)-2-oxo-2,3-dihydro-1H-imidazo[4,5-b]pyrazin-5-yl)-N-((dimethylamino)methylene) benzamide (0.209 g, 0.514 mmol) in acetic acid (10 mL). After stirring at room temperature for 2 h, the solution was condensed under reduced pressure and the product was purified by reverse-phase semi-preparatory HPLC (5-70% acetonitrile+0.1% TFA in H$_2$O+0.1% TFA, over 30 min). Fractions containing clean product were neutralized with potassium carbonate and extracted with ethyl acetate. Organic fractions were pooled, dried over magnesium sulfate, filtered, and solvent was removed under reduced pressure. The resulting material was dried under vacuum to give (0.020 g, 10% yield). $^1$H NMR (400 MHz, CD$_3$OD) δ 8.49 (s, 1H) 8.39 (s, 1H), 8.16 (m, 4H), 3.87 (d, J=7.2, 2H), 2.02 (m, 1H), 1.74 (m, 5H) 1.26 (m, 5H); MS (ESI) m/z 334.4 [M+1]$^+$; mp 336-338° C.

5.1.83 Example 83

SYNTHESIS OF 1-(CYCLOHEXYLMETHYL)-6-PHENYL-1H-IMIDAZO[4,5-B]PYRAZIN-2(3H)-ONE

A. 1-(Cyclohexylmethyl)-6-phenyl-1H-imidazo[4,5-b] pyrazin-2(3H)-one. 6-Bromo-1-(cyclohexylmethyl)-1H-imidazo[4,5-b]pyrazin-2(3H)-one (See Example 55. B) (150 mg, 0.48 mmol), phenylboronic acid (71 mg, 0.58 mmol), dichloro[1,1'-bis(diphenylphosphino) ferrocene]palladium (II) dichloromethane (40 mg, 0.05 mmol) and potassium phosphate (407 mg, 1.92 mmol) in DMF (10 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL), heated at 100° C. until completely dissolved. Water was added upon cooling and the desired product precipitated out of solution. The precipitate was collected by vacuum filtration, washed with water and dried under high vacuum to provide the title compound (22 mg, 15% yield) as a tan solid. $^1$H NMR (400 MHz, DMSO-d$_6$) δ 12.03 (s, 1H), 8.49 (s, 1H), 8.02 (d, J=8.8, 2H), 7.49 (t, J=7.6, 2H), 7.40 (d, J=7.2, 1H), 3.73 (d, J=6.8, 2H), 1.90 (m, 1H), 1.67 (m, 5H), 1.17 (m, 3H), 1.05 (m, 2H); MS (ESI) m/z 309.1 [M+1]$^+$; mp 253-255° C.

5.1.84 Example 84

SYNTHESIS OF 1-(CYCLOHEXYLMETHYL)-6-(1H-PYRAZOL-5-YL)-1H-IMIDAZO[4,5-B]PYRAZIN-2(3H)-ONE

A. 1-(Cyclohexylmethyl)-6-(1H-pyrazol-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (250 mg, 0.80 mmol), pyrazole-4-boronic acid (108 mg, 0.96 mmol), dichloro[1,1'-bis(diphenylphosphino)ferrocene]palladium (II) dichloromethane (66 mg, 0.08 mmol) and potassium phosphate (680 mg, 3.2 mmol) in DMF (10 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (93 mg, 39% yield) as a white solid. $^1$H NMR (300 MHz, DMSO-d$_6$) δ 13.01 (s, 1H), 11.97 (s, 1H), 8.44 (s, 1H), 7.82 (s, 1H), 6.75 (s, 1H), 3.70 (d, J=7.2, 2H), 1.90 (m, 1H), 1.65 (m, 5H), 1.17 (m, 3H), 1.06-1.01 (m, 2H); MS (ESI) m/z 299.1 [M+1]$^+$; mp 264-266° C.

5.1.85 Example 85

SYNTHESIS OF 1-(CYCLOHEXYLMETHYL)-6-(1H-PYRAZOL-4-YL)-1H-IMIDAZO[4,5-B]PYRAZIN-2(3H)-ONE

A. 1-(Cyclohexylmethyl)-6-(1H-pyrazol-4-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (250 mg, 0.80 mmol), pyrazole-4-boronic acid (108 mg, 0.96 mmol), dichloro[1,1'-bis(diphenylphosphino)ferrocene]palladium (II) dichloromethane (66 mg, 0.08 mmol) and potassium phosphate (680 mg, 3.2 mmol) in DMF (10 mL) and water (1 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (17 mg, 7% yield) as a white solid. $^1$H NMR (300 MHz, DMSO-d$_6$) δ 12.97 (s, 1H), 11.85 (s, 1H), 8.15 (m, 2H), 7.96 (s, 1H), 3.65 (d, J=5.4, 2H), 1.88 (m, 1H), 1.66-1.59 (m, 5H), 1.16 (m, 3H), 1.04-0.99 (m, 2H); MS (ESI) m/z 299.1 [M+1]$^+$; mp 246-248° C.

5.1.86 Example 86

SYNTHESIS OF 6-(3-(1H-TETRAZOL-5-YL)PHENYL)-1-(CYCLOHEXYLMETHYL)-1H-IMIDAZO[4,5-B]PYRAZIN-2(3H)-ONE

A. 6-(3-(1H-Tetrazol-5-yl)phenyl)-1-(cyclohexylmethyl)-1H-imidazo[4,5-b]pyrazin-2(3H)-one. A solution of 3-(3-(cyclohexylmethyl)-2-oxo-2,3-dihydro-1H-imidazo[4,5-b]pyrazin-5-yl)benzonitrile (See Example 61.A) (140 mg, 0.42 mmol) in dry toluene (2 mL) was treated with azidotributyltin (350 μL, 1.26 mmol) for 21 h at 110° C. Toluene was removed under reduced pressure. Dioxane (3 mL) and 6N HCl (2 mL) were added and the resulting reaction mixture was stirred at rt for 3 h. The volatiles were removed under reduced pressure, the crude product was dissolved in DMSO and purified by reverse-phase semi-preparatory HPLC (30-100% acetonitrile+0.1% TFA in H$_2$O+0.1% TFA, over 30 min). The desired fractions were concentrated and the residue was taken up in DMSO (2 mL), heated at 100° C. until completely dissolved. Water was added upon cooling and the desired product precipitated out of solution. The precipitate was collected by vacuum filtration, washed with water and dried under high vacuum to provide the title compound (22 mg, 14% yield) as a white powder. $^1$H NMR (400 MHz, DMSO-d$_6$) δ 8.68 (s, 1H), 8.51 (s, 1H), 8.22 (d, J=8.4, 1H), 8.04 (d, J=8.0, 1H), 7.69 (t, J=8.0, 1H), 3.87 (d, J=7.2, 2H), 2.02 (m, 1H), 1.75 (m, 4H), 1.66 (m, 1H), 1.25 (m, 3H), 1.14 (m, 2H); MS (ESI) m/z 364.2 [M+1]$^+$; mp 248-250° C.

5.1.87 Example 87

SYNTHESIS OF 1-(CYCLOHEXYLMETHYL)-6-(2-OXOINDOLIN-5-YL)-1H-IMIDAZO[4,5-B]PYRAZIN-2(3H)-ONE

A. 5-(4,4,5,5-Tetramethyl-1,3,2-dioxaborolan-2-yl)indolin-2-one. Bis(pinacolato)diboron (1.31 g, 4.71 mmol), dichloro[1,1'-bis(diphenylphosphino) ferrocene]palladium (II) dichloro-methane (385 mg, 0.47 mmol) and potassium acetate (1.38 g, 14.1 mmol) were successively added to a solution of 5-bromooxindole (1.0 g, 4.71 mmol) in methylene chloride (25 mL), followed by DMSO (15 mL). The crude mixture was diluted with water, extracted with methylene chloride (3×). the combined organic fractions were washed with water, brine, dried over magnesium sulfate, filtered, and the volatiles were removed under reduced pressure. The crude product was triturated with diethyl ether, sonicated, and the precipitate was collected by filtration to afford the title compound (165 mg, 14%). MS (ESI) m/z 260.3 [M+1]$^+$.

B. 1-(Cyclohexylmethyl)-6-(2-oxoindolin-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (165 mg, 0.53 mmol), 5-(4,4,5,5-tetramethyl-1,3,2-dioxaborolan-2-yl)indolin-2-one (165 mg, 0.63 mmol), dichloro[1,1'-bis(diphenylphosphino) ferrocene]palladium (II) dichloromethane (41 mg, 0.05 mmol) and potassium phosphate (450 mg, 2.12 mmol) in DMF (12 mL) and water (5 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated and the residue was taken up in DMSO (2 mL), heated at 100° C. until completely dissolved. Water was added upon cooling and the desired product precipitated out of solution. The precipitate was collected by vacuum filtration, washed with water and dried under high vacuum to provide the title compound (25 mg, 13% yield) as a tan solid. $^1$H NMR (400 MHz, DMSO-d$_6$) δ 11.95 (s, 1H), 10.52 (s, 1H), 8.38 (s, 1H), 7.85 (d, J=8.0, 2H), 6.92 (d, J=8.0, 2H), 3.72 (d, J=7.2, 2H), 3.57 (s, 2H), 1.89 (m, 1H), 1.66 (m, 5H), 1.17 (m, 3H), 1.03 (m, 2H); MS (ESI) m/z 364.2 [M+1]$^+$; mp 313-316° C.

5.1.88 Example 88

SYNTHESIS OF 1-(CYCLOHEXYLMETHYL)-6-(1H-INDAZOL-5-YL)-1H-IMIDAZO[4,5-B]PYRAZIN-2(3H)-ONE

A. 1-(Cyclohexylmethyl)-6-(1H-indazol-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.300 g, 0.96 mmol), indazole-5-boronic acid (0.283 g, 1.16 mmol), and [1,1'-bis(diphenylphosphino) ferrocene] dichloropalladium(II) complex with dichloromethane (1:1) (0.082 g, 0.1 mmol), potassium phosphate (0.818 g, 3.86 mmol), water (2 ml) and dimethylformamide (10 mL) were reacted according to General Procedure B. The solution was condensed under reduced pressure and the product was purified by reverse-phase semi-preparatory HPLC (5-70% acetonitrile+0.1% TFA in $H_2O$+0.1% TFA, over 30 min). Fractions containing clean product were neutralized with potassium carbonate and extracted with ethyl acetate. Organic fractions were pooled, dried over magnesium sulfate, filtered and concentrated under reduced pressure. The resulting solid was dried under high vacuum to give the product (0.020 g, 10% yield). $^1$H NMR (400 MHz, $CD_3OD$), δ 8.44 (s, 1H) 8.40 (s, 1H), 8.14 (s, 1H), 8.07 (dd, J=8.8, 1.6, 1H), 7.64 (d, J=8.8, 2H), 3.87 (d, J=7.2, 2H), 2.03 (m, 1H), 1.74 (m, 5H) 1.26 (m, 5H); MS (ESI) m/z 349.4 [M+1]$^+$; mp 311-313° C.

5.1.89 Example 89

SYNTHESIS OF 1-(CYCLOHEXYLMETHYL)-6-(6-METHOXYPYRIDIN-3-YL)-1H-IMIDAZO[4,5-B]PYRAZIN-2(3H)-ONE

A. 1-(Cyclohexylmethyl)-6-(6-methoxypyridin-3-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.300 g, 0.96 mmol), 2-methoxypyridine-5-boronic acid (0.177 g, 1.16 mmol), and [1,1'-bis(diphenylphosphino)ferrocene]dichloropalladium(II) complex with dichloromethane (1:1) (0.082 g, 0.1 mmol), potassium phosphate (0.818 g, 3.86 mmol), water (2 ml) and dimethylformamide (10 mL) were reacted according to General Procedure B. The solution was condensed under reduced pressure and the product was purified by reverse-phase semi-preparatory HPLC (5-70% acetonitrile+0.1% TFA in $H_2O$+0.1% TFA, over 30 min). Fractions containing clean product were neutralized with potassium carbonate and extracted with ethyl acetate. Organic fractions were pooled, dried over magnesium sulfate, filtered and concentrated under reduced pressure. The resulting solid was dried under high vacuum to give the product (0.133 g, 40% yield). $^1$H NMR (400 MHz, $CD_3OD$), δ 8.44 (s, 1H) 8.74 (d, J=2.4, 1H), 8.35 (s, 1H), 8.28 (dd, J=8.8, 2.4, 1H), 6.91 (d, J=8.8, 1H), 3.96 (s, 3H), 3.84 (d, J=7.2, 2H), 2.02 (m, 1H) 1.73 (m, 5H), 1.28 (m, 5H); MS (ESI) m/z 340.4 [M+1]$^+$; mp 235-237° C.

5.1.90 Example 90

SYNTHESIS OF 6-(4-HYDROXYPHENYL)-1-(TETRAHYDRO-2H-PYRAN-4-YL)-1H-IMIDAZO[4,5-B]PYRAZIN-2(3H)-ONE

A. 6-(4-Hydroxyphenyl)-1-(tetrahydro-2H-pyran-4-yl)-1H-imidazo[4,5-b]pyrazin-2(3H)-one. 4-(6-Bromo-5-(N,N-bis-boc-amino)pyrazin-2-yl)phenol (see Example 46.F) (100 mg, 0.2 mmol), tetrahydro-2H-pyran-4-amine (0.22 g, 2 mmol), and N-methylpyrrolidinone (2 mL) were heated in a Biotage Emrys Optimizer microwave reactor at 150° C. for 10 min. The reaction was extracted with water and ethyl acetate. The organic layer was dried over magnesium sulfate and concentrated. The resulting residue was purified using Biotage silica gel chromatography (0-100% ethyl acetate in hexanes) to give a white solid. Product fractions were concentrated and then triturated with ether to give a white solid (36 mg, 54% yield). $^1$H NMR (400 MHz, DMSO-$d_6$) δ 11.96 (s, 1H), 9.71 (s, 1H), 8.36 (s, 1H), 7.85 (d, J=9.0, 2H), 6.88 (d, J=8.6, 2H), 4.49 (tt, J=12.4, 4.4, 1H), 4.01 (dd, J=11.5, 3.3, 2H), 3.47 (t, J=11.1, 2H), 2.60 (td, J=12.6, 4.5, 1H), 1.73 (dd, J=12.3, 2.9, 2H); MS (ESI) m/z 313.4 [M+1]$^+$; mp 382-383° C.

5.1.91 Example 91

SYNTHESIS OF 6-(4-HYDROXYPHENYL)-1-(PIPERIDIN-4-YLMETHYL)-1H-IMIDAZO[4,5-B]PYRAZIN-2(3H)-ONE

A. 6-(4-Hydroxyphenyl)-1-(piperidin-4-ylmethyl)-1H-imidazo[4,5-b]pyrazin-2(3H)-one. 4-(6-Bromo-5-(N,N-bis-boc-amino)pyrazin-2-yl)phenol (see Example 46.F) (100 mg, 0.2 mmol), tert-butyl 4-(aminomethyl)piperidine-1-carboxylate (0.46 g, 2 mmol), and N-methylpyrrolidinone (2 mL) were heated in a Biotage Emrys Optimizer microwave reactor at 150° C. for 10 min. The reaction was extracted with water and ethyl acetate. The organic layer was dried over magnesium sulfate and concentrated. The residue was purified using Biotage silica gel chromatography (0-100% ethyl acetate in hexanes) to give an oil. The oil was treated with 4N hydrochloric acid in dioxane. The reaction was concentrated and then passed through Strata XC-ion exchange column. Product was released from the column with ammonium hydroxide in methanol (5%). Fractions containing product were combined and concentrated under reduced pressure. The resulting material was triturated with ether to give a yellow solid (56 mg, 80% yield). $^1$H NMR (400 MHz, DMSO-$d_6$) δ 8.31 (s, 1H), 7.83 (d, J=8.6, 2H), 6.86 (d, J=9.0, 2H), 3.72 (d, J=7.0, 2H), 2.94 (d, J=12.1, 2H), 2.43 (t, J=10.7, 2H), 2.00 (m, 1H), 1.55 (d, J=13.3, 2H), 1.11-1.21 (m, 2H); MS (ESI) m/z 326.1 [M+1]$^+$; mp 300° C. dec.

5.1.92 Example 92

SYNTHESIS OF 1-(((1R,4R)-4-AMINOCYCLOHEXYL)METHYL)-6-(4-HYDROXYPHENYL)-1H-IMIDAZO[4,5-B]PYRAZIN-2(3H)-ONE

A. 2-(((1r,4r)-4-(Dibenzylamino)cyclohexyl)methyl) isoindoline-1,3-dione. ((1r,4r)-4-(Dibenzylamino)cyclohexyl)methanol (5.0 g, 16 mmol), phthalimide (2.6 g, 18 mmol), and triphenylphosphine (4.7 g, 18 mmol) were dissolved in tetrahydrofuran. Diisopropyl azodicarboxylate (3.4 mL, 18 mmol) was added and the reaction was stirred at room temperature overnight. The reaction was extracted with 1N hydrochloric acid and ethyl acetate. The aqueous layer was neutralized with 1M sodium hydroxide and then extracted with ethyl acetate. The organic layer was dried over magnesium sulfate, filtered and concentrated to give a white solid (3.1 g, 44% yield). MS (ESI) m/z 439.1 [M+1]$^+$.

B. (1r,4r)-4-(Aminomethyl)-N,N-dibenzylcyclohexanamine. A solution of 2-(((1r,4r)-4-(dibenzylamino)cyclohexyl)methyl)isoindoline-1,3-dione (1.5 g, 3.4 mmol) and hydrazine hydrate (2 mL) in ethanol (10 mL) was heated to 50° C. for 1 h. The reaction was triturated with water and ethyl acetate to give a white solid (0.7 g, 69% yield). MS (ESI) m/z 309.3 [M+1]+.

C. 1-(((1r,4r)-4-(Dibenzylamino)cyclohexyl)methyl)-6-(4-hydroxyphenyl)-1H-imidazo[4,5-b]pyrazin-2(3H)-one. 4-(6-Bromo-5-(N,N-bis-boc-amino)pyrazin-2-yl)phenol (see Example 46.F) (100 mg, 0.2 mmol), (1r,4r)-4-(aminomethyl)-N,N-dibenzylcyclohexanamine (0.32 g, 2 mmol), and N-methylpyrrolidinone (2 mL) were heated in an oil-bath to 150° C. for 16 h. The reaction was extracted with water and ethyl acetate. The organic layer was dried over magnesium sulfate, filtered and concentrated. The residue was purified using Biotage silica gel chromatography (0-100% ethyl acetate in hexanes) to give a white solid (100 mg, 60% yield). MS (ESI) m/z 520.3 [M+1]+.

D. 1-(((1r,4r)-4-Aminocyclohexyl)methyl)-6-(4-hydroxyphenyl)-1H-imidazo[4,5-b]pyrazin-2(3H)-one. 1-(((1r,4r)-4-(Dibenzylamino)cyclohexyl)methyl)-6-(4-hydroxyphenyl)-1H-imidazo[4,5-b]pyrazin-2(3H)-one (100 mg, 0.2 mmol), palladium hydroxide (100 mg), and methanol (5 mL) were stirred under a hydrogen balloon for 16 h. The reaction solution was filtered through celite and the filtrate was concentrated before purification by reverse-phase semi-preparatory HPLC (5-40% acetonitrile+0.1% TFA in $H_2O$+0.1% TFA, over 30 min). Product fractions were passed through StrataXC ion-exchange column to remove trifluoroacetic acid and then released by treatment with 2M ammonium hydroxide in methanol. The solution was concentrated and then triturated with ether to give a white solid (17 mg, 26% yield). $^1$H NMR (400 MHz, DMSO-$d_6$) δ 8.26 (s, 1H), 7.81 (d, J=8.6, 2H), 6.85 (d, J=9.0, 2H), 3.67 (d, J=7.0, 2H), 2.58 (m, 1H), 1.78 (m, 3H), 1.64 (m, 2H), 1.05 (m, 4H); MS (ESI) m/z 340.5 [M+1]+; mp 290° C. dec.

5.1.93 Example 93

SYNTHESIS OF 1-(CYCLOHEXYLMETHYL)-6-(1-OXOISOINDOLIN-5-YL)-1H-IMIDAZO[4,5-B]PYRAZIN-2(3H)-ONE

A. 5-Bromoisoindolin-1-one. A solution of methyl 4-bromo-2-bromomethyl benzoate (2.0 g, 6.5 mmol) was treated with a solution of ammonia in methanol (7.0M, 5 mL) and ammonium hydroxide (1 mL). The resulting reaction mixture was allowed to stir overnight at rt. The reaction mixture was partitioned between water and methylene chloride. The organic layer was washed with brine, dried over magnesium sulfate, filtered and the volatiles were removed under reduced pressure. The crude product (620 mg) was used without further purification. MS (ESI) m/z 212.0 [M+1]+.

B. 5-(4,4,5,5-Tetramethyl-1,3,2-dioxaborolan-2-yl)isoindolin-1-one. Bis (pinacolato)diboron (815 mg, 3.21 mmol), dichloro[1,1'-bis(diphenylphosphino) ferrocene]palladium (II) dichloromethane (240 mg, 0.29 mmol) and potassium acetate (860 mg, 8.76 mmol) were successively added to a solution of 5-bromoisoindolin-1-one (620 mg, 2.92 mmol) in methylene chloride (15 mL), followed by DMSO (5 mL).). The resulting reaction mixture was heated at 100° C. for 4 h. Upon cooling, the crude mixture was diluted with water, extracted with methylene chloride (3×); the combined organic fractions were washed with water, brine, dried over magnesium sulfate, filtered, and the volatiles were removed under reduced pressure. The crude product was taken into hexanes, sonicated, and the precipitate was collected by filtration to afford the desired product (250 mg, 33%). MS (ESI) m/z 260.3 [M+1]+.

C. 1-(Cyclohexylmethyl)-6-(1-oxoisoindolin-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (250 mg, 0.80 mmol), 5-(4,4,5,5-tetramethyl-1,3,2-dioxaborolan-2-yl)isoindolin-1-one (250 mg, 0.96 mmol), dichloro[1,1'-bis(diphenylphosphino)ferrocene]palladium (II) dichloromethane (65 mg, 0.08 mmol) and potassium phosphate (680 mg, 3.2 mmol) in DMF (25 mL) and water (4 mL) were reacted according to General Procedure B. The product was purified by reverse-phase semi-preparatory HPLC (30-100% acetonitrile+0.1% TFA in $H_2O$+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (51 mg, 17% yield) as a tan solid. $^1$H NMR (400 MHz, DMSO-$d_6$) δ 12.12 (s, 1H), 8.61 (s, 1H), 8.58 (s, 1H), 8.20 (s, 1H), 8.14 (d, J=8.0, 2H), 7.76 (d, J=8.0, 2H), 4.46 (s, 2H), 3.74 (d, J=7.2, 2H), 1.91 (m, 1H), 1.68 (m, 4H), 1.60 (m, 1H), 1.17 (m, 3H), 1.05 (m, 2H); MS (ESI) m/z 364.2 [M+1]+; mp 337-339° C.

5.1.94 Example 94

SYNTHESIS OF 1-(CYCLOHEXYLMETHYL)-6-(2-METHOXYPYRIDIN-4-YL)-1H-IMIDAZO[4,5-B]PYRAZIN-2(3H)-ONE

A. 1-(Cyclohexylmethyl)-6-(2-methoxypyridin-4-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.300 g, 0.96 mmol), 2-methoxypyridine-4-boronic acid (0.177 g, 1.16 mmol), and [1,1'-bis(diphenylphosphino)ferrocene]dichloropalladium(II) complex with dichloromethane (1:1) (0.082 g, 0.1 mmol), potassium phosphate (0.818 g, 3.86 mmol), water (2 ml) and dimethylformamide (10 mL) were reacted according to General Procedure B. The solution was condensed under reduced pressure and the product was isolated using Biotage silica gel chromatography (0-10% methanol in dichloromethane). Fractions containing product were concentrated to give the product (0.145 g, 44% yield). $^1$H NMR (400 MHz, CD$_3$OD), δ 8.65 (s, 1H) 8.26 (dd, J=5.6, 1.6, 1H), 7.64 (dd, J=5.6, 1.6, 1H), 7.43 (d, J=0.8, 1H), 3.90 (s, 3H), 3.74 (d, J=7.2, 2H), 1.92 (m, 1H), 2.02 (m, 1H) 1.68 (m, 5H), 1.18 (m, 5H); MS (ESI) m/z 340.4 [M+1]+; mp 295-297° C.

5.1.95 Example 95

SYNTHESIS OF 1-(CYCLOHEXYLMETHYL)-6-(6-HYDROXYPYRIDIN-3-YL)-1H-IMIDAZO[4,5-B]PYRAZIN-2(3H)-ONE

A. 1-(Cyclohexylmethyl)-6-(6-hydroxypyridin-3-yl)-1H-imidazo[4,5-b]pyrazin-2(3H)-one. 1-(Cyclohexylmethyl)-6-(2-methoxypyridin-4-yl)-1H-imidazo[4,5-b]pyrazin-2(3H)-one (See Example 94.A) (0.125 g, 0.369 mmol) was added to aqueous hydrobromic acid 48% (6 mL) and heated to 100° C. for 1 h. The solution was condensed under reduced pressure and the product was purified by reverse-phase semi-preparatory HPLC (5-70% acetonitrile+0.1% TFA in $H_2O$+0.1% TFA, over 30 min). Fractions containing clean product were neutralized with potassium carbonate and extracted with ethyl acetate. Organic fractions were pooled, dried over magnesium sulfate, filtered and concentrated under reduced pressure. The resulting solid was dried under high vacuum to give the product (0.008 g, 8.0% yield). $^1$H NMR (400 MHz, CD$_3$OD), δ 8.32 (s, 1H), 8.12 (dd, J=9.6, 2.8, 1H), 8.02 (s, 1H), 6.48 (d, J=9.2, 1H), 3.70 (d, J=7.2, 2H), 3.84 (d, J=7.2, 2H), 1.90 (m, 1H), 1.65 (m, 5H), 1.19 (m, 3H), 1.05 (m, 2H); MS (ESI) m/z 326 [M+1]$^+$; mp >400° C.

5.1.96 Example 96

SYNTHESIS OF 4-(3-((1R,4R)-4-HYDROXYCYCLOHEXYL)-2-OXO-2,3-DIHYDRO-1H-IMIDAZO[4,5-B]PYRAZIN-5-YL)BENZAMIDE

A. (1r,4r)-4-(3-Amino-6-bromopyrazin-2-ylamino)cyclohexanol. 3,5-Dibromopyrazin-2-amine (5.00 g, 19.9 mmol), (1r,4r)-4-aminocyclohexanol (4.58 g, 39.8 mmol), diisopropylethylamine (3.842 g, 39.8 mmol), and n-butanol (120 mL) were heated in a sealed tube at 130° C. for 18 h. The solution was condensed under reduced pressure and the product was purified by reverse-phase preparatory HPLC (30-100% acetonitrile+0.1% TFA in H$_2$O+0.1% TFA, over 30 min). Fractions containing product were concentrated to give the title compound (3.9 g, 68% yield). MS (ESI) m/z 288.2 [M+1]$^+$.

B. 6-Bromo-1-((1r,4r)-4-hydroxycyclohexyl)-1H-imidazo[4,5-b]pyrazin-2(3H)-one. (1r,4r)-4-(3-Amino-6-bromopyrazin-2-ylamino)cyclohexanol (3.90 g, 13.6 mmol), 1,1'-carbonyldiimidazole (2.76 g, 17.0 mmol), and tetrahydrofuran (60 mL) were heated in a sealed tube at 120° C. for 18 h. The solution was condensed under reduced pressure and the product was purified by reverse-phase preparatory HPLC (30-100% acetonitrile+0.1% TFA in H$_2$O+0.1% TFA, over 30 min). Fractions containing product were concentrated to give the product (0.884 g, 21% yield). MS (ESI) m/z 314.2 [M+1]$^+$.

C. 4-(3-((1r,4r)-4-Hydroxycyclohexyl)-2-oxo-2,3-dihydro-1H-imidazo[4,5-b]pyrazin-5-yl)benzamide. 6-Bromo-1-((1r,4r)-4-hydroxycyclohexyl)-1H-imidazo[4,5-b]pyrazin-2 (3H)-one (0.300 g, 0.96 mmol), 4-carboxamidephenylboronic acid (0.190 g, 1.15 mmol), and [1,1'-bis(diphenylphosphino)ferrocene]dichloropalladium(II) complex with dichloromethane (1:1) (0.082 g, 0.1 mmol), potassium phosphate (0.812 g, 3.83 mmol), water (2 ml) and dimethylformamide (7 mL) were reacted according to General Procedure B. The solution was condensed under reduced pressure and the product was crystallized from ethyl acetate to give the product (0.302 g, 89% yield). $^1$H NMR (400 MHz, CD$_3$OD), δ 8.34 (s, 1H) 8.08 (d, J=8.4, 2H), 7.96 (d, J=8.8, 2H), 7.43 (d, J=0.8, 1H), 4.41 (m, 1H), 3.74 (m, 1H), 2.66 (m, 2H), 2.12 (d, J=10.4, 2H) 1.87 (d, J=10.8, 2H), 1.52 (m, 2H); MS (ESI) m/z 354.4 [M+1]$^+$; mp 301-303° C.

5.1.97 Example 97

SYNTHESIS OF 2-(4-(3-(CYCLOHEXYLMETHYL)-2-OXO-2,3-DIHYDRO-1H-IMIDAZO[4,5-B]PYRAZIN-5-YL)PHENYL)ACETIC ACID

A. Methyl 2-(4-(4,4,5,5-tetramethyl-1,3,2-dioxaborolan-2-yl)phenyl)acetate. In a sealed vessel, a solution of 2-(4-(4,4,5,5-tetramethyl-1,3,2-dioxaborolan-2-yl)phenyl)acetic acid (650 mg, 2.47 mmol) in methanol (10 mL) was treated with concentrated hydrochloric acid (few drops). The resulting reaction mixture was allowed to stir at rt. Upon completion of the reaction, the volatiles were removed under reduced pressure. The crude product (650 mg, 100% yield) was used without purification in the next step. MS (ESI) m/z 277.3 [M+1]$^+$.

B. Methyl 2-(4-(3-(cyclohexylmethyl)-2-oxo-2,3-dihydro-1H-imidazo[4,5-b]pyrazin-5-yl)phenyl)acetate. Bromo-1-(cyclohexylmethyl)-4-imidazolino[4,5-b]pyrazin-2-one (200 mg, 0.64 mmol), methyl 2-[4-(4,4,5,5-tetramethyl-1,3,2-dioxaborolan-2-yl)phenyl]acetate (213 mg, 0.77 mmol), dichloro[1,1'-bis(diphenylphosphino)ferrocene]palladium (II) dichloromethane (53 mg, 0.06 mmol) and potassium phosphate (543 mg, 2.56 mmol) in DMF (20 mL) and water (5 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (95 mg, 39 yield) as a tan solid. MS (ESI) m/z 381.4 [M+1]$^+$.

C. 2-(4-(3-(Cyclohexylmethyl)-2-oxo-2,3-dihydro-1H-imidazo[4,5-b]pyrazin-5-yl)phenyl)acetic acid A solution of methyl 2-(4-(3-(cyclohexylmethyl)-2-oxo-2,3-dihydro-1H-imidazo[4,5-b]pyrazin-5-yl)phenyl)acetate (40 mg, 0.13 mmol) in tetrahydrofuran (1 mL) was treated with 1N lithium hydroxide (1 mL). After 2 h, the reaction was complete. Tetrahydrofuran was removed under reduced pressure and the residue was treated with acetic acid until pH ~5. A white precipitate formed and was collected by filtration to provide the title compound (20 mg, 55% yield). $^1$H NMR (400 MHz, DMSO-d$_6$) δ 12.38 (s, 1H), 12.02 (s, 1H) 8.47 (s, 1H), 7.96 (d, J=8.4, 2H), 7.37 (d, J=8.4, 2H), 3.73 (d, J=7.2, 2H), 3.62 (s, 2H), 2.08 (m, 1H), 1.66 (m, 5H), 1.17 (m, 3H), 1.15 (m, 2H); MS (ESI) m/z 367.2 [M+1]$^+$.

5.1.98 Example 98

SYNTHESIS OF 2-(4-(3-(CYCLOHEXYLMETHYL)-2-OXO-2,3-DIHYDRO-1H-IMIDAZO[4,5-B]PYRAZIN-5-YL)PHENYL)ACETAMIDE

A. 2-(4-(3-(Cyclohexylmethyl)-2-oxo-2,3-dihydro-1H-imidazo[4,5-b]pyrazin-5-yl)phenyl)acetamide. A solution of methyl 2-(4-(3-(cyclohexylmethyl)-2-oxo-2,3-dihydro-1H-imidazo[4,5-b]pyrazin-5-yl)phenyl)acetate (See Example 97.B) (40 mg, 0.13 mmol) was treated with a solution of ammonia in methanol (7N, 2 mL) and ammonium hydroxide. The resulting solution was allowed to stir at rt. Upon completion of the reaction, the volatiles were removed under reduced pressure. The residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (50 mg, 47% yield). $^1$H NMR (400 MHz, DMSO-d$_6$) δ 12.01 (s, 1H), 8.46 (s, 1H). 7.94 (d, J=8.0, 2H), 7.49 (s, 1H), 7.37 (d, J=8.4 2H), 6.92 (s, 1H), 3.73 (d, J=7.2, 2H), 3.62 (s, 2H), 1.90 (m, 1H), 1.66 (m, 5H), 1.17 (m, 3H), 1.03 (m, 2H); MS (ESI) m/z 366.1 [M+1]$^+$; mp 272-274° C.

5.1.99 Example 99

SYNTHESIS OF 1-(CYCLOHEXYLMETHYL)-6-(2-OXOINDOLIN-6-YL)-1H-IMIDAZO[4,5-B]PYRAZIN-2(3H)-ONE

A. 6-(Trimethylstannyl)indolin-2-one. A solution of 6-bromoindole (0.5 g, 2.35 mmol) in dry toluene (30 mL) was treated with hexamethylditin (1.07 g, 3.29 mmol) and tetrakis(triphenylphosphine)palladium(0) (271 mg, 0.23 mmol) in a sealed tube at 92° C. for 1.5 h. The volatiles were removed under reduced pressure and the crude product was purified by biotage (0-30% EtOAc in hexanes) to afford the title compound (265 mg, 38%). MS (ESI) m/z 298.2 [M+1]$^+$.

B. 1-(Cyclohexylmethyl)-6-(2-oxoindolin-6-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (100 mg, 0.32 mmol), 6-(trimethylstannyl)indolin-2-one (114 mg, 0.38 mmol), dichlorobis(triphenylphosphine)palladium(II) (44 mg, 0.06 mmol) in DMF (5 mL) were reacted for 1 h at 115° C. The product was purified by reverse-phase semi-preparatory HPLC (30-100% acetonitrile+0.1% TFA in H$_2$O+0.1% TFA, over 30 min). The desired fractions were concentrated, the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (29 mg, 24% yield) as a tan solid. $^1$H NMR (400 MHz, DMSO-d$_6$) δ 12.03 (s, 1H), 10.49 (s, 1H), 8.42 (s, 1H), 7.58 (d, J=8.0, 1H), 7.44 (s, 1H), 7.39 (d, J=8.0, 1H), 3.72 (d, J=7.2, 2H), 3.52 (s, 2H), 1.90 (m, 1H), 1.66 (m, 5H), 1.17 (m, 3H), 1.03 (m, 2H); MS (ESI) m/z 364.0 [M+1]$^+$; mp 334-336° C.

5.1.100 Example 100

SYNTHESIS OF 4-(3-(CYCLOHEXYLMETHYL)-2-OXO-2,3-DIHYDRO-1H-IMIDAZO[4,5-B]PYRAZIN-5-YL)-3-METHYLBENZOIC ACID

A. 3-Methyl-4-(4,4,5,5-tetramethyl-1,3,2-dioxaborolan-2-yl)benzoic acid. Bis(pinacolato)diboron (3.07 g, 12.09 mmol), dichloro[1,1'-bis(diphenylphosphino) ferrocene]palladium (II) dichloromethane (114 mg, 0.14 mmol) and triethylamine (1.95 mL, 13.95 mmol) were successively added to a solution of 4-bromo-3-methyl-benzoic acid (1.0 g, 4.65 mmol) in dioxane (15 ml). The resulting reaction mixture was allowed to stir at rt for 20 min, before being heated at 80° C. in a sealed tube. The volatiles were removed under reduced pressure, and the residual oil was partitioned between water and ethyl acetate. The aqueous phase was extracted with ethyl acetate (2×). The combined organic fractions were dried over magnesium sulfate, filtered and concentrated. The crude product was used without further purification. MS (ESI) m/z 263.2 [M+1]$^+$.

B. 4-(3-(Cyclohexylmethyl)-2-oxo-2,3-dihydro-1H-imidazo[4,5-b]pyrazin-5-yl)-3-methyl benzoic acid. 6-Bromo-1-(cyclohexylmethyl)-1H-imidazo[4,5-b]pyrazin-2(3H)-one (See Example 55.B) (300 mg, 0.96 mmol), 3-methyl-4-(4,4,5,5-tetramethyl-1,3,2-dioxaborolan-2-yl)benzoic acid (303 mg, 1.15 mmol), dichloro[1,1'-bis(diphenylphosphino)ferrocene]palladium (II) dichloromethane (80 mg, 0.09 mmol) and potassium phosphate (815 mg, 3.84 mmol) in DMF (25 mL) and water (5 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (43 mg, 12% yield) as a colorless solid. $^1$H NMR (400 MHz, DMSO-d$_6$) δ 12.99 (s, 1H), 12.11 (s, 1H), 8.07 (s, 1H), 7.88 (s, 1H), 7.85 (d, J=8.0, 1H), 7.53 (d, J=8.0, 1H), 3.67 (d, J=7.2, 1H), 1.88 (m, 1H), 1.64 (m, 2H), 1.61 (m, 2H), 1.14 (m, 3H), 1.01 (m, 2H); MS (ESI) m/z 367.2 [M+1]$^+$; mp 244-247° C.

5.1.101 Example 101

SYNTHESIS OF N-METHYL-4-(2-OXO-3-((TETRAHYDRO-2H-PYRAN-4-YL)METHYL)-2,3-DIHYDRO-1H-IMIDAZO[4,5-B]PYRAZIN-5-YL)BENZAMIDE

A. 6-Bromo-N$^2$-((tetrahydro-2H-pyran-4-yl)methyl)pyrazine-2,3-diamine. In a sealed tube, a solution of 5-bromopyrazine-2,3-diamine (6.98 g, 2.78 mmol), (tetrahydro-2H-pyran-4-yl)methanamine (4.0 g, 3.47 mmol), diisopropylethylamine (6.06 mL, 3.47 mmol) in n-butanol (100 mL) was heated at 120° C. for 17 h. The volatiles were removed under reduced pressure. The residue was taken up in hexanes/diethylether and sonicated. The resulting precipitate was collected by filtration to provide the desired product (5.10 g, 64% yield). MS (ESI) m/z 289.1 [M+1]$^+$.

B. 6-Bromo-1-((tetrahydro-2H-pyran-4-yl)methyl)-1H-imidazo[4,5-b]pyrazin-2(3H)-one. In a sealed tube, a solution of 6-bromo-N$^2$-((tetrahydro-2H-pyran-4-yl)methyl)pyrazine-2,3-diamine (5.05 g, 0.017 mmol), 1,1'-carbonyldiimidazole (3.52 g, 0.021 mmol) in tetrahydrofuran (40 mL) was heated at 95° C. More 1,1'-carbonyldiimidazole (1.7 g, 10 mmol) was added and the reaction mixture was heated for an additional 12 h. The volatiles were removed under reduced pressure. The residue was taken into hexanes/diethylether and sonicated. The resulting precipitate was collected by filtration, rinsed with hexanes, and dried in vacuum oven to afford the title compound (3.5 g, 67% yield) as a tan solid. MS (ESI) m/z 315.9 [M+1]$^+$.

C. N-Methyl-4-(2-oxo-3-((tetrahydro-2H-pyran-4-yl)methyl)-2,3-dihydro-1H-imidazo[4,5-b]pyrazin-5-yl)benzamide. 6-Bromo-1-((tetrahydro-2H-pyran-4-yl)methyl)-1H-imidazo[4,5-b]pyrazin-2(3H)-one (300 mg, 0.95 mmol), [4-(N-methylaminocarbonyl)phenyl]boronic acid (205 mg, 1.15 mmol), dichloro[1,1'-bis(diphenylphosphino)ferrocene]palladium (II) dichloromethane (80 mg, 0.09 mmol) and potassium phosphate (805 mg, 3.8 mmol) in DMF (30 mL) and water (8 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL), heated at 100° C. until completely dissolved. Water was added upon cooling and the desired product precipitated out of solution. The precipitate was collected by vacuum filtration, washed with water and dried under high vacuum to provide the title compound (165 mg, 47% yield) as a colorless solid. $^1$H NMR (400 MHz, DMSO-d$_6$) δ 12.11 (s, 1H), 8.58 (s, 1H), 8.50 (d, J=4.8, 1H), 8.12 (d, J=8.4, 1H), 7.93 (d, J=8.4, 1H), 3.82 (m, 2H), 3.79 (d, J=7.2, 2H), 3.25 (m, 2H), 2.14 (m, 1H), 1.57 (m, 2H), 1.31 (m, 2H); MS (ESI) m/z 368.1 [M+1]$^+$; mp 328-330° C.

5.1.102 Example 102

SYNTHESIS OF 4-(2-OXO-3-((TETRAHYDRO-2H-PYRAN-4-YL)METHYL)-2,3-DIHYDRO-1H-IMIDAZO[4,5-B]PYRAZIN-5-YL)BENZAMIDE

A. 4-(2-oxo-3-((Tetrahydro-2H-pyran-4-yl)methyl)-2,3-dihydro-1H-imidazo[4,5-b]pyrazin-5-yl)benzamide.

6-Bromo-1-((tetrahydro-2H-pyran-4-yl)methyl)-1H-imidazo[4,5-b]pyrazin-2(3H)-one (See Example 101.B) (500 mg, 1.59 mmol), (4-aminocarbonylphenyl)boronic acid (317 mg, 1.92 mmol), dichloro[1,1'-bis(diphenylphosphino)ferrocene]palladium (II) dichloromethane (130 mg, 0.16 mmol) and potassium phosphate (1.35 g, 6.36 mmol) in DMF (40 mL) and water (10 mL) were reacted according to General Procedure B. The product was purified by reverse-phase semi-preparatory HPLC (30-100% acetonitrile+0.1% TFA in $H_2O$+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (165 mg, 47% yield) as a colorless solid. $^1H$ NMR (400 MHz, DMSO-$d_6$) δ 12.11 (s, 1H), 8.59 (s, 1H), 8.12 (d, J=8.4, 2H), 8.03 (s, 1H), 7.97 (d, J=8.4, 2H), 7.42 (s, 1H), 3.82 (m, 2H), 3.79 (d, J=7.2, 2H), 3.25 (m, 2H), 2.14 (m, 1H), 1.57 (m, 2H), 1.32 (m, 2H); MS (ESI) m/z 354.1 [M+1]$^+$; mp 273-275° C.

5.1.103 Example 103

SYNTHESIS OF 7-(4-HYDROXYPHENYL)-1-(3-METHOXYBENZYL)-3,4-DIHYDROPYRAZINO[2,3-B]PYRAZIN-2(1H)-ONE

A. Methyl 2-(3,5-dibromopyrazin-2-ylamino)acetate. 3,5-Dibromopyrazin-2-amine (2.5 g, 26 mmol), ethyl glyoxalate (50% in toluene, 8 mL, 39 mmol), dibutyltin dichloride (0.4 g, 1.3 mmol), and methanol (20 mL) were stirred together at room temperature for 16 h. Sodium borohydride (1.5 g, 39 mmol) was added in small portions. The reaction was concentrated and then purified on silica gel column (0-100% ethyl acetate in hexanes) to give the desired product (0.8 g, 19% yield) as a white solid. MS (ESI) m/z 246.1 [M+1]$^+$.

B. 7-Bromo-1-(3-methoxybenzyl)-3,4-dihydropyrazino[2,3-b]pyrazin-2(1H)-one. Methyl 2-(3,5-dibromopyrazin-2-ylamino)acetate (0.58 g, 1.8 mmol), 3-methoxybenzylamine (227 µL, 1.8 mmol), diisopropylethylamine (1 mL), and dimethylsulfoxide (1 mL) were heated to 100° C. for 3 d under nitrogen. The reaction was extracted with ethyl acetate and water. The organic layer was dried with magnesium sulfate, filtered and concentrated. The residue was purified on silica gel column (0-100% ethyl acetate in hexanes) to give the title compound (124 mg, 20% yield) as a pink solid. MS (ESI) m/z 349.0 [M+1]$^+$.

C. 7-(4-Hydroxyphenyl)-1-(3-methoxybenzyl)-3,4-dihydropyrazino[2,3-b]pyrazin-2(1H)-one. 7-Bromo-1-(3-methoxybenzyl)-3,4-dihydropyrazino[2,3-b]pyrazin-2(1H)-one (124 mg, 0.35 mmol), 4-hydroxyphenylboronic acid (54 mg, 0.39 mmol), dichloro[1,1'-bis(diphenylphosphino)ferrocene]palladium(II) dichloromethane adduct (13 mg, 0.017 mmol), 1M sodium carbonate (1 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layer was dried over magnesium sulfate, filtered and concentrated. The residue was purified using Biotage silica gel chromatography (0-100% ethyl acetate in hexanes) to give a white solid (49 mg, 38% yield). $^1H$ NMR (400 MHz, DMSO-$d_6$) δ 9.56 (s, 1H), 8.09 (s, 1H), 7.71 (d, J=8.6, 2H), 7.45 (s, 1H), 7.21 (t, J=7.8, 1H), 6.96 (s, 1H), 6.92 (d, J=7.8, 1H), 6.78 (d, J=8.6, 2H), 5.23 (s, 2H), 4.25 (s, 2H), 3.69 (s, 3H); MS (ESI) m/z 363.0 [M+1]$^+$.

5.1.104 Example 104

SYNTHESIS OF 6-(4-(2-HYDROXYPROPAN-2-YL)PHENYL)-1-((TETRAHYDRO-2H-PYRAN-4-YL)METHYL)-1H-IMIDAZO[4,5-B]PYRAZIN-2(3H)-ONE

A. Methyl 4-(2-oxo-3-((tetrahydro-2H-pyran-4-yl)methyl)-2,3-dihydro-1H-imidazo[4,5-b]pyrazin-5-yl)benzoate. 6-Bromo-1-((tetrahydro-2H-pyran-4-yl)methyl)-1H-imidazo[4,5-b]pyrazin-2(3H)-one (See Example 101.B) (500 mg, 1.59 mmol), 4-(methoxycarbonyl)phenylboronic acid (317 mg, 1.92 mmol), dichloro[1,1'-bis(diphenylphosphino)ferrocene]palladium (II) dichloromethane (130 mg, 0.16 mmol) and potassium phosphate (1.35 g, 6.36 mmol) in DMF (40 mL) and water (10 mL) were reacted according to General Procedure B. The product was purified by reverse-phase semi-preparatory HPLC (30-100% acetonitrile+0.1% TFA in $H_2O$+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (180 mg, 31% yield) as a colorless solid. MS (ESI) m/z 369.2 [M+1]$^+$.

B. 6-(4-(2-Hydroxypropan-2-yl)phenyl)-1-((tetrahydro-2H-pyran-4-yl)methyl)-1H-imidazo[4,5-b]pyrazin-2(3H)-one. Methyl 4-(2-oxo-3-((tetrahydro-2H-pyran-4-yl)methyl)-2,3-dihydro-1H-imidazo[4,5-b]pyrazin-5-yl)benzoate (0.150 g, 0.408 mmol) was dissolved in tetrahydrofuran (15 mL) and cooled to −78° C. Methylmagnesium bromide (1.4M in toluene/tetrahydrofuran, 1.16 mL, 1.63 mmol) was added and the reaction was allowed to warm to rt and stirred for 4 h. The reaction was quenched with water and extracted with ethyl acetate. The product was purified using reverse-phase semi-preparatory HPLC (30-70% acetonitrile+0.1% TFA in $H_2O$+0.1% TFA, over 40 min). Fractions containing the desired material were combined and concentrated under reduced pressure. The residue was dissolved in hot DMSO and water added to induce precipitation. The resulting solid was filtered, washed with water and dried under vacuum to afford the title compound (0.067 g, 45% yield). $^1H$ NMR (400 MHz, DMSO-$d_6$) δ 12.02 (s, 1H), 8.45 (s, 1H), 7.94 (d, J=8.4, 2H), 8.03 (s, 1H), 7.56 (d, J=8.4, 2H), 3.82 (m, 2H), 3.78 (d, J=6.8, 2H), 3.25 (m, 2H), 2.14 (m, 1H), 1.57 (m, 2H), 1.45 (s, 6H), 1.32 (m, 2H); MS (ESI) m/z 369.1 [M+1]$^+$; mp 212-214° C.

5.1.105 Example 105

SYNTHESIS OF 6-(1H-INDOL-5-YL)-1-((TETRAHYDRO-2H-PYRAN-4-YL)METHYL)-1H-IMIDAZO [4,5-B]PYRAZIN-2(3H)-ONE

A. 6-(1H-Indol-5-yl)-1-((tetrahydro-2H-pyran-4-yl)methyl)-1H-imidazo[4,5-b]pyrazin-2(3H)-one. 6-Bromo-1-((tetrahydro-2H-pyran-4-yl)methyl)-1H-imidazo[4,5-b]pyrazin-2(3H)-one (See Example 101.B) (300 mg, 0.95 mmol), 5-indolylboronic acid (185 mg, 1.15 mmol), dichloro[1,1'-bis(diphenylphosphino) ferrocene]palladium (II) dichloromethane (80 mg, 0.09 mmol) and potassium phosphate (812 mg, 3.83 mmol) in DMF (20 mL) and water (4 mL) were reacted according to General Procedure B. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (89 mg, 24% yield) as a tan solid. $^1$H NMR (400 MHz, DMSO-d$_6$) δ 11.93 (s, 1H), 11.21 (s, 1H), 8.45 (s, 1H), 8.20 (s, 1H), 7.78 (dd, J=8.4, 1.6, 1H), 7.48 (d, J=8.4, 1H), 7.39 (m, 1H), 6.52 (s, 1H), 3.84 (m, 2H), 3.80 (d, J=7.2, 2H), 3.26 (t, J=10, 2H), 2.15 (m, 1H), 1.58 (m, 2H), 1.33 (m, 2H); MS (ESI) m/z 350.1 [M+1]$^+$; mp 305-308° C.

5.1.106 Example 106

SYNTHESIS OF 6-(4-(4H-1,2,4-TRIAZOL-3-YL)PHENYL)-1-((TETRAHYDRO-2H-PYRAN-4-YL)METHYL)-1H-IMIDAZO[4,5-B]PYRAZIN-2(3H)-ONE

A. 6-(4-(4H-1,2,4-Triazol-3-yl)phenyl)-1-((tetrahydro-2H-pyran-4-yl)methyl)-1H-imidazo[4,5-b]pyrazin-2(3H)-one. A solution of 4-(2-oxo-3-((tetrahydro-2H-pyran-4-yl)methyl)-2,3-dihydro-1H-imidazo[4,5-b]pyrazin-5-yl)benzamide (See Example 102.A) (300 mg, 0.84 mmol) in DMF (3 mL) was treated with N,N-dimethylformamide dineopentyl acetal (2 mL). The resulting reaction mixture was heated at 80° C. for 1.5 h, and the volatiles were removed under reduced pressure. The residual oil was taken up in hydrazine (3 mL) and acetic acid (10 drops) was added. After 1.5 h, the reaction was found to be complete. The volatiles were removed under reduced pressure. The product was purified by reverse-phase preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (39 mg, 12% yield) as a tan solid. $^1$H NMR (400 MHz, DMSO-d$_6$) δ 12.09 (s, 1H), 8.65 (s, 1H), 8.56 (s, 1H), 8.22 (d, J=8.8, 1H), 8.08 (m, 4H), 3.85 (m, 2H), 3.80 (d, J=7.2, 2H), 3.26 (m, 2H), 2.15 (m, 1H), 1.58 (m, 2H), 1.32 (m, 2H); MS (ESI) m/z 378.1 [M+1]$^+$; mp 342-345° C.

5.1.107 Example 107

SYNTHESIS OF 6-(1H-BENZO[D]IMIDAZOL-5-YL)-1-(CYCLOHEXYLMETHYL)-1H-IMIDAZO[4,5-B]PYRAZIN-2(3H)-ONE

A. tert-Butyl 5-bromo-1H-benzo[d]imidazole-1-carboxylate. 5-Bromo-1H-benzo[d]imidazole (0.300 g, 1.52 mmol), di-tert-butyl dicarbonate (0.397 g, 1.82 mmol), triethyl amine (0.307 g, 3.04 mmol) and tetrahydrofuran (10 mL) were stirred at 25° C. for 18 h. The solution was condensed under reduced pressure and the product was isolated using Biotage silica gel chromatography (0-80% ethyl acetate in hexanes). Fractions containing product were concentrated to give (0.398 g, 88% yield). MS (ESI) m/z 298 [M+1]$^+$.

B. tert-Butyl 5-(4,4,5,5-tetramethyl-1,3,2-dioxaborolan-2-yl)-1H-benzo[d]imidazole-1-carboxylate. tert-Butyl 5-bromo-1H-benzo[d]imidazole-1-carboxylate (0.300 g, 1.01 mmol), bis(pinacolato)diboron (0.283 g, 1.11 mmol), [1,1'-bis(diphenylphosphino)ferrocene]dichloropalladium (II) complex with dichloromethane (1:1) (0.074 g, 0.09 mmol), potassium acetate (0.297 g, 3.03 mmol), dichloromethane (2 mL) and methylsulfoxide (1 mL) were combined in a sealed tube and heated to 100° C. for 18 h. The solution was condensed under reduced pressure and the product was used without purification in the next step (0.363 g). MS (ESI) m/z 345 [M+1]$^+$.

C. 6-(1H-Benzo[d]imidazol-5-yl)-1-(cyclohexylmethyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.219 g, 0.70 mmol), tert-butyl 5-(4,4,5,5-tetramethyl-1,3,2-dioxaborolan-2-yl)-1H-benzo[d]imidazole-1-carboxylate (0.290 g, 0.84 mmol), [1,1'-bis(diphenylphosphino) ferrocene]dichloropalladium(II) complex with dichloromethane (1:1) (0.057 g, 0.07 mmol), potassium phosphate (0.596 g, 2.81 mmol), water (2 ml) and dimethylformamide (7 mL) were reacted according to General Procedure B. The solution was condensed under reduced pressure and the product was purified by reverse-phase semi-preparatory HPLC (5-70% acetonitrile+0.1% TFA in H$_2$O+0.1% TFA, over 30 min). Fractions containing clean product were neutralized with potassium carbonate and extracted with ethyl acetate, dried over magnesium sulfate, filtered, concentrated and dried under vacuum to give (0.060 g, 20% yield). $^1$H NMR (400 MHz, CD$_3$OD), δ 8.44 (s, 1H) 8.26 (s, 1H), 8.22 (s, 1H), 7.94 (dd, J=8.8, 1.6, 1H), 7.70 (s, 1H), 3.88 (d, J=7.2, 2H), 2.04 (m, 1H), 1.76 (m, 5H), 1.29 (m, 5H); MS (ESI) m/z 349 [M+1]$^+$; mp 217-220° C.

5.1.108 Example 108

SYNTHESIS OF 4-(2-OXO-3-(2-(TETRAHYDRO-2H-PYRAN-4-YL)ETHYL)-2,3-DIHYDRO-1H-IMIDAZO[4,5-B]PYRAZIN-5-YL)BENZAMIDE

A. 6-Bromo-N$^2$-(2-(tetrahydro-2H-pyran-4-yl)ethyl)pyrazine-2,3-diamine. 3,5-Dibromopyrazin-2-amine (5.05 g, 20.1 mmol), 2-(tetrahydro-2H-pyran-4-yl)ethanamine (4.00 g, 24.1 mmol), N,N-diisopropylethylamine (5.19 g, 40.2 mmol), and n-butanol (120 mL) were heated in a sealed tube at 130° C. for 18 h. The solution was condensed under reduced pressure and the product was recrystallized from methanol to give (5.8 g, 96% yield). MS (ESI) m/z 302.2 [M+1]$^+$.

B. 6-Bromo-1-(2-(tetrahydro-2H-pyran-4-yl)ethyl)-1H-imidazo[4,5-b]pyrazin-2(3H)-one. 6-Bromo-N$^2$-(2-(tetrahydro-2H-pyran-4-yl)ethyl)pyrazine-2,3-diamine (5.80 g, 19.3 mmol), 1,1'-carbonyldiimidazole (3.92 g, 24.1 mmol), and tetrahydrofuran (40 mL) were heated in a sealed tube at 120° C. for 18 h. The solution was condensed under reduced pressure and the product was purified by reverse-phase preparatory HPLC (30-100% acetonitrile+0.1% TFA in H$_2$O+0.1% TFA, over 30 min). Fractions containing product recrystallized from methanol to give (5.3 g, 84% yield). MS (ESI) m/z 328.2 [M+1]$^+$.

C. 4-(2-oxo-3-(2-(Tetrahydro-2H-pyran-4-yl)ethyl)-2,3-dihydro-1H-imidazol-[4,5-b]pyrazin-5-yl)benzamide. 6-Bromo-1-(2-(tetrahydro-2H-pyran-4-yl)ethyl)-1H-imidazo[4,5-b]pyrazin-2(3H)-one (0.400 g, 1.22 mmol), 4-carboxamide-phenylboronic acid (0.241 g, 1.46 mmol), [1,1'-bis(diphenylphosphino)ferrocene]dichloropalladium(II) complex with dichloromethane (1:1) (0.098 g, 0.12 mmol), potassium phosphate (1.03 g, 4.88 mmol), water (2 ml) and dimethylformamide (7 mL) were reacted according to General Procedure B. The solution was condensed under reduced pressure and the product was crystallized from dichloromethane to give (0.400 g, 89% yield). $^1$H NMR (400 MHz, CD$_3$OD) δ 8.54 (s, 1H) 8.40 (s, 1H), 8.09 (d, J=8.4, 2H), 7.94 (d, J=8.4, 1H), 4.08 (t, J=6.8, 2H), 3.92 (dd, J=11.2, 3.2, 2H), 3.64 (m, 2H), 1.83 (m, 4H), 1.59 (m, 1H), 1.38 (qd, J=12.8, 4.4, 2H); MS (ESI) m/z 368.4 [M+1]$^+$; mp 233-236° C.

5.1.109 Example 109

SYNTHESIS OF 6-(3-(2H-1,2,3-TRIAZOL-4-YL) PHENYL)-1-(CYCLOHEXYLMETHYL)-1H-IMI-DAZO[4,5-B]PYRAZIN-2(3H)-ONE

A. 1-(Cyclohexylmethyl)-6-(trimethylstannyl)-1H-imidazo[4,5-b]pyrazin-2(3H)-one. A solution of 6-bromo-1-(cyclohexylmethyl)-1H-imidazo[4,5-b]pyrazin-2(3H)-one (See Example 55.B) (100 mg, 0.32 mmol), hexamethylditin (150 mg, 0.45 mmol), tetrakis(triphenylphosphine)palladium(0) (37 mg, 0.032 mmol) in toluene (10 mL) was heated at 100° C. for 2 h. Upon completion of the reaction, toluene was removed under reduced pressure, and the residue was purified by biotage (0-50% ethyl acetate in hexanes) to afford the title compound (100 mg, 79%). MS (ESI) m/z 309.2[M+1]$^+$.

B. 6-(3-(2H-1,2,3-Triazol-4-yl)phenyl)-1-(cyclohexylmethyl)-1H-imidazo[4,5-b]pyrazin-2(3H)-one. A solution of 1-(cyclohexylmethyl)-6-(trimethylstannyl)-1H-imidazo[4,5-b]pyrazin-2(3H)-one (100 mg, 0.25 mmol), 4-(3-bromophenyl)-2H-1,2,3-triazole (70 mg, 0.30 mmol), and dichlorobis(triphenylphosphine) palladium(II) (18 mg, 0.02 mmol) in DMF (5 mL) was heated for 1.5 h at 90° C. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (4 mg, 4% yield) as a tan solid. $^1$H NMR (400 MHz, DMSO-d$_6$) δ 12.03 (s, 1H), 10.49 (s, 1H), 8.42 (s, 1H), 7.58 (d, J=8.0, 1H), 7.44 (s, 1H), 7.39 (d, J=8.0, 1H), 3.72 (d, J=7.2, 2H), 3.52 (s, 2H), 1.90 (m, 1H), 1.66 (m, 5H), 1.17 (m, 3H), 1.03 (m, 2H); MS (ESI) m/z 376.2 [M+1]$^+$; mp 299-301° C.

5.1.110 Example 110

SYNTHESIS OF 6-(4-(1H-IMIDAZOL-1-YL)PHENYL)-1-(CYCLOHEXYLMETHYL)-1H-IMI-DAZO[4,5-B]PYRAZIN-2(3H)-ONE

A. 6-(4-(1H-Imidazol-1-yl)phenyl)-1-(cyclohexylmethyl)-1H-imidazo[4,5-b]pyrazin-2(3H)-one. 1-(Cyclohexylmethyl)-6-(trimethylstannyl)-1H-imidazo[4,5-b]pyrazin-2 (3H)-one (See Example 109.A) (200 mg, 0.506 mmol), 1-(4-bromophenyl)imidazole (94 mg, 0.42 mmol), dichlorobis (triphenylphosphine)palladium(II) (104 mg, 0.10 mmol) in DMF (10 mL) were reacted for 1.5 h at 90° C. The product was purified by reverse-phase semi-preparatory HPLC (30-100% acetonitrile+0.1% TFA in H$_2$O+0.1% TFA, over 30 min). The desired fractions were concentrated, the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (16 mg, 10% yield) as a tan solid. $^1$H NMR (400 MHz, DMSO-d$_6$) δ 12.11 (s, 1H), 8.61 (s, 1H), 8.24 (d, J=8.8, 2H), 7.87 (d, J=8.8, 2H), 4.02 (d, J=8.8, 1H), 3.75 (d, J=8.8, 1H), 1.68 (m, 2H), 1.24 (m, 4H), 1.17 (m, 4H); MS (ESI) m/z 375.1 [M+1]$^+$; mp 284-287° C.

5.1.111 Example 111

SYNTHESIS OF 6-(4-(1H-1,2,4-TRIAZOL-3-YL) PHENYL)-1-((1R,4R)-4-HYDROXYCYCLO-HEXYL)-1H-IMIDAZO[4,5-B]PYRAZIN-2(3H)-ONE

A. (1r,4r)-4-(3-Amino-6-bromopyrazin-2-ylamino)cyclohexanol. 3,5-Dibromopyrazin-2-amine (5.00 g, 19.9 mmol), 4-aminocyclohexan-1-ol (4.58 g, 39.8 mmol), diisopropyl ethyl amine (3.84 g, 39.8 mmol) and n-butanol (120 mL) were heated at 130° C. for 18 h. The solution was condensed under reduced pressure and the product was purified by reverse-phase preparatory HPLC (30-100% acetonitrile+0.1% TFA in H$_2$O+0.1% TFA, over 30 min). Fractions containing product were condensed to give (3.9 g, 68% yield). MS (ESI) m/z 288.2 [M+1]$^+$.

B. 6-Bromo-1-((1r,4r)-4-hydroxycyclohexyl)-1H-imidazo[4,5-b]pyrazin-2(3H)-one. (1r,4r)-4-(3-Amino-6-bromopyrazin-2-ylamino)cyclohexanol (3.90 g, 13.6 mmol), 1,1'-carbonyldiimidazole (2.76 g, 17.0 mmol), and tetrahydrofuran (60 mL) were heated in a sealed tube at 120° C. for 18 h. The solution was condensed under reduced pressure and the product was purified by reverse-phase preparatory HPLC (30-100% acetonitrile+0.1% TFA in H$_2$O+0.1% TFA, over 30 min). Fractions containing product were condensed to give (0.884 g, 21% yield). MS (ESI) m/z 314.2 [M+1]$^+$.

C. 4-(3-((1r,4r)-4-Hydroxycyclohexyl)-2-oxo-2,3-dihydro-1H-imidazo[4,5-b]pyrazin-5-yl)benzamide. 6-Bromo-1-((1r,4r)-4-hydroxycyclohexyl)-1H-imidazo[4,5-b]pyrazin-2 (3H)-one (0.300 g, 0.96 mmol), 4-carboxamidephenylboronic acid (0.190 g, 1.15 mmol), [1,1'-bis(diphenylphosphino)ferrocene]dichloropalladium(II) complex with dichloromethane (1:1) (0.082 g, 0.10 mmol), potassium phosphate (0.812 g, 3.83 mmol), water (2 ml) and dimethylformamide (7 mL) were reacted according to General Procedure B. The solution was condensed under reduced pressure and the product was crystallized from ethyl acetate to give (0.297 g, 88% yield). MS (ESI) m/z 354.4 [M+1]$^+$.

D. (E)-N-((Dimethylamino)methylene)-4-(3-((1r,4r)-4-hydroxycyclohexyl)-2-oxo-2,3-dihydro-1H-imidazo[4,5-b] pyrazin-5-yl)benzamide. 4-(3-((1r,4r)-4-Hydroxycyclohexyl)-2-oxo-2,3-dihydro-1H-imidazo[4,5-b]pyrazin-5-yl) benzamide (0.272 g, 0.77 mmol) and N,N-dimethylformamide dineopentyl acetal (5.0 mL, 17.9 mmol) were heated together in a Biotage Emrys Optimizer microwave reactor at 100° C. for 45 min. Upon consumption of the starting material, the product was filtered to give (0.249 g, 79% yield). MS (ESI) m/z 409.5 [M+1]$^+$.

E. 6-(4-(1H-1,2,4-Triazol-3-yl)phenyl)-1-((1r,4r)-4-hydroxycyclohexyl)-1H-imidazo[4,5-b]pyrazin-2(3H)-one. (E)-N-((Dimethylamino)methylene)-4-(3-((1r,4r)-4-hydroxycyclohexyl)-2-oxo-2,3-dihydro-1H-imidazo[4,5-b] pyrazin-5-yl)benzamide (0.249 g, 0.61 mmol) was added to acetic acid (10 mL) and cooled to 0° C. Hydrazine (0.548 g, 17.1 mmol) was added dropwise and reaction was stirred at 25° C. for 4 h. The solution was condensed under reduced pressure and the product was purified by reverse-phase preparatory HPLC (20-70% acetonitrile+0.1% TFA in H$_2$O+0.1% TFA, over 30 min). Fractions containing product were condensed and converted to hydrochloride salt with ethanol (300 mL) and 12M HCl (10 mL) to give (0.010 g, 4.3% yield). $^1$H NMR (400 MHz, CD$_3$OD), δ 8.95 (s, 1H) 8.52 (s, 1H), 8.23 (d, J=6.4, 2H), 8.13 (d, J=6.4, 1H), 4.45 (m, 1H), 3.75 (m, 1H), 2.65 (qd, J=12.8, 2.8, 2H), 2.14 (m, 2H) 1.93 (m, 2H), 1.54 (m, 2H); MS (ESI) m/z 378.4 [M+1]$^+$; mp 303-305° C.

5.1.112 Example 112

SYNTHESIS OF 6-(4-(2H-TETRAZOL-5-YL)PHENYL)-1-(CYCLOHEXYLMETHYL)-1H-IMIDAZO[4,5-B]PYRAZIN-2(3H)-ONE

A. 6-(4-(2H-tetrazol-5-yl)phenyl)-1-(cyclohexylmethyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.300 g, 0.964 mmol), 4-tetrazole phenyl boronic acid (0.220 g, 1.164 mmol), [1,1'-bis(diphenylphosphino)ferrocene]dichloropalladium(II) complex with dichloromethane (1:1) (0.082 g, 0.1 mmol), potassium phosphate (0.812 g, 3.83 mmol), water (2 ml) and dimethylformamide (7 mL) were reacted according to General Procedure B. The solution was condensed under reduced pressure and the product was purified by reverse-phase semi-preparatory HPLC (5-70% acetonitrile+0.1% TFA in H$_2$O+0.1% TFA, over 30 min). Fractions containing clean product were neutralized with potassium carbonate, extracted with ethyl acetate, dried over magnesium sulfate, filtered, concentrated, and dried under vacuum to give (0.184 g, 51% yield). $^1$H NMR (400 MHz, CD$_3$OD), δ 8.24 (s, 1H) 8.11 (d, J=8.4, 2H), 8.04 (d, J=8.4, 2H), 3.84 (d, J=7.6, 2H), 1.73 (m, 5H), 1.27 (m, 6H); MS (ESI) m/z 349 [M+1]$^+$; mp >400° C.

5.1.113 Example 113

SYNTHESIS OF 1-(CYCLOHEXYLMETHYL)-6-(2-HYDROXYPYRIDIN-4-YL)-1H-IMIDAZO[4,5-B]PYRAZIN-2(3H)-ONE

A. 1-(Cyclohexylmethyl)-6-(2-hydroxypyridin-4-yl)-1H-imidazo[4,5-b]pyrazin-2(3H)-one. 1-(Cyclohexylmethyl)-6-(2-methoxypyridin-4-yl)-1H-imidazo[4,5-b]pyrazin-2(3H)-one (See Example 94.A) (0.120 g, 0.354 mmol) was added to hydrobromic acid/acetic acid solution (10 mL) and heated at 100° C. for 0.5 h. The solution was condensed under reduced pressure and the product was purified by reverse-phase semi-preparatory HPLC (20-70% acetonitrile+0.1% TFA in H$_2$O+0.1% TFA, over 30 min). Fractions containing product were condensed and converted to the hydrochloride salt with ethanol (300 mL) and 12M HCl (10 mL) to give (0.045 g, 39% yield). $^1$H NMR (400 MHz, CD$_3$OD), δ 8.70 (s, 1H) 8.05 (d, J=6.4, 2H), 7.774 (m, 2H), 3.85 (d, J=7.2, 2H), 2.01 (m, 1H), 1.75 (m, 5H), 1.28 (m, 6H); MS (ESI) m/z 326.4 [M+1]$^+$; mp 311-313° C.

5.1.114 Example 114

SYNTHESIS OF 6-(4-(1H-1,2,4-TRIAZOL-3-YL)PHENYL)-1-(2-(TETRAHYDRO-2H-PYRAN-4-YL)ETHYL)-1H-IMIDAZO[4,5-B]PYRAZIN-2(3H)-ONE

A. (E)-N-((Dimethylamino)methylene)-4-(2-oxo-3-(2-(tetrahydro-2H-pyran-4-yl)ethyl)-2,3-dihydro-1H-imidazo[4,5-b]pyrazin-5-yl)benzamide. 4-(2-Oxo-3-(2-(tetrahydro-2H-pyran-4-yl)ethyl)-2,3-dihydro-1H-imidazo[4,5-b]pyrazin-5-yl)benzamide (See Example 108.C) (0.40 g, 1.09 mmol), N,N-dimethylformamide dineopentyl acetal (10.0 mL, 35.8 mmol) were heated together at 100° C. for 180 min. Upon consumption of the starting material, the product was filtered to give (0.539 g, crude product). MS (ESI) m/z 423.5 [M+1]$^+$.

B. 6-(4-(1H-1,2,4-Triazol-3-yl)phenyl)-1-(2-(tetrahydro-2H-pyran-4-yl)ethyl)-1H-imidazo[4,5-b]pyrazin-2(3H)-one. (E)-N-((Dimethylamino)methylene)-4-(2-oxo-3-(2-(tetrahydro-2H-pyran-4-yl)ethyl)-2,3-dihydro-1H-imidazo[4,5-b]pyrazin-5-yl)benzamide (0.250 g, 0.592 mmol) was added to acetic acid (10 mL) and cooled to 0° C. Hydrazine (0.532 g, 16.6 mmol) was added dropwise and reaction was stirred at 25° C. for 4 h. The solution was condensed under reduced pressure and the product was purified by reverse-phase preparatory HPLC (20-70% acetonitrile+0.1% TFA in H$_2$O+0.1% TFA, over 30 min). Fractions containing product were condensed and converted to the hydrochloride salt with ethanol (300 mL) and 12M HCl (10 mL) to give (0.091 g, 39% yield). $^1$H NMR (400 MHz, CD$_3$OD), δ 9.18 (s, 1H) 8.56 (s, 1H), 8.27 (m, 2H), 8.13 (m, 2H), 4.11 (t, J=7.2, 2H), 3.93 (m, 2H), 3.80 (m, 2H), 1.85 (m, 4H), 1.61 (m, 1H), 1.39 (m, 2H); MS (ESI) m/z 378.4 [M+1]$^+$; mp 263-266° C.

5.1.115 Example 115

SYNTHESIS OF 6-(4-(1H-IMIDAZOL-2-YL)PHENYL)-1-(CYCLOHEXYLMETHYL)-1H-IMIDAZO[4,5-B]PYRAZIN-2(3H)-ONE

A. 6-(4-(1H-Imidazol-2-yl)phenyl)-1-(cyclohexylmethyl)-1H-imidazo[4,5-b]pyrazin-2(3H)-one. 1-(Cyclohexylmethyl)-6-(trimethylstannyl)-1H-imidazo[4,5-b]pyrazin-2(3H)-one (See Example 109.A) (200 mg, 0.506 mmol), 1-(4-bromophenyl)imidazole (94 mg, 0.42 mmol), dichlorobis(triphenylphosphine)palladium(II) (104 mg, 0.10 mmol) in DMF (10 mL) were reacted for 1.5 h at 90° C. The product was purified by reverse-phase semi-preparatory HPLC (30-100% acetonitrile+0.1% TFA in H$_2$O+0.1% TFA, over 30 min). The desired fractions were concentrated, the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the desired product (5 mg, 3% yield) as a tan solid. $^1$H NMR (400 MHz, DMSO-d$_6$) δ 12.1 (s, 1H), 8.60 (s, 1H), 8.19 (d, J=8.4, 1H), 8.07 (d, J=8.4, 1H), 7.45 (s, 1H), 3.75 (d, J=7.2, 2H), 1.91 (m, 1H), 1.68 (m, 4H), 1.60 (m, 1H), 1.85 (m, 3H), 1.06 (m, 2H); MS (ESI) m/z 375.1 [M+1]$^+$; mp 349-351° C.

5.1.116 Example 116

SYNTHESIS OF 6-(4-(1H-1,2,3-TRIAZOL-1-YL)PHENYL)-1-(CYCLOHEXYLMETHYL)-1H-IMIDAZO[4,5-B]PYRAZIN-2(3H)-ONE

A. 1-Azido-4-bromobenzene. tert-Butanol (8 mL) was added to sodium azide (1.13 g, 17.43 mmol) followed by water (1.7 mL), 4-bromoaniline (1 g, 5.81 mmol) and tert-butyl nitrite (8.35 mL, 69.7 mmol). The resulting reaction mixture was brought to 70° C. for 2 h. Water (20 mL) was added and the reaction mixture was extracted ethyl acetate (3×). The combined organic fractions were dried over magnesium sulfate, filtered and concentrated under reduced pressure. The crude product was purified by biotage (0-40% ethyl acetate in hexanes) to afford the desire product (730 mg, 63% yield).

B. 1-(4-Bromophenyl)-1H-1,2,3-triazole. In a sealed tube, a solution of 1-azido-4-bromobenzene and vinyl acetate was heated at 100° C. for 14 h. After removing the volatiles under reduced pressure, the residue was recrystallized from methanol to provide the title compound (430 mg, 52%).

C. 1-(4-(Trimethylstannyl)phenyl)-1H-1,2,3-triazole. A solution of 1-(4-bromophenyl)-1H-1,2,3-triazole (0.43 g, 1.91 mmol) in dry toluene (30 mL) was treated with hexamethylditin (0.75 g, 2.29 mmol) and tetrakis(triphenylphosphine)palladium(0) (220 mg, 0.19 mmol) in a sealed tube at 110° C. for 2.5 h. The volatiles were removed under reduced pressure and the crude product was purified by biotage (0-35% ethyl acetate in hexanes) to afford the desired product (447 mg, 76%). MS (ESI) m/z 309.2[M+1]$^+$.

D. 6-(4-(1H-1,2,3-Triazol-1-yl)phenyl)-1-(cyclohexylmethyl)-1H-imidazo[4,5-b]pyrazin-2(3H)-one. A solution of 6-Bromo-1-(cyclohexylmethyl)-1H-imidazo[4,5-b]pyrazin-2(3H)-one (See Example 55.B) (235 mg, 0.75 mmol), 1-(4-(trimethylstannyl)phenyl)-1H-1,2,3-triazole (300 mg, 0.97 mmol), and dichlorobis(triphenylphosphine)palladium(II) (53 mg, 0.075 mmol) in DMF (10 mL) was heated for 1.5 h at 110° C. The product was purified by reverse-phase semi-preparatory HPLC (30-100% acetonitrile+0.1% TFA in H$_2$O+0.1% TFA, over 30 min). The desired fractions were concentrated. The residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (17 mg, 6% yield) as a tan solid. $^1$H NMR (400 MHz, DMSO-d$_6$) δ 12.19 (s, 1H), 8.98 (s, 1H), 8.70 (s, 1H), 8.34 (d, J=11.2, 2H), 8.13 (d, J=11.2, 2H), 8.10 (s, 1H), 3.84 (d, J=9.6, 2H), 2.0 (m, 1H), 1.78 (m, 5H), 1.27 (m, 3H), 1.15 (m, 2H); MS (ESI) m/z 375.1 [M+1]$^+$; mp 276-278° C.

5.1.117 Example 117

SYNTHESIS OF 6-(4-(2-HYDROXYPROPAN-2-YL)PHENYL)-1-(2-(TETRAHYDRO-2H-PYRAN-4-YL)ETHYL)-1H-IMIDAZO[4,5-B]PYRAZIN-2(3H)-ONE

A. Methyl 4-(2-oxo-3-(2-(tetrahydro-2H-pyran-4-yl)ethyl)-2,3-dihydro-1H-imidazo[4,5-b]pyrazin-5-yl)benzoate. 6-Bromo-1-(2-(tetrahydro-2H-pyran-4-yl)ethyl)-1H-imidazo[4,5-b]pyrazin-2(3H)-one (See Example 108.B) (0.400 g, 1.22 mmol), 4-methoxycarbonyl phenylboronic acid (0.262 g, 1.46 mmol), and [1,1'-bis(diphenylphosphino)ferrocene]dichloropalladium(II) complex with dichloromethane (1:1) (0.098 g, 0.12 mmol), potassium phosphate (1.03 g, 4.88 mmol), water (2 ml) and dimethylformamide (7 mL) were reacted according to General Procedure B. The solution was condensed under reduced pressure and the product was purified by Biotage silica gel chromatography (0-80% ethyl acetate in hexanes). Fractions containing product were concentrated to give (0.058 g, 12% yield). MS (ESI) m/z 383.4 [M+1]$^+$.

B. 6-(4-(2-Hydroxypropan-2-yl)phenyl)-1-(2-(tetrahydro-2H-pyran-4-yl)ethyl)-1H-imidazo[4,5-b]pyrazin-2(3H)-one. Methyl 4-(2-oxo-3-(2-(tetrahydro-2H-pyran-4-yl)ethyl)-2,3-dihydro-1H-imidazo[4,5-b]pyrazin-5-yl)benzoate (0.058 g, 0.152 mmol) is added to tetrahydrofuran (5 mL) and cooled to −78° C. Methylmagnesium bromide (3.0 M, 0.073 g, 0.61 mmol) was added dropwise and reaction was stirred and allowed to reach 25° C. over 18 h. The solution was quenched with methanol, condensed under reduced pressure and the product was purified by reverse-phase preparatory HPLC (20-70% acetonitrile+0.1% TFA in H$_2$O+0.1% TFA, over 30 min). Fractions containing product were neutralized with ammonium hydroxide, condensed and recrystallized from methyl sulfoxide and water to give (0.027 g, 47% yield). $^1$H NMR (400 MHz, DMSO-d$_6$) δ 8.40 (s, 1H) 7.95 (d, J=8.4, 2H), 7.59 (d, J=8.4, 2H), 4.09 (m, 2H), 3.92 (m, 2H), 3.37 (m, 2H), 1.83 (m, 4H), 1.59 (m, 1H), 1.59 (s, 6H), 1.38 (qd, J=12.4, 4.4, 2H); MS (ESI) m/z 392.4 [M+1]$^+$; mp 263-266° C.

5.1.118 Example 118

SYNTHESIS OF 1-(CYCLOHEXYLMETHYL)-6-(4-(5-METHYL-1H-1,2,4-TRIAZOL-3-YL)PHENYL)-1H-IMIDAZO[4,5-B]PYRAZIN-2(3H)-ONE

A. Ethyl 4-(3-(cyclohexylmethyl)-2-oxo-2,3-dihydro-1H-imidazo[4,5-b]pyrazin-5-yl)benzimidate hydrochloride. 4-(3-(Cyclohexylmethyl)-2-oxo-2,3-dihydro-1H-imidazo[4,5-b]pyrazin-5-yl)benzonitrile (See Example 69.A) (0.142 g, 0.43 mmol) was added to ethanol (100 mL) and cooled to 0° C. Hydrochloride gas is bubbled through the solution for 15 min. The solution was allowed to stir at rt for 18 h. The solution was condensed under reduced pressure to give (0.182 g). MS (ESI) m/z 380.4 [M+1]$^+$.

B. 1-(Cyclohexylmethyl)-6-(4-(5-methyl-1H-1,2,4-triazol-3-yl)phenyl)-1H-imidazo[4,5-b]pyrazin-2(3H)-one. Ethyl 4-(3-(cyclohexylmethyl)-2-oxo-2,3-dihydro-1H-imidazo[4,5-b]pyrazin-5-yl)benzimidate hydrochloride (0.182 g, 0.480 mmol), acetic acid hydrazide (0.142 g, 1.92 mmol) and methanol (4 mL) were reacted according to General Procedure F. The solution was condensed under reduced pressure and the product was purified by Biotage silica gel chromatography (0-80% ethyl acetate in hexanes). Fractions containing product were concentrated to give (0.488 g, 37% yield). $^1$H NMR (400 MHz, CD$_3$OD), δ 8.47 (s, 1H) 8.13 (dd, J=18.4, 8.4, 4H), 3.87 (d, J=7.2, 2H), 2.50 (s, 3H), 2.02 (m, 1H), 1.75 (m, 5H), 1.29 (m, 5H); MS (ESI) m/z 390.5 [M+1]$^+$; mp 315-318° C.

5.1.119 Example 119

SYNTHESIS OF 6-(4-(1H-PYRAZOL-3-YL)PHENYL)-1-(CYCLOHEXYLMETHYL)-1H-IMIDAZO[4,5-B]PYRAZIN-2(3H)-ONE

A. 3-(4-(Trimethylstannyl)phenyl)-1H-pyrazole. A solution of 3-(4-bromophenyl)-1H-pyrazole (0.50 g, 2.24 mmol) in dry toluene (15 mL) was treated with hexamethylditin (0.88 g, 2.68 mmol) and tetrakis(triphenylphosphine)palladium(0) (255 mg, 0.22 mmol) in a sealed tube at 110° C. for 2.5 h. The volatiles were removed under reduced pressure and the crude product was purified by biotage (0-35% ethyl acetate in hexanes) to afford the desired product (420 mg, 76%). MS (ESI) m/z 307.2[M+1]$^+$.

B. 6-(4-(1H-Pyrazol-3-yl)phenyl)-1-(cyclohexylmethyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (250 mg, 0.81 mmol), 3-(4-(trimethylstannyl)phenyl)-1H-pyrazole (212 mg, 0.68 mmol), dichlorobis(triphenylphosphine)palladium(II) (57 mg, 0.081 mmol) in DMF (10 mL) were reacted for 1.5 h at 110° C. The product was purified by reverse-phase semi-preparatory HPLC (30-100% acetonitrile+0.1% TFA in H$_2$O+0.1% TFA, over 30 min). The desired fractions were concentrated, the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (28 mg, 11% yield) as a colorless solid. $^1$H NMR (400 MHz, CD$_3$OD) δ 8.41 (s, 1H), 8.00 (m, 4H), 7.69 (d, J=8.4, 2H), 3.85 (d, J=7.2, 2H), 2.02 (m, 1H), 1.74 (m, 4H), 1.67 (m, 1H), 1.25 (m, 3H), 1.13 (m, 2H); MS (ESI) m/z 375.1 [M+1]$^+$; mp 292-294° C.

5.1.120 Example 120

SYNTHESIS OF 6-(4-(1H-PYRAZOL-4-YL)PHENYL)-1-(CYCLOHEXYLMETHYL)-1H-IMIDAZO[4,5-B]PYRAZIN-2(3H)-ONE

A. 4-(4-(Trimethylstannyl)phenyl)-1H-pyrazole. A solution of 4-(4-bromophenyl)-1H-pyrazole (1.0 g, 4.48 mmol) in dry toluene (20 mL) was treated with hexamethylditin (1.8 g, 5.38 mmol) and tetrakis(triphenylphosphine)palladium(0) (510 mg, 0.44 mmol) in a sealed tube at 110° C. for 2.5 h. The volatiles were removed under reduced pressure and the crude product was purified by biotage (0-35% ethyl acetate in hexanes) to afford the desired product (940 mg, 76%). MS (ESI) m/z 307.2 [M+1]$^+$.

B. 6-(4-(1H-Pyrazol-4-yl)phenyl)-1-(cyclohexylmethyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (250 mg, 0.81 mmol), 4-(4-(trimethylstannyl)phenyl)-1H-pyrazole (212 mg, 0.68 mmol), dichlorobis(triphenylphosphine)palladium(II) (57 mg, 0.081 mmol) in DMF (10 mL) were reacted for 1.5 h at 110° C. The product was purified by reverse-phase semi-preparatory HPLC (30-100% acetonitrile+0.1% TFA in H$_2$O+0.1% TFA, over 30 min). The desired fractions were concentrated and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (28 mg, 11% yield) as a colorless solid. $^1$H NMR (400 MHz, CD$_3$OD) δ 8.98 (s, 1H), 8.70 (s, 1H), 8.06 (m, 2H), 7.91 (m, 2H), 7.71 (s, 1H), 6.73 (s, 1H), 3.86 (d, J=7.2, 2H), 2.03 (m, 1H), 1.75 (m, 4H), 1.67 (m, 1H), 1.25 (m, 3H), 1.13 (m, 2H); MS (ESI) m/z 375.1 [M+1]$^+$; mp 305-307° C.

5.1.121 Example 121

SYNTHESIS OF 6-(4-(5-(AMINOMETHYL)-1H-1,2,4-TRIAZOL-3-YL)PHENYL)-1-(CYCLOHEXYLMETHYL)-1H-IMIDAZO[4,5-B]PYRAZIN-2(3H)-ONE

A. tert-Butyl (3-(4-(3-(cyclohexylmethyl)-2-oxo-2,3-dihydro-1H-imidazo[4,5-b]pyrazin-5-yl)phenyl)-1H-1,2,4-triazol-5-yl)methylcarbamate. Ethyl 4-(3-(cyclohexylmethyl)-2-oxo-2,3-dihydro-1H-imidazo[4,5-b]pyrazin-5-yl)benzimidate hydrochloride (See Example 118.A) (0.196 g, 0.517 mmol) and boc-glycine hydrazide (0.392 g, 2.07 mmol) (0.392 g, 2.07 mmol) and methanol (4 mL) were reacted according to General Procedure F. The solution was condensed under reduced pressure and the product was purified by Biotage silica gel chromatography (0-20% methanol in dichloromethane). Fractions containing product were concentrated to give (0.099 g, 39% yield). MS (ESI) m/z 505.5 [M+1]$^+$.

B. 6-(4-(5-(Aminomethyl)-1H-1,2,4-triazol-3-yl)phenyl)-1-(cyclohexylmethyl)-1H-imidazo[4,5-b]pyrazin-2(3H)-one hydrochloride. tert-Butyl (3-(4-(3-(cyclohexylmethyl)-2-oxo-2,3-dihydro-1H-imidazo[4,5-b]pyrazin-5-yl)phenyl)-1H-1,2,4-triazol-5-yl)methylcarbamate (0.099 g, 0.196 mmol) and 4.0 M hydrogen chloride in dioxane (5 mL) were stirred at 25° C. for 90 min. The solution was condensed under reduced pressure to give (0.071 g, 90% yield) of the hydrochloride salt. $^1$H NMR (400 MHz, CD$_3$OD) δ 8.51 (s, 1H) 8.21 (d, J=8.8, 4H), 8.10 (d, J=8.8, 2H), 4.31 (s, 2H), 3.86 (d, J=7.2, 2H), 2.02 (m, 1H), 1.75 (m, 5H), 1.28 (m, 5H); MS (ESI) m/z 405.5 [M+1]$^+$; mp 326-329° C.

5.1.122 Example 122

SYNTHESIS OF 1-(CYCLOHEXYLMETHYL)-6-(4-(5-(TRIFLUOROMETHYL)-1H-1,2,4-TRIAZOL-3-YL)PHENYL)-1H-IMIDAZO[4,5-B]PYRAZIN-2(3H)-ONE

A. 1-(Cyclohexylmethyl)-6-(4-(5-(trifluoromethyl)-1H-1,2,4-triazol-3-yl)phenyl)-1H-imidazo[4,5-b]pyrazin-2(3H)-one. Ethyl 4-(3-(cyclohexylmethyl)-2-oxo-2,3-dihydro-1H-imidazo[4,5-b]pyrazin-5-yl)benzimidate hydrochloride (See Example 118.A) (0.196 g, 0.517 mmol), trifluoroacetic acid hydrazide (0.265 g, 2.07 mmol) and methanol (4 mL) were reacted according to General Procedure F. The solution was condensed under reduced pressure and the product was purified by reverse-phase preparatory HPLC (20-70% acetonitrile+0.1% TFA in H$_2$O+0.1% TFA, over 30 min). Fractions containing product were neutralized with ammonium hydroxide, condensed and recrystallized from methyl sulfoxide and water to give (0.019 g, 8% yield). $^1$H NMR (400 MHz, CD$_3$OD), δ 8.52 (s, 1H) 8.21 (d, J=8.4, 2H), 8.10 (d, J=8.4, 2H), 3.87 (d, J=7.2, 2H), 2.02 (m, 1H), 1.76 (m, 5H), 1.26 (m, 5H); MS (ESI) m/z 444.7 [M+1]$^+$; mp 303-305° C.

5.1.123 Example 123

SYNTHESIS OF 6-(4-HYDROXYPHENYL)-1-((1R,4R)-4-METHOXYCYCLOHEXYL)-1H-IMIDAZO[4,5-B]PYRAZIN-2(3H)-ONE

A. tert-Butyl (1r,4r)-4-hydroxycyclohexylcarbamate. (1r,4r)-4-Aminocyclohexanol (2.9 g, 25 mmol) was stirred in 2-propanol (30 mL). di-tert-Butyl dicarbonate (11 g, 50 mmol) was added and the reaction was stirred for 16 h at room temperature. The reaction was concentrated and the product purified on a silica gel column (0-10% ethyl acetate in methanol) to give a white solid (4.5 g, 83% yield).

B. (1r,4r)-4-Methoxycyclohexanamine hydrochloride. tert-Butyl (1r,4r)-4-hydroxycyclohexylcarbamate (4.5 g, 21 mmol) was dissolved in tetrahydrofuran (100 mL) followed by the addition of 15-crown-5 (4.4 mL, 22 mmol) and 95% sodium hydride (0.75 g, 31 mmol). Iodomethane (1.3 mL, 21 mmol) was added and the reaction was stirred for 2 h at room temperature. The reaction was extracted with ethyl acetate and water. The organic layer was dried over magnesium sulfate, filtered and concentrated. The resulting solid was purified by silica gel chromatography (0-100% ethyl acetate in hexanes) to give the methylated product as a solid. The solid was treated with 4N hydrogen chloride in dioxane for 2 h. The solvent was removed under reduced pressure and the residue was triturated with ether to a give solid (2.5 g, 65% yield over two steps).

C. 6-Bromo-N-((1r,4r)-4-methoxycyclohexyl)pyrazine-2,3-diamine. 3,5-Dibromopyrazin-2-amine (253 mg, 1 mmol), (1r,4r)-4-methoxycyclohexanamine hydrochloride (165 mg, 1 mmol), diisopropylethylamine (0.5 mL), and n-butanol (2 mL) were heated in a Biotage Emrys Optimizer microwave reactor at 200° C. for 2 h. The reaction was purified on silica gel column (0-10% methanol in ethyl acetate) to give a tan solid (210 mg, 70% yield). MS (ESI) m/z 303.3 [M+1]$^+$.

D. 6-Bromo-1-((1r,4r)-4-methoxycyclohexyl)-1H-imidazo[4,5-b]pyrazin-2(3H)-one 6-bromo-N$^2$-((1r,4r)-4-methoxycyclohexyl)pyrazine-2,3-diamine (210 mg, 0.7 mmol), 1,1'-carbonyldiimidazole (340 mg, 2 mmol), and dioxane (2 mL) were heated in a Biotage Emrys Optimizer microwave reactor at 200° C. for 1 h. The reaction was purified on silica gel column (0-10% methanol in ethyl acetate) to give a tan solid (130 mg, 57% yield). MS (ESI) m/z 327.0 [M+1]$^+$.

E. 6-(4-Hydroxyphenyl)-1-((1r,4r)-4-methoxycyclohexyl)-1H-imidazo[4,5-b]pyrazin-2(3H)-one. 6-Bromo-1-((1r,4r)-4-methoxycyclohexyl)-1H-imidazo[4,5-b]pyrazin-2(3H)-one (130 mg, 0.4 mmol), 4-hydroxyphenylboronic acid (55 mg, 0.44 mmol), dichloro[1,1'-bis(diphenylphosphino)ferrocene]palladium(II) dichloromethane adduct (15 mg, 0.02 mmol), 1M sodium carbonate (1 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layers were combined, concentrated and then purified by reverse-phase semi-preparative HPLC (10-70% acetonitrile+0.1% TFA in H$_2$O+0.1% TFA, over 30 min). The product fractions were concentrated and then triturated with ether to give a white solid (70 mg, 52% yield). $^1$H NMR (400 MHz, DMSO-d$_6$) δ 11.92 (s, 1H), 9.70 (s, 1H), 8.35 (s, 1H), 7.85 (d, J=8.6, 2H), 6.85-6.89 (m, 2H), 4.26 (t, J=12.3, 1H), 3.23-3.32 (m, 5H), 2.35-2.46 (m, 2H), 2.15 (d, J=11.7, 2H), 1.82 (d, J=11.3, 2H), 1.24-1.35 (m, 2H); MS (ESI) m/z 341.0 [M+1]$^+$; mp 288-290° C.

5.1.124 Example 124

SYNTHESIS OF 6-(4-HYDROXYPHENYL)-1-((TETRAHYDROFURAN-2-YL)METHYL)-1H-IMIDAZO[4,5-B]PYRAZIN-2(3H)-ONE

A. 6-(4-Hydroxyphenyl)-1-((tetrahydrofuran-2-yl)methyl)-1H-imidazo[4,5-b]pyrazin-2(3H)-one. 4-(6-Bromo-5-(N,N-bis-boc-amino)pyrazin-2-yl)phenol (See Example 46.F) (466 mg, 1 mmol), (tetrahydrofuran-2-yl)methanamine (1 g, 10 mmol), and n-butanol (2 mL) were heated in a Biotage Emrys Optimizer microwave reactor at 150° C. for 4 h. The reaction was purified by reverse-phase semi-preparatory HPLC (10-70% acetonitrile+0.1% TFA in H$_2$O+0.1% TFA, over 30 min). The product fractions were concentrated and then triturated with ether to give a white solid (98 mg, 32% yield). $^1$H NMR (400 MHz, DMSO-d$_6$) δ 11.95 (s, 1H), 9.70 (s, 1H), 8.37 (s, 1H), 7.83-7.88 (m, 2H), 6.84-6.90 (m, 2H), 4.29-4.36 (m, 1H), 3.94 (dd, J=14.1, 7.4, 1H), 3.77-3.84 (m, 2H), 3.60-3.66 (m, 1H), 1.88-1.99 (m, 2H), 1.79-1.87 (m, 1H), 1.68-1.78 (m, 1H); MS (ESI) m/z 313.1 [M+1]$^+$; mp 256-258° C.

5.1.125 Example 125

SYNTHESIS OF 6-(3-(1H-1,2,4-TRIAZOL-3-YL)PHENYL)-1-(CYCLOHEXYLMETHYL)-1H-IMIDAZO[4,5-B]PYRAZIN-2(3H)-ONE

A. 3-(3-Bromophenyl)-1H-1,2,4-triazole. In a sealed tube, a solution of 3-bromobenzaldehyde (1.0 g, 5.0 mmol) was treated with dimethylformamide dimethylacetal (5 mL) at 100° C. for 6 h. Upon completion of the reaction, the volatiles were removed under reduced pressure. The crude product was treated with hydrazine (2 mL) and acetic acid (10 drops) at room temperature for 1 h. The volatiles were removed under reduced pressure. The crude product was dried under high vacuum, and used without further purification in the next step. MS (ESI) m/z 226.1[M+1]$^+$.

B. 3-(3-(Trimethylstannyl)phenyl)-1H-1,2,4-triazole. A solution of 3-(3-bromophenyl)-1H-1,2,4-triazole (0.5 g, 2.25 mmol) in dry toluene (20 mL) was treated with hexamethylditin (0.88 g, 2.70 mmol) and tetrakis(triphenylphosphine)palladium(0) (255 mg, 0.22 mmol) in a sealed tube at 110° C. for 2.5 h. The volatiles were removed under reduced pressure and the crude product was purified by biotage (0-50% ethyl acetate in hexanes) to afford the desired stannane (200 mg, 29%). MS (ESI) m/z 310.3[M+1]$^+$.

C. 6-(3-(1H-1,2,4-Triazol-3-yl)phenyl)-1-(cyclohexylmethyl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (253 mg, 0.81 mmol), 3-(3-(trimethylstannyl)phenyl)-1H-1,2,4-triazole (300 mg, 0.97 mmol), dichlorobis(triphenylphosphine)palladium(II) (57 mg, 0.081 mmol) in DMF (10 mL) were reacted for 1.5 h at 110° C. The product was purified by reverse-phase semi-preparatory HPLC (30-100% acetonitrile+0.1% TFA in H$_2$O+0.1% TFA, over 30 min). The desired fractions were concentrated, and the residue was taken up in DMSO (2 mL) and heated at 100° C. until completely dissolved. Water was added upon cooling and the desired product precipitated out of solution. The precipitate was collected by vacuum filtration, washed with water and dried under high vacuum to provide the title compound (11 mg, 11% yield) as a colorless solid. $^1$H NMR (400 MHz, DMSO-d$_6$) δ 12.09 (s, 1H), 8.64 (s, 1H), 8.51 (s, 1H), 8.04 (m, 3H), 7.60 (m, 1H), 3.75 (d, J=6.8, 2H), 1.93 (m, 1H), 1.68 (m, 3H), 1.59 (m, 2H), 1.18 (m, 3H), 1.07 (m, 2H); MS (ESI) m/z 376.2 [M+1]$^+$; mp 305-307° C.

5.1.126 Example 126

SYNTHESIS OF 1-((1R,4R)-4-(HYDROXYMETHYL)CYCLOHEXYL)-6-(4-HYDROXYPHENYL)-1H-IMIDAZO[4,5-B]PYRAZIN-2(3H)-ONE

A. (1r,4r)-4-(tert-Butoxycarbonylamino)cyclohexanecarboxylic acid (1r,4r)-4-Aminocyclohexanecarboxylic acid (2 g, 14 mmol) was placed in THF (30 mL). Aqueous sodium hydroxide (14 mL, 1M) was added, followed by di-t-butyl-dicarbonate (6.7 g, 31 mmol). The reaction was stirred at room temperature for 16 h. The reaction was extracted with ethyl acetate, the aqueous layer was acidified to pH 4 with 1 N hydrochloric acid and extracted with ethyl acetate. Organic layers were pooled, dried over sodium sulfate, filtered and concentrated. The resulting material was triturated with hexanes to give the title compound as a white solid (1.2 g, 35% yield). $^1$H NMR (300 MHz, DMSO-d$_6$) δ 6.72 (d, J=8.1, 1H), 3.13 (m, 1H), 2.06 (m, 1H), 1.84 (m, 4H), 1.37 (s, 9H), 1.33 (m, 2H), 1.15 (m, 2H).

B. tert-Butyl (1r,4r)-4-(hydroxymethyl)cyclohexylcarbamate A solution of (1r,4r)-4-(tert-butoxycarbonylamino)cyclohexanecarboxylic acid (1.2 g, 4.9 mmol), isobutylchloroformate (0.65 mL, 4.9 mmol) and N-methyl morpholine (1.6 mL, 15 mmol) in anhydrous tetrahydrofuran (10 mL) was stirred at rt, under nitrogen, for 30 min. Sodium borohydride (0.56 g, 15 mmol) was added in small portions and the mixture stirred a further 30 min. The reaction was quenched with methanol and treated with water and ethyl acetate. The organic layer was dried over magnesium sulfate, filtered and concentrated to yield the title compound as an oil (1.05 g, 95% yield). $^1$H NMR (300 MHz, DMSO-$d_6$) δ 6.72 (d, J=8.1, 1H), 4.36 (m, 1H), 3.18 (m, 2H), 3.12 (m, 1H), 1.72 (m, 4H), 1.1 (m, 2H), 0.9 (m, 2H).

C. ((1r,4r)-4-Aminocyclohexyl)methanol hydrochloride tert-Butyl (1r,4r)-4-(hydroxymethyl)cyclohexylcarbamate (0.33 g, 1.45 mmol) was placed in 1,4-dioxane (4 mL) and 1M hydrochloric acid in 1,4-dioxane (1 mL) was added. The reaction mixture was stirred overnight. The solvent was removed, the residue was treated with ethyl acetate, filtered and dried to yield the title compound as a solid (0.13 g, 56% yield). $^1$H NMR (400 MHz, DMSO-$d_6$) δ 7.81 (bs, 2H), 3.2 (m, 2H), 2.89 (m, 1H), 1.92 (m, 2H), 1.75 (m, 2H), 1.27 (m, 3H), 0.93 (m, 2H).

D. ((1r,4r)-4-(3-Amino-6-bromopyrazin-2-ylamino)cyclohexyl)methanol. 2-Amino-3,5-dibromopyrazine (0.3 g, 1.2 mmol), ((1r,4r)-4-aminocyclohexyl)methanol hydrochloride (0.22 g, 1.33 mmol) and diisopropylethylamine (0.51 g, 4 mmol) were reacted according to General Procedure A and purified using silica gel chromatography (30-100% ethyl acetate in hexanes) to afford the title compound (0.19 g, 47.7% yield). MS (ESI) m/z 301 [M+1]$^+$.

E. ((1r,4r)-4-(6-Bromo-2-oxo-2,3-dihydro-1H-imidazo[4,5-b]pyrazin-1-yl)cyclohexyl)methyl 1H-imidazole-1-carboxylate. ((1r,4r)-4-(3-Amino-6-bromopyrazin-2-ylamino)cyclohexyl)methanol (0.19 g, 0.63 mmol) and 1,1'-carbonyldiimidazole (0.13 g, 0.79 mmol) were reacted in tetrahydrofuran according to General Procedure D1 and purified using silica gel chromatography (50-100% ethyl acetate in hexanes) to afford the title compound (0.2 g, 75% yield). MS (ESI) m/z 421 [M+1]$^+$.

F. 1-((1r,4r)-4-(Hydroxymethyl)cyclohexyl)-6-(4-hydroxyphenyl)-1H-imidazo[4,5-b]pyrazin-2(3H)-one. ((1r,4r)-4-(6-Bromo-2-oxo-2,3-dihydro-1H-imidazo[4,5-b]pyrazin-1-yl)cyclohexyl)methyl 1H-imidazole-1-carboxylate (0.2 g, 0.47 mmol), 4-hydroxybenzene boronic acid (0.065 g, 0.47 mmol), dichloro[1,1'-bis(diphenylphosphino)ferrocene]palladium(II) dichloromethane adduct (0.038 g. 0.047 mmol), and sodium carbonate (0.25 g, 2.35 mmol) were combined in 1,4-dioxane (6 mL) and water (2 mL) and heated in a Biotage Emrys Optimizer microwave reactor at 150° C. for 20 min. The product was purified by reverse-phase semi-preparatory HPLC (20-100% acetonitrile+0.1% TFA in H$_2$O+0.1% TFA, over 30 min). Product fractions were concentrated and triturated with ethyl ether to yield an off-white solid (22.4 mg, 14% yield). $^1$H NMR (400 MHz, DMSO-$d_6$) δ 11.90 (s, 1H), 9.69 (s, 1H), 8.35 (s, 1H), 7.85 (d, J=8.8, 2H), 6.87 (d, J=8.8, 2H), 4.48 (t, J=5.0, 1H), 4.21 (t, J=12, 1H), 3.28 (t, J=6, 2H), 2.39 (m, 2H), 1.89 (d, J=12, 2H), 1.81 (d, J=12, 2H), 1.47 (m, 1H), 1.08 (m, 2H); MS (ESI) m/z 341.3[M+1]$^+$; mp 324-326° C.

5.1.127 Example 127

SYNTHESIS OF 6-(4-HYDROXYPHENYL)-1-((1S,4S)-4-METHOXYCYCLOHEXYL)-1H-IMIDAZO[4,5-B]PYRAZIN-2(3H)-ONE

A. tert-Butyl (1s,4s)-4-hydroxycyclohexylcarbamate. (1s,4s)-4-Aminocyclohexanol hydrochloride (4 g, 26 mmol) was stirred in 1M sodium hydroxide (26 mL, 26 mmol), and 2-propanol (30 mL). di-tert-Butyl dicarbonate (7 g, 32 mmol) was added and the reaction was stirred for 3 h at room temperature. The reaction was extracted with ethyl acetate and water. The organic layer was dried over magnesium sulfate, filtered and concentrated to give a white solid (4.3 g, 77% yield).

B. (1s,4s)-4-Methoxycyclohexanamine hydrochloride. tert-Butyl (1s,4s)-4-hydroxy-cyclohexylcarbamate (3.8 g, 17.6 mmol) was dissolved in tetrahydrofuran (50 mL) followed by the addition of 15-crown-5 (0.35 mL, 2 mmol) and 95% sodium hydride (850 mg, 17 mmol). Iodomethane (1.2 mL, 19 mmol) was added and the reaction was stirred for 6 h at room temperature. The reaction was extracted with ethyl acetate and water. The organic layer was dried over magnesium sulfate, filtered and concentrated. The oil was purified by silica gel chromatography (0-20% ethyl acetate in hexanes) to give the methylated product as an oil. The solid was treated with 4N hydrogen chloride in dioxane for 2 h. The solvent was removed under reduced pressure and the residue was triturated with ether to a give solid (2.3 g, 79% yield over 2 steps).

C. 6-Bromo-N$^2$-((1s,4s)-4-methoxycyclohexyl)pyrazine-2,3-diamine. 3,5-Dibromopyrazin-2-amine (253 mg, 1 mmol), (1s,4s)-4-methoxycyclohexanamine hydrochloride (200 mg, 1.2 mmol), diisopropylethylamine (0.5 mL), and n-butanol (2 mL) were heated in a Biotage Emrys Optimizer microwave reactor at 200° C. for 2 h. The reaction was purified on silica gel column (0-10% methanol in ethyl acetate) to give a tan solid (110 mg, 36% yield). MS (ESI) m/z 301.0 [M+1]$^+$.

D. 6-Bromo-1-((1s,4s)-4-methoxycyclohexyl)-1H-imidazo[4,5-b]pyrazin-2(3H)-one. 6-Bromo-N$^2$-((1s,4s)-4-methoxycyclohexyl)pyrazine-2,3-diamine (110 mg, 0.36 mmol), 1,1'-carbonyldiimidazole (178 mg, 1.1 mmol), and dioxane (2 mL) were heated in a Biotage Emrys Optimizer microwave reactor at 200° C. for 1 h. The reaction was purified on silica gel column (0-10% methanol in ethyl acetate) to give a tan solid (75 mg, 63% yield). MS (ESI) m/z 327.0 [M+1]$^+$.

E. 6-(4-Hydroxyphenyl)-1-((1s,4s)-4-methoxycyclohexyl)-1H-imidazo[4,5-b]pyrazin-2(3H)-one. 6-Bromo-1-((1s,4s)-4-methoxycyclohexyl)-1H-imidazo[4,5-b]pyrazin-2(3H)-one (75 mg, 0.22 mmol), 4-hydroxyphenylboronic acid (35 mg, 0.25 mmol), dichloro[1,1'-bis(diphenylphosphino)ferrocene]palladium(II) dichloromethane adduct (8 mg, 0.01 mmol), 1M sodium carbonate (0.6 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layer was concentrated and the resulting material was purified by reverse-phase semi-preparatory HPLC (10-70% acetonitrile+0.1% TFA in H$_2$O+0.1% TFA, over 30 min). The product fractions were concentrated and the resulting residue was triturated with ether to give a white solid (70 mg, 52% yield). $^1$H NMR (400 MHz, DMSO-$d_6$) δ 11.88 (s, 1H), 9.70 (s, 1H), 8.36 (s, 1H), 7.89 (d, J=9.0, 2H), 6.86 (d, J=8.6, 2H), 4.24-4.32 (m, 1H), 3.47 (s, 1H), 3.30 (s, 3H), 2.60-2.72 (m, 2H), 2.03 (d, J=12.9, 2H), 1.47-1.57 (m, 4H); MS (ESI) m/z 341.0 [M+1]$^+$; mp 256-258° C.

5.1.128 Example 128

SYNTHESIS OF 6-(4-HYDROXYPHENYL)-1-((1R,4R)-4-(METHOXYMETHYL)CYCLOHEXYL)-1H-IMIDAZO[4,5-B]PYRAZIN-2(3H)-ONE

A. tert-Butyl (1r,4r)-4-(methoxymethyl)cyclohexylcarbamate. Sodium hydride (0.055 g, 2.29 mmol, 60% by weight suspension in mineral oil) was washed three times with hexanes (10 mL portions) and suspended in anhydrous tetrahydrofuran (8 mL). The mixture was cooled to 0° C. under nitrogen. tert-Butyl (1r,4r)-4-(hydroxymethyl)cyclohexylcarbamate (See Example 126.B) (0.35 g, 1.53 mmol) and 15-crown-5 (0.354 g, 1.6 mmol) were added and the mixture was allowed to stir for 30 min at 0° C. Methyl iodide was added dropwise (0.227 g, 1.6 mmol) and stirred at 0° C. for another 30 min. The ice bath was removed and the reaction mixture stirred at rt overnight. Excess hydride was quenched by the slow addition of water and the mixture was extracted with ethyl acetate. The organic layers were combined and concentrated. The resulting material was purified using silica gel chromatography (25-70% ethyl acetate in hexanes) to afford the title compound (0.31 g, 83% yield). MS (ESI) m/z 244.1 [M+1]+.

B. (1r,4r)-4-(Methoxymethyl)cyclohexanamine hydrochloride. tert-Butyl (1r,4r)-4-(methoxymethyl)cyclohexylcarbamate (0.31 g, 1.27 mmol) was treated with 1N HCl in 1,4-dioxane (4 mL) and stirred at rt overnight. The solvent was removed and the residue dried under high vacuum to yield the title compound as a white solid (0.21 g, 92% yield). MS (ESI) m/z 144.3 [M+1]+.

C. 6-Bromo-$N^2$-((1r,4r)-4-(methoxymethyl)cyclohexyl)pyrazine-2,3-diamine. 2-Amino-3,5-dibromopyrazine (0.317 g, 1.25 mmol), (1r,4r)-4-(methoxymethyl)cyclohexanamine hydrochloride (0.21 g, 1.16 mmol) and diisopropylethylamine (0.45 g, 3.5 mmol) were reacted according to General Procedure A and purified using silica gel chromatography (30-100% ethyl acetate in hexanes) to afford the title compound (0.15 g, 41% yield). MS (ESI) m/z 315 [M+1]+.

D. 4-(5-Amino-6-((1r,4r)-4-(methoxymethyl)cyclohexylamino)pyrazin-2-yl)phenol 6-Bromo-$N^2$-((1r,4r)-4-(methoxymethyl)cyclohexyl)pyrazine-2,3-diamine (0.15 g, 0.47 mmol), 4-hydroxybenzene boronic acid (0.065 g, 0.47 mmol), dichloro[1,1'-bis(diphenylphosphino)ferrocene]palladium(II) dichloromethane adduct (0.04 g. 0.047 mmol) and sodium carbonate (0.25 g, 2.38 mmol) were combined in 1,4-dioxane (3 mL) and water (2 mL) and heated in a Biotage Emrys Optimizer microwave reactor at 150° C. for 20 min. The resulting material was purified using silica gel chromatography (10% hexanes in ethyl acetate) to afford the title compound (0.15 g, 96% yield). MS (ESI) m/z 329 [M+1]+.

E. 6-(4-Hydroxyphenyl)-1-((1r,4r)-4-(methoxymethyl)cyclohexyl)-1H-imidazo[4,5-b]pyrazin-2(3H)-one. A solution of 4-(5-amino-6-((1r,4r)-4-(methoxymethyl)cyclohexylamino)pyrazin-2-yl)phenol (0.15 g, 0.45 mmol) and urea (0.055 g, 0.91 mmol) in dimethylformamide (2 mL) was reacted according to General Procedure D2. The solvent was removed and the residue purified using silica gel chromatography (30% hexanes in ethyl acetate) followed by reverse-phase semi-preparatory HPLC (20-100% acetonitrile+0.1% TFA in H$_2$O+0.1% TFA, over 30 min). Product fractions were concentrated and washed with water to yield the title compound (0.033 g, 20% yield). $^1$H NMR (400 MHz, DMSO-d$_6$) δ 11.90 (s, 1H), 9.69 (s, 1H), 8.35 (s, 1H), 7.85 (d, J=8.4, 2H), 6.87 (d, J=8.4, 2H), 4.21 (m, 1H), 3.26 (s, 3H), 3.2 (d, J=6, 2H), 2.37 (m, 2H), 1.84 (m, 4H), 1.65 (m, 1H), 1.13 (m, 2H); MS (ESI) m/z 355.3 [M+1]+; mp 300-303° C.

5.1.129 Example 129

SYNTHESIS OF 6-(1-METHYL-1H-PYRAZOL-4-YL)-1-((TETRAHYDRO-2H-PYRAN-4-YL)METHYL)-1H-IMIDAZO[4,5-B]PYRAZIN-2(3H)-ONE

A. 6-(1-Methyl-1H-pyrazol-4-yl)-1-((tetrahydro-2H-pyran-4-yl)methyl)-1H-imidazo[4,5-b]pyrazin-2(3H)-one. 6-Bromo-1-((tetrahydro-2H-pyran-4-yl)methyl)-1H-imidazo[4,5-b]pyrazin-2(3H)-one (See Example 101.B) (0.2 g, 0.63 mmol), 1-methyl-4-(4,4,5,5-tetramethyl-1,3,2-dioxaborolan-2-yl)-1H-pyrazole (0.16 g, 0.76 mmol), dichloro[1,1'-bis(diphenyl-phosphino)ferrocene]palladium(II) dichloromethane adduct (0.05 g, 0.063 mmol) and potassium phosphate (0.53 g, 2.5 mmol) were combined in dimethylformamide (5 mL) and water (1 mL) in a sealed tube and reacted according to General Procedure B. The reaction solution was concentrated and purified by silica gel chromatography (ethyl acetate) followed by reverse-phase semi-preparatory HPLC (20-100% acetonitrile+0.1% TFA in H$_2$O+0.1% TFA, over 30 min) to yield the title compound (0.018 g, 9% yield). $^1$H NMR (400 MHz, DMSO-d$_6$) δ 11.89 (s, 1H), 8.22 (s, 2H), 7.96 (s, 1H), 3.89 (s, 3H), 3.82 (d, 2H), 3.73 (d, J=7, 2H), 3.25 (t, J=8, 2H), 2.12 (m, 1H), 1.55 (d, 2H), 1.3 (m, 2H); MS (ESI) m/z 315.3 [M+1]+; mp 224-226° C.

5.1.130 Example 130

SYNTHESIS OF 1-(((1R,4R)-4-HYDROXYCYCLOHEXYL)METHYL)-6-(4-HYDROXYPHENYL)-1H-IMIDAZO[4,5-B]PYRAZIN-2(3H)-ONE

A. (1r,4r)-4-Hydroxycyclohexanecarboxamide. (1r,4r)-4-Hydroxycyclohexanecarboxylic acid (5.4 g, 38 mmol), ammonium chloride (2.2 g, 41 mmol), O-(benzotriazol-1-yl)-N,N,N'N'-tetramethyluronium hexafluorophosphate (15.6 g, 41 mmol), triethylamine (16 mL, 113 mmol), and acetonitrile (80 ml) were stirred together at room temperature for 16 h. The reaction filtered and rinsed with acetonitrile. The filtrate was concentrated and triturated with ethyl acetate to give a white solid (3.7 g, 69% yield). MS (ESI) m/z 144.1 [M+1]+.

B. (1r,4r)-4-(Aminomethyl)cyclohexanol hydrochloride. (1r,4r)-4-Hydroxycyclohexane carboxamide (1.4 g, 10 mmol) was dissolved in tetrahydrofuran (15 mL). Chloroborane methylsulfide complex (2.1 mL, 20 mmol) was added and the reaction was heated to reflux under nitrogen for 16 h. The reaction was quenched by slow addition of methanol. 4N Hydrogen chloride in dioxane (5 mL) was added to the reaction and the solution was concentrated. The residue was triturated with 10% methanol in ethyl acetate to give a white solid after filtration (1.2 g, 75% yield). MS (ESI) m/z 303.3 [M+1]+.

C. (1r,4r)-4-((3-Amino-6-bromopyrazin-2-ylamino)methyl)cyclohexanol 3,5-Dibromo-pyrazin-2-amine (253 mg, 1 mmol), (1r,4r)-4-(aminomethyl)cyclohexanol hydrochloride (200 mg, 1.2 mmol), diisopropylethylamine (1 mL), and n-butanol (2 mL) were heated in a Biotage Emrys Optimizer microwave reactor at 200° C. for 2 h. The reaction was purified on silica gel column (0-10% methanol in ethyl acetate) to give a tan solid (138 mg, 46% yield). MS (ESI) m/z 303.3 [M+1]+.

D. 6-Bromo-1-(((1r,4r)-4-hydroxycyclohexyl)methyl)-1H-imidazo[4,5-b]pyrazin-2(3H)-one (1r,4r)-4-((3-Amino-6-bromopyrazin-2-ylamino)methyl)cyclohexanol (138 mg, 0.45 mmol), 1,1'-carbonyldiimidazole (223 mg, 1.4 mmol), and dioxane (2 mL) were heated in a Biotage Emrys Optimizer microwave reactor at 200° C. for 1 h. The reaction was purified on silica gel column (0-10% methanol in ethyl acetate) to give a tan solid (125 mg, 83% yield). MS (ESI) m/z 311.3 [M+1]+.

E. 1-(((1r,4r)-4-Hydroxycyclohexyl)methyl)-6-(4-hydroxyphenyl)-1H-imidazo[4,5-b]pyrazin-2(3H)-one. 6-Bromo-1-(((1r,4r)-4-hydroxycyclohexyl)methyl)-1H-imidazo[4,5-b]pyrazin-2(3H)-one (125 mg, 0.4 mmol), 4-hydroxyphenylboronic acid (61 mg, 0.44 mmol), dichloro[1,1'-bis(diphenylphosphino)ferrocene]palladium(II)

dichloromethane adduct (15 mg, 0.02 mmol), 1M sodium carbonate (1 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layer was concentrated and the resulting material was purified by reverse-phase semi-preparatory HPLC (10-70% acetonitrile+0.1% TFA in H$_2$O+0.1% TFA, over 30 min). The product fractions were concentrated and then triturated with ether to give a white solid (53 mg, 35% yield). $^1$H NMR (400 MHz, DMSO-d$_6$) δ 11.91 (s, 1H), 9.69 (s, 1H), 8.35 (s, 1H), 7.82-7.86 (m, 2H), 6.85-6.89 (m, 2H), 4.49 (d, J=4.3, 1H), 3.70 (d, J=7.0, 2H), 1.80 (s, 3H), 1.66 (s, 2H), 1.07 (t, J=10.3, 4H); MS (ESI) m/z 341.5 [M+1]$^+$; mp 332-334° C.

5.1.131 Example 131

SYNTHESIS OF 6-(4-HYDROXYPHENYL)-1-((TETRAHYDROFURAN-3-YL)METHYL)-1H-IMIDAZO[4,5-B]PYRAZIN-2(3H)-ONE

A. (Tetrahydrofuran-3-yl)methanamine hydrochloride. A solution of tetrahydrofuran-3-carboxaldehyde (50 wt. % in water, 5 mL, 25 mmol), ammonium chloride (13 g, 25 mmol), Raney nickel (2 mL slurry) in methanol was reacted in a Parr shaker under 40 psi of hydrogen for 16 h at room temperature. The reaction was filtered through celite and the filtrate concentrated to an oil. The oil was added with dioxane (50 mL), 1M sodium hydroxide (50 mL), and di-tert-butyl dicarbonate (5.5 g, 25 mmol). The solution was stirred at room temperature for 16 h. The reaction was extracted with ethyl acetate and water. The organic layer was dried over magnesium sulfate, filtered and concentrated to an oil. The oil was purified on silica gel column (0-20% ethyl acetate in hexanes) to give a clear oil. The oil was treated with 4N hydrogen chloride in dioxane. The solution was concentrated and triturated with ether to give a white solid, (0.33 g, 10% yield). MS (ESI) m/z 101.9 [M+1]$^+$.

B. 6-Bromo-N$^2$-((tetrahydrofuran-3-yl)methyl)pyrazine-2,3-diamine. 3,5-Dibromopyrazin-2-amine (253 mg, 1 mmol), (tetrahydrofuran-3-yl)methanamine hydrochloride (0.33 g, 2.4 mmol), diisopropylethylamine (0.5 mL), and n-butanol (2 mL) were heated in a Biotage Emrys Optimizer microwave reactor at 200° C. for 2 h. The reaction was purified on silica gel column (0-10% methanol in ethyl acetate) to give a tan solid (140 mg, 51% yield). MS (ESI) m/z 303.3 [M+1]$^+$.

C. 6-Bromo-1-((tetrahydrofuran-3-yl)methyl)-1H-imidazo[4,5-b]pyrazin-2(3H)-one. 6-Bromo-N$^2$-((tetrahydrofuran-3-yl)methyl)pyrazine-2,3-diamine (140 mg, 0.5 mmol), 1,1'-carbonyldiimidazole (250 mg, 1.5 mmol), and dioxane (5 mL) were heated to reflux for 3 h. The reaction was purified on silica gel column (0-100% ethyl acetate in hexanes) to give a white solid (90 mg, 60% yield). MS (ESI) m/z 299.0 [M+1]$^+$.

D. 6-(4-Hydroxyphenyl)-1-((tetrahydrofuran-3-yl)methyl)-1H-imidazo[4,5-b]pyrazin-2(3H)-one. 6-Bromo-1-((tetrahydrofuran-3-yl)methyl)-1H-imidazo[4,5-b]pyrazin-2(3H)-one (90 mg, 0.3 mmol), 4-hydroxyphenylboronic acid (50 mg, 0.36 mmol), dichloro[1,1'-bis(diphenylphosphino)ferrocene]palladium(II) dichloromethane adduct (11 mg, 0.017 mmol), 1M sodium carbonate (1 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layer was concentrated and then purified by reverse-phase semi-preparatory HPLC (10-70% acetonitrile+0.1% TFA in H$_2$O+0.1% TFA, over 30 min). The product fractions were concentrated and then triturated with ether to give a white solid (60 mg, 64% yield). $^1$H NMR (400 MHz, DMSO-d$_6$) δ 11.96 (s, 1H), 9.70 (s, 1H), 8.37 (s, 1H), 7.85 (d, J=9.0, 2H), 6.87 (d, J=8.6, 2H), 3.86 (d, J=7.4, 2H), 3.80 (td, J=8.1, 5.7, 1H), 3.65-3.71 (m, 1H), 3.57-3.64 (m, 2H), 2.77-2.86 (m, 1H), 1.92-2.01 (m, 1H), 1.66-1.74 (m, 1H); MS (ESI) m/z 313.5 [M+1]$^+$; mp 256-258° C.

5.1.132 Example 132

SYNTHESIS OF 1-(((1S,4S)-4-HYDROXYCYCLOHEXYL)METHYL)-6-(4-HYDROXYPHENYL)-1H-IMIDAZO[4,5-B]PYRAZIN-2(3H)-ONE

A. (1s,4s)-4-Hydroxycyclohexanecarboxamide. (1s,4s)-4-Hydroxycyclohexanecarboxylic acid (5.4 g, 38 mmol), ammonium chloride (2.2 g, 41 mmol), O-(benzotriazol-1-yl)-N,N,N'N'-tetramethyluronium hexafluorophosphate (15.6 g, 41 mmol), triethylamine (16 mL, 113 mmol), and acetonitrile (80 ml) were stirred together at room temperature for 16 h. The reaction was filtered and rinsed with acetonitrile. The filtrate was concentrated and then triturated with ethyl acetate to give a white solid (2.1 g, 39% yield). MS (ESI) m/z 144.1 [M+1]$^+$.

B. (1s,4s)-4-(Aminomethyl)cyclohexanol hydrochloride. (1s,4s)-4-Hydroxycyclo-hexane carboxamide (1.4 g, 10 mmol) was dissolved in tetrahydrofuran (15 mL). Chloroborane methylsulfide complex (2.1 mL, 20 mmol) was added and the reaction was heated to reflux under nitrogen for 16 h. The reaction was quenched by slow addition of methanol. 4N Hydrogen chloride in dioxane (5 mL) was added to the reaction and the solution was concentrated. The residue was triturated with 10% methanol in ethyl acetate to give a white solid after filtration, (0.2 g, 10% yield). MS (ESI) m/z 130.1 [M+1]$^+$.

C. (1s,4s)-4-((3-Amino-6-bromopyrazin-2-ylamino)methyl)cyclohexanol 3,5-Dibromo-pyrazin-2-amine (253 mg, 1 mmol), (1s,4s)-4-(aminomethyl)cyclohexanol hydrochloride (200 mg, 1.2 mmol), diisopropylethylamine (1 mL), and n-butanol (2 mL) were heated in a Biotage Emrys Optimizer microwave reactor at 200° C. for 2 h. The reaction was purified on silica gel column (0-10% methanol in ethyl acetate) to give a tan solid (135 mg, 45% yield). MS (ESI) m/z 303.3 [M+1]$^+$.

D. 6-Bromo-1-(((1s,4s)-4-hydroxycyclohexyl)methyl)-1H-imidazo[4,5-b]pyrazin-2(3H)-one. (1s,4s)-4-((3-Amino-6-bromopyrazin-2-ylamino)methyl)cyclohexanol (135 mg, 0.45 mmol), 1,1'-carbonyldiimidazole (218 mg, 1.3 mmol), and dioxane (3 mL) were heated in a Biotage Emrys Optimizer microwave reactor at 200° C. for 1 h. The reaction was purified on silica gel column (0-10% methanol in ethyl acetate) to give a tan solid (80 mg, 44% yield). MS (ESI) m/z 311.3 [M+1]$^+$.

E. 1-(((1s,4s)-4-Hydroxycyclohexyl)methyl)-6-(4-hydroxyphenyl)-1H-imidazo[4,5-b]pyrazin-2(3H)-one. 6-Bromo-1-(((1s,4s)-4-hydroxycyclohexyl)methyl)-1H-imidazo[4,5-b]pyrazin-2(3H)-one (80 mg, 0.2 mmol), 4-hydroxyphenylboronic acid (33 mg, 0.24 mmol), dichloro[1,1'-bis(diphenylphosphino)ferrocene]palladium(II) dichloromethane adduct (7 mg, 0.02 mmol), 1M sodium carbonate (0.6 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layer was concentrated and then purified by reverse-phase semi-preparatory HPLC (10-70% acetonitrile+0.1% TFA in H$_2$O+0.1% TFA, over 30 min). The product fractions were concentrated and then triturated with ether to give a white solid (25 mg, 37% yield). $^1$H NMR (400 MHz, DMSO-d$_6$) δ 11.92 (s, 1H), 9.70 (s, 1H), 8.35 (s, 1H), 7.85 (d, J=8.6, 2H), 6.87 (d, J=8.6, 2H), 4.34 (d, J=3.5, 1H), 3.75 (d, J=7.0, 2H), 3.71 (s, 1H), 1.95 (s, 1H), 1.56-1.66 (m, 2H), 1.34-1.46 (m, 6H); MS (ESI) m/z 341.8 [M+1]$^+$; mp 314-316° C.

5.1.133 Example 133

SYNTHESIS OF 6-(1H-BENZO[D]IMIDAZOL-5-YL)-1-((TETRAHYDRO-2H-PYRAN-4-YL)METHYL)-1H-IMIDAZO[4,5-B]PYRAZIN-2(3H)-ONE

A. tert-Butyl 5-bromo-1H-benzo[d]imidazole-2-carboxylate. A solution of 5-bromo-1H-benzimidazole (1.06 g, 5.38 mmol), di-tert-butyl dicarbonate (1.3 g, 5.91 mmol), triethylamine (0.9 mL, 6.45 mmol) and dimethylaminopyridine (few crystals) in anhydrous tetrahydrofuran (15 mL) was allowed to stir at room temperature overnight. The reaction mixture was concentrated under reduced pressure and the crude product was purified by Biotage chromatography (0-55% ethyl acetate in hexanes) to provide the desired product (0.85 g, 54%) as a white solid. MS (ESI) m/z 297.3 [M+1]$^+$.

B. tert-Butyl 5-(trimethylstannyl)-1H-benzo[d]imidazole-2-carboxylate. A solution of tert-butyl 5-bromo-1H-benzo[d]imidazole-2-carboxylate (500 mg, 1.68 mmol), hexamethylditin (0.45 mL, 2.02 mmol), tetrakis(triphenylphosphine)palladium(0) (195 mg, 0.17 mmol) in toluene (10 mL) was heated at 100° C. for 2 h. Upon completion of the reaction, toluene was removed under reduced pressure and the resulting residue was purified by Biotage chromatography (0-50% ethyl acetate in hexanes) to afford the title compound (640 mg, 100%). MS (ESI) m/z 383.2 [M+1]$^+$.

C. 6-(1H-Benzo[d]imidazol-5-yl)-1-((tetrahydro-2H-pyran-4-yl)methyl)-1H-imidazol-[4,5-b]pyrazin-2(3H)-one hydrochloride. tert-Butyl 5-(trimethylstannyl)-1H-benzo[d]imidazole-2-carboxylate (640 mg, 1.7 mmol), 6-bromo-1-((tetrahydro-2H-pyran-4-yl)methyl)-1H-imidazo[4,5-b]pyrazin-2(3H)-one (See Example 101.B) (420 mg, 1.3 mmol), dichlorobis(triphenylphosphine)palladium(II) (90 mg, 0.13 mmol) in DMF (25 mL) were reacted for 1.5 h at 90° C. The product was purified by reverse-phase semi-preparatory HPLC (30-100% acetonitrile+0.1% TFA in H$_2$O+0.1% TFA, over 30 min). The desired fractions were concentrated, treated with 4N hydrochloric acid in diethyl ether (few drops), and sonicated. This procedure was repeated twice more to provide 6-(1H-benzo[d]imidazol-5-yl)-1-((tetrahydro-2H-pyran-4-yl)methyl)-1H-imidazo[4,5-b]pyrazin-2(3H)-one (48 mg, 10% yield) as the hydrochloride salt. $^1$H NMR (400 MHz, DMSO-d$_6$) δ 12.07 (s, 1H), 8.55 (s, 1H), 8.52 (s, 1H), 8.33 (s, 1H), 8.06 (dd, J=8.0, 1.6, 1H), 7.80 (d, J=8.8, 1H), 3.81 (m, 2H), 3.80 (d, J=7.2, 2H), 3.27 (d, J=11.6, 2H), 2.14 (m, 1H), 1.59 (m, 2H), 1.33 (m, 2H); MS (ESI) m/z 351.2 [M+1]$^+$.

5.1.134 Example 134

SYNTHESIS OF 6-(4-(5-(MORPHOLINOMETHYL)-1H-1,2,4-TRIAZOL-3-YL)PHENYL)-1-((TETRAHYDRO-2H-PYRAN-4-YL)METHYL)-1H-IMIDAZO[4,5-B]PYRAZIN-2(3H)-ONE

A. 4-[2-Oxo-3-(2H-3,4,5,6-tetrahydropyran-4-ylmethyl)-4-imidazolino[4,5-e]pyrazin-5-yl]benzenecarbonitrile. 6-Bromo-1-(2H-3,4,5,6-tetrahydropyran-4-ylmethyl)-4-imidazolino[4,5-b]pyrazin-2-one (0.700 g, 2.24 mmol), 4-cyanophenylboronic acid, (0.395 g, 2.69 mmol), [1,1'-bis(diphenylphosphino)ferrocene]dichloropalladium(II) complex with dichloromethane (1:1) (0.183 g, 0.224 mmol), potassium carbonate (1.90 g, 8.96 mmol), dimethylformamide (15 mL) and water (5 mL) were combined in a sealed tube and heated to 100° C. for 3 h. The solution was condensed under reduced pressure and the resulting material portioned between water and ethyl acetate. Organic layers were collected, dried over magnesium sulfate, filtered and concentrated. The resulting residue was taken up in methanol and sonicated for 10 min. Product precipitated and was filtered off to give the title compound (0.497 g, 66%). MS (ESI) m/z 336.4 [M+1]$^+$.

B. Ethyl 4-(2-oxo-3-((tetrahydro-2H-pyran-4-yl)methyl)-2,3-dihydro-1H-imidazo[4,5-b]pyrazin-5-yl)benzimidate. A solution of 4-[2-oxo-3-(2H-3,4,5,6-tetrahydropyran-4-ylmethyl)-3-hydrobenzimidazol-5-yl]benzenecarbonitrile (0.497 g, 1.48 mmol) in ethanol (100 mL) was cooled to 0° C. and hydrogen chloride gas was bubbled through the solution for 10 min. The resulting solution was allowed to warm to room temperature and was stirred for 18 h. The reaction was concentrated under reduced pressure and the resulting solid was used directly in the next step as the hydrochloride salt (0.637 g, 95%). MS (ESI) m/z 382 [M+1]$^+$.

C. 6-(4-(5-(Morpholinomethyl)-1H-1,2,4-triazol-3-yl)phenyl)-1-((tetrahydro-2H-pyran-4-yl)methyl)-1H-imidazo[4,5-b]pyrazin-2(3H)-one. A solution of ethyl 4-(2-oxo-3-((tetrahydro-2H-pyran-4-yl)methyl)-2,3-dihydro-1H-imidazo[4,5-b]pyrazin-5-yl)benzimidate (0.20 g, 0.525 mmol), 2-morpholinoacetohydrazide (0.334 g, 2.1 mmol), and triethylamine (1.46 mL, 10.5 mmol) and methanol (4 mL) were reacted as described in General Procedure F. The reaction was concentrated and the resulting residue was taken up in methylene chloride. Purification using Biotage column chromatography (0-80% ethyl acetate in hexanes) provided clean product 95.9% pure (0.11 g, 44%). $^1$H NMR (400 MHz, CD$_3$OD) δ 8.50 (s, 1H), 8.13 (m, 4H), 3.96 (m, 4H), 3.75 (m, 7H), 3.43 (m, 2H), 2.58 (s, 4H), 2.50 (m, 1H), 2.30 (m, 1H), 1.67 (m, 2H), 1.52 (m, 2H); MS (ESI) m/z 477.5 [M+1]$^+$; mp 281-283° C.

5.1.135 Example 135

SYNTHESIS OF 6-(4-HYDROXYPHENYL)-1-(3-(2-OXOPYRROLIDIN-1-YL)PROPYL)-1H-IMIDAZO[4,5-B]PYRAZIN-2(3H)-ONE

A. 1-(3-(3-Amino-6-bromopyrazin-2-ylamino)propyl)pyrrolidin-2-one. 3,5-Dibromo-pyrazin-2-amine (253 mg, 1 mmol), 1-(3-aminopropyl)pyrrolidin-2-one (426 mg, 1 mmol), and n-butanol (2 mL) were stirred at 100° C. under nitrogen for 3 d. The reaction was purified on silica gel column (0-100% ethyl acetate in hexanes) to give the title compound (250 mg, 80% yield) as a white solid. MS (ESI) m/z 315.9 [M+1]$^+$.

B. 6-Bromo-1-(3-(2-oxopyrrolidin-1-yl)propyl)-1H-imidazo[4,5-b]pyrazin-2(3H)-one. 1-(3-(3-Amino-6-bromopyrazin-2-ylamino)propyl)pyrrolidin-2-one (250 mg, 0.8 mmol), 1,1'-carbonyldiimidazole (387 mg, 2.4 mmol), and dioxane (5 mL) were heated to reflux for 3 h. The reaction was purified on silica gel column (0-100% ethyl acetate in hexanes) to give a clear oil. MS (ESI) m/z 342.1 [M+1]$^+$.

C. 6-(4-Hydroxyphenyl)-1-(3-(2-oxopyrrolidin-1-yl)propyl)-1H-imidazo[4,5-b]pyrazin-2(3H)-one. 6-Bromo-1-(3-(2-oxopyrrolidin-1-yl)propyl)-1H-imidazo[4,5-b]pyrazin-2

(3H)-one (119 mg, 0.35 mmol), 4-hydroxyphenylboronic acid (53 mg, 0.39 mmol), dichloro[1,1'-bis(diphenylphosphino)ferrocene]palladium(II) dichloromethane adduct (13 mg, 0.017 mmol), 1M sodium carbonate (1 mL, 0.8 mmol), and dioxane (2 mL) were heated in a Biotage Emrys Optimizer microwave reactor at 150° C. for 10 min. The reaction was adjusted to pH 7 with 1N hydrochloric acid and then extracted with water and ethyl acetate. The organic layer was concentrated and the resulting material was purified by reverse-phase semi-preparatory HPLC (10-70% acetonitrile+ 0.1% TFA in $H_2O$+0.1% TFA, over 30 min). The product fractions were concentrated and the residue was triturated with ether to give a white solid (69 mg, 24% yield). $^1$H NMR (400 MHz, DMSO-$d_6$) δ 11.93 (s, 1H), 9.70 (s, 1H), 8.36 (s, 1H), 7.86 (d, J=8.6, 2H), 6.86 (d, J=8.6, 2H), 3.84 (t, J=7.2, 2H), 3.35-3.39 (m, 2H), 3.25 (t, J=7.0, 2H), 2.16 (t, J=8.0, 2H), 1.94-2.02 (m, 2H), 1.86-1.93 (m, 2H); MS (ESI) m/z 354.4 [M+1]$^+$; mp 305-306° C.

5.1.136 Example 136

SYNTHESIS OF 6-(4-HYDROXYPHENYL)-1-(2-MORPHOLINOETHYL)-1H-IMIDAZO[4,5-B]PYRAZIN-2(3H)-ONE

A. 6-Bromo-$N^2$-(2-morpholinoethyl)pyrazine-2,3-diamine. In a sealed tube, a solution of 5-bromopyrazine-2,3-diamine (5.0 g, 19.7 mmol), 2-morpholinoethanamine (5.14 g, 39.5 mmol), diisopropylethylamine (6.9 mL, 39.5 mmol) in n-butanol (100 mL) was heated at 120° C. for 17 h. The volatiles were removed under reduced pressure. The residue was taken up in hexanes and diethylether and sonicated. The resulting precipitate was collected by filtration to provide the title compound (5.23 g, 88%). MS (ESI) m/z 304.2 [M+1]$^+$.

B. 6-Bromo-1-(2-morpholinoethyl)-1H-imidazo[4,5-b]pyrazin-2(3H)-one. In a sealed tube, a solution of 6-bromo-$N^2$-(2-morpholinoethyl)pyrazine-2,3-diamine (5.23 g, 17.2 mmol), 1,1'-carbonyldiimidazole (4.2 g, 25.89 mmol) in tetrahydrofuran (50 mL) was heated at 110° C. The volatiles were removed under reduced pressure. The resulting residue was taken into hexanes and diethylether, sonicated, and the precipitate was collected by filtration, rinsed with hexanes, and dried in vacuum oven to afford the product (4.65 g, 82% yield) as a tan solid. MS (ESI) m/z 328.2[M+1]$^+$.

C. 6-(4-Hydroxyphenyl)-1-(2-morpholinoethyl)-1H-imidazo[4,5-b]pyrazin-2(3H)-one hydrochloride. 6-Bromo-1-(2-morpholinoethyl)-1H-imidazo[4,5-b]pyrazin-2(3H)-one (300 mg, 0.95 mmol), [4-(N-methylaminocarbonyl)phenyl] boronic acid (205 mg, 1.15 mmol), dichloro[1,1'-bis(diphenylphosphino)ferrocene]palladium (II) dichloromethane (80 mg, 0.09 mmol) and potassium phosphate (805 mg, 3.8 mmol) in DMF (30 mL) and water (8 mL) were reacted according to General Procedure C. The product was purified by reverse-phase semi-preparatory HPLC (30-100% acetonitrile+0.1% TFA in $H_2O$+0.1% TFA, over 30 min). The desired fractions were concentrated, treated with 4N hydrochloric acid in diethylether (few drops) and sonicated. This procedure was repeated twice more to provide 6-(4-hydroxyphenyl)-1-(2-morpholinoethyl)-1H-imidazo[4,5-b]pyrazin-2(3H)-one (67 mg, 16%) as a colorless solid hydrochloride salt. $^1$H NMR (400 MHz, $CD_3OD$-$d_6$) δ 8.38 (s, 1H), 8.84 (d, J=8.4, 2H), 7.44 (s, 1H), 7.39 (d, J=8.4, 2H), 4.45 (t, J=5.6, 2H), 4.07 (d, J=12.4, 2H), 3.82 (d, J=12.4, 2H), 3.69-3.64 (m, 4H); MS (ESI) m/z 342.15 [M+1]$^+$.

5.1.137 Example 137

SYNTHESIS OF 1-(CYCLOHEXYLMETHYL)-6-(4-(OXAZOL-5-YL)PHENYL)-1H-IMIDAZO[4,5-B]PYRAZIN-2(3H)-ONE

A. 5-(4-Bromophenyl)oxazole. A solution of 2,4'-dibromoacetophenone (2.5 g, 9.0 mmol) in formamide (40 mL) was heated in a sealed tube at 110° C. for 2.5 h. Upon cooling, the reaction mixture was poured in water, extracted with methylene chloride (2×), dried over magnesium sulfate, filtered and concentrated under reduced pressure. The crude product was purified by Biotage chromatography (0-50% ethyl acetate in hexanes) to afford the title compound (380 mg, 19%). MS (ESI) m/z 226.1 [M+1]$^+$.

B. 5-(4-(Trimethylstannyl)phenyl)oxazole. A solution of 5-(4-bromophenyl)oxazole (380 mg, 1.70 mmol), hexamethylditin (0.45 mL, 2.02 mmol), tetrakis(triphenylphosphine)palladium(0) (195 mg, 0.17 mmol) in toluene (10 mL) was heated at 100° C. for 2 h. Upon completion of the reaction, toluene was removed under reduced pressure, and the residue was purified by Biotage chromatography (0-50% EtOAc in hexanes) to afford the desired product (250 mg, 47%). MS (ESI) m/z 305.8[M+1]$^+$.

C. 1-(Cyclohexylmethyl)-6-(4-(oxazol-5-yl)phenyl)-1H-imidazo[4,5-b]pyrazin-2(3H)-one. 5-(4-(Trimethylstannyl) phenyl)oxazole (250 mg, 0.8 mmol), 6-bromo-1-(cyclohexylmethyl)-1H-imidazo[4,5-b]pyrazin-2(3H)-one (See Example 55. B) (208 mg, 0.66 mmol), dichlorobis-(triphenylphosphine)palladium(II) (42 mg, 0.06 mmol) in DMF (10 mL) were reacted for 2 h at 90° C. The product was purified by reverse-phase semi-preparatory HPLC (10-100% acetonitrile+0.1% TFA in $H_2O$+0.1% TFA, over 30 min). The desired fractions were concentrated, and treated with aqueous 6N ammonium hydroxide (few drops). The volatiles were removed under reduced pressure, and the residue was taken up in water (2 mL), and the solid was filtered and rinsed with water. The resulting solid was dried under vacuum to provide the title compound (20 mg, 8% yield). $^1$H NMR (400 MHz, DMSO-$d_6$) δ 12.06 (s, 1H), 8.71 (s, 1H), 8.55 (s, 1H), 8.51 (s, 1H), 8.11 (d, J=8.4, 2H), 7.91 (d, J=8.4, 2H), 3.74 (d, J=7.2, 2H), 1.92 (m, 1H), 1.68 (m, 3H), 1.60 (m, 2H), 1.18 (m, 3H), 1.03 (m, 2H); MS (ESI) m/z 376.2 [M+1]$^+$.

5.1.138 Example 138

SYNTHESIS OF 6-(2-METHYL-1H-BENZO[D]IMIDAZOL-5-YL)-1-((TETRAHYDRO-2H-PYRAN-4-YL)METHYL)-1H-IMIDAZO[4,5-B]PYRAZIN-2(3H)-ONE

A. tert-Butyl 6-bromo-2-methyl-1H-benzo[d]imidazole-1-carboxylate. A solution of 6-bromo-2-methyl-1H-benzo[d]imidazole (1 g, 4.73 mmol), di-tert-butyl dicarbonate (1.09 g, 5.21 mmol), triethylamine (0.72 mL, 5.67 mmol) and N,N-dimethylpyridin-4-amine (few crystals) in anhydrous tetrahydrofuran (15 mL) was allowed to stir at room temperature overnight. The reaction mixture was concentrated under reduced pressure and the crude product was purified by Biotage chromatography (0-55% ethyl acetate in hexanes) to provide the desired product (0.22 g, 15%) as a white solid. MS (ESI) m/z 313.2[M+1]$^+$.

B. tert-Butyl 2-methyl-6-(trimethylstannyl)-1H-benzo[d]imidazole-1-carboxylate. A solution of tert-butyl 6-bromo-2-methyl-1H-benzo[d]imidazole-1-carboxylate (0.22 g, 0.70 mmol), hexamethylditin (0.19 mL, 0.84 mmol), tetrakis (triphenylphosphine)palladium(0) (0.081 g, 0.07 mmol) in toluene (10 mL) was heated at 100° C. for 2 h. Upon completion of the reaction, toluene was removed under reduced pressure, and the residue was purified by Biotage chromatography (0-50% ethyl acetate in hexanes) to afford the title compound (120 mg, 44%). MS (ESI) m/z 397.3[M+1]$^+$.

C. 6-(2-Methyl-1H-benzo[d]imidazol-5-yl)-1-((tetrahydro-2H-pyran-4-yl)methyl)-1H-imidazo[4,5-b]pyrazin-2(3H)-one hydrochloride. tert-Butyl 2-methyl-6-(trimethylstannyl)-1H-benzo[d]imidazole-1-carboxylate (120 mg, 0.30 mmol), 6-bromo-1-((tetrahydro-2H-pyran-4-yl)methyl)-1H-imidazo[4,5-b]pyrazin-2(3H)-one (See Example 101.B) (96 mg, 0.3 mmol), dichlorobis(triphenylphosphine)palladium (II) (21 mg, 0.03 mmol) in DMF (5 mL) were reacted for 1.5 h at 90° C. The product was purified by reverse-phase semi-preparatory HPLC (10-100% acetonitrile+0.1% TFA in H$_2$O+0.1% TFA, over 30 min). The desired fractions were concentrated, and treated with 4N hydrochloric acid in diethyl ether (few drops), sonicated and concentrated. This procedure was repeated twice more to provide the title compound (8 mg, 6.5% yield). $^1$H NMR (400 MHz, DMSO-d$_6$) δ 12.12 (s, 1H), 8.62 (s, 1H), 8.31 (s, 1H), 8.15 (d, J=8.4, 1H), 7.82 (d, J=8.4, 1H), 3.85 (m, 2H), 3.81 (d, J=8.0, 2H), 3.26 (t, J=11.2, 2H), 1.90 (m, 1H), 1.61 (m, 2H), 1.35-1.23 (m, 3H), 0.89-0.86 (m, 2H); MS (ESI) m/z 365.1 [M+1]$^+$.

5.1.139 Example 139

SYNTHESIS OF 6-(4-(5-(METHOXYMETHYL)-1H-1,2,4-TRIAZOL-3-YL)PHENYL)-1-((TETRAHYDRO-2H-PYRAN-4-YL)METHYL)-1H-IMIDAZO[4,5-B]PYRAZIN-2(3H)-ONE

A. 6-(4-(5-(Methoxymethyl)-1H-1,2,4-triazol-3-yl)phenyl)-1-((tetrahydro-2H-pyran-4-yl)methyl)-1H-imidazo[4,5-b]pyrazin-2(3H)-one. A solution of ethyl 4-(2-oxo-3-((tetrahydro-2H-pyran-4-yl)methyl)-2,3-dihydro-1H-imidazo[4,5-b]pyrazin-5-yl)benzimidate (See Example 134.B) (0.205 g, 0.538 mmol), 2-methoxyacetohydrazide (0.224 g, 2.15 mmol), triethylamine (1.5 mL, 10.8 mmol) and methanol (4 mL) were reacted as described in General Procedure F. The reaction was concentrated under reduced pressure and the resulting residue was taken up in methylene chloride. Purification using Biotage column chromatography (0-20% methanol in dichloromethane) provided clean product 98.6% pure (0.076 g, 34%). $^1$H NMR (400 MHz, CD$_3$OD) δ 8.49 (s, 1H), 8.16 (m, 4H), 4.63 (s, 2H), 3.96 (m, 5H), 3.47 (s, 3H), 3.42 (m, 3H), 2.32 (m, 1H), 1.67 (m, 2H), 1.52 (m, 2H); MS (ESI) m/z 422.5 [M+1]$^+$; mp 273-276° C.

5.1.140 Example 140

SYNTHESIS OF 1-((1S,4S)-4-(HYDROXYMETHYL)CYCLOHEXYL)-6-(4-HYDROXYPHENYL)-1H-IMIDAZO[4,5-B]PYRAZIN-2(3H)-ONE

A. (1s,4s)-4-(tert-Butoxycarbonylamino)cyclohexanecarboxylic acid. (1s,4s)-4-Amino-cyclohexane carboxylic acid (2 g, 14 mmol) was dissolved in 1,4-dioxane (40 mL) and di-t-butyl-dicarbonate (6.1 g, 28 mmol) and sodium bicarbonate (4.06 g, 48 mmol) dissolved in water (25 mL) were added. The mixture was stirred at rt overnight. Saturated potassium hydrogensulfate solution was added dropwise until gas evolution stopped. The solvent was removed, and the residue taken up in ethyl acetate and washed with water. The organic fractions were pooled, dried over magnesium sulfate and concentrated under high vacuum to yield the title compound (3.4 g, 100% yield). MS (ESI) m/z 244.4[M+1]$^+$.

B. tert-Butyl (1s,4s)-4-(hydroxymethyl)cyclohexylcarbamate (1s,4s)-4-(tert-Butoxy-carbonylamino)cyclohexanecarboxylic acid (3.4 g, 14 mmol) was dissolved in anhydrous tetrahydrofuran (20 mL) and the solution was cooled to −10° C. (ice/methanol bath). N-Methylmorpholine (1.41 g, 14 mmol) and isobutylchloroformate (1.91 g, 14 mmol) were added and the reaction was stirred for 10 min. Sodium borohydride (1.59 g, 42 mmol) was added in one portion, the reaction was warmed to 0° C. and methanol added dropwise (5 mL). The reaction was stirred for 30 min at 0° C. and quenched with saturated potassium hydrogensulfate solution (5 mL), extracted with ethyl acetate, dried over magnesium sulfate and concentrated to yield the title compound as an oil that solidified upon standing (3.2 g, 100% yield). MS (ESI) m/z 230.6[M+1]$^+$.

C. ((1s,4s)-4-Aminocyclohexyl)methanol hydrochloride tert-Butyl (1s,4s)-4-(hydroxymethyl)cyclohexylcarbamate (1.0 g, 4.36 mmol) was placed in 1,4-dioxane (4 mL) at room temperature and 4N hydrochloric acid in 1,4-dioxane (3.5 mL, 13.1 mmol) was added and the resulting solution was stirred overnight. The solvent was removed, the residue was treated with ether, sonicated and filtered. The resulting solid was dried under high vacuum to yield the title compound as a white solid (0.61 g, 84.7% yield). MS (ESI) m/z 130.1 [M+1]$^+$.

D. ((1s,4s)-4-(3-Amino-6-bromopyrazin-2-ylamino)cyclohexyl)methanol 2-Amino-3,5-dibromopyrazine (1.53 g, 6 mmol), ((1s,4s)-4-aminocyclohexyl)methanol hydrochloride (1.0 g, 6 mmol) and diisopropylethylamine (2.32 g, 18 mmol) were dissolved in n-butanol (3 mL) and reacted according to General Procedure A. The mixture was purified using silica gel chromatography (30-100% ethyl acetate in hexanes) to afford the title compound (0.42 g, 23% yield). MS (ESI) m/z 301.3 [M]$^+$, 303.3 [M+2]$^+$.

E. 4-(5-Amino-6-((1s,4s)-4-(hydroxymethyl)cyclohexylamino)pyrazin-2-yl)phenol ((1s,4s)-4-(3-Amino-6-bromopyrazin-2-ylamino)cyclohexyl)methanol (0.42 g, 1.39 mmol), 4-hydroxybenzene boronic acid (0.192 g, 1.39 mmol), dichloro[1,1'-bis(diphenylphosphino)ferrocene]palladium(II) dichloromethane adduct (0.113 g, 0.139 mmol) and sodium carbonate (0.74 g, 6.97 mmol) were reacted in 1,4-dioxane (4 mL) according to General Procedure B2 and purified using silica gel chromatography (50-100% ethyl acetate in hexanes) to afford the title compound (0.175 g, 40% yield). MS (ESI) m/z 315.5 [M+1]$^+$.

F. 1-((1s,4s)-4-(Hydroxymethyl)cyclohexyl)-6-(4-hydroxyphenyl)-1H-imidazo[4,5-b]pyrazin-2(3H)-one 4-(5-Amino-6-((1s,4s)-4-(hydroxymethyl)cyclohexylamino) pyrazin-2-yl)phenol (0.175 g, 0.557 mmol), 1,1'-carbonyldiimidazole (0.27 g, 1.67 mmol), and tetrahydrofuran (3 mL) were combined in a sealed tube and heated to 120° C. for 3 h. The mixture was cooled, potassium carbonate (1 g, 7.2 mmol) in methanol (3 mL) was added and stirred at room temperature overnight. The product was purified by reverse-phase semi-preparatory HPLC (20-100% acetonitrile+0.1% TFA in H$_2$O+0.1% TFA, over 30 min). Product fractions were concentrated to yield an off-white solid (17.0 mg, 9% yield). $^1$H NMR (400 MHz, DMSO-d$_6$) δ 11.9 (s, 1H), 9.71 (s, 1H), 8.35 (s, 1H), 7.85 (d, J=8.8, 2H), 6.86 (d, J=8.8, 2H), 4.58 (t, J=5.6, 1H), 4.23 (m, 1H), 3.64 (t, J=5.6, 2H), 1.86 (m, 2H), 1.79 (m, 2H), 1.55 (m, 4H); MS (ESI) m/z 341.3[M+1]$^+$; mp 208-210° C.

5.1.141 Example 141

SYNTHESIS OF 6-(3-METHYL-1H-PYRAZOL-4-YL)-1-((TETRAHYDRO-2H-PYRAN-4-YL)METHYL)-1H-IMIDAZO[4,5-B]PYRAZIN-2(3H)-ONE

A. tert-Butyl 4-bromo-3-methyl-1H-pyrazole-1-carboxylate. 4-Bromo-3-methyl-1H-pyrazole (0.3 g, 1.86 mmol), di-t-butyl dicarbonate (0.65 g, 2.98 mmol) and sodium hydroxide (0.082 g, 2.05 mmol) were placed in 1,4-dioxane (10 mL) and stirred at room temperature overnight. The solvent was removed and the residue treated with ethyl acetate and filtered. The filtrate was concentrated to yield the title compound (0.48 g, 100% yield). MS (ESI) m/z 261.3 $[M]^+$, 263.3 $[M+2]^+$.

B. 3-Methyl-4-(4,4,5,5-tetramethyl-1,3,2-dioxaborolan-2-yl)-1H-pyrazole. tert-Butyl 4-bromo-3-methyl-1H-pyrazole-1-carboxylate (0.48 g, 1.84 mmol), bis(pinacolato)diboron (0.535 g, 2.1 mmol), dichloro[1,1'-bis(diphenylphosphino)ferrocene]palladium(II) dichloromethane adduct (0.156 g, 0.19 mmol) and potassium acetate (0.56 g, 5.7 mmol) were placed in a sealed tube, in DMSO (5 mL). The system was flushed with nitrogen, sealed and heated to 90° C. for 18 h. The solvent was removed and the desired product isolated using silica gel chromatography (50% ethyl acetate in hexanes) to afford the title compound (0.2 g, 50% yield). MS (ESI) m/z 209.1 $[M+1]^+$.

C. tert-Butyl 3-methyl-4-(4,4,5,5-tetramethyl-1,3,2-dioxaborolan-2-yl)-1H-pyrazole-1-carboxylate. 3-Methyl-4-(4,4,5,5-tetramethyl-1,3,2-dioxaborolan-2-yl)-1H-pyrazole (0.2 g, 0.96 mmol), di-t-butyldicarbonate (0.4 g, 1.8 mmol) and triethylamine (0.18 g, 1.79 mmol) were placed in 1,4-dioxane (5 mL) and stirred, under nitrogen, at rt for two days. The solvent was removed and the desired product isolated using silica gel chromatography (25% ethyl acetate in hexanes) to afford the title compound (0.175 g, 59% yield). MS (ESI) m/z 309.4 $[M+1]^+$.

D. 6-(3-Methyl-1H-pyrazol-4-yl)-1-((tetrahydro-2H-pyran-4-yl)methyl)-1H-imidazo[4,5-b]pyrazin-2(3H)-one. 6-Bromo-1-((tetrahydro-2H-pyran-4-yl)methyl)-1H-imidazo[4,5-b]pyrazin-2(3H)-one (See Example 101.B) (0.16 g, 0.51 mmol), tert-butyl 3-methyl-4-(4,4,5,5-tetramethyl-1,3,2-dioxaborolan-2-yl)-1H-pyrazole-1-carboxylate (0.175 g, 0.56 mmol), dichloro[1,1'-bis(diphenylphosphino)ferrocene] palladium(II) dichloromethane adduct (0.04 g, 0.05 mmol) and potassium phosphate (0.43 g, 2.05 mmol) were combined in DMF (3 mL) and water (0.2 mL), the mixture purged with nitrogen and heated in a sealed tube at 100° C. overnight. The solvent was removed and the crude purified on silica gel chromatography (100% ethyl acetate) to afford the title compound as a white solid (0.036 g, 22% yield). $^1$H NMR (400 MHz, DMSO-$d_6$) δ 12.77 (s, 1H), 11.87 (s, 1H), 8.17 (s, 1H), 7.92 (s, 1H), 3.82 (d, J=12, 2H), 3.72 (d, J=7.2, 2H), 3.23 (t, J=10, 2H), 2.54 (s, 3H), 2.13 (m, 1H), 1.54 (d, J=12, 2H), 1.26 (m, 2H); MS (ESI) m/z 315.1 $[M+1]^+$; mp 222-224° C.

5.1.142 Example 142

SYNTHESIS OF 6-(1H-PYRAZOL-4-YL)-1-((TETRAHYDRO-2H-PYRAN-4-YL)METHYL)-1H-IMIDAZO[4,5-B]PYRAZIN-2(3H)-ONE

A. 6-(1H-Pyrazol-4-yl)-1-((tetrahydro-2H-pyran-4-yl)methyl)-1H-imidazo[4,5-b]pyrazin-2(3H)-one. 6-Bromo-1-((tetrahydro-2H-pyran-4-yl)methyl)-1H-imidazo[4,5-b]pyrazin-2(3H)-one (See Example 101.B) (0.25 g, 0.8 mmol), pyrazole-4-boronic acid (0.1 g, 0.89 mmol), dichloro[1,1'-bis(diphenylphosphino)ferrocene]palladium(II) dichloromethane adduct (0.065 g, 0.08 mmol) and potassium phosphate (0.68 g, 3.2 mmol) were combined in DMF (3 mL) and water (0.2 mL), the mixture purged with nitrogen and heated in a sealed tube at 100° C. overnight. The solvent was removed and the crude purified on silica gel chromatography (100% ethyl acetate) to afford the title compound as an off-white solid (0.075 g, 31% yield). $^1$H NMR (400 MHz, DMSO-$d_6$) δ 13.06 (s, 1H), 11.88 (s, 1H), 8.26 (s, 1H), 8.02 (s, 1H), 3.82 (d, J=11.6, 2H), 3.74 (d, J=7.2, 2H), 3.25 (t, J=11.2, 2H), 2.12 (m, 1H), 1.54 (d, J=10.8, 2H), 1.30 (m, 2H); MS (ESI) m/z 301.3 $[M+1]^+$; mp 238-240° C.

5.1.143 Example 143

SYNTHESIS OF 6-(2-AMINO-1H-BENZO[D]IMIDAZOL-5-YL)-1-((TETRAHYDRO-2H-PYRAN-4-YL)METHYL)-1H-IMIDAZO[4,5-B]PYRAZIN-2(3H)-ONE

A. tert-Butyl 2-(bis(tert-butoxycarbonyl)amino)-5-bromo-1H-benzo[d]imidazole-1-carboxylate. A solution of 5-bromo-1H-benzimidazole-2-amine (1 g, 4.71 mmol), di-t-butyl dicarbonate (3.81 g, 17.45 mmol), triethylamine (1.44 mL, 10.36 mmol) and 4-dimethylaminopyridine (few crystals) in anhydrous tetrahydrofuran (15 mL) was allowed to stir at room temperature overnight. The reaction mixture was concentrated under reduced pressure, and the crude product was purified by Biotage chromatography (0-40% EtOAc in hexanes) to provide the desired product (1.690 g, 70%) as a white solid. MS (ESI) m/z 514.2$[M+1]^+$.

B. tert-Butyl 2-(bis(tert-butoxycarbonyl)amino)-5-(trimethylstannyl)-1H-benzo[d]imidazole-1-carboxylate. A solution of tert-butyl 2-(bis(tert-butoxycarbonyl)amino)-5-bromo-1H-benzo[d]imidazole-1-carboxylate (0.30 g, 0.58 mmol), hexamethylditin (0.15 mL, 0.70 mmol), and tetrakis(triphenylphosphine)palladium(0) (0.067 g, 0.06 mmol) in toluene (10 mL) was heated at 100° C. for 2 h. Upon completion of the reaction, toluene was removed under reduced pressure and the residue was purified by Biotage chromatography (0-40% EtOAc in hexanes) to afford the title compound (120 mg, 34%). MS (ESI) m/z 598.4$[M+1]^+$.

C. 6-(2-Amino-1H-benzo[d]imidazol-5-yl)-1-((tetrahydro-2H-pyran-4-yl)methyl)-1H-imidazo[4,5-b]pyrazin-2(3H)-one dihydrochloride. A solution of tert-butyl 2-(bis(tert-butoxycarbonyl)amino)-5-(trimethylstannyl)-1H-benzo[d]imidazole-1-carboxylate (120 mg, 0.20 mmol), 6-Bromo-1-((tetrahydro-2H-pyran-4-yl)methyl)-1H-imidazo[4,5-b]pyrazin-2(3H)-one (See Example 101.B) (63 mg, 0.2 mmol), and dichlorobis(triphenylphosphine)palladium(II) (14 mg, 0.02 mmol) in DMF (5 mL) was reacted for 1.5 h at 90° C. The product was purified by reverse-phase semi-preparatory HPLC (20-100% acetonitrile+0.1% TFA in H$_2$O+0.1% TFA, over 30 min). The desired fractions were concentrated, and treated with 4N hydrochloric acid in diethyl ether (few drops), sonicated and concentrated. This procedure was repeated twice more to provide the title compound (10.2 mg, 12.7% yield). $^1$H NMR (400 MHz, DMSO-$d_6$) δ 12.54 (d, J=11.2, 2H), 12.09 (s, 1H), 8.53 (s, 1H), 8.49 (s, 1H), 7.97 (s, 1H), 7.90 (d, J=8.4, 1H), 7.44 (d, J=8.4, 1H), 3.84 (d, J=10.8, 2H), 3.79 (d, J=10.8, 2H), 3.26 (t, J=10.8, 2H), 2.13 (m, 1H), 1.58 (m, 2H), 1.35-1.23 (m, 3H); MS (ESI) m/z 366.1 $[M+1]^+$.

5.1.144 Example 144

SYNTHESIS OF 6-(4-(5-(2-HYDROXYPROPAN-2-YL)-1H-1,2,4-TRIAZOL-3-YL)PHENYL)-1-((TETRAHYDRO-2H-PYRAN-4-YL)METHYL)-1H-IMIDAZO[4,5-B]PYRAZIN-2(3H)-ONE

A. 6-(4-(5-(2-Hydroxypropan-2-yl)-1H-1,2,4-triazol-3-yl)phenyl)-1-((tetrahydro-2H-pyran-4-yl)methyl)-1H-imidazo[4,5-b]pyrazin-2(3H)-one. A solution of ethyl 4-(2-oxo-3-((tetrahydro-2H-pyran-4-yl)methyl)-2,3-dihydro-1H-imidazo[4,5-b]pyrazin-5-yl)benzimidate (See Example 134.B) (0.20 g, 0.525 mmol), 1-hydroxy-isopropyl hydrazide (0.248 g, 2.10 mmol), triethylamine (1.46 mL, 10.5 mmol) and methanol (4 mL) were reacted as described in General Procedure F. The solution was condensed under reduced pressure and the product was purified by reverse-phase preparatory HPLC (20-70% acetonitrile+0.1% TFA in $H_2O$+0.1% TFA, over 30 min). Clean fractions were combined, neutralized with ammonium hydroxide and then extracted with ethyl acetate, dried over magnesium sulfate, filtered and solvent removed under reduced pressure. The resulting material was dried under vacuum overnight to afford the title compound as an off white solid, 99.9% pure, (15 mg, 7%). $^1$H NMR (400 MHz, $CD_3OD$) δ 8.49 (s, 1H), 8.12 (s, 4H), 3.96 (m, 4H), 3.43 (m, 4H), 2.29 (m, 1H), 1.67 (m, 8H), 1.52 (m, 2H); MS (ESI) m/z 436.5 [M+1]$^+$; mp 249-253° C.

5.1.145 Example 145

SYNTHESIS OF 6-(4-(5-ISOPROPYL-1H-1,2,4-TRIAZOL-3-YL)PHENYL)-1-((TETRAHYDRO-2H-PYRAN-4-YL)METHYL)-1H-IMIDAZO[4,5-B]PYRAZIN-2(3H)-ONE

A. 6-(4-(5-Isopropyl-1H-1,2,4-triazol-3-yl)phenyl)-1-((tetrahydro-2H-pyran-4-yl)methyl)-1H-imidazo[4,5-b]pyrazin-2(3H)-one. A solution of ethyl 4-(2-oxo-3-((tetrahydro-2H-pyran-4-yl)methyl)-2,3-dihydro-1H-imidazo[4,5-b]pyrazin-5-yl)benzimidate (See Example 134.B) (0.20 g, 0.525 mmol), 2-methylpropanohydrazide (0.214 g, 2.1 mmol), triethylamine (1.46 mL, 10.5 mmol) and methanol (4 mL) were reacted as described in General Procedure F. The reaction was concentrated under reduced pressure and purified using reverse-phase semi-preparatory HPLC (20-70% acetonitrile+0.1% TFA in $H_2O$+0.1% TFA, over 30 min). Clean fractions were combined, neutralized with ammonium hydroxide and then extracted with ethyl acetate, dried over magnesium sulfate, filtered and solvent removed under reduced pressure. The resulting material was dried under vacuum overnight to afford the title compound as an off white solid, 99.9% pure, (27 mg, 12%). $^1$H NMR (400 MHz, $CD_3OD$) δ 8.49 (s, 1H), 8.14 (m, 4H), 3.96 (m, 4H), 3.43 (m, 3H), 2.28 (m, 1H), 1.67 (m, 2H), 1.41 (d, J=6.4, 6H); MS (ESI) m/z 420.5 [M+1]$^+$; mp 305-308° C.

5.1.146 Example 146

SYNTHESIS OF 4-(2-METHOXY-1-(2-MORPHOLINOETHYL)-1H-IMIDAZO[4,5-B]PYRAZIN-6-YL)BENZAMIDE HYDROCHLORIDE

A. 4-(3-(2-Morpholinoethyl)-2-oxo-2,3-dihydro-1H-imidazo[4,5-b]pyrazin-5-yl)benzamide. 6-Bromo-1-(2-morpholinoethyl)-1H-imidazo[4,5-b]pyrazin-2(3H)-one (See Example 136.B) (500 mg, 1.52 mmol), (4-aminocarbonylphenyl)boronic acid (302 mg, 1.82 mmol), dichloro[1,1'-bis(diphenylphosphino)ferrocene]palladium (II) dichloromethane (124 mg, 0.09 mmol) and potassium phosphate (1280 mg, 6.08 mmol) in DMF (30 mL) and water (8 mL) were reacted according to General Procedure C. The product was purified by reverse-phase semi-preparatory HPLC (10-80% acetonitrile+0.1% TFA in $H_2O$+0.1% TFA, over 30 min). The desired fractions were concentrated and the material was used in the next step as a TFA salt. MS (ESI) m/z 369.1 [M+1]$^+$.

B. 4-(2-Methoxy-1-(2-morpholinoethyl)-1H-imidazo[4,5-b]pyrazin-6-yl)benzamide hydrochloride. In a sealed tube, the TFA salt of 4-(3-(2-morpholinoethyl)-2-oxo-2,3-dihydro-1H-imidazo[4,5-b]pyrazin-5-yl)benzamide (200 mg, 0.41 mmol) was treated with N,N-dimethylformamide dineopentyl acetal at 96° C. for 2 h. The product was purified by reverse-phase semi-preparatory HPLC (10-80% acetonitrile+0.1% TFA in $H_2O$+0.1% TFA, over 30 min). The desired fractions were concentrated, and treated with 4N hydrochloric acid in diethylether (few drops), sonicated and concentrated. This procedure was repeated twice more to provide the title compound (19 mg, 11%). $^1$H NMR (400 MHz, DMSO-$d_6$) δ 8.71 (s, 1H), 8.16 (d, J=8.4, 2H), 8.03 (bs, 1H), 7.99 (d, J=8.4, 2H), 4.38 (t, J=5.6, 2H), 3.98-3.88 (m, 2H), 3.75-3.60 (m, 6H), 3.39 (s, 3H); MS (ESI) m/z 383.1 [M+1]$^+$.

5.1.147 Example 147

SYNTHESIS OF 4-(1-((1S,4S)-4-HYDROXYCYCLOHEXYL)-2-METHOXY-1H-IMIDAZO[4,5-B]PYRAZIN-6-YL)BENZAMIDE

A. 4-(3-((1s,4s)-4-Hydroxycyclohexyl)-2-oxo-2,3-dihydro-1H-imidazo[4,5-b]pyrazin-5-yl)benzamide. 6-Bromo-1-((1s,4s)-4-hydroxycyclohexyl)-1H-imidazo[4,5-b]pyrazin-2(3H)-one (250 mg, 0.79 mmol), (4-aminocarbonylphenyl)boronic acid (160 mg, 1.2 mmol), dichloro[1,1'-bis(diphenylphosphino)ferrocene]palladium (II) dichloromethane (65 mg, 0.08 mmol) and potassium phosphate (676 mg, 3.19 mmol) in DMF (20 mL) and water (4 mL) were reacted according to General Procedure C. The product was purified by reverse-phase semi-preparatory HPLC (10-80% acetonitrile+0.1% TFA in $H_2O$+0.1% TFA, over 30 min). The desired fractions were concentrated and the product was used in the next step as a TFA salt. MS (ESI) m/z 354.2[M+1]$^+$.

B. 4-(1-((1s,4s)-4-Hydroxycyclohexyl)-2-methoxy-1H-imidazo[4,5-b]pyrazin-6-yl)benzamide. In a sealed tube, the TFA salt of 4-(3-((1s,4s)-4-hydroxycyclohexyl)-2-oxo-2,3-dihydro-1H-imidazo[4,5-b]pyrazin-5-yl)benzamide (172 mg, 0.41 mmol) was treated with N,N-dimethylformamide dineopentyl acetal at 96° C. for 2 h. The product was purified by reverse-phase semi-preparatory HPLC (10-100% acetonitrile+0.1% TFA in $H_2O$+0.1% TFA, over 30 min). The desired fractions were concentrated, and treated with 4N hydrochloric acid in diethylether (few drops) and concentrated. This procedure was repeated twice more to provide the title compound (21 mg, 15%). $^1$H NMR (400 MHz, DMSO-$d_6$) δ 8.66 (s, 1H), 8.15 (d, J=8.4, 2H), 8.05 (bs, 1H), 7.97 (d, J=8.4, 2H), 4.31 (m, 1H), 3.91 (s, 1H), 2.79 (q, J=12.4, 2H), 1.85-1.81 (m, 1H), 1.62-1.52 (m, 3H), 1.28-1.23 (m, 2H), 0.89-0.86 (m, 1H); MS (ESI) m/z 368.1 [M+1]$^+$.

5.1.148 Example 148

SYNTHESIS OF 6-(4-HYDROXYPHENYL)-1-((1S,4S)-4-(METHOXYMETHYL)CYCLOHEXYL)-1H-IMIDAZO[4,5-B]PYRAZIN-2(3H)-ONE

A. tert-Butyl (1s,4s)-4-(methoxymethyl)cyclohexylcarbamate Sodium hydride (0.204 g, 8.5 mmol, 60% by weight suspension in mineral oil) was washed three times with hexanes (10 mL portions), suspended in anhydrous tetrahydrofuran (10 mL) and cooled to 0° C. under a nitrogen atmosphere. To this suspension, tert-butyl (1s,4s)-4-(hydroxymethyl)cyclohexylcarbamate (See Example 140.B) (1.5 g, 6.55 mmol) and 15-crown-5 (1.52 g, 6.9 mmol) were added. The reaction mixture stirred at 0° C. for 30 min. Methyl iodide was added dropwise (0.98 g, 6.9 mmol) and stirring continued at 0° C. for 30 min. The ice bath was removed and the reaction mixture stirred at rt overnight. Excess hydride was quenched by the slow addition of water and the product was extracted with ethyl acetate. The organic layers were pooled and concentrated. The resulting material was purified using silica gel chromatography (25-70% ethyl acetate in hexanes) to afford the title compound (0.70 g, 44% yield). MS (ESI) m/z 244.1 [M+1]$^+$.

B. (1s,4s)-4-(Methoxymethyl)cyclohexanamine hydrochloride tert-Butyl (1s,4s)-4-(methoxymethyl)cyclohexylcarbamate (0.70 g, 2.63 mmol) was placed in 1,4-dioxane (2 mL) at room temperature and 4N hydrochloric acid in 1,4-dioxane (2.5 mL, 10.5 mmol) was added and the resulting mixture was stirred overnight. The solvent was removed, the resulting residue was treated with ether and methanol, sonicated, concentrated and dried under high vacuum to yield the title compound as a white solid (0.51 g, 98.6% yield). MS (ESI) m/z 130.1[M+1]$^+$.

C. 6-Bromo-N$^2$-((1s,4s)-4-(methoxymethyl)cyclohexyl)pyrazine-2,3-diamine. 2-Amino-3,5-dibromopyrazine (0.845 g, 3.34 mmol), (1s,4s)-4-(methoxymethyl)cyclohexanamine hydrochloride (0.5 g, 2.78 mmol) and diisopropylethylamine (0.72 g, 5.57 mmol) were dissolved in n-butanol (3 mL) and reacted according to General Procedure A. The mixture was purified using silica gel chromatography (50% ethyl acetate in hexanes) to afford the title compound (0.348 g, 40% yield). MS (ESI) m/z 315.5 [M]$^+$, 317.5 [M+2]$^+$.

D. 4-(5-Amino-6-((1s,4s)-4-(methoxymethyl)cyclohexylamino)pyrazin-2-yl)phenol. (3-6-Bromo-N$^2$-((1s,4s)-4-(methoxymethyl)cyclohexyl)pyrazine-2,3-diamine (0.348 g, 1.1 mmol), 4-hydroxybenzene boronic acid (0.168 g, 1.2 mmol), dichloro[1,1'-bis(diphenylphosphino)ferrocene]palladium(II) dichloromethane adduct (0.09 g, 0.11 mmol) and potassium phosphate (0.93 g, 4.3 mmol) were combined in DMF (3 mL) and water (0.2 mL) and heated together in a sealed tube at 150° C. for 2 h. The product was purified using silica gel chromatography (1:9 hexanes in ethyl acetate) to afford the title compound (0.34 g, 94% yield). MS (ESI) m/z 329.5 [M+1]$^+$.

E. 6-(4-Hydroxyphenyl)-1-((1s,4s)-4-(methoxymethyl)cyclohexyl)-1H-imidazo[4,5-b]pyrazin-2(3H)-one. 4-(5-Amino-6-((1s,4s)-4-(methoxymethyl)cyclohexylamino)pyrazin-2-yl)phenol (0.34 g, 1.0 mmol), 1,1'-carbonyldiimidazole (0.67 g, 4 mmol), and tetrahydrofuran (5 mL) were combined in a sealed tube and heated to 80° C. for 48 h. The mixture was cooled to room temperature, potassium carbonate (0.15 g, 1.1 mmol) and methanol (3 mL) were added and the mixture stirred at room temperature overnight. The product was purified by silica gel chromatography (1:2 hexanes in ethyl acetate) to yield the title compound as a light yellow solid (0.12 g, 34% yield). $^1$H NMR (400 MHz, DMSO-d$_6$) δ 11.9 (s, 1H), 9.71 (s, 1H) 8.37 (s, 1H), 7.88 (d, J=8.8, 2H), 6.85 (d, J=8.8, 2H), 4.25 (m, 1H), 3.6 (d, J=7.6, 2H), 3.35 (s, 3H), 2.46 (m, 2H), 1.99 (m, 1H), 1.85 (m, 1H), 1.81 (m, 1H), 1.58 (m, 4H); MS (ESI) m/z 355.3 [M+1]$^+$; mp 236-238° C.

5.1.149 Example 149

SYNTHESIS OF 6-(3H-IMIDAZO[4,5-B]PYRIDIN-6-YL)-1-((TETRAHYDRO-2H-PYRAN-4-YL)METHYL)-1H-IMIDAZO[4,5-B]PYRAZIN-2(3H)-ONE

A. tert-Butyl 6-bromo-3H-imidazo[4,5-b]pyridine-3-carboxylate. A solution of 6-bromo-3H-imidazo[4,5-b]pyridine (0.700 g, 3.53 mmol), di-tert-butyl dicarbonate (0.847 g, 3.88 mmol), and triethylamine (0.984 mL, 7.1 mmol) in tetrahydrofuran (10 mL) was stirred at room temp for 18 h. The reaction was concentrated under reduced pressure to give the product as a solid (1.03 g, 98%). The material was used directly in the next step without further purification or characterization. MS (ESI) m/z 299 [M+1]$^+$.

B. tert-Butyl 6-(trimethylstannyl)-3H-imidazo[4,5-b]pyridine-3-carboxylate. A solution of tert-butyl 6-bromo-3H-imidazo[4,5-b]pyridine-3-carboxylate (0.167 g, 0.560 mmol), hexamethylditin (0.220 g, 0.672 mmol), and tetrakis (triphenylphosphine)palladium(0) (0.0647 g, 0.07 mmol) in toluene (4 mL) was heated in a sealed tube at 115° C. for 90 min. The reaction was concentrated under reduced pressure. Purification using Biotage column chromatography (0-20% methanol in dichloromethane) provided clean product (0.165 g, 64%). MS (ESI) m/z 382.9 [M+1]$^+$.

C. 6-(3H-imidazo[4,5-b]pyridin-6-yl)-1-((tetrahydro-2H-pyran-4-yl)methyl)-1H-imidazo[4,5-b]pyrazin-2(3H)-one. A solution of 6-bromo-1-((tetrahydro-2H-pyran-4-yl)methyl)-1H-imidazo[4,5-b]pyrazin-2(3H)-one (See Example 101.B) (0.135 g, 0.432 mmol), tert-butyl 6-(trimethylstannyl)-3H-imidazo[4,5-b]pyridine-3-carboxylate (0.165 g, 0.432 mmol), dichlorobis(triphenylphosphine)palladium(II) (0.028 g, 0.04 mmol) in dimethylformamide (2 mL) was heated in a sealed tub at 115° C. for 2 h. The reaction was concentrated under reduced pressure and purification using Biotage column chromatography (0-20% methanol in dichloromethane) provided clean product (0.053 g, 44%). $^1$H NMR (400 MHz, CD$_3$OD) δ 9.05 (s, 1H), 8.61 (s, 1H), 8.52 (s, 1H), 8.45 (s, 1H), 3.96 (m, 4H), 3.42 (m, 2H), 2.31 (m, 1H), 1.68 (m, 2H), 1.52 (m, 2H); MS (ESI) m/z 352.4 [M+1]$^+$; mp 367-370° C.

5.1.150 Example 150

SYNTHESIS OF 1-(2-(2,2-DIMETHYLTETRAHYDRO-2H-PYRAN-4-YL)ETHYL)-6-(4-HYDROXYPHENYL)-1H-IMIDAZO[4,5-B]PYRAZIN-2(3H)-ONE

A. 6-Bromo-1-(2-(2,2-dimethyltetrahydro-2H-pyran-4-yl)ethyl)-1H-imidazo[4,5-b]pyrazin-2(3H)-one. 3,5-Dibromopyrazin-2-amine (161 mg, 0.6 mmol), 2-(2,2-dimethyltetrahydro-pyran-4-yl)-ethylamine hydrochloride (100 mg, 0.5 mmol), diisopropylethylamine (0.5 mL), and dimethylsulfoxide (2 mL) were heated in a Biotage Emrys Optimizer microwave reactor to 150° C. for 2 h to give crude 6-bromo-N$^2$-(2-(2,2-dimethyltetrahydro-2H-pyran-4-yl)ethyl)pyrazine-2,3-diamine. MS (ESI) m/z 329.5, 331.5 [M+1]$^+$. 1,1'-Carbonyldiimidazole (194 mg, 1.2 mmol) was added to the reaction mixture and then heated again in a Biotage Emrys Optimizer microwave reactor to 150° C. for 10 min. The product was purified by reverse-phase semi-preparatory HPLC (10-70% acetonitrile+0.1% TFA in H$_2$O+0.1% TFA, over 30 min). Product containing fractions were concentrated and then triturated with ether to give a white solid (90 mg, 42% yield over two steps). MS (ESI) m/z 355.4 [M]$^+$, 357.4 [M+2]$^+$.

B. 1-(2-(2,2-Dimethyltetrahydro-2H-pyran-4-yl)ethyl)-6-(4-hydroxyphenyl)-1H-imidazo[4,5-b]pyrazin-2(3H)-one. 6-Bromo-1-(2-(2,2-dimethyltetrahydro-2H-pyran-4-yl) ethyl)-1H-imidazo[4,5-b]pyrazin-2(3H)-one (90 mg, 0.25 mmol), 4-hydroxyphenylboronic acid (46 mg, 0.33 mmol), dichloro[1,1'-bis(diphenylphosphino)ferrocene]palladium (II) dichloromethane adduct (9 mg, 0.012 mmol), 1M sodium carbonate (0.75 mL, 0.0.75 mmol), and dioxane (1.5 mL) were heated in a Biotage Emrys Optimizer microwave reactor at 150° C. for 10 min. The reaction was adjusted to pH 7 with 1N hydrochloric acid and then extracted with water and ethyl acetate. The organic layer was concentrated and the resulting residue was purified by reverse-phase semi-preparatory HPLC (10-70% acetonitrile+0.1% TFA in H$_2$O+0.1% TFA, over 30 min). The product fractions were concentrated and then triturated with ether to give a white solid (45 mg, 48% yield). $^1$H NMR (400 MHz, DMSO-d$_6$) δ 11.90 (s, 1H), 9.69 (s, 1H), 8.35 (s, 1H), 7.84 (d, J=8.6 Hz, 2H), 6.83 (d, J=9.0, 2H), 3.82-3.94 (m, 2H), 3.50-3.56 (m, 1H), 3.39-3.48 (m, 2H), 1.64-1.73 (m, 2H), 1.51-1.63 (m, 3H), 0.99-1.08 (m, 4H), 0.91-0.98 (m, 4H); MS (ESI) m/z 354.4 [M+1]$^+$; mp 232-234° C.

5.1.151 Example 151

SYNTHESIS OF 6-(4-(1H-PYRAZOL-1-YL)PHENYL)-1-((TETRAHYDRO-2H-PYRAN-4-YL)METHYL)-1H-IMIDAZO[4,5-B]PYRAZIN-2(3H)-ONE

A. 1-(4-(Trimethylstannyl)phenyl)-1H-pyrazole. A solution of 1-(4-bromophenyl)-1H-pyrazole (1.0 g, 4.48 mmol), hexamethylditin (1.08 mL, 4.93 mmol), tetrakis(triphenylphosphine)palladium(0) (0.508 g, 0.06 mmol) in toluene (15 mL) was heated at 100° C. for 2 h. Upon completion of the reaction, toluene was removed under reduced pressure, and the residue was purified by Biotage chromatography (0-40% ethyl acetate in hexanes) to afford the desired product (1.20 g, 87%). MS (ESI) m/z 309.3[M+1]$^+$.

B. 6-(4-(1H-Pyrazol-1-yl)phenyl)-1-((tetrahydro-2H-pyran-4-yl)methyl)-1H-imidazo[4,5-b]pyrazin-2(3H)-one. 1-(4-(Trimethylstannyl)phenyl)-1H-pyrazole (300 mg, 0.97 mmol), 6-bromo-1-((tetrahydro-2H-pyran-4-yl)methyl)-1H-imidazo[4,5-b]pyrazin-2(3H)-one (See Example 101.B) (304 mg, 0.97 mmol), dichlorobis(triphenylphosphine) palladium (II) (68 mg, 0.097 mmol) in DMF (15 mL) were reacted for 1.5 h at 90° C. The product was purified by reverse-phase semi-preparatory HPLC (10-60% acetonitrile+0.1% TFA in H$_2$O+0.1% TFA, over 30 min). The desired fractions were concentrated and treated with aqueous 6N ammonium hydroxide (few drops). The volatiles were removed under reduced pressure, and the residue was taken up in water (2 mL), and the solid was filtered and rinsed with water to provide the title compound (14.5 mg, 4% yield). $^1$H NMR (400 MHz, DMSO-d$_6$) δ 8.57 (s, 1H), 8.32 (d, J=8.8, 2H), 8.01 (d, J=8.8, 2H), 7.68 (s, 2H), 2.27-2.33 (m, 2H), 1.66-1.63 (m, 2H), 1.51-1.49 (m, 2H), 1.27 (m, 2H), 0.88-0.84 (m, 2H); MS (ESI) m/z 377.3 [M+1]$^+$; mp 294-296° C.

5.1.152 Example 152

SYNTHESIS OF 6-(4-(4H-1,2,4-TRIAZOL-3-YL)PHENYL)-1-(2-MORPHOLINOETHYL)-1H-IMIDAZO[4,5-B]PYRAZIN-2(3H)-ONE

A. 4-(3-(2-Morpholinoethyl)-2-oxo-2,3-dihydro-1H-imidazo[4,5-b]pyrazin-5-yl)benzonitrile. 6-Bromo-1-(2-(morpholinoethyl)-1H-imidazo[4,5-b]pyrazin-2(3H)-one (See Example 136.B) (700 mg, 2.13 mmol), (4-cyanophenyl)boronic acid (376 mg, 2.56 mmol), dichloro[1,1'-bis(diphenylphosphino)ferrocene]palladium (II) dichloromethane (171 mg, 0.21 mmol) and potassium phosphate (1.80 mg, 6.52 mmol) in DMF (30 mL) and water (8 mL) were reacted according to General Procedure C. The product was purified by reverse-phase semi-preparatory HPLC (10-80% acetonitrile+0.1% TFA in H$_2$O+0.1% TFA, over 30 min). The desired fractions were concentrated and the desired product (410 mg, 41%) was used in the next step as a TFA salt. MS (ESI) m/z 351.4[M+1]$^+$.

B. Ethyl 4-(3-(2-morpholinoethyl)-2-oxo-2,3-dihydro-1H-imidazo[4,5-b]pyrazin-5-yl)benzimidate. HCl gas was bubbled in a suspension of 4-(3-(2-morpholinoethyl)-2-oxo-2,3-dihydro-1H-imidazo[4,5-b]pyrazin-5-yl)benzonitrile (410 mg, 0.88 mmol) in anhydrous ethanol (30 mL) at 0° C. The flask was capped, and the reaction mixture was stirred overnight at room temperature. Upon complete conversion to product (monitored by LCMS), the volatiles were removed under reduced pressure, and the resulting solid was dried in a vacuum oven to give the desired product (460 mg, 1.16 mmol). The material was used in the next step without further purification. MS (ESI) m/z 397.3[M+1]$^+$.

C. 6-(4-(4H-1,2,4-Triazol-3-yl)phenyl)-1-(2-morpholinoethyl)-1H-imidazo[4,5-b]pyrazin-2(3H)-one. Ethyl 4-(3-(2-morpholinoethyl)-2-oxo-2,3-dihydro-1H-imidazo[4,5-b] pyrazin-5-yl)benzimidate (460 mg, 1.16 mmol) in methanol (15 mL) was treated with formic hydrazide (278 mg, 4.64 mmol) and triethylamine (3.23 mL, 2.32 mmol), and the resulting reaction mixture was stirred at 110° C. for 3 h. The volatiles were removed under reduced pressure and the crude product was purified by reverse-phase semi-preparatory HPLC (10-80% acetonitrile+0.1% TFA in H$_2$O+0.1% TFA, over 30 min). The desired fractions were concentrated, and treated with aqueous 6N ammonium hydroxide (few drops). The volatiles were removed under reduced pressure, and the residue was taken up in water (2 mL), the solid was filtered and rinsed with water to provide the title compound (71 mg, 15.5%). $^1$H NMR (400 MHz, DMSO-d$_6$) δ 12.09 (s, 1H), 8.65 (s, 1H), 8.57 (d, J=8.4, 2H), 8.12 (d, J=8.4, 2H), 4.04 (t, J=6.4, 2H), 3.45 (t, J=4.0, 4H), 3.34 (s, 4H), 2.70 (t, J=6.4, 2H); MS (ESI) m/z 393.1 [M+1]$^+$; mp 295-297° C.

5.1.153 Example 153

SYNTHESIS OF 6-(4-(1H-BENZO[D]IMIDAZOL-2-YL)PHENYL)-1-((TETRAHYDRO-2H-PYRAN-4-YL)METHYL)-1H-IMIDAZO[4,5-B]PYRAZIN-2(3H)-ONE

A. 2-(4-Bromophenyl)-1H-benzo[d]imidazole. 1,2-Phenyldiamine (2.16 g, 20 mmol) and iodine (0.1 g, 0.4 mmol) were placed in tetrahydrofuran (4 mL) and water (4 mL) and 4-bromobenzaldehyde (3.7 g, 20 mmol) was added. The mixture was stirred at rt for 2 h, extracted with ethyl acetate and concentrated. The resulting solid was treated with ethyl acetate (30 mL) and subjected to sonication. The resulting suspension was filtered to provided the desired product (1 g, 18% yield). MS (ESI) m/z 273.3.3 [M]$^+$, 275.3 [M+2]$^+$.

B. 2-(4-(4,4,5,5-Tetramethyl-1,3,2-dioxaborolan-2-yl) phenyl)-1H-benzo[d]imidazole. 2-(4-Bromophenyl)-1H-benzo[d]imidazole (0.3 g, 1.1 mmol), bis(pinacolato)diboron (0.31 g, 1.2 mmol), dichloro[1,1'-bis(diphenylphosphino)ferrocene]palladium(II) dichloromethane adduct (0.09 g, 0.11 mmol) and potassium acetate (0.32 g, 3.2 mmol) were placed in a sealed tube in DMSO (4 mL). The system was flushed with nitrogen, sealed and heated to 90° C. for 2 h. The solvent was removed and the desired product purified using silica gel chromatography (50% ethyl acetate in hexanes) to afford the title compound (0.2 g, 57% yield). MS (ESI) m/z 321.4 [M+1]$^+$.

C. 6-(4-(1H-Benzo[d]imidazol-2-yl)phenyl)-1-((tetrahydro-2H-pyran-4-yl)methyl)-1H-imidazo[4,5-b]pyrazin-2 (3H)-one. 2-(4-(4,4,5,5-Tetramethyl-1,3,2-dioxaborolan-2-yl)phenyl)-1H-benzo[d]imidazole (0.2 g, 0.6 mmol), 6-bromo-1-((tetrahydro-2H-pyran-4-yl)methyl)-1H-imidazo[4,5-b]pyrazin-2(3H)-one (See Example 101.B) (0.20 g, 0.6 mmol), dichloro[1,1'-bis(diphenylphosphino)ferrocene] palladium(II) dichloromethane adduct (0.052 g, 0.06 mmol) and potassium phosphate (0.54 g, 2.5 mmol) were combined in DMF (3 mL) and water (0.5 mL), the mixture purged with nitrogen and heated in a sealed tube at 100° C. overnight. The solvent was removed and the crude material was purified using silica gel chromatography (100% ethyl acetate) to afford the title compound as a white solid (0.04 g, 16% yield). $^1$H NMR (400 MHz, DMSO-d$_6$) δ 12.98 (s, 1H), 12.13 (s, 1H), 8.63 (s, 1H), 8.29 (d, J=8.8, 2H), 8.23 (d, J=8, 2H), 7.69 (d, J=7.6, 1H), 7.56 (d, J=8, 1H), 7.22 (m, 2H), 3.83 (m, 4H), 3.27 (t, J=11.6, 2H), 2.16 (m, 1H), 1.59 (d, J=12, 2H), 1.33 (m, 2H); MS (ESI) m/z 427.2 [M+1]$^+$; mp >300° C.

5.1.154 Example 154

SYNTHESIS OF 6-(4-(1H-IMIDAZOL-2-YL)PHENYL)-1-((TETRAHYDRO-2H-PYRAN-4-YL)METHYL)-1H-IMIDAZO [4,5-B]PYRAZIN-2(3H)-ONE HYDROCHLORIDE

A. 2-(4-(Trimethylstannyl)phenyl)-1H-imidazole. A solution of 2-(4-bromophenyl)-1H-imidazole (1.0 g, 4.48 mmol), hexamethylditin (1.08 mL, 4.93 mmol), tetrakis(triphenylphosphine)palladium(0) (0.508 g, 0.06 mmol) in toluene (15 mL) was heated at 100° C. for 2 h. Upon completion of the reaction, toluene was removed under reduced pressure, and the residue was purified by Biotage chromatography (0-40% EtOAc in hexanes) to afford the desired stannane (635 mg, 46%). MS (ESI) m/z 309.2[M+1]$^+$.

B. 6-(4-(1H-Imidazol-2-yl)phenyl)-1-((tetrahydro-2H-pyran-4-yl)methyl)-1H-imidazo[4,5-b]pyrazin-2(3H)-one hydrochloride. 2-(4-(Trimethylstannyl)phenyl)-1H-imidazole (400 mg, 1.29 mmol), 6-bromo-1-((tetrahydro-2H-pyran-4-yl)methyl)-1H-imidazo[4,5-b]pyrazin-2(3H)-one (See Example 101.B) (406 mg, 1.29 mmol), dichlorobis(triphenylphosphine)palladium(II) (90 mg, 0.13 mmol) in DMF (15 mL) were reacted for 1.5 h at 90° C. The product was purified by reverse-phase semi-preparatory HPLC (10-100% acetonitrile+0.1% TFA in H$_2$O+0.1% TFA, over 30 min). The desired fractions were concentrated, treated with 4N hydrochloric acid in diethylether (few drops) and concentrated. This procedure was repeated twice more to provide the title compound (4.0 mg, 0.75% yield). $^1$H NMR (400 MHz, DMSO-d$_6$) δ 8.57 (s, 1H), 8.32 (d, J=8.8, 2H), 8.01 (d, J=8.8, 2H), 7.68 (s, 2H), 2.27-2.33 (m, 2H), 1.66-1.63 (m, 2H), 1.51-1.49 (m, 2H), 1.27 (m, 2H), 0.88-0.84 (m, 2H); MS (ESI) m/z 377.3 [M+1]$^+$.

5.1.155 Example 155

SYNTHESIS OF 6-(4-(5-(HYDROXYMETHYL)-1H-1,2,4-TRIAZOL-3-YL)PHENYL)-1-((TETRAHYDRO-2H-PYRAN-4-YL)METHYL)-1H-IMIDAZO[4,5-B]PYRAZIN-2(3H)-ONE

A. 2-Hydroxyacetohydrazide. A solution of ethyl 2-hydroxyacetate (1.00 g, 9.60 mmol), hydrazine (0.324 mg, 10.1 mmol), and ethanol (20 mL) were combined and heated to 85° C. for 3 h. The reaction was concentrated to afford the title compound (0.702 g, 81%). MS (ESI) m/z 91.1 [M+1]$^+$.

B. 6-(4-(5-(Hydroxymethyl)-1H-1,2,4-triazol-3-yl)phenyl)-1-((tetrahydro-2H-pyran-4-yl)methyl)-1H-imidazo[4,5-b]pyrazin-2(3H)-one. A solution of ethyl 4-(2-oxo-3-((tetrahydro-2H-pyran-4-yl)methyl)-2,3-dihydro-1H-imidazo[4,5-b]pyrazin-5-yl)benzimidate (See Example 134.B) (0.280 g, 0.367 mmol), 2-hydroxyacetohydrazide (0.265 g, 1.47 mmol), triethylamine (2.04 mL, 7.34 mmol) and methanol (4 mL) were reacted as described in General Procedure F. The reaction was concentrated under reduced pressure and purified using reverse-phase semi-preparatory HPLC (20-70% acetonitrile+0.1% TFA in H$_2$O+0.1% TFA, over 30 min). Clean fractions were combined, neutralized with ammonium hydroxide, extracted with ethyl acetate, dried over magnesium sulfate, filtered and solvent removed under reduced pressure. The resulting material was dried under vacuum overnight to afford the title compound as an off white solid, 99.9% pure, (211 mg, 71%). $^1$H NMR (400 MHz, DMSO-d$_6$) δ 12.1 (br s, 1H), 8.56 (s, 1H), 8.13 (br s, 2H), 3.85 (m, 4H), 3.23 (m, 3H), 2.15 (m, 1H), 1.59 (m, 2H), 1.36 (m, 2H); MS (ESI) m/z 408.5 [M+1]$^+$; mp 258-260° C.

5.1.156 Example 156

SYNTHESIS OF 6-(4-(1H-IMIDAZOL-5-YL)PHENYL)-1-((TETRAHYDRO-2H-PYRAN-4-YL)METHYL)-1H-IMIDAZO[4,5-B]PYRAZIN-2(3H)-ONE HYDROCHLORIDE

A. 2-(4-Bromophenyl)-4-tosyloxazole. 4-Bromobenzaldehyde (700 mg, 3.78 mmol) in ethanol (20 mL) was treated with tosyl-methyl-isocyanate (722 mg, 3.70 mmol) and sodium cyanide (181 mg, 3.70 mmol). The resulting suspension was allowed to stir overnight at room temperature. The volatiles were removed under reduced pressure. The residue was taken up in diethyl ether, sonicated, filtered and rinsed with diethyl ether to provide the product (820 mg, 57%) as a yellow solid. MS (ESI) m/z 380.2 [M+1]$^+$.

B. 5-(4-Bromophenyl)-1H-imidazole. 2-(4-Bromophenyl)-4-tosyloxazole (820 mg, 2.17 mmol) was treated with a 7N solution of ammonia in methanol. The resulting reaction mixture was allowed to stir overnight at room temperature. The volatiles were removed under reduced pressure. The residue was taken up in diethyl ether, sonicated, filtered and rinsed with diethyl ether to provide the product (100 mg, 21%) as a white solid. MS (ESI) m/z 225.1 [M+1]$^+$.

C. 5-(4-(Trimethylstannyl)phenyl)-1H-imidazole. A solution of 5-(4-bromophenyl)-1H-imidazole (100 mg, 0.44 mmol), hexamethylditin (0.11 mL, 0.49 mmol), tetrakis (triphenylphosphine)palladium(0) (0.050 g, 0.006 mmol) in toluene (5 mL) was heated at 100° C. for 2 h. Upon completion of the reaction, toluene was removed under reduced pressure, and the residue was purified by Biotage chromatography (0-40% ethyl acetate in hexanes) to afford the title compound (50 mg, 36%). MS (ESI) m/z 309.3 [M+1]$^+$.

D. 6-(4-(1H-Imidazol-5-yl)phenyl)-1-((tetrahydro-2H-pyran-4-yl)methyl)-1H-imidazo[4,5-b]pyrazin-2(3H)-one hydrochloride. 5-(4-(Trimethylstannyl)phenyl)-1H-imidazole (50 mg, 0.16 mmol), 6-bromo-1-((tetrahydro-2H-pyran-4-yl)methyl)-1H-imidazo[4,5-b]pyrazin-2(3H)-one (See Example 101.B) (51 mg, 0.16 mmol), dichlorobis(triphenylphosphine)palladium(II) (11 mg, 0.016 mmol) in DMF (5 mL) were reacted for 1.5 h at 115° C. The product was purified by reverse-phase semi-preparatory HPLC (10-100% acetonitrile+0.1% TFA in H$_2$O+0.1% TFA, over 30 min). The desired fractions were concentrated, treated with 4N hydrochloric acid in diethylether (few drops) and concentrated. This procedure was repeated twice more to provide the title compound (24.2 mg, 37% yield). $^1$H NMR (400 MHz, CD$_3$OD-d$_6$) δ 8.46 (s, 1H), 8.12 (d, J=8.8, 2H), 7.84 (d, J=8.8, 2H), 7.59 (s, 2H), 3.97-3.91 (m, 2H), 1.67-1.63 (m, 2H), 1.50-1.42 (m, 2H), 1.27 (m, 2H), 0.97-0.84 (m, 2H); MS (ESI) m/z 378.1 [M+1]$^+$.

5.1.157 Example 157

SYNTHESIS OF 6-(4-HYDROXYPHENYL)-1-((5-OXOPYRROLIDIN-2-YL)METHYL)-1H-IMIDAZO[4,5-B]PYRAZIN-2(3H)-ONE

A. 6-Bromo-1-((5-oxopyrrolidin-2-yl)methyl)-1H-imidazo[4,5-b]pyrazin-2(3H)-one. 3,5-Dibromopyrazin-2-amine (253 mg, 1 mmol), 5-(aminomethyl)pyrrolidin-2-one hydrochloride (150 mg, 1 mmol), diisopropylethylamine (0.5 mL), and dimethylsulfoxide (2 mL) were heated in a Biotage Emrys Optimizer microwave reactor at 150° C. for 2 h to afford crude 5-((3-amino-6-bromopyrazin-2-ylamino)methyl)pyrrolidin-2-one. MS (ESI) m/z 286.0 [M]$^+$, 288.0 [M+2]$^+$. 1,1'-Carbonyldiimidazole (243 mg, 1.5 mmol) was added to the reaction mixture and the solution was heated again in a Biotage Emrys Optimizer microwave reactor at 150° C. for 10 min. The product was purified by reverse-phase semi-preparatory HPLC (10-70% acetonitrile+0.1% TFA in H$_2$O+0.1% TFA, over 30 min). The product fractions were concentrated and then triturated with ether to give a white solid. MS (ESI) m/z 312.0 [M]$^+$, 314.0 [M+2]$^+$.

B. 6-(4-Hydroxyphenyl)-1-((5-oxopyrrolidin-2-yl)methyl)-1H-imidazo[4,5-b]pyrazin-2(3H)-one. 6-Bromo-1-((5-oxopyrrolidin-2-yl)methyl)-1H-imidazo[4,5-b]pyrazin-2(3H)-one (312 mg, 1 mmol), 4-hydroxyphenylboronic acid (152 mg, 1.1 mmol), dichloro[1,1'-bis(diphenylphosphino)ferrocene]palladium(II) dichloromethane adduct (37 mg, 0.05 mmol), 1M sodium carbonate (3 mL, 3 mmol), and dioxane (6 mL) were heated in a Biotage Emrys Optimizer microwave reactor at 150° C. for 20 min. The reaction was adjusted to pH 7 with 1N hydrochloric acid and then extracted with water and ethyl acetate. The organic layer was concentrated and then purified by reverse-phase semi-preparatory HPLC (10-70% acetonitrile+0.1% TFA in H$_2$O+0.1% TFA, over 30 min). The product fractions were concentrated and the resulting material triturated with ether to give a white solid (42 mg, 13% yield over 2 steps). $^1$H NMR (400 MHz, DMSO-d$_6$) δ 11.92 (s, 1H), 9.69 (s, 1H), 8.36 (s, 1H), 7.86 (d, J=8.6, 2H), 7.82 (s, 1H), 6.85 (d, J=8.6, 2H), 4.11 (m, 1H), 3.92 (dd, J=13.7, 6., 1H), 3.82 (dd, J=13.7, 6.2, 1H), 2.24 (m, 1H), 2.11 (m, 1H), 1.85 (dd, J=13.7, 6.2, 1H); MS (ESI) m/z 326.1 [M+1]$^+$; mp 338-340° C.

5.1.158 Example 158

SYNTHESIS OF 6-(4-(4,5-DIMETHYL-1H-IMIDAZOL-2-YL)PHENYL)-1-((TETRAHYDRO-2H-PYRAN-4-YL)METHYL)-1H-IMIDAZO[4,5-B]PYRAZIN-2(3H)-ONE

A. 2-(4-Bromophenyl)-4,5-dimethyl-1H-imidazole 4-Bromobenzaldehyde (1.39 g, 7.5 mmol), 2,3-butanedione (0.43 g, 5 mmol) and ammonium acetate (3.85 g, 50 mmol) were combined in glacial acetic acid (10 mL) and heated to 60° C. overnight. The solvent was removed and the residue treated with satd. sodium bicarbonate and extracted into ethyl acetate. The organic layer was further washed with water, dried over magnesium sulfate, filtered and concentrated. The resulting solid was purified on silica gel chromatography (100% ethyl acetate) to yield the title compound as a light yellow solid (0.8 g, 64% yield). $^1$H NMR (400 MHz, CDCl$_3$) δ 7.63 (d, J=8.4, 2H), 7.49 (d, J=8.8, 2H), 2.2 (s, 6H); MS (ESI) m/z 251.1 [M]$^+$, 253.1 [M+2]$^+$.

B. 4,5-Dimethyl-2-(4-(4,4,5,5-tetramethyl-1,3,2-dioxaborolan-2-yl)phenyl)-1H-imidazole A solution of 2-(4-bromophenyl)-4,5-dimethyl-1H-imidazole (0.4 g, 1.59 mmol), bis(pinacolato) diboron (0.44 g, 1.75 mmol), dichloro[1,1'-bis(diphenylphosphino)ferrocene]palladium(II) dichloromethane adduct (0.13 g, 0.159 mmol) and potassium acetate (0.47 g, 4.77 mmol) in DMSO (5 mL) was heated in a sealed tube at 90° C. for 2 h. Upon cooling to rt, the reaction mixture was filtered through celite and washed with methanol and ethyl acetate. The filtrate and wash were combined and concentrated under reduced pressure. The resulting material was treated with water and extracted into ethyl acetate. The organic layers were combined, dried over magnesium sulfate, filtered and concentrated to afford a solid precipitate. The product was isolated by filtration to yield the title compound (0.16 g, 34% yield). MS (ESI) m/z 299.5 [M+1]$^+$.

C. 6-(4-(4,5-Dimethyl-1H-imidazol-2-yl)phenyl)-1-((tetrahydro-2H-pyran-4-yl)methyl)-1H-imidazo[4,5-b]pyrazin-2(3H)-one 4,5-Dimethyl-2-(4-(4,4,5,5-tetramethyl-1,3,2-dioxaborolan-2-yl)phenyl)-1H-imidazole (0.16 g, 0.53 mmol), 6-bromo-1-((tetrahydro-2H-pyran-4-yl)methyl)-1H-imidazo[4,5-b]pyrazin-2(3H)-one (See Example 101.B) (0.168 g, 0.53 mmol), dichloro[1,1'-bis(diphenylphosphino)ferrocene]palladium(II) dichloromethane adduct (0.044 g, 0.053 mmol) and potassium phosphate (0.45 g, 2.14 mmol) were reacted in DMF (2 mL) according to General Procedure B2, except reaction was heated for 2 h. Purification by silica gel chromatography (10% methanol in ethyl acetate) gave the title compound as an off-white solid (40.0 mg, 19% yield). $^1$H NMR (400 MHz, DMSO-d$_6$) δ 12.1 (s, 1H), 8.52 (s, 1H), 8.06 (d, J=8.6, 2H), 7.93 (d, J=8.20, 2H), 4.0-3.69 (m, 4H), 3.26 (t, J=11.1, 2H), 2.2 (s, 3H), 2.15 (m, 1H), 2.05 (s, 3H), 1.7 (m, 2H), 1.13 (m, 2H); MS (ESI) m/z 405.4[M+1]$^+$; mp 250-254° C. (dec.)

5.1.159 Example 159

SYNTHESIS OF 6-(4-(1H-1,2,4-TRIAZOL-5-YL)PHENYL)-1-(((1S,4S)-4-METHOXYCYCLOHEXYL)METHYL)-1H-IMIDAZO[4,5-B]PYRAZIN-2(3H)-ONE

A. tert-Butyl ((1s,4s)-4-hydroxycyclohexyl)methylcarbamate. (1s,4s)-4-Hydroxycyclohexanecarboxamide (See Example 132.A) (3.5 g) was added with tetrahydrofuran (60 mL) and monochloroborane dimethylsulfide (5.1 mL, 48 mmol). The reaction was heated to 60° C. for 16 h. The reaction was quenched by slow addition of methanol and then concentrated to a thick oil. The oil was added with triethylamine (10 mL, 72 mmol), 2-propanol (40 mL), and di-t-butyldicarbonate (10.5 g, 48 mmol). The reaction mixture was heated to 60° C. for 2 h. The reaction was concentrated and then purified on silica gel column (0-80% ethyl acetate in hexanes) to give a white solid (1.2 g, 15% yield over 2-steps). MS (ESI) m/z 230.4 [M+1]$^+$.

B. ((1s,4s)-4-Methoxycyclohexyl)methanamine hydrochloride. Sodium hydride (326 mg, 14 mmol) was added to a solution of tert-butyl ((1s,4s)-4-hydroxycyclohexyl)methylcarbamate (1.2 g, 4.5 mmol) in tetrahydrofuran (40 mL), followed by the addition of iodomethane (283 µL, 4.5 mmol). The reaction was stirred at room temperature for 16 h. Additional sodium hydride was added and the mixture continued stirring. The reaction was quenched by slow addition of water and then extracted with ethyl acetate (3×). The organic layers were pooled and dried over magnesium sulfate, filtered, and concentrated to give a colorless oil. The oil was purified on silica gel column (0-50% ethyl acetate in hexanes) to give a colorless oil. The oil was treated with 4N hydrogen chloride in dioxane for 30 min. The reaction was concentrated and then triturated with 10% methanol in diethyl ether to give a white solid (0.38 g, 47% yield). MS (ESI) m/z 144.4 [M+1]$^+$.

C. 6-Bromo-1-(((1s,4s)-4-methoxycyclohexyl)methyl)-1H-imidazo[4,5-b]pyrazin-2(3H)-one. 3,5-Dibromopyrazin-2-amine (537 mg, 2.1 mmol), ((1s,4s)-4-methoxycyclohexyl) methanamine hydrochloride (380 mg, 2.1 mmol), diisopropylethylamine (1 mL), and dimethylsulfoxide (2 mL) were heated in a Biotage Emrys Optimizer microwave reactor at 150° C. for 2 h to give the crude 6-bromo-N$^2$-(((1s,4s)-4-methoxycyclohexyl)methyl)pyrazine-2,3-diamine. MS (ESI) m/z 315.0, 317.0 [M+1]$^+$. 1,1'-Carbonyldiimidazole (680 mg, 4.2 mmol) was added and the reaction mixture was heated in a Biotage Emrys Optimizer microwave reactor at 150° C. for 10 min. The reaction was concentrated and the product was purified by reverse-phase semi-preparatory HPLC (10-70% acetonitrile+0.1% TFA in H$_2$O+0.1% TFA, over 30 min). Product containing fractions were concentrated and then triturated with either to give a white solid (450 mg, 63% yield over two steps). MS (ESI) m/z 341.0, 343.0 [M+1]$^+$.

D. 4-(1H-1,2,4-Triazol-5-yl)phenylboronic acid hydrochloride. A solution of 4-cyanophenylboronic acid (5.5 g, 37 mmol) in ethanol (200 mL) was cooled on an ice-bath. Hydrogen chloride gas was bubbled into the reaction for 15 min and the resulting solution was allowed to stir at rt for 3 d. The solution was concentrated under reduced pressure to give the imidate hydrochloride salt as white solid. The imidate was combined with 2-propanol (15 mL), triethylamine (16 mL, 112 mmol), and formic hydrazide (6.7 g, 112 mmol). The mixture was heated to 100° C. for 2 h. The reaction was concentrated under reduced pressure and the resulting material was purified on a silica gel column (0-100% (5% methanol in ethyl acetate) in hexanes) to give a thick oil. The oil was treated with 4N hydrogen chloride in dioxane. The solution was concentrated under reduced pressure to give the product as the hydrochloride salt. The salt was triturated with 10% methanol in diethyl ether, filtered and dried to give a white solid (7.2 g, 86% yield). $^1$H NMR (400 MHz, DMSO-d$_6$) δ 11.24 (br. s., 2H), 8.69 (s, 1H), 8.23 (s, 2H), 8.02 (d, J=8.0, 2H), 7.91 (d, J=8.6, 2H); MS (ESI) m/z 190.1 [M+1]$^+$.

E. 6-(4-(1H-1,2,4-Triazol-5-yl)phenyl)-1-(((1s,4s)-4-methoxycyclohexyl)methyl)-1H-imidazo[4,5-b]pyrazin-2 (3H)-one. 6-Bromo-1-(((1s,4s)-4-methoxycyclohexyl)methyl)-1H-imidazo[4,5-b]pyrazin-2(3H)-one (450 mg, 1.3 mmol), 4-(1H-1,2,4-triazol-5-yl)phenylboronic acid hydrochloride (356 mg, 1.6 mmol), dichloro[1,1'-bis(diphenylphosphino)ferrocene]palladium(II) dichloromethane adduct (48 mg, 0.06 mmol), 1M sodium carbonate (4 mL, 4 mmol), and dioxane (8 mL) were heated in a Biotage Emrys Optimizer microwave reactor at 150° C. for 1 h. The reaction was purified by reverse-phase semi-preparatory HPLC (10-70% acetonitrile+0.1% TFA in H$_2$O+0.1% TFA, over 30 min). The product fractions were passed through a Strata-XC ion-exchange column and then released from the column with 2M ammonia in methanol. The solution was concentrated and then triturated with diethyl ether to give a white solid (31 mg, 6% yield). $^1$H NMR (400 MHz, DMSO-d$_6$) δ 12.10 (s, 1H), 8.57 (s, 1H), 8.13 (m, 4H), 3.76 (d, J=7.0, 2H), 3.20 (s, 3H), 1.99 (br. s., 1H), 1.81 (d, J=4.3, 1H), 1.37 (m, 6H); MS (ESI) m/z 406.5 [M+1]$^+$; mp 294-296° C.

5.1.160 Example 160

SYNTHESIS OF 6-(4-(1H-1,2,4-TRIAZOL-5-YL) PHENYL)-1-(((1R,4R)-4-METHOXYCYCLO-HEXYL)METHYL)-1H-IMIDAZO[4,5-B] PYRAZIN-2(3H)-ONE

A. tert-Butyl ((1r,4r)-4-hydroxycyclohexyl)methylcarbamate. (1r,4r)-4-Hydroxycyclo-hexanecarboxamide (See Example 130.A) (5 g) was dissolved in tetrahydrofuran (60 mL), monochloroborane dimethylsulfide (7.3 mL, 70 mmol) was added and the reaction was heated to 60° C. for 16 h. The reaction was quenched by slow addition of methanol and concentrated down to a thick oil. The oil was combined with triethylamine (16 mL, 105 mmol), 2-propanol (50 mL), and di-t-butyldicarbonate (15 g, 70 mmol). The reaction was heated to 60° C. for 2 h. The reaction was concentrated and the resulting material was purified on silica gel column (0-80% ethyl acetate in hexanes) to give a white solid (3 g, 52% yield for 2-steps). MS (ESI) m/z 230.3 [M+1]$^+$.

B. ((1r,4r)-4-Methoxycyclohexyl)methanamine hydrochloride. To a solution of tert-Butyl ((1r,4r)-4-hydroxycyclohexyl)methylcarbamate (3 g, 11 mmol) in tetrahydrofuran (40 mL), sodium hydride (815 mg, 34 mmol) and iodomethane (707 µL, 11 mmol) were added sequentially. The reaction was stirred at room temperature for 16 h. Additional sodium hydride was added to complete the reaction. Upon completion (monitored by TLC) the reaction was quenched by slow addition of water and then extracted with ethyl acetate (3×). The organic layers were pooled, dried over magnesium sulfate, filtered, and concentrated to give a colorless oil. The oil was purified on a silica gel column (0-50% ethyl acetate in hexanes) to give a colorless oil. The oil was treated with 4N hydrogen chloride in dioxane for 30 min. The reaction was concentrated and the resulting material was triturated with 10% methanol in diethyl ether to give a white solid (1 g, 20% yield). MS (ESI) m/z 144.4 [M+1]$^+$.

C. 6-Bromo-1-(((1r,4r)-4-methoxycyclohexyl)methyl)-1H-imidazo[4,5-b]pyrazin-2(3H)-one. 3,5-Dibromopyrazin-2-amine (537 mg, 2.1 mmol), ((1r,4r)-4-methoxycyclohexyl) methanamine hydrochloride (380 mg, 2.1 mmol), diisopropylethylamine (1 mL), and dimethylsulfoxide (2 mL) were heated in a Biotage Emrys Optimizer microwave reactor at 150° C. for 2 h to provide the crude 6-bromo-N$^2$-(((1r,4r)-4-methoxycyclohexyl)methyl)pyrazine-2,3-diamine. MS (ESI) m/z 315.0 [M]$^+$, 317.0 [M+2]$^+$. 1,1'-Carbonyl-diimidazole (680 mg, 4.2 mmol) was added to the reaction mixture and the solution was heated a Biotage Emrys Optimizer microwave reactor at 150° C. for 10 min. The reaction mixture was condensed and the product was purified by reverse-phase semi-preparatory HPLC (10-70% acetonitrile+0.1%

TFA in H$_2$O+0.1% TFA, over 30 min). The product fractions were concentrated and triturated with either to give a white solid (400 mg, 56% yield over two steps). MS (ESI) m/z 341.0 [M]$^+$, 343.0 [M+2]$^+$.

D. 6-(4-(1H-1,2,4-Triazol-5-yl)phenyl)-1-(((1r,4r)-4-methoxycyclohexyl)methyl)-1H-imidazo[4,5-b]pyrazin-2(3H)-one. 6-Bromo-1-(((1r,4r)-4-methoxycyclohexyl)methyl)-1H-imidazo[4,5-b]pyrazin-2(3H)-one (400 mg, 1.2 mmol), 4-(1H-1,2,4-triazol-5-yl)phenylboronic acid hydrochloride (See Example 159.D) (395 mg, 1.7 mmol), dichloro[1,1'-bis(diphenylphosphino)ferrocene]palladium(II) dichloromethane adduct (48 mg, 0.06 mmol), 1M sodium carbonate (4 mL, 4 mmol), and dioxane (8 mL) were heated in a Biotage Emrys Optimizer microwave reactor at 150° C. for 1 h. The reaction was concentrated and the resulting material was purified by reverse-phase semi-preparatory HPLC (10-70% acetonitrile+0.1% TFA in H$_2$O+0.1% TFA, over 30 min). Product containing fractions were passed through a Strata-XC ion-exchange column and then released from the column with 2M ammonia in methanol. The solution was concentrated and the resulting material was triturated with either to give a white solid (36 mg, 8% yield). $^1$H NMR (400 MHz, DMSO-d$_6$) δ 12.09 (s, 1H), 8.57 (s, 1H), 8.13 (br. s., 4H), 3.76 (d, J=6.6, 2H), 3.21 (s, 3H), 3.09 (br. s., 1H), 1.99 (d, J=8.6, 2H), 1.87 (br. s., 1H), 1.73 (d, J=11.7, 2H), 1.08 (m, 4H). MS (ESI) m/z 406.4 [M+1]$^+$. mp 286-288° C.

5.1.161 Example 161

SYNTHESIS OF 6-(6-(1H-1,2,4-TRIAZOL-3-YL)PYRIDIN-3-YL)-1-((TETRAHYDRO-2H-PYRAN-4-YL)METHYL)-1H-IMIDAZO[4,5-B]PYRAZIN-2(3H)-ONE

A. (E)-5-bromo-N-((dimethylamino)methylene)picolinamide. A solution of 5-bromopicolinamide (0.500 g, 2.49 mmol) and dimethylformamide dimethylacetal (20 mL), were heated to 85° C. for 3 h. The reaction was concentrated and the product was used directly in the next step (0.604 g, 95%). MS (ESI) m/z 257.1 [M+1]$^+$.

B. 5-Bromo-2-(1H-1,2,4-triazol-3-yl)pyridine. A solution of (E)-5-bromo-N-((dimethylamino)methylene)picolinamide (0.604 mg, 2.36 mmol) and hydrazine (2.12 g, 66.1 mmol) was stirred at 25° C. for 3 h. The reaction was concentrated and diluted with water. The resulting precipitate was collected by filtration and dried under vacuum to give the title compound (0.442 g, 83%). MS (ESI) m/z 226.1 [M+1]$^+$.

C. 5-Bromo-2-(1-(tetrahydro-2H-pyran-2-yl)-1H-1,2,4-triazol-3-yl)pyridine. A solution of 5-bromo-2-(1H-1,2,4-triazol-3-yl)pyridine (0.342 mg, 1.52 mmol), 3,4-dihydro-2H-pyran (0.256 g, 3.04 mmol) and 4-methylbenzenesulfonic acid (0.058 g, 0.30 mmol) in tetrahydrofuran was heated to 75° C. for 6 h. The reaction was concentrated and purified using Biotage column chromatography (0-20% methanol in dichloromethane) to provide semi-clean product as an oil (0.614 g, >100%). MS (ESI) m/z 310.2 [M+1]$^+$.

D. 2-(1-(Tetrahydro-2H-pyran-2-yl)-1H-1,2,4-triazol-3-yl)-5-(trimethylstannyl)pyridine. A solution of 5-bromo-2-(1-(tetrahydro-2H-pyran-2-yl)-1H-1,2,4-triazol-3-yl)pyridine (0.200 g, 0.647 mmol), hexamethylditin (0.254 g, 0.776 mmol), tetrakis(triphenylphosphine)palladium(0) (0.069 g, 0.06 mmol) in toluene (3 mL) was heated in a sealed tube at 115° C. for 90 min. The reaction was concentrated under reduced pressure. Purification using Biotage column chromatography (0-20% methanol in dichloromethane) provided clean product (0.153 g, 60%). MS (ESI) m/z 382.9 [M+1]$^+$.

E. 6-(6-(1-(Tetrahydro-2H-pyran-2-yl)-1H-1,2,4-triazol-3-yl)pyridin-3-yl)-1-((tetrahydro-2H-pyran-4-yl)methyl)-1H-imidazo[4,5-b]pyrazin-2(3H)-one. A solution of 6-bromo-1-((tetrahydro-2H-pyran-4-yl)methyl)-1H-imidazo[4,5-b]pyrazin-2(3H)-one (See Example 101.B) (0.122 g, 0.389 mmol), 2-(1-(tetrahydro-2H-pyran-2-yl)-1H-1,2,4-triazol-3-yl)-5-(trimethylstannyl)pyridine (0.153 g, 0.389 mmol), dichlorobis(triphenylphosphine)palladium(II) (0.027 g, 0.04 mmol) in dimethylformamide (3 mL) heated to 115° C. in a sealed tube and for 2 h. The reaction was concentrated under reduced pressure. Purification using Biotage column chromatography (0-20% methanol in dichloromethane) provided clean product (0.098 g, 55%); MS (ESI) m/z 463.5 [M+1]$^+$.

F. 6-(6-(1H-1,2,4-Triazol-3-yl)pyridin-3-yl)-1-((tetrahydro-2H-pyran-4-yl)methyl)-1H-imidazo[4,5-b]pyrazin-2(3H)-one. A solution of 6-(6-(1-(tetrahydro-2H-pyran-2-yl)-1H-1,2,4-triazol-3-yl)pyridin-3-yl)-1-((tetrahydro-2H-pyran-4-yl)methyl)-1H-imidazo[4,5-b]pyrazin-2(3H)-one (0.098 g, 0.212 mmol) and 4.0M hydrochloric acid in dioxane (4.0 mL) was stirred at 25° C. for 3 h. The reaction was concentrated under reduced pressure and the resulting material was purified using reverse-phase semi-preparatory HPLC (20-70% acetonitrile+0.1% TFA in H$_2$O+0.1% TFA, over 30 min). Clean fractions were combined, neutralized with ammonium hydroxide and then extracted with ethyl acetate, dried over magnesium sulfate, filtered and solvent removed under reduced pressure. The resulting material was dried under vacuum overnight to afford the title compound as an off white solid, 99.9% pure, (30.4 mg, 38%). $^1$H NMR (400 MHz, DMSO-d$_6$) δ 9.29 (d, J=1.6, 1H), 8.52 (m, 2H), 8.25 (s, 1H), 8.14 (d, J=8.4, 1H), 3.85 (m, br, 2H), 3.75 (d, J=7.2, 1H), 3.3 (m, 2H), 2.14 (m, 1H), 1.56 (m, br, 2H), 1.36 (m, 2H); MS (ESI) m/z 379.4 [M+1]$^+$; mp 353-356° C.

5.1.162 Example 162

SYNTHESIS OF 6-(4-(1H-1,2,4-TRIAZOL-3-YL)PHENYL)-1-(2-(2-OXOPYRROLIDIN-1-YL)ETHYL)-1H-IMIDAZO[4,5-B]PYRAZIN-2(3H)-ONE

A. 6-(4-(1H-1,2,4-Triazol-3-yl)phenyl)-1-(2-(2-oxopyrrolidin-1-yl)ethyl)-1H-imidazo[4,5-b]pyrazin-2(3H)-one 6-Bromo-1-(2-(2-oxopyrrolidin-1-yl)ethyl)-1H-imidazo[4,5-b]pyrazin-2(3H)-one (See Example 157.A) (290 mg, 0.8 mmol), 4-(1H-1,2,4-triazol-5-yl)phenylboronic acid hydrochloride (See Example 159.D) (224 mg, 0.99 mmol), dichloro[1,1'-bis(diphenylphosphino)ferrocene]palladium(II) dichloromethane adduct (30 mg, 0.04 mmol), 1M sodium carbonate (2.5 mL, 2.5 mmol), and dioxane (5 mL) were heated in a Biotage Emrys Optimizer microwave reactor at 150° C. for 1 h. The reaction was purified by reverse-phase semi-preparatory HPLC (10-70% acetonitrile+0.1% TFA in H$_2$O+0.1% TFA, over 30 min). The product fractions were passed through a Strata-XC ion-exchange column and the product was released from the column with 2M ammonia in methanol. The solution was concentrated and the resulting material was triturated with either to give a white solid (23 mg, 7% yield). $^1$H NMR (400 MHz, DMSO-d$_6$) δ 8.58 (s, 1H), 8.48 (br, 1H), 8.20 (d, J=10.0, 2H), 8.13 (d, J=10.0, 2H), 4.06 (m, 2H), 3.58 (m, 2H), 3.52 (t, J=6.8, 2H), 1.85 (d, J=7.8, 2H), 1.74 (m, 2H); MS (ESI) m/z 391.5 [M+1]$^+$; mp 300-301° C.

5.1.163 Example 163

SYNTHESIS OF 3-(1-PHENYLETHYL)-5-(QUINOLIN-5-YL)-1H-IMIDAZO[4,5-B]PYRIDIN-2(3H)-ONE

A. 6-Chloro-3-nitro-N-(1-phenylethyl)pyridin-2-amine. To a solution of 2,6-dichloro-3-nitropyridine (2.0 g, 10.4 mmol) in tetrahydrofuran (18 mL) at −78° C. was added diisopropylethylamine (2.17 mL, 12.4 mmol) and 1-phenylethanamine (1.51 g, 12.4 mmol). The reaction was maintained at −78° C. for 2 h and then allowed to slowly warm to room temperature overnight. Solvent was removed under reduced pressure and the crude product was purified by silica gel chromatography to afford the title compound (2.24 g, 78% yield). $^1$H NMR (400 MHz, DMSO-d$_6$) δ 8.68 (d, J=7.5, 1H), 8.42 (d, J=8.5, 1H), 7.45 (d, J=7.5, 2H), 7.34 (t, J=7.5, 2H), 7.25 (t, J=7.5, 1H), 6.80 (d, J=8.5, 1H), 5.36 (app quint, J=7, 1H), 1.57 (d, J=7, 3H).

B. 3-Nitro-N-(1-phenylethyl)-6-(quinolin-5-yl)pyridin-2-amine. To a solution of 6-chloro-3-nitro-N-(1-phenylethyl)pyridin-2-amine (2.24 g, 8.07 mmol) and quinolin-5-ylboronic acid (1.81 g, 10.5 mmol) in DMF (150 mL) was added potassium carbonate (4.46 g, 32.3 mmol) in water (25 mL). The reaction solution was purged with a stream of nitrogen followed by the addition of tetrakis(triphenylphosphine)palladium(0) (932 mg, 0.81 mmol). After heating at 85° C. for 2 h, the solvent was removed under reduced pressure. The crude product was purified by silica gel chromatography to afford the title compound (2.36 g, 79% yield). MS (ESI) m/z 371.3 [M+1]$^+$.

C. N$^2$-(1-Phenylethyl)-6-(quinolin-5-yl)pyridine-2,3-diamine. A solution of 3-nitro-N-(1-phenylethyl)-6-(quinolin-5-yl)pyridin-2-amine (2.36 g, 6.37 mmol) in ethanol (175 mL) was purged with nitrogen for several min. Following addition of palladium on carbon (245 mg, 2.29 mmol), the flask was evacuated and a hydrogen filled balloon was placed on the reaction. After stirring at room temperature for 18 h, the reaction was filtered and the solvent removed under reduced pressure to afford the title compound (1.89 g, 87% yield). MS (ESI) m/z 341.3 [M+1]$^+$.

D. 3-(1-Phenylethyl)-5-(quinolin-5-yl)-1H-imidazo[4,5-b]pyridin-2(3H)-one A solution of N$^2$-(1-phenylethyl)-6-(quinolin-5-yl)pyridine-2,3-diamine (0.500 g, 1.47 mmol) and urea (0.265 g, 4.41 mmol) in 1-methylpyrrolidin-2-one (2 mL) was heated at 185° C. for 1 h. The solvent was removed under reduced pressure and the crude material dissolved in DMSO. Purification using reverse phase HPLC (10-100% acetonitrile in water, over 18 min) afforded the title compound (110 mg, 21% yield). $^1$H NMR (300 MHz, DMSO-d$_6$) δ 11.40 (s, 1H), 8.90-8.92 (m, 1H), 8.37 (d, J=8, 1H), 8.05 (d, J=8, 1H), 7.80 (t, J=7, 1H), 7.70 (d, J=7, 1H), 7.49 (d, J=8, 1H), 7.28-7.42 (m, 7H), 5.73 (q, J=7.5, 1H), 1.95 (d, J=7.5, 3H); MS (ESI) m/z 366.8 [M+1]$^+$.

5.1.164 Example 164

SYNTHESIS OF (R)-3-(1-PHENYLETHYL)-5-(QUINOLIN-5-YL)-1H-IMIDAZO[4,5-B]PYRIDIN-2(3H)-ONE

A. (R)-6-Chloro-3-nitro-N-(1-phenylethyl)pyridin-2-amine. To a solution of 2,6-dichloro-3-nitropyridine (1.0 g, 5.18 mmol) in tetrahydrofuran (8 mL) at −78° C. was added diisopropylethylamine (1.08 mL, 6.22 mmol) followed by (R)-1-phenylethanamine (0.75 g, 6.22 mmol) in tetrahydrofuran (2 mL). The reaction was kept at −78° C. for 2 h and then allowed to slowly warm to room temperature overnight. The solvent was removed under reduced pressure and the crude product was purified by silica gel chromatography to afford the title compound (1.12 g, 78% yield). $^1$H NMR (400 MHz, DMSO-d$_6$) δ 8.67 (d, J=7.5, 1H), 8.43 (d, J=−8.5, 1H), 7.46 (d, J=7.5, 2H), 7.35 (t, J=7.5, 2H), 7.25 (t, J=7.5, 1H), 6.80 (d, J=8.5, 1H), 5.38 (app quint, J=7, 1H), 1.59 (d, J=7, 3H).

B. (R)-3-Nitro-N-(1-phenylethyl)-6-(quinolin-5-yl)pyridin-2-amine. To a solution of (R)-6-chloro-3-nitro-N-(1-phenylethyl)pyridin-2-amine (1.12 g, 4.03 mmol) and quinolin-5-ylboronic acid (0.91 g, 5.24 mmol) in DMF (75 mL) was added potassium carbonate (2.23 g, 16.1 mmol) in water (25 mL). The reaction solution was purged with a stream of nitrogen followed by the addition of tetrakis(triphenylphosphine)palladium(0) (0.466 g, 0.403 mmol). After heating at 85° C. for 2 h, the solvent was removed under reduced pressure. The crude product was purified by silica gel chromatography to afford the title compound (1.1 g, 74% yield). MS (ESI) m/z 371.3 [M+1]$^+$.

C. (R)—N$^2$-(1-Phenylethyl)-6-(quinolin-5-yl)pyridine-2,3-diamine. A solution of (R)-3-nitro-N-(1-phenylethyl)-6-(quinolin-5-yl)pyridin-2-amine (1.10 g, 2.97 mmol) in ethanol (95 mL) was purged with nitrogen for several minutes. Following addition of palladium on carbon (0.125 g, 1.18 mmol), the flask was evacuated and a hydrogen filled balloon was placed on the reaction. After stirring at room temperature for 18 h, the reaction was filtered and the solvent removed under reduced pressure to afford the title compound (0.77 g, 76% yield). MS (ESI) m/z 341.3 [M+1]$^+$.

D. (R)-3-(1-Phenylethyl)-5-(quinolin-5-yl)-1H-imidazo[4,5-b]pyridin-2(3H)-one. A solution of (R)—N$^2$-(1-phenylethyl)-6-(quinolin-5-yl)pyridine-2,3-diamine (0.30 g, 0.881 mmol) and urea (0.16 g, 2.64 mmol) in 1-methylpyrrolidin-2-one (1.2 mL) was heated at 185° C. for 1 h. Purification of the crude material by reverse phase HPLC (10-100% acetonitrile in water, over 18 min) afforded the title compound (55 mg, 17% yield). $^1$H NMR (400 MHz, DMSO-d$_6$) δ 11.42 (s, 1H), 8.92 (dd, J=2, 4, 1H), 8.38 (d, J=8, 1H), 8.07 (d, J=8, 1H), 7.82 (t, J=7, 1H), 7.70 (dd, J=1, 7, 1H), 7.51 (d, J=8, 1H), 7.29-7.44 (m, 7H), 5.75 (q, J=7.5, 1H), 1.96 (d, J=7.5, 3H); MS (ESI) m/z 366.8 [M+1]$^+$.

5.1.165 Example 165

SYNTHESIS OF (S)-3-(1-HYDROXY-3-METHYLBUTAN-2-YL)-5-(5-ISOPROPYL-2-METHOXYPHENYL)-1H-IMIDAZO[4,5-B]PYRIDIN-2(3H)-ONE

A. (S)-2-(6-Chloro-3-nitropyridin-2-ylamino)-3-methylbutan-1-ol. To a solution of 2,6-dichloro-3-nitropyridine (1.0 g, 5.18 mmol) in tetrahydrofuran (8 mL) at −78° C. was added diisopropylethylamine (1.08 mL, 6.22 mmol) followed by (S)-2-amino-3-methylbutan-1-ol (0.641 g, 6.22 mmol) in tetrahydrofuran (2 mL). The reaction was kept at −78° C. for 2 h and then allowed to slowly warm to room temperature overnight. The solvent was removed under reduced pressure and the crude product was purified by silica gel chromatography to afford the title compound (0.810 g, 60% yield). MS (ESI) m/z 260.2 [M+1]$^+$.

B. (S)-2-(6-(5-Isopropyl-2-methoxyphenyl)-3-nitropyridin-2-ylamino)-3-methylbutan-1-ol. To a solution of (S)-2-(6-Chloro-3-nitropyridin-2-ylamino)-3-methylbutan-1-ol (0.80 g, 3.08 mmol) and 5-isopropyl-2-methoxyphenylboronic acid (0.78 g, 4.00 mmol) in DMF (50 mL) was added potassium carbonate (1.7 g, 12.3 mmol) in water (8 mL). The reaction solution was purged with a stream of nitrogen followed by the addition of tetrakis(triphenylphosphine) palladium(0) (0.358 g, 0.308 mmol). After heating at 85° C. for 2 h, the solvent was removed under reduced pressure. The crude product was purified by silica gel chromatography to afford the title compound (1.11 g, 96% yield). MS (ESI) m/z 374.3 [M+1]$^+$.

C. (S)-2-(3-Amino-6-(5-isopropyl-2-methoxyphenyl)pyridin-2-ylamino)-3-methylbutan-1-ol. A solution of (S)-2-(6-(5-isopropyl-2-methoxyphenyl)-3-nitropyridin-2-ylamino)-3-methylbutan-1-ol (0.33 g, 0.88 mmol) in ethanol (30 mL) was purged with nitrogen for several min. Following addition of palladium on carbon (0.038 g, 0.35 mmol), the flask was evacuated and a hydrogen filled balloon was placed on the reaction. After stirring at room temperature for 18 h, the reaction was filtered and the solvent removed under reduced pressure to afford the title compound (0.30 g, 99% yield). MS (ESI) m/z 344.3 [M+1]$^+$.

D. (S)-3-(1-Hydroxy-3-methylbutan-2-yl)-5-(5-isopropyl-2-methoxyphenyl)-1H-imidazo[4,5-b]pyridin-2(3H)-one. To a thick-wall borosilicate glass vial was added (S)-2-(3-Amino-6-(5-isopropyl-2-methoxyphenyl)pyridin-2-ylamino)-3-methylbutan-1-ol (0.70 g, 2.04 mmol), urea (0.245 g, 4.08 mmol) and DMF (14 mL). The reaction vial was sealed and placed in a Biotage Emrys Optimizer microwave reactor and irradiated at 220° C. for 2700 (s). After cooling to ambient temperature, the solution was condensed and the crude material was purified by reverse phase HPLC (10-100% acetonitrile in water, over 18 min). Fractions containing product were combined and concentrated under reduced pressure. The material was further purified by silica gel chromatography to afford the title compound (0.04 g, 5% yield). $^1$H NMR (300 MHz, DMSO-d$_6$) δ 11.05 (s, 1H), 7.61 (s, 1H), 7.55 (d, J=8, 1H), 7.36 (d, J=8, 1H), 7.21 (d, J=7.5, 1H), 7.04 (d, J=7.5, 1H), 4.87 (t, J=5, 1H), 4.21-4.32 (m, 1H), 4.04-4.15 (m, 1H), 3.80-3.86 (m, 1H), 3.80 (s, 3H), 2.81-2.88 (m, 1H), 2.42-2.50 (m, 1H), 1.21 (d, J=7, 6H), 1.05 (d, J=7, 3H), 0.75 (d, J=7, 3H); MS (ESI) m/z 370.3 [M+1]$^+$.

5.1.166 Example 166

SYNTHESIS OF (R)-1-(1-PHENYLETHYL)-6-(QUINOLIN-5-YL)-1H-IMIDAZO[4,5-B]PYRIDIN-2(3H)-ONE

A. Ethyl pyridine-2-yl carbonate. To a mixture of 2-hydroxy pyridine (2.0 g, 21.0 mmol) and potassium carbonate (7.3 g, 52.6 mmol) in acetone (40 mL) was added ethyl chloroformate (5.7 g, 52.6 mmol). After heating at 40° C. overnight, the reaction mixture was passed through a celite plug and the solvent removed under reduced pressure. The crude material was dissolved in ethyl acetate, washed with water (4×), dried over sodium sulfate, filtered, and condensed to yield the title compound (2.8 g, 80%). MS (ESI) m/z 168.2 [M+1]$^+$.

B. Ethyl 6-bromo-2-oxo-2,3-dihydro-1H-imidazo[4,5-b]pyridine-1-carboxylate. A solution of 6-bromo-1H-imidazo[4,5-b]pyridin-2(3H)-one (2 g, 9.3 mmol), ethyl pyridine-2-yl carbonate (2.1 g, 12.5 mmol) and potassium carbonate (1.8 g, 12.5 mmol) in acetonitrile (20 mL) and DMF (20 mL) was heated at 75° C. overnight. Following concentration under reduced pressure, water was added followed by 1 N HCl until the mixture reached pH of 1. The resultant precipitate was filtered, washed with water and dried in a vacuum oven to afford the title compound (2.3 g, 85%). $^1$H NMR (400 MHz, DMSO-d$_6$) δ 12.17 (br s, 1H), 8.18 (d, J=2, 1H), 7.98 (d, J=2, 1H), 4.42 (q, J=7, 2H), 1.35 (t, J=7, 3H); MS (ESI) m/z 286.0 [M+1]$^+$.

C. tert-Butyl 6-bromo-2-oxo-1H-imidazo[4,5-b]pyridine-3(2H)-carboxylate. To a solution of ethyl 6-bromo-2-oxo-2,3-dihydro-1H-imidazo[4,5-b]pyridine-1-carboxylate (1.6 g, 5.59 mmol) and di-tert-butyl dicarbonate (1.47 g, 6.71 mmol) in tetrahydrofuran (20 mL) was added 4-dimethylaminopyridine (0.102 g, 0.839 mmol). The reaction was stirred for 90 min at room temperature and isopropyl amine (0.40 g, 6.71 mmol) was added. After stirring for an additional 30 min, the solvent was removed under reduced pressure and the crude product triturated with diethyl ether (3×2 mL) to afford the title compound (1.6 g, 91%). MS (ESI) m/z 314.0 [M+1]$^+$.

D. (R)-tert-Butyl 6-bromo-2-oxo-1-(1-phenylethyl)-1H-imidazo[4,5-b]pyridine-3(2H)-carboxylate. To a solution of tert-butyl 6-bromo-2-oxo-1H-imidazo[4,5-b]pyridine-3(2H)-carboxylate (1.6 g, 5.09 mmol), (S)-1-phenylethanol (0.75 g, 6.11 mmol) and triphenylphosphine (1.6 g, 6.11 mmol) in tetrahydrofuran (45 mL) was added diisopropyl azodicarboxylate (1.19 mL, 6.11 mmol). After stirring at room temperature for 1 h, the solvent was removed under reduced pressure. The crude product was purified by silica gel chromatography to afford the title compound (0.60 g, 28% yield). MS (ESI) m/z 418.2 [M+1]$^+$.

E. (R)-6-Bromo-1-(1-phenylethyl)-1H-imidazo[4,5-b]pyridin-2(3H)-one hydrochloride. (R)-tert-Butyl 6-bromo-2-oxo-1-(1-phenylethyl)-1H-imidazo[4,5-b]pyridine-3(2H)-carboxylate (0.60 g, 1.43 mmol) was treated with 4.0 M hydrochloric acid in dioxane (30 mL) at room temperature overnight. The solvent was removed under reduced pressure to afford the title compound (0.50 g, 98% yield). MS (ESI) m/z 318.1 [M+1]$^+$.

F. (R)-1-(1-Phenylethyl)-6-(quinolin-5-yl)-1H-imidazo[4,5-b]pyridin-2(3H)-one. To a thick-wall borosilicate glass vial containing a solution of (R)-6-bromo-1-(1-phenylethyl)-1H-imidazo[4,5-b]pyridin-2(3H)-one hydrochloride (0.25 g, 0.705 mmol) and quinolin-5-ylboronic acid (0.16 g, 0.916 mmol) in DMF (18 mL) was added potassium carbonate (0.39 g, 2.82 mmol) in water (2 mL). The reaction solution was purged with a stream of nitrogen followed by the addition of tetrakis(triphenylphosphine)palladium(0) (0.090 g, 0.078 mmol). The reaction vial was sealed and placed in a Biotage Emrys Optimizer microwave reactor at 150° C. for 15 min. After cooling to ambient temperature, the solvent was removed under reduced pressure. The crude product was purified by silica gel chromatography and washed with methanol to afford the title compound (0.09 g, 35% yield). $^1$H NMR (400 MHz, DMSO-d$_6$) δ 11.34 (s, 1H), 8.94 (dd, J=1.5, 4, 1H), 8.24 (d, J=8, 1H), 8.08 (d, J=8.5, 1H), 8.03 (d, J=2, 1H), 7.83 (dd, J=7, 8.5, 1H), 7.60 (dd, J=1, 7, 1H), 7.48-7.54 (m, 3H), 7.40 (d, J=2, 1H), 7.36 (t, J=7.5, 2H), 7.28 (t, J=7.5, 1H), 5.78 (q, J=7, 1H), 2.02 (d, J=7, 3H); MS (ESI) m/z 367.2 [M+1]$^+$.

5.1.167 Example 167

SYNTHESIS OF 1-(1-PHENYLETHYL)-6-(QUINOLIN-5-YL)-1H-IMIDAZO[4,5-B]PYRIDIN-2(3H)-ONE

A. tert-Butyl 6-bromo-2-oxo-1-(1-phenylethyl)-1H-imidazo[4,5-b]pyridine-3(2H)-carboxylate. To a solution of tert-butyl 6-bromo-2-oxo-1H-imidazo[4,5-b]pyridine-3(2H)-carboxylate (See Example 166.C) (0.60 g, 1.97 mmol), 1-phenylethanol (0.289 g, 2.37 mmol) and triphenylphosphine (0.62 g, 2.37 mmol) in tetrahydrofuran (15 mL) was added diisopropyl azodicarboxylate (0.46 mL, 2.37 mmol). After stirring at room temperature for 1 h, the solvent was removed under reduced pressure. The crude product was purified by silica gel chromatography to afford the title compound (0.30 g, 36% yield). MS (ESI) m/z 418.2 [M+1]+.

B. 6-Bromo-1-(1-phenylethyl)-1H-imidazo[4,5-b]pyridin-2(3H)-one hydrochloride. tert-Butyl 6-bromo-2-oxo-1-(1-phenylethyl)-1H-imidazo[4,5-b]pyridine-3(2H)-carboxylate (0.30 g, 0.72 mmol) was treated with 4.0 M hydrochloric acid in dioxane (20 mL) at room temperature overnight. The solvent was removed under reduced pressure to afford the title compound (0.23 g, 90% yield). MS (ESI) m/z 318.1 [M+1]+.

C. 1-(1-Phenylethyl)-6-(quinolin-5-yl)-1H-imidazo[4,5-b]pyridin-2(3H)-one. To a thick-wall borosilicate glass vial containing a solution of 6-bromo-1-(1-phenylethyl)-1H-imidazo[4,5-b]pyridin-2(3H)-one hydrochloride (0.125 g, 0.352 mmol) and quinolin-5-ylboronic acid (0.080 g, 0.458 mmol) in DMF (9 mL) was added potassium carbonate (0.195 g, 1.41 mmol) in water (1 mL). The reaction solution was purged with a stream of nitrogen followed by the addition of tetrakis(triphenylphosphine)palladium(0) (0.045 g, 0.039 mmol). The reaction vial was sealed and placed in a Biotage Emrys Optimizer microwave reactor at 150° C. for 15 minutes. After cooling to ambient temperature, the solvent was removed under reduced pressure. The crude product was purified by silica gel chromatography and washed with methanol to afford the title compound (0.02 g, 16% yield). $^1$H NMR (400 MHz, DMSO-$d_6$) δ 11.34 (s, 1H), 8.94 (dd, J=1.7, 4, 1H), 8.24 (d, J=8, 1H), 8.08 (d, J=8.5, 1H), 8.03 (d, J=7, 1H), 7.83 (dd, J=7, 8.5, 1H), 7.60 (dd, J=1, 7, 1H), 7.48-7.54 (m, 3H), 7.40 (d, J=2, 1H), 7.36 (t, J=7.5, 2H), 7.28 (t, J=7.5, 1H), 5.78 (q, J=7, 1H), 2.02 (d, J=7, 3H); MS (ESI) m/z 367.2 [M+1]+.

5.1.168 Example 168

SYNTHESIS OF (R)-1-(1-PHENYLETHYL)-6-(QUINOLIN-5-YL)-1H-IMIDAZO[4,5-C]PYRIDIN-2(3H)-ONE

A. ((1R)-1-phenylethyl)(2-bromo-5-nitro(4-pyridyl))amine. To a solution containing 2,4-dibromo-5-nitropyridine (500 mg, 1.75 mmol) and diisopropylethylamine (314 uL, 1.80 mmol) in tetrahydrofuran (8 mL) at 0° C. was added (R)-(+)-1-phenylethylamine (225 mg, 1.86 mmol). The reaction was allowed to come to room temperature and stirred for 18 h. Upon complete consumption of starting material (monitored by LCMS), the solution was condensed under reduced pressure. The residue was dissolved in ethyl acetate, washed with water and dried over sodium sulfate, filtered and condensed to give (5.6 g, 99%) of product. MS (ESI) m/z 322 [M+1]+.

B. ((1R)-1-Phenylethyl)(5-nitro-2-(5-quinolyl)(4-pyridyl))amine. ((1R)-1-Phenylethyl)(2-bromo-5-nitro(4-pyridyl))amine (5.6 g, 1.75 mmol) and 5-quinolineboronic acid (393 mg, 2.27 mmole) were dissolved in DMF (25 ml). Nitrogen gas was bubbled into solution for 2 min. Potassium carbonate (970 mg, 7.00 mmol) in water (5 mL) was then added followed by tetrakis(triphenylphosphine)palladium (0) (0.175 mmol). The solution was then heated to 85° C. under nitrogen for 1 h. The solution was condensed under reduced pressure and the crude product was diluted with ethyl acetate and filtered through a plug of silica-gel. The resultant filtrate was condensed under reduced pressure to afford the title compound (502 mg, 77%). MS (ESI) m/z 371 [M+1]+.

C. ((1R)-1-phenylethyl)(3-amino-6-(5-quinolyl)(4-pyridyl))amine ((1R)-1-Phenylethyl)(5-nitro-2-(5-quinolyl)(4-pyridyl))amine (500 mg, 1.35 mmol) was dissolved in ethanol (100 mL). Palladium on carbon (70 mg) was added followed by a hydrogen balloon. The reaction was stirred at room temperature for 18 h, then filtered through celite. The filtrate was condensed under reduced pressure to afford the desired product (450 mg, 97.9%). (MS (ESI) m/z 341 [M+1]+.

D. 1-((1R)-1-phenylethyl)-6-(5-quinolyl)-4-imidazolino[4,5-c]pyridine-2-one. ((1R)-1-Phenylethyl)(3-amino-6-(5-quinolyl)(4-pyridyl))amine (150 mg, 0.44 mmol) and urea (52.8 mg, 0.88 mmol) were combined in 1-methylpyrrolidin-2-one (4 mL) and heated at 185° C. for 2 h. Water (10 mL) was added and the crude product was collected by filtration. The product was purified by reverse-phase preparative HPLC (20-95% acetonitrile in water, over 30 min) to give the title compound (52.3 mg, 32.4%) as an off-white solid. $^1$H NMR (400 MHz, DMSO-$d_6$) δ 11.45 (s, 1H) 8.91 (dd, J=4.10, 1.56, 1H) 8.39 (d, J=0.78, 1H) 8.33 (ddd, J=8.74, 1.71, 0.88, 1H) 8.05 (d, J=8.49, 1H) 7.80 (dd, J=8.49, 7.13, 1H) 7.59 (dd, J=7.22, 1.37, 1H) 7.41-7.46 (m, 3H) 7.30-7.40 (m, 3H), 5.75 (d, J=7.22, 1H), 4.16 (d, J=0.98, 1H), 1.87 (d, J=7.22, 3H); MS (ESI) m/z 367.0 [M+1]+.

5.1.169 Example 169

SYNTHESIS OF (S)-1-(1-PHENYLETHYL)-6-(QUINOLIN-5-YL)-1H-IMIDAZO[4,5-C]PYRIDIN-2(3H)-ONE

A. ((1S)-1-phenylethyl)(2-bromo-5-nitro(4-pyridyl))amine. To a solution containing 2,4-dibromo-5-nitropyridine (500 mg, 1.75 mmol) and diisopropylethylamine (314 uL, 1.80 mmol) in tetrahydrofuran (8 mL) at 0° C. was added (S)-(-)-1-phenylethylamine (225 mg, 1.86 mmol). The reaction was allowed to come to room temperature and stirred for 18 h. The reaction was complete via LCMS and the solution was condensed under reduced pressure. The residue was dissolved in ethyl acetate, washed with water, dried over sodium sulfate, filtered and concentrated to give the desired product (5.6 g, 99%). MS (ESI) m/z 322 [M+1]+.

B. ((1S)-1-Phenylethyl)(5-nitro-2-(5-quinolyl)(4-pyridyl))amine. ((1S)-1-Phenylethyl)(2-bromo-5-nitro(4-pyridyl))amine (5.6 g, 1.75 mmol) and 5-quinolineboronic acid (393 mg, 2.27 mmole) were dissolved in DMF (25 ml). Nitrogen gas was bubbled into solution for 2 min. Potassium carbonate (970 mg, 7.00 mmol) in water (5 mL) was then added followed by tetrakis(triphenylphosphine)palladium (0) (0.175 mmol). The solution was then heated to 85° C. under nitrogen for 1 h. The solution was condensed under reduced pressure and the crude product was diluted with ethyl acetate and filtered through a plug of silica-gel. The resultant filtrate was condensed under reduced pressure to afford the title compound (500 mg, 77%). MS (ESI) m/z 371 [M+1]+.

C. ((1S)-1-Phenylethyl)(3-amino-6-(5-quinolyl)(4-pyridyl))amine. ((1S)-1-Phenylethyl)(5-nitro-2-(5-quinolyl)(4-pyridyl))amine (500 mg, 1.35 mmol) was dissolved in ethanol (100 mL). Palladium on carbon (80 mg) was added followed by a hydrogen balloon. The reaction was stirred at room temperature for 18 h then filtered through celite. The filtrate was condensed under reduced pressure to afford the crude product (450 mg, 97.9%). (MS (ESI) m/z 341 [M+1]+.

D. (S)-1-(1-Phenylethyl)-6-(quinolin-5-yl)-1H-imidazo[4,5-c]pyridin-2(3H)-one ((1S)-1-Phenylethyl)(3-amino-6-(5-quinolyl)(4-pyridyl))amine (450 mg, 1.32 mmol) and urea (158 mg, 2.64 mmol) were combined in 1-methylpyrrolidin-2-one (4 mL) and heated at 185° C. for 2 h. Water (10 mL) was added and the crude product was collected by filtration. The product was purified by reverse-phase preparative HPLC (20-95% acetonitrile in water, over 30 min) to give the product (92.9 mg, 19%) as an off-white solid. $^1$H NMR (400 MHz, DMSO-$d_6$) δ 11.45 (s, 1H), 8.91 (dd, J=4.10, 1.76, 1H), 8.39 (d, J=0.78, 1H), 8.33 (ddd, J=8.00, 1.27, 1.07, 1H), 8.05 (d, J=8.40, 1H), 7.80 (dd, J=8.49, 7.13, 1H), 7.59 (dd, J=7.13, 1.27, 1H), 7.41-7.47 (m, 3H), 7.29-7.41 (m, 3H), 5.75 (d, J=7.22, 1H), 4.16 (d, J=0.78, 1H), 1.87 (d, J=7.22, 3H); MS (ESI) m/z 367.0 [M+1]$^+$.

5.1.170 Example 170

SYNTHESIS OF 1-(CYCLOHEXYLMETHYL)-6-(2-(METHYLAMINO)PYRIMIDIN-5-YL)-1H-IMIDAZO[4,5-B]PYRAZIN-2(3H)-ONE

A. 1-(Cyclohexylmethyl)-6-(2-(methylthio)pyrimidin-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.53 g, 1.7 mmol), 2-(methylthio)pyrimidin-5-ylboronic acid (0.35 g, 2.04 mmol), potassium phosphate (1.44 g, 6.81 mmol), and dichloro[1,1'-bis(diphenylphosphino) ferrocene]palladium (II) dichloromethane (0.14 g, 0.17 mmol) were combined together in DMF/water (9:1 v/v, 6 mL) and reacted according to General Procedure B2. The cooled reaction was diluted with ethyl acetate (50 mL) and 5% HCl (aq, 50 mL). The mixture was shaken and separated. The organic layer was washed with brine (50 mL), dried over sodium sulfate, filtered, and concentrated to about a 5 mL volume. The product precipitated from solution and was filtered (0.46 g, 76%). MS (ESI) m/z 357.4 [M+1]$^+$.

B. 1-(Cyclohexylmethyl)-6-(2-(methylsulfonyl)pyrimidin-5-yl)-1H-imidazo[4,5-b]pyrazin-2(3H)-one. 1-(Cyclohexylmethyl)-6-(2-(methylthio)pyrimidin-5-yl)-1H-imidazo[4,5-b]pyrazin-2(3H)-one (0.46 g, 1.29 mmol) was dissolved in chloroform (10 mL). To this solution was added m-chloroperoxybenzoic acid (0.6 g, 2.6 mmol). The mixture was stirred for 2 h at rt. The reaction was washed with 5% sodium bicarbonate (aq, 2×50 mL), water (50 mL), and then brine. The organic layer was dried over sodium sulfate, filtered, and concentrated to afford the product (0.48 g, 96%). MS (ESI) m/z 389.0 [M+1]$^+$.

C. 1-(Cyclohexylmethyl)-6-(2-(methylamino)pyrimidin-5-yl)-1H-imidazo[4,5-b]pyrazin-2(3H)-one. 1-(Cyclohexylmethyl)-6-(2-(methylsulfonyl)pyrimidin-5-yl)-1H-imidazo[4,5-b]pyrazin-2(3H)-one (0.05 g, 0.129 mmol) was dissolved in 2M methyl amine in tetrahydrofuran (3 mL). The mixture was stirred at 70° C. for 24 h. The reaction was concentrated and the residue purified by semi-preparatory HPLC (20-80% acetonitrile+0.1% TFA in H$_2$O+0.1% TFA, over 45 min). Concentration of the desired fractions afforded the product (10 mg, 23%, 99.7% pure by HPLC). $^1$H NMR (400 MHz, DMSO-d$_6$) δ 11.97 (s, 1H), 8.90 (s, 2H), 8.39 (s, 1H), 7.41 (d, J=4.4, 1H), 3.71 (d, J=6.8, 2H), 2.86 (d, J=4.8, 2H), 1.89 (m, 1H), 1.62 (m, 5H), 1.16 (m, 3H), 1.03 (m, 2H); MS (ESI) m/z 340.4 [M+1]$^+$.

5.1.171 Example 171

SYNTHESIS OF 1-(CYCLOHEXYLMETHYL)-6-(2-(2-METHOXYETHYLAMINO)PYRIMIDIN-5-YL)-1H-IMIDAZO[4,5-B]PYRAZIN-2(3H)-ONE

A. 1-(Cyclohexylmethyl)-6-(2-(2-methoxyethylamino) pyrimidin-5-yl)-1H-imidazo[4,5-b]pyrazin-2(3H)-one. 1-(Cyclohexylmethyl)-6-(2-(methylsulfonyl)pyrimidin-5-yl)-1H-imidazo[4,5-b]pyrazin-2(3H)-one (See Example 170.B) (0.05 g, 0.129 mmol) was dissolved in tetrahydrofuran (3 mL). To this solution was added 2-methoxyethanamine (0.097 g, 1.287 mmol). The mixture was stirred at 70° C. for 24 h. The reaction was concentrated and the residue purified by semi-preparatory HPLC (20-80% acetonitrile+0.1% TFA in H$_2$O+0.1% TFA, over 45 min). Concentration of the desired fractions afforded the product (15 mg, 30%, 100% pure by HPLC). $^1$H NMR (400 MHz, DMSO-d$_6$) δ 12.00 (s, 1H), 8.89 (s, 2H), 8.39 (s, 1H), 7.47 (t, J=5.6, 11H), 3.70 (d, J=7.2, 2H), 3.48 (d, J=5.2, 4H), 3.27 (s, 3H), 1.89 (m, 1H), 1.62 (m, 5H), 1.17 (m, 3H), 1.04 (m, 2H); MS (ESI) m/z 384.3 [M+1]$^+$; mp >250° C.

5.1.172 Example 172

SYNTHESIS OF (1R,4R)-4-(6-(4-HYDROXYPHENYL)-2-OXO-2,3-DIHYDRO-1H-IMIDAZO[4,5-B] PYRAZIN-1-YL)CYCLOHEXANECARBOXAMIDE

A. tert-Butyl (1r,4r)-4-carbamoylcyclohexylcarbamate. (1r,4r)-4-(tert-Butoxycarbonyl-amino)cyclohexanecarboxylic acid (1.7 g, 6.99 mmol), ammonium chloride (560 mg, 10.5 mmol), O-(benzotriazol-1-yl)-N,N,N'N'-tetramethyluronium hexafluorophosphate (2.66 g, 6.99 mmol), triethylamine (2.92 ml, 20.96 mmol), and acetonitrile (20 ml) were stirred at room temperature for 1 h. The reaction was filtered and rinsed with fresh acetonitrile. The solid was vacuum dried to give the product (1.57 g, 93% yield) as white solid. MS (ESI) m/z 242.9 [M+1]$^+$ B. (1r,4r)-4-(6-Bromo-2-oxo-2,3-dihydro-1H-imidazo[4,5-b]pyrazin-1-yl)cyclohexane carboxamide. tert-Butyl (1r,4r)-4-carbamoylcyclohexylcarbamate (0.5 g, 2.063 mmol) was treated with 4N hydrochloric acid in dioxane for 2 h at room temperature. The reaction was concentrated to give a white solid. The solid, (1r,4r)-4-aminocyclohexanecarboxamide, was combined with 3,5-dibromopyrazin-2-amine (0.522 g, 2.063 mmol), diisopropylethylamine (0.721 ml, 4.13 mmol), and methyl sulfoxide (4 ml) and heated in a Biotage Emrys Optimizer microwave reactor for 2 h at 150° C. The product was purified using silica gel chromatography (0-100% (5% methanol in ethyl acetate) in hexanes) to isolate the diamine, (1r,4r)-4-(3-amino-6-bromopyrazin-2-ylamino) cyclohexanecarboxamide. The diamine was combined with 1,1'-carbonyldiimidazole (0.669 g, 4.13 mmol) and dioxane (4 mL) and heated in a Biotage Emrys Optimizer microwave reactor for 10 min at 100° C. The material was purified on silica gel chromatography (0-100% (5% methanol in ethyl acetate) in hexanes). The isolated fractions were concentrated and then triturated with ether to give a white solid, (85 mg, 12% yield over 3 steps). MS (ESI) m/z 340.0 [M]$^+$, 342.0 [M+2]$^+$.

C. (1r,4r)-4-(6-(4-Hydroxyphenyl)-2-oxo-2,3-dihydro-1H-imidazo[4,5-b]pyrazin-1-yl)cyclo-hexanecarboxamide. (1r,4r)-4-(6-Bromo-2-oxo-2,3-dihydro-1H-imidazo[4,5-b] pyrazin-1-yl)cyclohexanecarboxamide (85 mg, 0.25 mmol), 4-hydroxyphenylboronic acid (41 mg, 0.3 mmol), dichloro [1,1'-bis(diphenylphosphino)ferrocene]palladium(II) dichloromethane adduct (10 mg, 0.012 mmol), 1M sodium carbonate (0.75 mL, 0.75 mmol), and dioxane (3 mL) were heated in a Biotage Emrys Optimizer microwave reactor at 150° C. for 1 h. The reaction was adjusted to pH 7 with 1N hydrochloric acid and then extracted with water and ethyl acetate. The organic layer was concentrated and then purified by reverse-phase semi-preparatory HPLC (10-70% acetonitrile+0.1% TFA in H$_2$O+0.1% TFA, over 30 min). The product fractions were concentrated and the resulting material triturated with 10% methanol in diethyl ether to give a white solid (37 mg, 42% yield). $^1$H NMR (400 MHz, DMSO-d$_6$) δ 11.92 (s, 1H), 9.71 (s, 1H), 8.36 (s, 1H), 7.86 (d, J=8.6, 2H), 7.31 (s, 1H), 6.87 (d, J=8.6, 2H), 6.77 (s, 1H), 4.23 (m, 1H), 2.38 (m, 2H), 2.22 (m, 1H), 1.88 (m, 4H), 1.52 (m, 2H); MS (ESI) m/z 354.3 [M+1]$^+$; mp 324-326° C.

5.1.173 Example 173

SYNTHESIS OF (1S,4S)-4-(6-(4-HYDROXYPHENYL)-2-OXO-2,3-DIHYDRO-1H-IMIDAZO[4,5-B]PYRAZIN-1-YL)CYCLOHEXANECARBOXAMIDE

A. tert-Butyl (1s,4s)-4-carbamoylcyclohexylcarbamate. (1s,4s)-4-(tert-Butoxycarbonyl-amino)cyclohexanecarboxylic acid (1.7 g, 6.99 mmol), ammonium chloride (560 mg, 10.5 mmol), O-(benzotriazol-1-yl)-N,N,N'N'-tetramethyluronium hexafluorophosphate (2.66 g, 6.99 mmol), triethylamine (2.92 ml, 20.96 mmol), and acetonitrile (20 ml) were stirred at room temperature for 1 h. The reaction was filtered and then rinsed with fresh acetonitrile. The solid was dried under vacuum to give the title compound (1.5 g, 89% yield) as white solid. MS (ESI) m/z 243.3 [M+1]$^+$ B. (1s,4s)-4-(6-Bromo-2-oxo-2,3-dihydro-1H-imidazo[4,5-b]pyrazin-1-yl)cyclohexane carboxamide. tert-Butyl (1s,4s)-4-carbamoylcyclohexylcarbamate (1.5 g, 6.2 mmol) was treated with 4N hydrochloric acid in dioxane (5 mL) for 2 h at room temperature. The reaction was concentrated to give a white solid. The solid was combined with 3,5-dibromopyrazin-2-amine (1.7 g, 7 mmol), diisopropylethylamine (3.6 ml, 21 mmol), and methyl sulfoxide (4 ml) and heated in a Biotage Emrys Optimizer microwave reactor for 2 h at 150° C. The material was purified on silica gel (0-100% (5% methanol in ethyl acetate) in hexanes) to isolate the diamine, (1s,4s)-4-(3-amino-6-bromopyrazin-2-ylamino)cyclohexanecarboxamide. The diamine was combined with 1,1'-carbonyldiimidazole (0.669 g, 4.13 mmol) and dioxane (4 mL) and heated in a Biotage Emrys Optimizer microwave reactor for 10 min at 100° C. The product was purified using silica gel chromatography (0-100% (5% methanol in ethyl acetate) in hexanes). The isolated fractions were concentrated to give the product. MS (ESI) m/z 340.0 [M]$^+$, 342.0 [M+2]$^+$.

C. (1s,4s)-4-(6-(4-Hydroxyphenyl)-2-oxo-2,3-dihydro-1H-imidazo[4,5-b]pyrazin-1-yl)cyclohexanecarboxamide. (1s,4s)-4-(6-Bromo-2-oxo-2,3-dihydro-1H-imidazo[4,5-b]pyrazin-1-yl)cyclohexanecarboxamide (200 mg, 0.59 mmol), 4-hydroxyphenylboronic acid (97 mg, 0.71 mmol), dichloro[1,1'-bis(diphenylphosphino)ferrocene]palladium (II) dichloromethane adduct (24 mg, 0.029 mmol), 1M sodium carbonate (1.7 mL, 1.7 mmol), and dioxane (3 mL) were heated in a Biotage Emrys Optimizer microwave reactor at 150° C. for 1 h. The reaction was adjusted to pH 7 with 1N hydrochloric acid and then extracted with water and ethyl acetate. The organic layer was concentrated and purified by reverse-phase semi-preparatory HPLC (10-70% acetonitrile+0.1% TFA in H$_2$O+0.1% TFA, over 30 min). The product fractions were concentrated and the resulting material triturated with 10% methanol in diethyl ether to give a white solid (90 mg, 43% yield). $^1$H NMR (400 MHz, DMSO-d$_6$) δ 11.86 (s, 1H), 9.67 (s, 1H), 8.36 (s, 1H), 7.91 (d, J=9.0, 2H), 7.27 (s, 1H), 6.92 (s, 1H), 6.87 (d, J=8.6, 2H), 4.22 (m, 1H), 2.61 (m, 3H), 2.45 (br. s., 1H), 2.21 (d, J=13.7, 2H), 1.57 (m, 4H); MS (ESI) m/z 354.3 [M+1]$^+$; mp 310-312° C.

5.1.174 Example 174

SYNTHESIS OF 6-(5-(HYDROXYMETHYL)THIOPHEN-2-YL)-1-((TETRAHYDRO-2H-PYRAN-4-YL)METHYL)-1H-IMIDAZO[4,5-B]PYRAZIN-2(3H)-ONE

A. 6-(5-(Hydroxymethyl)thiophen-2-yl)-1-((tetrahydro-2H-pyran-4-yl)methyl)-1H-imidazo[4,5-b]pyrazin-2(3H)-one. To a solution of 5-formylthiophen-2-ylboronic acid (100 mg, 0.639 mmol) in methanol (2 mL) was added sodium borohydride (242 mg, 6.39 mmol). The mixture was stirred at 25° C. for 10 min. 6-Bromo-1-((tetrahydro-2H-pyran-4-yl)methyl)-1H-imidazo[4,5-b]pyrazin-2(3H)-one (See Example 101.B) (100 mg, 0.319 mmol), dichloro[1,1'-bis(diphenyl-phosphino)ferrocene]palladium (II) dichloromethane (0.05 g, 0.06 mmol), water (2 ml), and dioxane (2 ml) were added and the reaction mixture was heated in a Biotage Emrys Optimizer microwave reactor at 140° C. for 30 min. The reaction mixture was then extracted with ethyl acetate (3×25 mL) and washed with aqueous sodium bicarbonate (3×25 ml). The organic layers were combined, dried over sodium sulfate, filtered, and concentrated. The crude material was subjected to silica gel chromatography (100% ethyl acetate). Concentration of the desired fractions afforded the title compound as an off white solid (0.085 g, 77%). $^1$H NMR (400 MHz, DMSO-d$_6$) δ 12.03 (s, 1H), 8.41 (s, 1H), 7.56 (d, J=3.6, 1H), 7.56 (d, J=3.6, 1H), 6.96 (d, J=3.6, 1H), 5.53 (t, J=5.6, 1H), 4.64 (d, J=5.6, 2H), 3.84-3.82 (m, 2H), 3.73 (d, J=6.8, 2H), 3.28-3.22 (m, 2H), 2.11 (m, 1H), 1.57-1.54 (m, 2H), 1.35-1.25 (m, 2H); MS (ESI) m/z 347.1 [M+1]$^+$.

5.1.175 Example 175

SYNTHESIS OF 6-(3-(HYDROXYMETHYL)THIOPHEN-2-YL)-1-((TETRAHYDRO-2H-PYRAN-4-YL)METHYL)-1H-IMIDAZO[4,5-B]PYRAZIN-2(3H)-ONE

A. 6-(3-(Hydroxymethyl)thiophen-2-yl)-1-((tetrahydro-2H-pyran-4-yl)methyl)-1H-imidazo[4,5-b]pyrazin-2(3H)-one. To a solution of 3-formylthiophen-2-ylboronic acid (0.156 g, 1 mmol) in methanol (2 mL) was added sodium tetrahydroborate (0.378 g, 10.00 mmol). The mixture was stirred at 25° C. for 10 min. 6-Bromo-1-((tetrahydro-2H-pyran-4-yl)methyl)-1H-imidazo[4,5-b]pyrazin-2(3H)-one (See Example 101.B) (0.157 g, 0.500 mmol), dichloro[1,1'-bis(diphenylphosphino)ferrocene]palladium (II) dichloromethane (0.041 g, 0.050 mmol), potassium carbonate (0.138 g, 1.000 mmol), 1,4-dioxane (2 mL), and water (6.00 ml) were then added. The reaction mixture was heated in a Biotage Emrys Optimizer microwave reactor at 140° C. for 30 min. The reaction mixture was then extracted with ethyl acetate (3×25 mL) and washed with aqueous sodium bicarbonate (3×25 ml). The organic layers were combined, dried over sodium sulfate, filtered, and concentrated. The crude material was subjected to silica gel chromatography (100% ethyl acetate). Concentration of the desired fractions afforded the title compound (0.070 g, 40.4%) as an off white solid. $^1$H NMR (400 MHz, DMSO-d$_6$) δ 12.09 (s, 1H), 8.20 (s, 1H), 7.54 (d, J=5.2, 1H), 7.21 (d, J=5.2, 1H), 5.30 (t, J=5.4, 1H), 4.67 (d, J=5.6, 2H), 3.85-3.82 (m, 2H), 3.73 (d, J=7.2, 2H), 3.27-3.22 (m, 2H), 2.15-2.07 (m, 1H), 1.57-1.54 (m, 2H), 1.34-1.23 (m, 2H); MS (ESI) m/z 347.1 [M+1]$^+$.

5.1.176 Example 176

SYNTHESIS OF 6-(5-(2-HYDROXYETHYL)THIOPHEN-2-YL)-1-((TETRAHYDRO-2H-PYRAN-4-YL)METHYL)-1H-IMIDAZO[4,5-B]PYRAZIN-2(3H)-ONE

A. 6-(5-(2-Hydroxyethyl)thiophen-2-yl)-1-((tetrahydro-2H-pyran-4-yl)methyl)-1H-imidazo[4,5-b]pyrazin-2(3H)-one. To a solution of 2-(5-bromothiophen-2-yl)ethanol (0.207 g, 1 mmol) [JACS 2001, p 11600] in DMSO (3 mL) was added potassium acetate (0.294 g, 3 mmol), dichloro[1,1'-bis(diphenylphosphino)ferrocene]palladium (II) dichloromethane (0.041 g, 0.050 mmol), 4,4,4',4',5,5,5',5'-octamethyl-2,2'-bi(1,3,2-dioxaborolane) (0.381 g, 1.5 mmol). The mixture was stirred at 80° C. for 16 h. To the reaction mixture was added 6-bromo-1-((tetrahydro-2H-pyran-4-yl)methyl)-H-imidazo[4,5-b]pyrazin-2(3H)-one (See Example 101.B) (0.157 g, 0.500 mmol), potassium carbonate (0.138 g, 1.000 mmol), dichloro[1,1'-bis(diphenylphosphino) ferrocene]palladium (II) dichloromethane (0.041 g, 0.050 mmol), water (2 mL), and 1,4-dioxane (8 mL). The reaction mixture heated in a Biotage Emrys Optimizer microwave reactor at 140° C. for 30 min. The reaction mixture was then extracted with ethyl acetate (3×25 mL) and washed with aqueous sodium bicarbonate (3×25 mL). The organic layers were combined, dried over sodium sulfate, filtered, and concentrated. The crude material was subjected to silica gel chromatography (5% methanol in ethyl acetate). Concentration of the desired fractions afforded the title compound as an off white solid (0.047 g, 26%). $^1$H NMR (400 MHz, DMSO-d$_6$) δ 12.02 (s, 1H), 8.38 (s, 1H), 7.54 (d, J=3.6, 1H), 6.88 (d, J=3.6, 1H), 4.85 (t, J=5.2, 1H), 3.84-3.82 (m, 2H), 3.72 (d, J=7.2, 2H), 3.67-3.62 (m, 2H), 3.27-3.22 (m, 2H), 2.96-2.92 (m, 2H), 2.15-2.07 (m, 1H), 1.56-1.53 (m, 2H), 1.34-1.23 (m, 2H); MS (ESI) m/z 361.0 [M+1]$^+$.

5.1.177 Example 177

SYNTHESIS OF 6-(4-HYDROXYPHENYL)-1-(PYRROLIDIN-2-YLMETHYL)-1H-IMIDAZO[4,5-B]PYRAZIN-2(3H)-ONE

A. tert-Butyl 2-((3-amino-6-bromopyrazin-2-ylamino)methyl)pyrrolidine-1-carboxylate 3,5-Dibromopyrazyn-2-amine (2.24 g., 8.85 mmol), tert-butyl 2-(aminomethyl)pyrrolidine-1-carboxylate (1.95 g., 9.54 mmol) and diisopropylethylamine (1.74 g, 17 mmol) were dissolved in n-butanol (3 mL) and heated in a sealed tube to 110° C. for 48 h. The mixture was purified using silica gel chromatography (20% ethanol in ethyl acetate) to afford the title compound (2 g, 62.5% yield). MS (ESI) m/z 372.2 [M]$^+$, 374.2 [M+2]$^+$.

B. tert-Butyl 2-((6-bromo-2-oxo-2,3-dihydro-1H-imidazo[4,5-b]pyrazin-1-yl)methyl)pyrrolidine-1-carboxylate tert-Butyl 2-((3-amino-6-bromopyrazin-2-ylamino)methyl)pyrrolidine-1-carboxylate (2.0 g., 5.4 mmol), 1,1'-carbonyldiimidazole (1.75 g., 10.80 mmol), and tetrahydrofuran (7 mL) were combined in a sealed tube and heated to 120° C. overnight. The solvent was removed and the crude purified using silica gel chromatography (20% hexane in ethyl acetate) to yield the title compound (1.73 g., 80% yield). MS (ESI) m/z 398 [M]$^+$, 400 [M+2]$^+$.

C. tert-Butyl 2-((6-(4-hydroxyphenyl)-2-oxo-2,3-dihydro-1H-imidazo[4,5-b]pyrazin-1-yl)methyl)pyrrolidine-1-carboxylate, tert-Butyl 2-((6-bromo-2-oxo-2,3-dihydro-1H-imidazo[4,5-b]pyrazin-1-yl)methyl)pyrrolidine-1-carboxylate (0.5 g., 1.25 mmol), 4-hydroxyphenylboronic acid (0.17 g., 1.25 mmol), dichloro[1,1'-bis(diphenylphosphino) ferrocene]palladium(II) dichloromethane adduct (0.103 g. 0.126 mmol) and sodium carbonate (0.665 g., 6.28 mmol) were reacted for 40 min in 1,4-dioxane (4 mL) according to General Procedure B2 and purified using silica gel chromatography (60% ethyl acetate in hexanes) to afford the title compound (0.21 g, 41.4% yield). MS (ESI) m/z 412.4 [M+1]$^+$.

D. 6-(4-Hydroxyphenyl)-1-(pyrrolidin-2-ylmethyl)-1H-imidazo[4,5-b]pyrazin-2(3H)-one hydrochloride. tert-Butyl 2-((6-(4-hydroxyphenyl)-2-oxo-2,3-dihydro-1H-imidazo[4,5-b]pyrazin-1-yl)methyl)pyrrolidine-1-carboxylate (0.21 g., 0.52 mmol) was dissolved in 1,4-dioxane (3 mL), 1M hydrochloric acid in 1,4-dioxane (1 mL) was added and the mixture was stirred at rt for 48 h. The solvent was removed, the resulting residue was triturated with methanol and filtered to yield the title compound (0.11 g., 61% yield). $^1$H NMR (400 MHz, DMSO-d$_6$) δ 12.09 (s, 1H), 9.768 (s, 1H), 9.4 (bs, 1H), 8.68 (bs, 1H), 8.415 (s, 1H), 7.906 (d, J=8.8, 2H), 6.873 (d, J=8.8, 2H), 4.19 (d, J=6.8, 2H), 3.89 (m, 1H), 3.30 (m, 1H), 3.13 (m, 1H), 2.14 (m, 1H), 1.97 (m, 2H), 1.79 (m, 1H); MS (ESI) m/z 312.1[M+1]$^+$; mp 178-180° C.

5.1.178 Example 178

SYNTHESIS OF 6-(4-(4H-1,2,4-TRIAZOL-3-YL)PHENYL)-1-(2-(PIPERIDIN-1-YL)ETHYL)-1H-IMIDAZO[4,5-B]PYRAZIN-2(3H)-ONE

A. 6-Bromo-N$^2$-(2-(piperidin-1-yl)ethyl)pyrazine-2,3-diamine. 3,5-Dibromopyrazyn-2-amine (1.54 g., 5.91 mmol), 2-(piperidin-1-yl)ethanamine and diisopropylethylamine (1.74 g, 17 mmol) were dissolved in n-butanol (5 mL) and heated in a sealed tube at 110° C. overnight. The mixture was purified using silica gel chromatography (20% ethanol in ethyl acetate) to afford the title compound (1.3 g, 73.3% yield). MS (ESI) m/z 300 [M]$^+$, 302 [M+2]$^+$ B. 6-Bromo-1-(2-(piperidin-1-yl)ethyl)-1H-imidazo[4,5-b]pyrazin-2(3H)-one 6-Bromo-N$^2$-(2-(piperidin-1-yl)ethyl)pyrazine-2,3-diamine (1.27 g., 4.23 mmol), 1,1'-carbonyldiimidazole (1.37 g., 8.46 mmol), and tetrahydrofuran (5 mL) were combined in a sealed tube and heated to 110° C. overnight. The solvent was removed and the residue treated with water and extracted into ethyl acetate, dried over magnesium sulfate, filtered and concentrated. Upon standing the desired product precipitated and was collected by filtration to give the title compound as a tan solid (1.2 g., 87% yield). MS (ESI) m/z 326.2 [M]$^+$, 328.2 [M+2]$^+$ C. 4-(2-Oxo-3-(2-(piperidin-1-yl)ethyl)-2,3-dihydro-1H-imidazo[4,5-b]pyrazin-5-yl)benzonitrile. 6-Bromo-1-(2-(piperidin-1-yl)ethyl)-1H-imidazo[4,5-b]pyrazin-2(3H)-one (1.2 g., 3.68 mmol), 4-cyanophenylboronic acid (0.595 g., 4.05 mmol), dichloro[1,1'-bis(diphenylphosphino)ferrocene]palladium(II) dichloromethane adduct (0.3 g., 0.368 mmol) and potassium phosphate (3.12 g., 14.7 mmol) were combined in DMF (9 mL) and heated in a sealed tube to 100° C. overnight. The flask was cooled to rt and the reaction mixture was filtered through celite, washed with methanol and ethyl acetate. The filtrate and washes were combined, concentrated and treated with water. The product was extracted into ethyl acetate, the organic layer was concentrated and the resulting material was subjected to silica gel chromatography (60-100% ethyl acetate in hexanes) to yield the title compound (0.5 g., 39% yield). MS (ESI) m/z 349.3 [M+1]$^+$.

D. Ethyl 4-(2-oxo-3-(2-(piperidin-1-yl)ethyl)-2,3-dihydro-1H-imidazo[4,5-b]pyrazin-5-yl)benzimidate hydrochloride. 4-(2-Oxo-3-(2-(piperidin-1-yl)ethyl)-2,3-dihydro-1H-imidazo[4,5-b]pyrazin-5-yl)benzonitrile (0.5 g., 1.43 mmol) was placed in anhydrous ethanol (5 mL) and cooled on an ice bath. The mixture was charged with hydrogen chloride gas for 15 min, capped and allowed to stir overnight while warming to rt. The solvent was removed and the residue treated with ether, filtered and dried under high vacuum to yield the title compound (0.4 g., 64.6% yield). MS (ESI) m/z 395.6 [M+1]$^+$ E. 6-(4-(4H-1,2,4-triazol-3-yl)phenyl)-1-(2-(piperidin-1-yl)ethyl)-1H-imidazo[4,5-b]pyrazin-2(3H)-one hydrochloride. Ethyl 4-(2-oxo-3-(2-(piperidin-1-yl)ethyl)-2,3-dihydro- 1H-imidazo[4,5-b]pyrazin-5-yl)benzimidate hydrochloride (0.4 g., 1.01 mmol), formic hydrazide (0.183 g., 3.04 mmol) and triethylamine (0.42 mL, 3.04 mmol) were combined in methanol (4 mL) and heated in a sealed tube at 100° C. for 3 h. The reaction mixture was cooled to room temperature and purified by reverse-phase semi-preparative HPLC (5-100% acetonitrile+0.1% TFA in $H_2O$+0.1% TFA, over 30 min). The clean fractions were collected and concentrated and the solid obtained was treated with hydrochloric acid in ether, filtered and dried under high vacuum to yield the title compound (0.035 g., 8.1% yield). $^1$H NMR (400 MHz, DMSO-$d_6$+$D_2O$) δ 8.64 (s, 1H), 8.50 (s, 1H), 8.20 (d, J=8.4, 2H), 8.15 (d, J=8.4, 2H), 4.34 (m, 2H), 3.76 (d, J=10.8, 2H), 3.53 (m, 2H), 2.98 (t, J=10.8, 2H), 1.86 (m, 2H), 1.70 (m, 2H), 1.5 (m, 2H); MS (ESI) m/z 391.5[M+1]$^+$; mp 194-197° C.

5.1.179 Example 179

SYNTHESIS OF 6-(2-AMINOBENZIMIDAZOL-5-YL)-1-(CYCLOHEXYLMETHYL)-4-IMIDA-ZOLINO[4,5-b]PYRAZIN-2-ONE

A. 6-(2-Aminobenzimidazol-5-yl)-1-(cyclohexylmethyl)-4-imidazolino[4,5-b]pyrazin-2-one dihydrochloride. tert-Butyl 2-(bis(tert-butoxycarbonyl)amino)-5-(trimethylstannyl)-1H-benzo[d]imidazole-1-carboxylate (480 mg, 0.80 mmol), 6-bromo-1-(cyclohexylmethyl)-1H-imidazo[4,5-b]pyrazin-2(3H)-one (See Example 55.B) (250 mg, 0.80 mmol), dichlorobis(triphenylphosphine)palladium(II) (56 mg, 0.008 mmol) in DMF (5 mL) were reacted for 1.5 h at 90° C. The product was purified by reverse-phase semi-preparatory HPLC (20-100% acetonitrile+0.1% TFA in $H_2O$+0.1% TFA, over 30 min). The desired fractions were concentrated, treated with 4N hydrochloric acid in diethyl ether (few drops), sonicated and concentrated. This procedure was repeated twice more to provide the title compound (11.4 mg, 3% yield). $^1$H NMR (400 MHz, DMSO-$d_6$) δ 12.52 (bs, 1H), 12.05 (s, 1H), 8.48 (bs, 2H), 7.95 (s, 1H), 7.88 (d, J=8.4, 1H), 7.43 (d, J=8.4, 1H), 3.73 (d, J=7.6, 2H), 1.93 (m, 1H), 1.68 (m, 2H), 1.28-1.23 (m, 2H), 1.18-1.16 (m, 2H), 1.02 (m, 1H), 0.89-0.85 (m, 2H); MS (ESI) m/z 364.2 [M+1]$^+$.

5.1.180 Example 180

SYNTHESIS OF 6-(2-(DIMETHYLAMINO)-1H-BENZO[D]IMIDAZOL-5-YL)-1-((TETRAHYDRO-2H-PYRAN-4-YL)METHYL)-1H-IMIDAZO[4,5-B]PYRAZIN-2(3H)-ONE

A. 6-Bromo-N,N-dimethyl-1H-benzo[d]imidazol-2-amine. A solution of 6-bromo-2-chloro-1H-benzo[d]imidazole (0.5 g, 2.16 mmol), dimethylamine (2.0 M in methanol, 4.3 mL, 8.6 mmol), diisopropylethylamine (1.50 mL, 8.60 mmol) in n-butanol (5 mL) was heated at 105° C. for 2.5 d. The reaction mixture was concentrated under reduced pressure and the crude product was purified by Biotage chromatography (0-80% ethyl acetate in hexanes) to provide the desired product (0.5 g, 100%) as a white solid. MS (ESI) m/z 241.3 [M+1]$^+$.

B. tert-Butyl 6-bromo-2-(dimethylamino)-1H-benzo[d]imidazole-1-carboxylate. A solution of 6-bromo-N,N-dimethyl-1H-benzo[d]imidazol-2-amine (0.5 g, 2.08 mmol), di-tert-butyl dicarbonate (0.54 g, 2.5 mmol), triethylamine (0.35 mL, 2.55 mmol) and dimethylaminopyridine (few crystals) in anhydrous tetrahydrofuran (10 mL) was allowed to stir at room temperature overnight. The reaction mixture was concentrated under reduced pressure and the crude product was purified by Biotage chromatography (0-55% ethyl acetate in hexanes) to provide the desired product (0.32 g, 54%) as a white solid. MS (ESI) m/z 341.3 [M+1]$^+$.

C. tert-Butyl 2-(dimethylamino)-6-(trimethylstannyl)-1H-benzo[d]imidazole-1-carboxylate A solution of tert-butyl 6-bromo-2-(dimethylamino)-1H-benzo[d]imidazole-1-carboxylate (320 mg, 0.93 mmol), hexamethylditin (0.22 mL, 1.03 mmol), tetrakis(triphenylphosphine) palladium(0) (107 mg, 0.09 mmol) in toluene (10 mL) was heated at 100° C. for 2 h. Upon completion of the reaction, toluene was removed under reduced pressure, and the resulting residue was purified by Biotage chromatography (0-50% ethyl acetate in hexanes) to afford the title compound (230 mg, 58%). MS (ESI) m/z 425.2 [M+1]$^+$.

D. 6-(2-(Dimethylamino)-1H-benzo[d]imidazol-5-yl)-1-((tetrahydro-2H-pyran-4-yl)methyl)-1H-imidazo[4,5-b]pyrazin-2(3H)-one. tert-Butyl 2-(dimethylamino)-6-(trimethyl-stannyl)-1H-benzo[d]imidazole-1-carboxylate (230 mg, 0.54 mmol), 6-bromo-1-((tetrahydro-2H-pyran-4-yl)methyl)-1H-imidazo[4,5-b]pyrazin-2(3H)-one (See Example 101.B) (170 mg, 0.54 mmol), dichlorobis(triphenylphosphine) palladium(II) (38 mg, 0.05 mmol) in DMF (5 mL) were reacted for 1.5 h at 105° C. The product was purified by reverse-phase semi-preparatory HPLC (30-100% acetonitrile+0.1% TFA in $H_2O$+0.1% TFA, over 30 min). The desired fractions were concentrated, treated with 4N hydrochloric acid in diethyl ether (few drops), and sonicated. This procedure was repeated twice more to provide the title compound (5.5 mg, 2.3% yield) as the hydrochloride salt. $^1$H NMR (400 MHz, DMSO-$d_6$) δ 8.44 (s, 1H), 8.03 (s, 1H), 8.33 (s, 1H), 7.95 (dd, J=8.4, 1.6, 1H), 7.46 (d, J=8.4, 1H), 3.95 (m, 2H), 3.92 (s, 3H), 3.90 (s, 3H), 2.25 (m, 1H), 1.65 (m, 2H), 1.49-1.41 (m, 2H), 1.27 (m, 2H), 0.95-0.88 (m, 2H); MS (ESI) m/z 394.2 [M+1]$^+$.

5.1.181 Example 181

SYNTHESIS OF 6-(4-HYDROXYPHENYL)-1-(PIPERIDIN-3-YLMETHYL)-1H-IMIDAZO[4,5-B]PYRAZIN-2(3H)-ONE

A. tert-Butyl 3-((3-amino-6-bromopyrazin-2-ylamino) methyl)piperidine-1-carboxylate. In a sealed tube, a solution of 5-bromopyrazine-2,3-diamine (1.88 g, 7.46 mmol), tert-butyl 3-(aminomethyl)piperidinecarboxylate (2.0 g, 9.33 mmol), diisopropylethylamine (1.95 mL, 11.19 mmol) in n-butanol (200 mL) was heated at 120° C. for 17 h. The volatiles were removed under reduced pressure. The residue was taken up in hexanes and sonicated. The resulting precipitate was collected by filtration to provide the title compound (1.7 g, 61%). MS (ESI) m/z 387.3 [M+1]$^+$.

B. tert-Butyl 3-((6-bromo-2-oxo-2,3-dihydro-1H-imidazo [4,5-b]pyrazin-1-yl)methyl)piperidine-1-carboxylate. In a sealed tube, a solution of tert-butyl 3-((3-amino-6-bromopyrazin-2-ylamino)methyl)piperidine-1-carboxylate (1.7 g, 4.41 mmol), 1,1'-carbonyldiimidazole (0.9 g, 5.51 mmol) in tetrahydrofuran (10 mL) was heated at 110° C. The volatiles were removed under reduced pressure. The resulting residue was taken into hexanes and diethylether, sonicated, and the precipitate was collected by filtration, rinsed with hexanes, and dried in vacuum oven to afford the product (0.59 g, 26% yield) as a tan solid. MS (ESI) m/z 413.3.2[M+1]$^+$.

C. 6-(4-Hydroxyphenyl)-1-(piperidin-3-ylmethyl)-1H-imidazo[4,5-b]pyrazin-2(3H)-one. tert-Butyl 3-((6-bromo-2-oxo-2,3-dihydro-1H-imidazo[4,5-b]pyrazin-1-yl)methyl)piperidine-1-carboxylate (0.5 g, 1.21 mmol), 4-hydroxyphenylboronic acid (0.16 g, 1.21 mmol) and dichloro[1,1'-bis(diphenylphosphino)ferrocene]palladium (II) dichloromethane (0.1 g, 0.12 mmol) were combined in DMF (30 mL). Potassium phosphate (1.02 g, 4.84 mmol) in water (10 mL) was added and the reaction stirred at 100° C. for 2 h. The cooled reaction solution was filtered through Celite and the filter cake was washed with ethyl acetate. Filtrate and ethyl acetate wash were combined and solvent removed under reduced pressure. Compound was purified using reverse-phase semi-preparatory HPLC (20-80% acetonitrile+0.1% TFA in $H_2O$+0.1% TFA, over 30 min). The desired fractions were concentrated, treated with 4N hydrochloric acid in diethyl ether (few drops), and sonicated. This procedure was repeated twice. The resulting material was dried under vacuum overnight to afford the title compound as an off white solid, 99.2% pure, (10.1 mg, 2.2%). $^1$H NMR (400 MHz, DMSO-$d_6$) δ 8.33 (s, 1H), 7.85 (d, J=8.4, 2H), 6.86 (d, J=8.4, 2H), 3.99 (m, 2H), 3.43-3.40 (m, 1H), 2.92-2.86 (m, 2H), 2.01-1.96 (m, 2H), 1.47-1.27 (m, 3H), 0.95-0.88 (m, 1H); MS (ESI) m/z 326.1 [M+1]$^+$.

5.1.182 Example 182

SYNTHESIS OF 6-(4-(5-OXOPYRROLIDIN-2-YL) PHENYL)-1-(2-(TETRAHYDRO-2H-PYRAN-4-YL)ETHYL)-1H-IMIDAZO[4,5-B]PYRAZIN-2(3H)-ONE

A. 7a-(4-Bromophenyl)-3-phenyltetrahydropyrrolo[2,1-b]oxazol-5(6H)-one. Racemic phenyl glycinol (6.40 g, 46.7 mmol), 4-(4-bromophenyl)-4-oxobutanoic acid (12.0 g, 46.7 mmol), and toluene (50 mL) were combined in a 100 mL round-bottom flask with a stirbar, stirred vigorously, and heated at 120° C. under a Dean-Stark apparatus under a reflux condenser under nitrogen for 16 h. Flash chromatography (15-30-50% ethyl acetate in hexane) gave the desired product as a white solid (12.77 g, 76%). $R_f$=0.23 (30% ethyl acetate in hexane); $^1$H NMR (400 MHz, DMSO-$d_6$) δ 7.51-7.56 (m, 2H), 7.42-7.47 (m, 2H), 7.15-7.26 (m, 3H), 7.05-7.10 (m, 2H), 5.06 (t, J=8.20, 1H), 4.78-4.84 (m, 1H), 3.63 (t, J=8.79, 1H), 2.98-3.10 (m, 1H), 2.51-2.59 (m, 2H), 2.17-2.27 (m, 1H); MS (ESI) m/z 359[M+1]$^+$.

B. 5-(4-Bromophenyl)pyrrolidin-2-one. 7a-(4-Bromophenyl)-3-phenyltetrahydropyrrolo[2,1-b]oxazol-5(6H),-one (8.61 g, 24.0 mmol) was dissolved in dichloromethane (120 mL) with stirring under nitrogen and cooled to −75° C. Titanium tetrachloride (3.95 mL, 36.1 mmol) was added and the resulting mixture stirred 5 min at −75° C. Triethylsilane (5.76 mL, 36.1 mmol) was added and the resulting mixture stirred 3 h while slowly warming to 10° C. Saturated ammonium chloride was added to quench the reaction. The resulting mixture was diluted with dichloromethane and stirred vigorously for 10 min. The mixture was filtered through Celite to remove white salts and the filter cake washed with dichloromethane. The layers of the filtrate were separated and the water layer extracted with dichloromethane. The combined organics were dried over magnesium sulfate, filtered, concentrated on a rotary evaporator, and dried under vacuum to give a yellow oil, which was used in the next step without purification. The yellow oil was dissolved in tetrahydrofuran (120 mL) and cooled to 0° C. with stirring under nitrogen. Thionyl chloride (3.50 mL, 48.1 mmol) was added. The cold bath was removed and the reaction mixture stirred 15 min while slowly warming to room temperature. More thionyl chloride (1 mL, 13.7 mmol) was added and the resulting mixture stirred for an additional 1 h. All volatiles were removed on a rotary evaporator. The residue was dissolved in ethanol (80 mL) at room temperature with stirring under nitrogen. Sodium ethoxide (45 mL of a 21 weight % solution in ethanol, 120 mmol) was added and the resulting cloudy mixture stirred 40 h at room temperature. All volatiles were removed on a rotary evaporator. The residue was treated with dichloromethane (100 mL) and 1 M sodium bisulfate in water (200 mL). The resulting mixture was shaken in a separatory funnel to give two clear layers. The layers were separated and the water layer extracted with dichloromethane. The combined organics were concentrated on a rotary evaporator. The residue was dissolved in tetrahydrofuran (175 mL) with stirring at 70° C. 1 M hydrochloric acid in water (48 mL) was added and the resulting mixture heated at 70° C. under a reflux condenser under nitrogen for 1.75 h. The tetrahydrofuran was removed on a rotary evaporator. Solid sodium bicarbonate (6.10 g) was added, followed by more water and dichloromethane. After all the acid had been neutralized, the mixture was shaken in a separatory funnel and the layers separated. The water layer was extracted with dichloromethane. The combined organics were dried over magnesium sulfate, filtered, and concentrated on a rotary evaporator nearly to dryness (solids precipitated). The resulting mixture was diluted with hexane and the solids collected by vacuum filtration. The solids were washed three times with hexane and dried under vacuum to give the desired product (4.74 g, 82%) as an off-white solid. $^1$H NMR (400 MHz, DMSO-$d_6$) δ 8.11 (s, 1H), 7.52-7.58 (m, 2H), 7.23-7.30 (m, 2H), 4.65 (t, J=7.03, 1H), 2.39-2.49 (m, 1H), 2.22 (t, J=8.00, 2H), 1.71 (m, 1H); MS (ESI) m/z 241[M+1]$^+$.

C. 6-Bromo-1-(2-(tetrahydro-2H-pyran-4-yl)ethyl)-1H-imidazo[4,5-b]pyrazin-2(3H)-one. 3,5-Dibromopyrazin-2-amine (9.79 g, 38.7 mmol) was dissolved in dimethylsulfoxide (12 mL) with stirring in a 150 mL sealable vessel. Diisopropylethylamine (13.5 mL, 77.4 mmol) was added followed by 2-(tetrahydro-2H-pyran-4-yl)ethanamine (5.00 g, 38.7 mmol). Nitrogen was blown into the vessel to blow out air and the vessel was sealed. The resulting reaction mixture was stirred vigorously and heated at 100° C. for 16 h and then cooled to room temperature. 1,1'-Carbonyldiimidazole (9.41 g, 58.0 mmol) was added and the resulting mixture heated at 70° C. Nitrogen was blown into the vessel to blow out air and the vessel was sealed. The resulting reaction mixture was stirred vigorously and heated at 70° C. for 3 h and then cooled to room temperature. More 1,1'-carbonyldiimidazole (3.14 g, 19.4 mmol) was added and the resulting mixture heated at 70° C. for 3.5 h and then cooled to room temperature. The resulting mixture was diluted with ethyl acetate and poured into a separatory funnel containing water and 50% ethyl acetate in hexane. Solids formed while the separatory funnel was being shaken. The solids were collected by vacuum filtration, washed three times with water and twice with ethyl ether, and dried under vacuum at 45° C. to give the desired product (5.57 g, 44%) as a tan-gray solid. A second batch of solids was collected from the filtrate to give the desired product (1.74 g, 14%) as a tan-gray solid. $^1$H NMR (400 MHz, DMSO-$d_6$) δ 12.20 (br. s., 1H), 8.03 (s, 1H), 3.82 (t, J=7.03, 4H), 3.23 (td, J=11.62, 1.76, 2H), 1.58-1.70 (m, 4H), 1.42-1.55 (m, 1H), 1.10-1.23 (m, 2H); MS (ESI) m/z 327[M+1]$^+$.

D. 1-(2-(Tetrahydro-2H-pyran-4-yl)ethyl)-6-(trimethylstannyl)-1H-imidazo[4,5-b]pyrazin-2(3H)-one. 6-Bromo-1-(2-(tetrahydro-2H-pyran-4-yl)ethyl)-1H-imidazo[4,5-b]pyrazin-2(3H)-one (1.00 g, 3.06 mmol), hexamethylditin (1.20 g, 3.67 mmol), tetrakis(triphenylphosphine)palladium (0) (0.71 g, 0.61 mmol), and 1,4-dioxane (10 mL) were combined in a 150 mL sealable vessel with a stirbar. Nitrogen was blown into the vessel to blow out air and the vessel was sealed. The resulting reaction mixture was stirred vigorously and heated at 100° C. for 5 h and then cooled to room temperature. The resulting mixture was diluted with ethyl acetate and filtered through Celite. The filter cake was washed thoroughly with ethyl acetate. The filtrate was concentrated on a rotary evaporator. Flash chromatography (30-60% ethyl acetate in hexane) gave the desired product (783 mg, 62%) as a yellow waxy solid. $R_f$=0.20 (50% ethyl acetate/hexane); $^1$H NMR (400 MHz, DMSO-$d_6$) δ 11.84 (s, 1H), 7.88 (s, 1H), 3.87 (t, J=6.64, 2H), 3.80 (dd, J=11.32, 3.12, 2H), 3.18 (t, J=10.93, 2H), 1.60-1.73 (m, 4H), 1.33-1.46 (m, 1H), 1.08-1.23 (m, 2H), 0.31 (s, 9H); MS (ESI) m/z 413[M+1]$^+$.

E. 6-(4-(5-Oxopyrrolidin-2-yl)phenyl)-1-(2-(tetrahydro-2H-pyran-4-yl)ethyl)-1H-imidazo[4,5-b]pyrazin-2(3H)-one. 5-(4-Bromophenyl)pyrrolidin-2-one (220 mg, 0.916 mmol), 1-(2-(tetrahydro-2H-pyran-4-yl)ethyl)-6-(trimethylstannyl)-1H-imidazo[4,5-b]pyrazin-2(3H)-one (396 mg, 0.962 mmol), tris(dibenzylidineacetone) dipalladium(0) (84 mg, 0.092 mmol), tri-o-tolylphosphine (56 mg, 0.183 mmol), triethylamine (0.38 mL, 2.75 mmol), and N,N-dimethylformamide (2.5 mL) were combined in a scintillation vial with a stirbar. The atmosphere in the vial was removed and replaced three times with nitrogen. The resulting mixture was stirred vigorously and heated at 100° C. under nitrogen for 2.5 h and then cooled to room temperature. The resulting mixture was diluted with methanol, filtered, and purified using reverse-phase semi-preparatory HPLC (50% acetonitrile+0.1% TFA in H$_2$O+0.1% TFA, isocratic). Fractions containing the desired product were combined and the acetonitrile removed on a rotary evaporator. Saturated aqueous sodium bicarbonate was added to neutralize the resulting mixture and it was then extracted with dichloromethane (5×20 mL). The combined organics were dried over magnesium sulfate, filtered, and concentrated on a rotary evaporator nearly to dryness (solids precipitated). The residual solvent was removed with a pipette. The remaining solids were washed twice with ethyl ether and dried under vacuum at 50° C. to give the desired product (68 mg, 18%) as a white solid. $^1$H NMR (400 MHz, DMSO-$d_6$) δ 12.05 (br. s., 1H), 8.49 (s, 1H), 8.15 (s, 1H), 8.00 (d, J=8.20, 2H), 7.41 (d, J=8.20, 2H), 4.72 (t, J=7.03, 1H), 3.93 (t, J=6.83, 2H), 3.82 (dd, J=10.93, 3.12, 2H), 3.21 (t, J=11.13, 2H), 2.44-2.55 (m, 1H), 2.26 (t, J=8.00, 2H), 1.65-1.84 (m, 5H), 1.44-1.57 (m, 1H), 1.20 (qd, J=12.10, 4.30, 2H); MS (ESI) m/z 408[M+1]$^+$.

5.1.183 Example 183

SYNTHESIS OF 6-(4-(4H-1,2,4-TRIAZOL-3-YL) PHENYL)-1-(2-METHYL-2-MORPHOLINOPROPYL)-1H-IMIDAZO[4,5-B]PYRAZIN-2(3H)-ONE

A. 6-Bromo-N$^2$-(2-methyl-2-morpholinopropyl)pyrazine-2,3-diamine. To a thick-wall borosilicate glass vial (5 mL) was added 2-amino-3,5-dibromo-pyrazine (559 mg, 2.21 mmol), 2-methyl-2-morpholinopropan-1-amine (350 mg, 2.212 mmol) and diisopropylethylamine (0.773 mL, 4.42 mmol), in ethanol. The solution was then heated in a Biotage Emrys Optimizer microwave reactor at 140° C. for 4 h. The reaction mixture was concentrated under reduced pressure and the crude product was purified by Biotage chromatography (0-15% methanol in dicholoromethane) to provide the desired product (555 mg, 76%) as a pale, yellow oil. $^1$H NMR (400 MHz, CD$_3$OD) δ 7.16 (s, 1H), 3.72-3.63 (m, 4H), 3.39 (s, 2H), 2.62 (br s, 4H), 1.12 (s, 6H); MS (ESI) m/z 330.1 [M+1]$^+$.

B. 6-Bromo-1-(2-methyl-2-morpholinopropyl)-1H-imidazo[4,5-b]pyrazin-2(3H)-one. A solution of phosgene in toluene (20%, 2.35 mL, 4.45 mmol) was added to 6-bromo-N$^2$-(2-methyl-2-morpholinopropyl)pyrazine-2,3-diamine (550 mg, 1.67 mmol) in tetrahydrofuran (16.7 mL) at room temperature and stirred for 16 h. The reaction mixture was concentrated under reduced pressure and the crude product was recrystallized from hot methanol yielding a tan solid (244 mg, 41%). $^1$H NMR (400 MHz, DMSO-$d_6$) δ 12.20 (s, 1H), 8.03 (s, 1H), 3.76 (s, 2H), 3.51 (t, J=4.30, 4H), 2.64-2.53 (m, 4H), 1.01 (s, 6H); MS (ESI) m/z 356.0 [M+1]$^+$.

C. 6-(4-(4H-1,2,4-triazol-3-yl)phenyl)-1-(2-methyl-2-morpholinopropyl)-1H-imidazo[4,5-b]pyrazin-2(3H)-one. 6-Bromo-1-(2-methyl-2-morpholinopropyl)-1H-imidazo[4,5-b]pyrazin-2(3H)-one (235 mg, 0.660 mmol), 4-(1H-1,2,4-triazol-5-yl)phenylboronic acid hydrochloride (See Example 159.D) (178 mg, 0.792 mmol), sodium carbonate (210 mg, 1.98 mmol) and dichloro[1,1'-bis(diphenylphosphino)ferrocene]palladium(II) dichloromethane adduct (26.9 mg, 0.033 mmol) were added to dioxane (5.5 mL) and water (0.5 mL) in a thick-wall borosilicate glass vial (20 mL). The solution was then heated in a Biotage Emrys Optimizer microwave reactor at 150° C. for 90 min. The reaction mixture was filtered and purified by reverse-phase semi-preparatory HPLC (5-70% acetonitrile+0.1% TFA in H$_2$O+0.1% TFA, over 30 min). Fractions containing clean product were passed through a Phenomenex Strata-X-C ion exchange column. The product was released from the column using 2M ammonia in methanol. The solution was concentrated under reduced pressure and dried under vacuum to give product as a white solid (6.8 mg, 2.5%). $^1$H NMR (400 MHz, DMSO-$d_6$) δ 12.08 (br s, 1H), 8.59 (s, 1H), 8.17-8.10 (m, 4H), 3.89 (s, 2H), 3.46 (br s, 4H), 2.66 (br s, 4H), 1.10 (s, 6H); MS (ESI) m/z 421.5 [M+1]$^+$.

5.1.184 Example 184

SYNTHESIS OF 6-(4-(4H-1,2,4-TRIAZOL-3-YL) PHENYL)-1-(1-MORPHOLINOPROPAN-2-YL)-1H-IMIDAZO[4,5-B]PYRAZIN-2(3H)-ONE

A. 6-Bromo-N$^2$-(1-morpholinopropan-2-yl)pyrazine-2,3-diamine. To a thick-wall borosilicate glass vial (5 mL) was added 2-amino-3,5-dibromo-pyrazine (789 mg, 3.12 mmol), 1-morpholinopropan-2-amine (450 mg, 3.12 mmol) and diisopropylethylamine (1.09 mL, 6.24 mmol), in ethanol. The solution was then heated in a Biotage Emrys Optimizer microwave reactor at 140° C. for 4 h. The reaction mixture was concentrated under reduced pressure and the crude product was purified by Biotage chromatography (0-15% methanol in dicholoromethane) to provide the desired product (601 mg, 61%) as a pale, yellow oil. $^1$H NMR (400 MHz, CD$_3$OD) δ 7.17 (s, 1H), 4.35 (br s, 1H), 3.71 (br s, 4H), 2.67 (br s, 6H), 1.26 (d, J=6.64, 3H); MS (ESI) m/z 316.0 [M+1]$^+$.

B. 6-Bromo-1-(1-morpholinopropan-2-yl)-1H-imidazo[4,5-b]pyrazin-2(3H)-one. A solution of phosgene in toluene (20%, 1.64 mL, 3.10 mmol) was added to 6-bromo-N$^2$-(1-morpholinopropan-2-yl)pyrazine-2,3-diamine (600 mg, 1.90 mmol) in THF (19 mL) at room temperature and stirred for 16 h. The reaction mixture was concentrated under reduced pressure and the crude product was recrystallized from hot methanol yielding a tan solid (324 mg, 50%). $^1$H NMR (400 MHz, DMSO-$d_6$) δ 12.35 (s, 1H), 8.08 (s, 1H), 4.99-4.82 (m, 1H), 4.11-3.32 (m, 8H), 3.25-3.01 (m, 2H), 1.53 (d, J=7.03, 3H); MS (ESI) m/z 342.0 [M+1]$^+$.

C. 6-(4-(4H-1,2,4-Triazol-3-yl)phenyl)-1-(1-morpholinopropan-2-yl)-1H-imidazo[4,5-b]pyrazin-2(3H)-one. 6-Bromo-1-(1-morpholinopropan-2-yl)-1H-imidazo[4,5-b]pyrazin-2(3H)-one (315 mg, 0.921 mmol), 4-(1H-1,2,4-triazol-5-yl)phenylboronic acid hydrochloride (See Example 159.D) (249 mg, 1.105 mmol), sodium carbonate (293 mg, 2.76 mmol) and dichloro[1,1'-bis(diphenylphosphino)ferrocene]palladium(II) dichloromethane adduct (37.6 mg, 0.046 mmol) were added to dioxane (7.6 mL) and water (0.5 mL) in a thick-wall borosilicate glass vial (20 mL). The solution was then heated in a Biotage Emrys Optimizer microwave reactor at 150° C. for 60 min. The reaction mixture was filtered and purified by reverse-phase semi-preparatory HPLC (5-70% acetonitrile+0.1% TFA in $H_2O$+0.1% TFA, over 30 min). Fractions containing clean product were passed through a Phenomenex Strata-X-C ion exchange column. The product was released from the column using 2M ammonia in methanol. The solution was concentrated under reduced pressure and dried under vacuum to give product as a white solid (32 mg, 9%). $^1$H NMR (400 MHz, DMSO-$d_6$) δ 12.06 (br s, 1H), 8.57 (s, 1H), 8.46 (br s, 1H), 8.20-8.05 (m, 4H), 4.79-4.68 (m, 1H), 3.43-3.30 (m, 4H), 3.21-3.14 (m, 1H), 2.60-2.50 (m, 2H), 2.26-2.21 (m, 2H), 1.57 (d, J=7.03, 3H); MS (ESI) m/z 407.0 [M+1]$^+$.

5.1.185 Example 185

SYNTHESIS OF 6-(4-(PYRROLIDIN-2-YL)PHENYL)-1-(2-(TETRAHYDRO-2H-PYRAN-4-YL)ETHYL)-1H-IMIDAZO[4,5-B]PYRAZIN-2(3H)-ONE

A. 6-(4-(Pyrrolidin-2-yl)phenyl)-1-(2-(tetrahydro-2H-pyran-4-yl)ethyl)-1H-imidazo[4,5-b]pyrazin-2(3H)-one. To lithium aluminum hydride (332 mg, 8.75 mmol) in a round-bottom flask with stirbar was added tetrahydrofuran (13 mL). The resulting gray mixture was stirred at room temperature under nitrogen for 5 min. 5-(4-Bromophenyl)pyrrolidin-2-one (700 mg, 2.92 mmol) was added and the resulting mixture heated at 70° C. under a reflux condenser under nitrogen for 2 h. The resulting mixture was cooled to 0° C. and quenched by adding a saturated aqueous solution of sodium sulfate dropwise, slowly. Ethyl ether was added to improve stirring and the quenched reaction mixture was stirred 20 min at room temperature. Di-tert-butyl dicarbonate (1.18 g, 5.41 mmol) was added and the resulting mixture stirred 1.5 h at room temperature under nitrogen. The resulting mixture was filtered through Celite and the filter cake washed thoroughly with ethyl acetate. The filtrate was concentrated on a rotary evaporator. Flash chromatography (10-30-50% ethyl acetate in hexane) gave 658 mg of a colorless oil which was a mixture of products. This mixture was carried on to the next step without further purification. 323 mg of the above-prepared mixture, 1-(2-(tetrahydro-2H-pyran-4-yl)ethyl)-6-(trimethylstannyl)-1H-imidazo[4,5-b]pyrazin-2(3H)-one (See Example 182.D) (407 mg, 0.990 mmol), tris(dibenzylidineacetone)dipalladium(0) (91 mg, 0.099 mmol), tri-o-tolylphosphine (60 mg, 0.198 mmol), triethylamine (0.41 mL, 2.97 mmol), and N,N-dimethylformamide (2.0 mL) were combined in a scintillation vial with a stirbar. The atmosphere in the vial was removed and replaced three times with nitrogen. The resulting mixture was stirred vigorously and heated at 100° C. under nitrogen for 1.5 h and then cooled to room temperature. The resulting mixture was diluted with methanol, filtered, and purified using reverse-phase preparatory HPLC (20-100% acetonitrile+0.1% TFA in $H_2O$+0.1% TFA, over 30 min). Fractions containing the desired product were combined and all of the solvent removed on a rotary evaporator. The residue was dissolved in ethanol (4 mL) at 80° C. with stirring. 6 N Hydrochloric acid (0.35 mL, 2.10 mmol) was added and the resulting clear solution heated at 80° C. under a reflux condenser under nitrogen for 30 min. The reaction mixture was filtered and purified reverse-phase preparatory HPLC (10-60% acetonitrile+0.1% TFA in $H_2O$+ 0.1% TFA, over 30 min). Vials containing product were combined and almost all the solvent removed on a rotary evaporator. Acetonitrile was added and the resulting mixture loaded on a Strata ion exchange column from Phenomenex. The column was washed successively with water, acetonitrile, methanol, and then 5% ammonium hydroxide in methanol. The product was released with the 5% ammonium hydroxide in methanol eluent and was concentrated on a rotary evaporator and dried under vacuum at 50° C. to give the desired product (64 mg, 16%) as a white solid. $^1$H NMR (400 MHz, DMSO-$d_6$) δ 8.45 (s, 1H), 7.93 (d, J=8.20, 2H), 7.46 (d, J=8.20, 2H), 4.09 (t, J=7.61, 1H), 3.92 (t, J=6.83, 2H), 3.82 (dd, J=11.52, 2.93, 2H), 3.51 (br. s., 2H), 3.21 (td, J=11.71, 1.95, 2H), 3.05 (ddd, J=9.96, 7.61, 5.47, 1H), 2.87-2.95 (m, 1H), 2.08-2.20 (m, 1H), 1.64-1.87 (m, 6H), 1.42-1.58 (m, 2H), 1.12-1.27 (m, 2H); MS (ESI) m/z 394 [M+1]$^+$.

5.1.186 Example 186

SYNTHESIS OF 6-(4-(5-OXOPYRROLIDIN-3-YL)PHENYL)-1-(2-(TETRAHYDRO-2H-PYRAN-4-YL)ETHYL)-1H-IMIDAZO[4,5-B]PYRAZIN-2(3H)-ONE

A. Ethyl 3-(4-bromophenyl)-4-nitrobutanoate. (E)-Ethyl 3-(4-bromophenyl)acrylate (12.0 g, 47.0 mmol), 1,1,3,3-tetramethylguanidine (1.0 mL), and nitromethane (100 mL) were combined in a 250 mL round-bottom flask with a stirbar, stirred vigorously, and heated at 50° C. under a reflux condenser under nitrogen for 36 h. The nitromethane solvent was removed on a rotary evaporator. Flash chromatography (10-30% ethyl acetate/hexane) gave the desired product (13.62 g, 92%) as a colorless oil. $R_f$=0.36 (30% ethyl acetate/hexane); $^1$H NMR (400 MHz, DMSO-$d_6$) δ 7.49-7.54 (m, 2H), 7.28-7.33 (m, 2H), 4.93-5.00 (m, 1H), 4.82-4.90 (m, 1H), 3.97 (qd, J=7.09, 2.15, 2H), 3.79 (tt, J=9.18, 6.05, 1H), 2.78-2.85 (m, 1H), 2.65-2.74 (m, 1H), 1.07 (t, J=7.03, 3H); MS (ESI) m/z 317[M+1]$^+$.

B. 4-(4-Bromophenyl)pyrrolidin-2-one. Ethyl 3-(4-bromophenyl)-4-nitrobutanoate (2.02 g, 6.39 mmol) was dissolved in ethanol (80 mL) and 4 M hydrochloric acid in 1,4-dioxane (16 mL, 63.9 mmol) with stirring and cooled to 0° C. under nitrogen. Zinc dust (4.18 g, 63.9 mmol) was added slowly in portions over ~10 min. Gas evolution was observed. After 30 min the cold bath was removed and the gray reaction mixture stirred 1 h at room temperature. The resulting mixture was filtered through Celite and the filter cake washed thoroughly with methanol. The filtrate was concentrated on a rotary evaporator. The residue was dissolved in ethanol (50 mL) with stirring at room temperature. Sodium ethoxide (24 mL of a 2.68 M solution in ethanol, 63.9 mmol) was added and the resulting cloudy mixture (pH is basic) stirred at room temperature overnight. The resulting cloudy mixture was poured into a separatory funnel containing dichloromethane (300 mL) and 1 M sodium bisulfate (80 mL). The mixture was shaken and the layers separated. The water layer was extracted once with dichloromethane. The combined organics were dried over magnesium sulfate, filtered, and concentrated on a rotary evaporator. The residue was dissolved in acetonitrile and water was added to induce precipitation of solids. The solids were collected by vacuum filtration, washed twice with water and twice with ether, and dried under vacuum at 45° C. to give the desired product (929 mg, 61%) as a slightly orange solid. $^1$H NMR (400 MHz, DMSO-$d_6$) δ 7.73 (br. s., 1H), 7.49-7.54 (m, 2H), 7.25-7.31 (m, 2H), 3.55-3.65 (m, 2H), 3.12-3.20 (m, 1H), 2.46-2.55 (m, 1H), 2.23-2.32 (m, 1H); MS (ESI) m/z 241 [M+1]$^+$.

C. 6-(4-(5-Oxopyrrolidin-3-yl)phenyl)-1-(2-(tetrahydro-2H-pyran-4-yl)ethyl)-1H-imidazo[4,5-b]pyrazin-2(3H)-one. 4-(4-Bromophenyl)pyrrolidin-2-one (215 mg, 0.894 mmol), 1-(2-(tetrahydro-2H-pyran-4-yl)ethyl)-6-(trimethylstannyl)-1H-imidazo[4,5-b]pyrazin-2(3H)-one (See Example 182.D) (386 mg, 0.939 mmol), tris(dibenzylideneacetone)dipalladium(0) (82 mg, 0.089 mmol), tri-o-tolylphosphine (54 mg, 0.179 mmol), triethylamine (0.37 mL, 2.68 mmol), and N,N-dimethylformamide (2.5 mL) were combined in a scintillation vial with a stirbar. The atmosphere in the vial was removed and replaced three times with nitrogen. The resulting mixture was stirred vigorously and heated at 100° C. under nitrogen for 2.5 h and then cooled to room temperature. The resulting mixture was diluted with methanol, filtered, and purified using reverse-phase preparatory HPLC (20-60% acetonitrile+0.1% TFA in $H_2O$+0.1% TFA, over 30 min). Fractions containing the desired product were combined and the acetonitrile removed on a rotary evaporator. Saturated aqueous sodium bicarbonate was added to neutralize the resulting mixture and it was then extracted with dichloromethane (4×20 mL). The combined organics were concentrated on a rotary evaporator. The residue was dissolved in hot dimethylsulfoxide and methanol was added to cause precipitation of solids. The solids were collected by vacuum filtration and washed successively with methanol, acetonitrile, and ethyl ether. This process was repeated and the solids dried under vacuum at 45° C. to give the desired product (60 mg, 16%) as a white solid. $^1$H NMR (400 MHz, DMSO-$d_6$) δ 12.03 (br. s., 1H), 8.48 (s, 1H), 7.97 (d, J=8.59, 2H), 7.75 (s, 1H), 7.43 (d, J=8.59, 2H), 3.92 (t, J=6.83, 2H), 3.82 (dd, J=11.32, 2.73, 2H), 3.61-3.72 (m, 2H), 3.16-3.27 (m, 3H), 2.52-2.58 (m, 1H), 2.29-2.40 (m, 1H), 1.66-1.76 (m, 4H), 1.44-1.57 (m, 1H), 1.14-1.26 (m, 2H); MS (ESI) m/z 408 [M+1]$^+$.

5.1.187 Example 187

SYNTHESIS OF 6-(4-(PYRROLIDIN-3-YL)PHENYL)-1-(2-(TETRAHYDRO-2H-PYRAN-4-YL)ETHYL)-1H-IMIDAZO[4,5-B]PYRAZIN-2(3H)-ONE

A. 6-(4-(Pyrrolidin-3-yl)phenyl)-1-(2-(tetrahydro-2H-pyran-4-yl)ethyl)-1H-imidazo[4,5-b]pyrazin-2(3H)-one. To lithium aluminum hydride (190 mg, 5.00 mmol) in a round-bottom flask with stirbar was added tetrahydrofuran (7 mL). The resulting gray mixture was stirred at room temperature under nitrogen for 5 min. 4-(4-Bromophenyl)pyrrolidin-2-one (400 mg, 1.67 mmol) was added and the resulting mixture heated at 65° C. under a reflux condenser under nitrogen for 1.25 h. The resulting mixture was cooled to 0° C. and quenched by adding a saturated aqueous solution of sodium sulfate dropwise slowly. Ethyl ether was added to improve stirring and the resulting quenched reaction mixture was stirred 20 min at room temperature. Di-tert-butyl dicarbonate (727 mg, 3.33 mmol) was added and the resulting mixture stirred 35 min at room temperature under nitrogen. The resulting mixture was filtered through Celite and the filter cake washed thoroughly with ethyl acetate. The filtrate was concentrated on a rotary evaporator. Flash chromatography (5-10-30% ethyl acetate in hexane) gave 204 mg of a colorless oil which was a mixture of products. This mixture was combined with 1-(2-(tetrahydro-2H-pyran-4-yl)ethyl)-6-(trimethylstannyl)-1H-imidazo[4,5-b]pyrazin-2(3H)-one (See Example 182.D) (205 mg, 0.499 mmol), tris(dibenzylidineacetone)dipalladium(0) (46 mg, 0.050 mmol), tri-o-tolylphosphine (30 mg, 0.100 mmol), triethylamine (0.21 mL, 1.50 mmol), and N,N-dimethylformamide (1.5 mL), in a scintillation vial with a stirbar. The atmosphere in the vial was removed and replaced three times with nitrogen. The resulting mixture was stirred vigorously and heated at 100° C. under nitrogen for 1 h and then cooled to room temperature. The resulting mixture was diluted with methanol, filtered, and purified using reverse-phase preparatory HPLC (20-100% acetonitrile+0.1% TFA in $H_2O$+0.1% TFA, over 30 min). Fractions containing the desired product were combined and all of the solvent removed on a rotary evaporator. The residue was dissolved in ethanol (4 mL) at 80° C. with stirring. 6 N hydrochloric acid (0.42 mL, 2.49 mmol) was added and the resulting clear solution heated at 80° C. under a reflux condenser under nitrogen for 70 min. The reaction mixture was filtered and purified reverse-phase preparatory HPLC (10-60% acetonitrile+0.1% TFA in $H_2O$+0.1% TFA, over 30 min). Vials containing product were combined and almost all the solvent removed on a rotary evaporator. Acetonitrile was added and the resulting mixture loaded on a Strata ion exchange column from Phenomenex. The column was washed successively with water, acetonitrile, methanol, and then 5% ammonium hydroxide in methanol. The product was released with the 5% ammonium hydroxide in methanol eluent and was concentrated on a rotary evaporator. The residue was triturated with ethyl ether to make a fine powder and dried under vacuum at 50° C. to give the desired product (41 mg, 6%) as a white solid. $^1$H NMR (400 MHz, DMSO-$d_6$) δ 8.41 (s, 1H), 7.92 (d, J=8.20, 2H), 7.37 (d, J=8.20, 2H), 3.90 (t, J=6.83, 2H), 3.82 (dd, J=11.32, 2.73, 2H), 3.59 (br. s., 1H), 3.15-3.31 (m, 5H), 3.02-3.10 (m, 1H), 2.96 (ddd, J=10.74, 7.81, 7.61, 1H), 2.72 (dd, J=10.15, 8.20, 1H), 2.13-2.24 (m, 1H), 1.65-1.81 (m, 5H), 1.42-1.55 (m, 1H), 1.13-1.26 (m, 2H); MS (ESI) m/z 394 [M+1]$^+$.

5.1.188 Example 188

SYNTHESIS OF 1-(CYCLOHEXYLMETHYL)-6-(PYRIMIDIN-5-YL)-1H-IMIDAZO[4,5-B]PYRAZIN-2(3H)-ONE

A. 1-(Cyclohexylmethyl)-6-(pyrimidin-5-yl)-1H-imidazo[4,5-b]pyrazin-2(3H)-one. 6-Bromo-1-(cyclohexylmethyl)-1H-imidazo[4,5-b]pyrazin-2(3H)-one (See Example 55.B) (0.324 g, 1.041 mmol), dichloro[1,1'-bis(diphenylphosphino)ferrocene]palladium(II) dichloromethane adduct (0.085 g, 0.104 mmol), potassium phosphate (0.884 g, 4.16 mmol), and pyrimidin-5-ylboronic acid (0.181 g, 1.458 mmol) were combined together in DMF:water (9:1 v/v, 5 mL) and reacted according to General Procedure B2. The reaction was cooled, diluted with ethyl acetate (50 mL), and washed with 5% hydrochloric acid (aq, 50 mL). The organic layer was dried over sodium sulfate, filtered, and concentrated. The resulting residue was purified via Biotage (50% hexanes in ethyl acetate). Concentration of the desired fractions afforded the product (0.014 g, 4%), 95.1% pure by HPLC. $^1$H NMR (400 MHz, DMSO-$d_6$) δ 12.23 (s, 1H), 9.41 (s, 2H), 9.22 (s, 1H), 8.67 (s, 1H), 3.74 (d, J=7.2, 2H), 1.91 (m, 1H), 1.66 (m, 5H), 1.18 (m, 3H), 1.09 (m, 2H); MS (ESI) m/z 311.3 [M+1]$^+$; mp >260° C.

5.1.189 Example 189

SYNTHESIS OF 6-(6-FLUOROPYRIDIN-3-YL)-1-((TETRAHYDRO-2H-PYRAN-4-YL)METHYL)-1H-IMIDAZO [4,5-B]PYRAZIN-2(3H)-ONE

A. 6-(6-Fluoropyridin-3-yl)-1-((tetrahydro-2H-pyran-4-yl)methyl)-1H-imidazo[4,5-b]pyrazin-2(3H)-one. 6-Bromo- 1-((tetrahydro-2H-pyran-4-yl)methyl)-1H-imidazo[4,5-b]pyrazin-2(3H)-one (See Example 101.B) (0.324 g, 1.041 mmol), 6-fluoropyridin-3-ylboronic acid (0.204 g, 1.449 mmol), dichloro[1,1'-bis(diphenylphosphino)ferrocene]palladium(II) dichloromethane adduct (0.085 g, 0.104 mmol), and potassium phosphate (0.878 g, 4.14 mmol) were combined together in DMF:water (9:1 v/v, 6 mL) and reacted according to General Procedure B2. The reaction was cooled, diluted with ethyl acetate (60 mL), and washed with 5% hydrochloric acid (aq, 50 mL). The organic layer was dried over sodium sulfate, filtered, and concentrated. The residue triturated with methanol and diethyl ether (5 mL), filtered, and dried to give the title compound (0.26 g, 76%), 91.7% pure by HPLC. $^1$H NMR (400 MHz, DMSO-d$_6$) δ 12.16 (s, 1H), 8.90 (d, J=2.4, 1H), 8.59 (m, 2H), 7.33 (dd, J=8.4, 2.8, 1H), 3.84 (m, 1H), 3.78 (d, J=7.6, 2H), 3.26 (d, J=9.2, 1H), 2.13 (m, 1H), 1.56 (d, J=10.8, 2H), 1.33 (m, 2H); MS (ESI) m/z 330.3 [M+1]$^+$; m.p.: 220-222° C.

5.1.190 Example 190

SYNTHESIS OF 6-(6-AMINOPYRIDIN-3-YL)-1-((TETRAHYDRO-2H-PYRAN-4-YL)METHYL)-1H-IMIDAZO[4,5-B]PYRAZIN-2(3H)-ONE

A. 6-(6-Aminopyridin-3-yl)-1-((tetrahydro-2H-pyran-4-yl)methyl)-1H-imidazo[4,5-b]pyrazin-2(3H)-one. In a Parr bomb, 6-(6-fluoropyridin-3-yl)-1-((tetrahydro-2H-pyran-4-yl)methyl)-1H-imidazo[4,5-b]pyrazin-2(3H)-one (See Example 189.A) (0.108 g, 0.328 mmol) was suspended in 7N ammonia in methanol (10 mL). The bomb was sealed and heated to 160° C. for 24 h. The mixture was concentrated and the residue subjected to semi-preparatory reverse-phase HPLC (5-40% acetonitrile+0.1% TFA in H$_2$O+0.1% TFA, over 30 min). The desired fractions were combined and subjected to ion exchange to liberate the product as a free base (50 mg, 47%), 99.3% pure by HPLC. $^1$H NMR (400 MHz, DMSO-d$_6$) δ 11.85 (br s, 1H), 8.59 (d, J=3.2, 1H), 8.33 (s, 1H), 8.00 (dd, J=12.0, 3.2, 1H), 6.54 (d, J=11.6, 1H), 6.23 (s, 2H), 3.84 (dd, J=12.4, 3.2, 2H), 3.76 (d, J=9.6, 2H), 2.11 (m, 1H), 1.55 (d, J=14.0, 2H), 1.31 (dq, J=15.6, 5.6, 2H); MS (ESI) m/z 327.1 [M+1]$^+$; m.p. >260° C.

5.1.191 Example 191

SYNTHESIS OF 6-(6-(METHYLAMINO)PYRIDIN-3-YL)-1-((TETRAHYDRO-2H-PYRAN-4-YL)METHYL)-1H-IMIDAZO[4,5-B]PYRAZIN-2(3H)-ONE

A. 6-(6-(Methylamino)pyridin-3-yl)-1-((tetrahydro-2H-pyran-4-yl)methyl)-1H-imidazo[4,5-b]pyrazin-2(3H)-one. In a Parr bomb apparatus 6-(6-fluoropyridin-3-yl)-1-((tetrahydro-2H-pyran-4-yl)methyl)-1H-imidazo[4,5-b]pyrazin-2(3H)-one (See Example 189.A) (0.102 g, 0.310 mmol), methanaminium chloride (0.627 g, 9.29 mmol), and triethylamine (1.254 g, 12.39 mmol) were combined in tetrahydrofuran (10 mL). The bomb was sealed and heated to 160° C. for 3d. The reaction was cooled to rt. The mixture was filtered and the filtrate was concentrated. The residue was purified by preparatory reverse-phase HPLC (0-50% acetonitrile+0.1% TFA in H$_2$O+0.1% TFA, over 30 min), and then by semi-preparatory reverse-phase HPLC (5-45% acetonitrile+0.1% TFA in H$_2$O+0.1% TFA, over 30 min). The desired fractions were subjected to ion exchange to liberate the title compound as the free base (8 mg, 8%), 97.7% pure by HPLC. $^1$H NMR (400 MHz, DMSO-d$_6$) δ 8.67 (d, J=2.8, 1H), 8.33 (s, 1H), 8.00 (dd, J=8.8, 2.8, 1H), 6.79 (dd, J=9.6, 4.8, 1H), 6.54 (dd, J=9.2, 0.8, 1H), 3.83 (d, J=12.0, 2H), 3.75 (d, J=7.2, 2H), 3.25 (t, J=10.8, 2H), 2.82 (d, J=4.8, 3H), 2.13 (m, 1H), 1.55 (d, J=10.8, 2H), 1.31 (dq, J=11.2, 4.4, 2H); MS (ESI) m/z 341.5 [M+1]$^+$; m.p. >260° C.

5.1.192 Example 192

SYNTHESIS OF N-(4-(2-OXO-3-(1-PHENYLETHYL)-2,3-DIHYDRO-1H-IMIDAZO[4,5-B]PYRAZIN-5-YL)PHENYL)METHANESULFONAMIDE

A. N-(4-(2-Oxo-3-(1-phenylethyl)-2,3-dihydro-1H-imidazo[4,5-b]pyrazin-5-yl)phenyl)methanesulfonamide. A solution of 6-bromo-1-(1-phenylethyl)-1H-imidazo[4,5-b]pyrazin-2(3H)-one (See Example 31.B) (0.125 g, 0.393 mmol), 4-(methylsulfonamido)phenyl boronic acid (0.084 g, 0.471 mmol), potassium phosphate (0.333 g, 1.57 mmol) and [1,1'-bis(diphenylphosphino)ferrocene]dichloropalladium(II) methylene chloride complex (0.032 g, 0.0393 mmol) in dimethylformamide (2 mL) and water (0.6 mL) was heated at 100° C. using an orbital hot plate. The reaction mixture was filtered through Celite and solvent was removed under reduced pressure. The crude material was purified by preparative HPLC (20-100% acetonitrile in water) to afford the title compound, 96.3% pure, (40 mg, 25%). $^1$H NMR (400 MHz, DMSO-d$_6$) δ 12.09 (s, 1H), 9.91 (s, 1H), 8.46 (s, 1H), 7.97 (d, J=8.6, 2H), 7.50 (d, J=7.0, 2H), 7.23-7.38 (m, 5H), 5.72 (q, J=7.3, 1H), 3.04 (s, 3H), 2.01 (d, J=7.0, 3H); MS (ESI) m/z 410.1 [M+1]$^+$.

5.1.193 Example 193

SYNTHESIS OF 99-PHENYL-2-(QUINOLIN-5-YL)-7H-PURIN-8(9H)-ONE

A. 2-Bromo-N$^4$-phenylpyrimidine-4,5-diamine. Aniline (0.566 g, 5.97 mmol) was added to 2-amino-3,5-dibromopyrazine (1.0 g, 3.98 mmol) in n-butanol (10 mL) and the resulting mixture was heated at 220° C. for 4500 s in the Emrys Optimizer microwave reactor. The reaction mixture was condensed to a brown oil. Purification using Biotage chromatography (10-60% ethyl acetate in hexanes) provided (0.599 g, 5.62 mmol, 56%) of 2-bromo-N$^4$-phenylpyrimidine-4,5-diamine. MS (ESI) m/z 265 [M]$^+$, 267 [M+2]$^+$.

B. N$^4$-Phenyl-2-(quinolin-5-yl)pyrimidine-4,5-diamine. 2-Bromo-N$^4$-phenylpyrimidine-4,5-diamine (0.599 g, 2.26 mmol), quinoline-5-boronic acid (0.469 g, 2.71 mmol), tetrakis(triphenylphosphine)palladium (0.261 g., 0.183 mmol), potassium carbonate (1.24 g., 9.04 mmol), water (6 mL) and dimethylformamide (25 mL) were reacted according to General Procedure B. The crude material was purified via Biotage silica gel chromatography (0-8% methanol in dichloromethane) to afford the title compound (0.140 g, 19.8% yield). MS (ESI) m/z 314.4[M+1]$^+$.

C. 9-Phenyl-2-(quinolin-5-yl)-7H-purin-8(9H)-one. N$^4$-Phenyl-2-(quinolin-5-yl)pyrimidine-4,5-diamine (0.140 g, 0.447 mmol) and urea (0.66 g, 1.11 mmol) were reacted according to General Procedure D2. The solution was condensed under reduced pressure and purified using preparative HPLC (10-60% acetonitrile in water) afford the title compound (0.41 g, 15% yield). $^1$H NMR (300 MHz, CD$_3$OD) δ 8.89 (m, J=7.8, 1H), 8.44 (d, J=7.8, 1H), 8.20 (s, 1H), 8.13 (d, J=7.8, 1H), 7.87 (t, J=8.4, 1H), 7.77 (d, J=6.9, 2H), 7.55 (d, J=6.3, 1H) 7.45 (m, 5H); MS (ESI) m/z 340.0 [M+1]$^+$.

5.1.194 Example 194

SYNTHESIS OF 6-(4-(5-METHYL-1H-1,2,4-TRIAZOL-3-YL)PHENYL)-1-(2-(2-OXOPYRROLIDIN-1-YL)ETHYL)-1H-IMIDAZO[4,5-B]PYRAZIN-2(3H)-ONE

A. 4-(5-Methyl-4H-1,2,4-triazol-3-yl)phenylboronic acid hydrochloride. 4-Cyano-phenylboronic acid (0.91 g, 6.2 mmol) was dissolved in abs. ethanol (100 mL) and cooled on an ice-bath. Hydrogen chloride gas was bubbled into the reaction for 15 min and allowed to stir for 3 d. The solution was concentrated and then rinsed with methanol. This process was repeated four times to remove all traces of hydrogen chloride to give a white solid. The solid was added with 2-propanol (10 mL), triethylamine (0.5 mL), and acetohydrazide (0.69 g, 9.3 mmol). The mixture was heated in a Biotage Emrys Optimizer microwave reactor to 100° C. for 10 min. The reaction was concentrated under reduced pressure, and then purified on silica gel column (0-100% ethyl acetate in hexanes, followed by 0-40% methanol in ethyl acetate) to give a clear oil. The oil was treated with 4N hydrogen chloride in dioxane. The solution was concentrated in vacuo to give the title compound. The salt was triturated with 10% methanol in diethyl ether to give a white solid (0.8 g, 54% yield). MS (ESI) m/z 204.1 [M+1]$^+$.

B. 6-(4-(5-Methyl-1H-1,2,4-triazol-3-yl)phenyl)-1-(2-(2-oxopyrrolidin-1-yl)ethyl)-1H-imidazo[4,5-b]pyrazin-2(3H)-one. 6-Bromo-1-(2-(2-oxopyrrolidin-1-yl)ethyl)-1H-imidazo[4,5-b]pyrazin-2(3H)-one (See Example 162.A) (203 mg, 0.62 mmol), 4-(5-methyl-4H-1,2,4-triazol-3-yl)phenylboronic acid hydrochloride (152 mg, 0.75 mmol), dichloro[1,1'-bis(diphenylphosphino)ferrocene]palladium(II) dichloromethane adduct (25 mg, 0.03 mmol), 1M sodium carbonate (1.9 mL, 1.9 mmol), and dioxane (3 mL) were heated in a Biotage Emrys Optimizer microwave reactor at 150° C. for 1 h. The reaction was purified by reverse-phase semi-preparatory HPLC (10-70% acetonitrile+0.1% TFA in H$_2$O+0.1% TFA, over 30 min). The product fractions were a Phenomenex Strata-X-C solid phase extraction column to remove TFA and then released from the column with 2M ammonia in methanol. The solution was concentrated and then triturated with ether to give a white solid (16 mg, 6% yield). $^1$H NMR (400 MHz, DMSO-d$_6$) δ 8.56 (s, 1H), 8.16 (m, 2H), 8.08 (m, 2H), 4.05 (m, 2H), 3.57 (m, 2H), 3.51 (t, J=6.8, 2H), 2.41 (br. s., 3H), 1.86 (m, 2H), 1.75 (t, J=7.4, 2H); MS (ESI) m/z 391.5 [M+1]$^+$; mp 315-316° C.

5.1.195 Example 195

SYNTHESIS OF 6-(3-METHYL-4-(1H-1,2,4-TRIAZOL-3-YL)PHENYL)-1-(TETRAHYDRO-2H-PYRAN-4-YL)METHYL)-1H-IMIDAZO[4,5-B]PYRAZIN-2(3H)-ONE

A. 4-Bromo-2-methylbenzamide. A solution of 4-bromo-2-methylbenzonitrile (1.0 g, 5.1 mmol), trifluoroacetic acid (4.0 mL) and sulfuric acid (1.0 mL) were combined and heated to 65° C. for 18 h. The reaction was poured into ice water and the product precipitated and was collected by filtration. The resulting material was dried under vacuum overnight to afford the title compound as a white solid (0.96 g, 88%). MS (ESI) m/z 420.5 [M+1]$^+$.

B. (Z)-4-Bromo-N-((dimethylamino)methylene)-2-methylbenzamide. A solution of 4-bromo-2-methylbenzamide (0.961 g, 4.49 mmol), 1,1-dimethoxy-N,N-dimethylmethanamine (10.0 mL) were combined and heated to 85° C. for 3 h. The reaction was concentrated under reduced pressure and used in the next step without further purification (0.500 g). MS (ESI) m/z 270 [M+1]$^+$.

C. 3-(4-Bromo-2-methylphenyl)-1H-1,2,4-triazole. (Z)-4-Bromo-N-((dimethylamino)methylene)-2-methylbenzamide (0.500 g, 1.86 mmol) was added to acetic acid (20.0 mL) and cooled to 0° C. Hydrazine (2.0 mL, 0.64 mmol) was added dropwise and the reaction was allowed to warm to room temperature with stirring for 2 h. The reaction was concentrated and diluted with water (20 mL). The resulting precipitate was collected by filtration and dried under high vacuum. The product was used in the next step without further purification (0.338 g). MS (ESI) m/z 239 [M+1]$^+$.

D. 3-(4-Bromo-2-Methylphenyl)-1-(tetrahydro-2H-pyran-2-yl)-1H-1,2,4-triazole. 3-(4-Bromo-2-methylphenyl)-1H-1,2,4-triazole (0.338 g, 1.42 mmol) is added to tetrahydrofuran (15.0 mL) followed by the addition of 3,4-dihydro-2H-pyran (0.239 g, 2.84 mmol) and 4-methylbenzenesulfonic acid (0.054 g, 0.28 mmol). The solution was heated to 75° C. for 2 h. The reaction was concentrated under reduced pressure and purified using Biotage column chromatography (0-80% hexanes in ethyl acetate) to provide clean product (0.239 g, 17%). MS (ESI) m/z 322.2 [M+1]$^+$.

E. 3-(2-Methyl-4-(4,4,5,5-Tetramethyl-1,3,2-Dioxaborolan-2-yl)phenyl)-1-(tetrahydro-2H-pyran-2-yl)-1H-1,2,4-triazole. 3-(4-Bromo-2-methylphenyl)-1-(tetrahydro-2H-pyran-2-yl)-1H-1,2,4-triazole (0.239 g, 0.742 mmol), 4,4,4',4',5,5,5',5'-octamethyl-2,2'-bi(1,3,2-dioxaborolane) (0.816 g, 0.816 mmol), [1,1'-bis(diphenylphosphino)ferrocene]dichloropalladium(II) complex with dichloromethane (1:1) (0.054 g, 0.07 mmol), potassium acetate (0.218 g, 2.23 mmol) and dimethylsulfoxide (2.0 mL) were combined in a sealed tube and heated at 90° C. for 2 h. The solution was condensed under reduced pressure and purified using Biotage column chromatography (0-80% hexanes in ethyl acetate) to give semi pure product (0.267 g), which was used directly in the next step. MS (ESI) m/z 370.3 [M+1]$^+$.

F. 6-(3-Methyl-4-(1-(tetrahydro-2H-pyran-2-yl)-1H-1,2,4-triazol-3-yl)phenyl)-1-((tetrahydro-2H-pyran-4-yl)methyl)-1H-imidazo[4,5-B]pyrazin-2(3H)-one. 3-(2-Methyl-4-(4,4,5,5-tetramethyl-1,3,2-dioxaborolan-2-yl)phenyl)-1-(tetrahydro-2H-pyran-2-yl)-1H-1,2,4-triazole (0.267 g, 0.723 mmol), 6-bromo-1-((tetrahydro-2H-pyran-4-yl)methyl)-1H-imidazo[4,5-b]pyrazin-2(3H)-one (See Example 101.B) (0.226 g, 0.722 mmol), [1,1'-bis(diphenylphosphino)ferrocene]dichloropalladium(II) complex with dichloromethane (1:1) (0.059 g, 0.07 mmol), potassium phosphate (0.153 g, 0.722 mmol), dimethylformamide (5.0 mL) and water (2.0 mL) were combined in a sealed tube and heated at 90° C. for 2 h. The solution was condensed under reduced pressure and purified using reverse-phase semi-preparatory HPLC (20-70% acetonitrile+0.1% TFA in H$_2$O+0.1% TFA, over 30 min) to give semi pure product (0.134 g), which was used directly in the next step. MS (ESI) m/z 476.5 [M+1]$^+$.

G. 6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one. 6-(3-Methyl-4-(1-(tetrahydro-2H-pyran-2-yl)-1H-1,2,4-triazol-3-yl)phenyl)-1-((tetrahydro-2H-pyran-4-yl)methyl)-1H-imidazo[4,5-B]pyrazin-2(3H)-one (0.134 g, 0.281 mmol) is added to 6.0 M hydrogen chloride in dioxane (4.0 mL) and stirred at 25° C. for 2 h. The solution was condensed under reduced pressure and purified using reverse-phase semi-preparatory HPLC (20-70% acetonitrile+0.1% TFA in H$_2$O+0.1% TFA, over 30 min). Clean fractions were combined, neutralized with ammonium hydroxide, concentrated, diluted with water (20.0 mL) and the desired product collected by filtration to afford the title compound as an off white solid, 99.9% pure, (0.040 g, 36%). $^1$H NMR (400 MHz, CD$_3$OD) δ 8.47 (s, 1H), 8.40 (s, 1H), 7.99 (s, 1H), 7.92-7.97 (m, 1H), 7.77 (d, J=8.20, 1H), 4.61 (br. s., 2H), 3.88-4.03 (m, 4H), 3.40 (td, J=11.62, 2.15, 2H), 2.60 (s, 3H), 2.19-2.36 (m, 1H), 1.66 (dd, J=12.49, 1.95, 2H), 1.39-1.55 (m, 2H); MS (ESI) m/z 408.5 [M+1]$^+$; mp 271-274° C.

5.1.196 Example 196

SYNTHESIS OF 6-(4-(1H-IMIDAZOL-2-YL)PHENYL)-1-(2-(TETRAHYDRO-2H-PYRAN-4-YL)ETHYL)-1H-IMIDAZO[4,5-B]PYRAZIN-2(3H)-ONE

A. 6-(4-(1H-imidazol-2-yl)phenyl)-1-(2-(tetrahydro-2H-pyran-4-yl)ethyl)-1H-imidazo[4,5-b]pyrazin-2(3H)-one. Ethyl 4-(2-oxo-3-(2-(tetrahydro-2H-pyran-4-yl)ethyl)-2,3-dihydro-1H-imidazo[4,5-b]pyrazin-5-yl)benzimidate (See Example 195.B) (0.300 g, 0.76 mmol), 2,2-diethoxyethanamine (100 mg, 0.76 mmol) and glacial acetic acid (0.114 mL, 1.9 mmol) were mixed well in a sealed tube and the resulting reaction mixture was stirred at 120° C. for 16 h. The resulting material was dissolved in methanol (10 mL) and the black insoluble residue was filtered. The filtrate was purified using reverse-phase semi-preparatory HPLC (15-40% acetonitrile+0.1% TFA in H$_2$O+0.1% TFA, over 30 min). Fractions containing clean product were passed through a Phenomenex Strata-X-C ion exchange column to remove TFA. The column was washed successively with water, methanol, and then 5% ammonium hydroxide in methanol. The product came off with the 5% ammonium hydroxide in methanol eluent and was concentrated on a rotary evaporator. The residue was triturated with ethyl ether in hexane to make a fine powder and dried under vacuum at 50° C. to give the desired product (0.093 g, 30%) as a white solid. $^1$H NMR (400 MHz, DMSO-d$_6$) δ 12.61 (br. s., 1H), 8.57 (s, 1H), 8.07-8.18 (m, 2H), 7.94-8.08 (m, 2H), 7.29 (br. s., 1H), 7.07 (br. s., 1H), 3.95 (t, J=6.64, 2H), 3.83 (dd, J=11.13, 3.32, 2H), 3.22 (t, J=10.93, 3H), 1.63-1.84 (m, 4H), 1.41-1.62 (m, 1H), 1.09-1.35 (m, 2H); MS (ESI) m/z 391.2 [M+1]$^+$; mp 293-295° C.

5.1.197 Example 197

SYNTHESIS OF 6-(4-(5-(AMINOMETHYL)-1H-1,2,4-TRIAZOL-3-YL)PHENYL)-1-(2-(TETRAHYDRO-2H-PYRAN-4-YL)ETHYL)-1H-IMIDAZO[4,5-B]PYRAZIN-2(3H)-ONE

A. 6-(4-(5-(Hydroxymethyl)-1H-1,2,4-triazol-3-yl)phenyl)-1-(2-(tetrahydro-2H-pyran-4-yl)ethyl)-1H-imidazo[4,5-b]pyrazin-2(3H)-one. Ethyl 4-(2-oxo-3-(2-(tetrahydro-2H-pyran-4-yl)ethyl)-2,3-dihydro-1H-imidazo[4,5-b]pyrazin-5-yl)benzimidate (See Example 195. B) (0.250 g, 0.63 mmol) in ethanol (20 mL) was treated with 2-hydroxyacetohydrazide (0.17 g, 1.9 mmol) and triethylamine (0.26 mL, 1.9 mmol), and the resulting reaction mixture was stirred in a sealed tube at 110° C. for 16 h. The cooled reaction solvent removed under reduced pressure. The resulting material was purified using reverse-phase semi-preparatory HPLC (15-50% acetonitrile+0.1% TFA in H$_2$O+0.1% TFA, over 30 min). Fractions containing clean product were passed through a Phenomenex Strata-X-C ion exchange column to remove TFA. The column was washed successively with water, methanol, and then 5% ammonium hydroxide in methanol. The product came off with the 5% ammonium hydroxide in methanol eluent and was concentrated on a rotary evaporator. The residue was triturated with ethyl ether in hexane to make a fine powder and dried under vacuum at 50° C. to give the desired product (0.130 g, 49%) as a white solid. MS (ESI) m/z 422.3 [M+1]$^+$ B. 6-(4-(5-(Chloromethyl)-1H-1,2,4-triazol-3-yl)phenyl)-1-(2-(tetrahydro-2H-pyran-4-yl)ethyl)-1H-imidazo[4,5-b]pyrazin-2(3H)-one. 6-(4-(5-(Hydroxymethyl)-1H-1,2,4-triazol-3-yl)phenyl)-1-(2-(tetrahydro-2H-pyran-4-yl)ethyl)-1H-imidazo[4,5-b]pyrazin-2(3H)-one (0.130 g, 0.31 mmol) in thionyl chloride (2 mL) was stirred in a sealed tube at 80° C. for 1 h. The cooled reaction solvent was removed under reduced pressure. The resulting material was dried under vacuum at 50° C. to give the desired product (0.110 g, 81%) as a white solid. MS (ESI) m/z 440.0 [M+1]$^+$.

C. 6-(4-(5-(Aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one. 6-(4-(5-(Chloromethyl)-1H-1,2,4-triazol-3-yl)phenyl)-1-(2-(tetrahydro-2H-pyran-4-yl)ethyl)-1H-imidazo[4,5-b]pyrazin-2(3H)-one (0.110 g, 0.250 mmol) in ethanol (20 mL) was treated with ammonium hydroxide (10 mL, 250 mmol), and the resulting reaction mixture was stirred in a sealed tube at 25° C. for 16 h. The reaction solvent was removed under reduced pressure. The resulting material was purified using reverse-phase semi-preparatory HPLC (15-50% acetonitrile+0.1% TFA in H$_2$O+0.1% TFA, over 30 min). Fractions containing clean product were passed through a Phenomenex Strata-X-C ion exchange column to remove TFA. The column was washed successively with water, methanol, and then 5% ammonium hydroxide in methanol. The product came off with the 5% ammonium hydroxide in methanol eluent and was concentrated on a rotary evaporator. The residue was triturated with ethyl ether in hexane to make a fine powder and dried under vacuum at 50° C. to give the desired product (0.074 g, 70.4%) as a white solid. $^1$H NMR (400 MHz, DMSO-d$_6$) δ 8.56 (s, 1H), 7.93-8.25 (m, 4H), 3.87-4.04 (m, 4H), 3.83 (dd, J=11.32, 2.73, 2H), 3.22 (t, J=10.74, 2H), 1.63-1.81 (m, 4H), 1.52 (ddd, 1H), 1.04-1.34 (m, 2H); MS (ESI) m/z 421.2 [M+1]$^+$; mp 258-260° C.

5.1.198 Example 198

SYNTHESIS OF 6-(1H-BENZO[D]IMIDAZOL-5-YL)-1-(2-(TETRAHYDRO-2H-PYRAN-4-YL)ETHYL)-1H-IMIDAZO[4,5-B]PYRAZIN-2(3H)-ONE

A. 6-(1H-benzo[d]imidazol-5-yl)-1-(2-(tetrahydro-2H-pyran-4-yl)ethyl)-1H-imidazo[4,5-b]pyrazin-2(3H)-one. 5-Bromo-1H-benzo[d]imidazole (0.100 g, 0.487 mmol), 1-(2-(tetrahydro-2H-pyran-4-yl)ethyl)-6-(trimethylstannyl)-1H-imidazo[4,5-b]pyrazin-2(3H)-one (See Example 182.D) (0.200 g, 0.487 mmol), tris(dibenzylidineacetone)dipalladium(0) (0.045 g, 0.049 mmol), tri-o-tolylphosphine (30 mg, 0.100 mmol), triethylamine (0.200 mL, 1.5 mmol), and N,N-dimethylformamide (6 mL) were combined in a scintillation vial with a stirbar. The atmosphere in the vial was removed and replaced three times with nitrogen. The resulting mixture was stirred vigorously and heated at 100° C. under nitrogen for 3 h and then cooled to room temperature. The resulting mixture was diluted with methanol, filtered, and purified using reverse-phase preparatory HPLC (20-60% acetonitrile+0.1% TFA in H$_2$O+0.1% TFA, over 30 min). Fractions containing the desired product were passed through a Phenomenex Strata-X-C ion exchange column to remove TFA. The column was washed successively with water, methanol, and then 5% ammonium hydroxide in methanol. The product came off with the 5% ammonium hydroxide in methanol eluent and was concentrated on a rotary evaporator. The residue was triturated with ethyl acetate in hexane to make a fine powder and the solids dried under vacuum at 45° C. to give the desired product (20 mg, 15%) as a white solid. $^1$H NMR (400 MHz, DMSO-d$_6$) δ 8.53 (s, 1H), 8.53 (s, 1H), 8.28 (s, 1H), 8.17 (br. s., 1H), 7.88 (br. s., 1H), 7.70 (br. s., 1H), 3.96 (t, J=6.83, 2H), 3.84 (dd, J=11.32, 2.73, 2H), 3.12-3.28 (m, 3H), 1.74 (q, J=7.16, 4H), 1.52 (m, 1H), 1.09-1.35 (m, 3H); MS (ESI) m/z 365.1 [M+1]$^+$.]$^+$; mp 264-265° C.

5.1.199 Example 199

SYNTHESIS OF 6-(2-AMINOPYRIMIDIN-5-YL)-1-(CYCLOHEXYLMETHYL)-1H-IMIDAZO[4,5-B]PYRAZIN-2(3H)-ONE

A. 6-(2-Aminopyrimidin-5-yl)-1-(cyclohexylmethyl)-1H-imidazo[4,5-b]pyrazin-2(3H)-one. 1-(Cyclohexylmethyl)-6-(2-(methylsulfonyl)pyrimidin-5-yl)-1H-imidazo[4,5-b]pyrazin-2(3H)-one (See Example 170.B) (0.5 g, 1.29 mmol) was dissolved in tetrahydrofuran (3 mL). The solution was cooled in an ice bath and then purged with ammonia (g) for 1 min. The mixture was stirred at 70° C. for 3 h. The reaction was concentrated and the residue purified by preparatory HPLC (20-70% acetonitrile+0.1% TFA in H$_2$O+0.1% TFA, over 30 min). Fractions containing the desired product were passed through a Phenomenex Strata-X-C ion exchange column to remove TFA. The column was washed successively with water, methanol, and then 7N ammonia in methanol (10 mL). The product eluted with the ammonia in methanol. Concentration of the eluant afforded the product (30 mg, 7%, 94.6% pure by HPLC). $^1$H NMR (400 MHz, DMSO-d$_6$) δ 11.96 (br s, 1H), 8.85 (s, 2H), 8.38 (s, 1H), 6.95 (s, 2H), 3.71 (d, J=6.8, 2H), 1.89 (m, 1H), 1.63 (m, 5H), 1.17 (m, 3H), 1.02 (m, 2H); MS (ESI) m/z 326.1 [M+1]$^+$; mp >250° C.

5.1.200 Example 200

SYNTHESIS OF 6-(4-HYDROXYPHENYL)-1-((1-METHYLPIPERIDIN-2-YL)METHYL)-1H-IMIDAZO[4,5-B]PYRAZIN-2(3H)-ONE

A. 6-Bromo-N-((1-methylpiperidin-2-yl)methyl)pyrazine-2,3-diamine. In a sealed flask, (1-methylpiperidin-2-yl)methanamine (1 g, 7.80 mmol), 3,5-dibromopyrazin-2-amine (1.578 g, 6.24 mmol) and diisopropylethylamine (1.635 ml, 9.36 mmol) were mixed in n-butanol (30 mL), and the resulting reaction mixture was heated overnight at 115° C. Upon cooling, the volatiles were removed under reduced pressure. The crude product was purified by Biotage column chromatography (0-65% ethyl acetate in hexanes) to provide the title compound (0.485 g, 1.616 mmol, 25.9% yield). MS (ESI) m/z 301.1 [M+1]$^+$.

B. 6-Bromo-1-((1-methylpiperidin-2-yl)methyl)-1H-imidazo[4,5-b]pyrazin-2(3H)-one. A solution of 6-bromo-N$^2$-((1-methylpiperidin-2-yl)methyl)pyrazine-2,3-diamine (0.48 g, 1.599 mmol) and 1,1'-carbonyldiimidazole (0.324 g, 1.999 mmol) in anhydrous tetrahydrofuran (15 mL) was heated overnight at 115° C. The volatiles were removed under reduced pressure, and the crude product was purified by Biotage column chromatography (0-15% methanol in dichloromethane) to provide the title compound (0.48 g, 1.472 mmol, 92% yield). MS (ESI) m/z 327.2 [M+1]$^+$.

C. 6-(4-Hydroxyphenyl)-1-((1-methylpiperidin-2-yl)methyl)-1H-imidazo[4,5-b]pyrazin-2(3H)-one hydrochloride. 6-Bromo-1-((1-methylpiperidin-2-yl)methyl)-1H-imidazo[4,5-b]pyrazin-2(3H)-one (0.25 g, 0.766 mmol), and dichloro [1,1'-bis(diphenylphosphino)ferrocene]palladium (II) dichloromethane (0.063 g, 0.077 mmol) were combined in DMF (30.0 mL). Potassium phosphate (0.65 g, 3.07 mmol) in water (8.0 mL) was added and the reaction stirred at 100° C. for 2 h. The cooled reaction solution was filtered through Celite and the filter cake was washed with ethyl acetate. Filtrate and ethyl acetate wash were combined and solvent removed under reduced pressure. The resulting material was purified using reverse-phase semi-preparatory HPLC (10-80% acetonitrile+0.1% TFA in H$_2$O+0.1% TFA, over 30 min). The desired fractions were concentrated, treated with 4N hydrochloric acid in diethyl ether (few drops), and sonicated. This procedure was repeated twice more to provide the desired product (0.045 g, 0.133 mmol, 17.30% yield) as the hydrochloride salt. $^1$H NMR (400 MHz, DMSO-d$_6$) δ 12.13 (s, 1H), 9.76 (s, 1H), 8.52 (s, 1H), 8.42 (s, 1H), 7.87 (d, J=8.4, 2H), 6.87 (d, J=8.4, 2H), 4.23 (dd, J=8.4 and 5.6, 2H), 4.15-4.12 (m, 1H), 2.07 (m, 1H), 1.84 (m, 1H), 1.76-1.73 (m, 2H), 1.64-1.57 (m, 2H), 1.28 (m, 3H), 0.89-0.85 (m, 2H); MS (ESI) m/z 340.1[M+1]$^+$.

5.1.201 Example 201

SYNTHESIS OF 6-(2-METHYL-4-(1H-1,2,4-TRIAZOL-3-YL)PHENYL)-1-(2-(TETRAHYDRO-2H-PYRAN-4-YL)ETHYL)-1H-IMIDAZO[4,5-B]PYRAZIN-2(3H)-ONE

A. 4-Bromo-3-methylbenzamide. A solution of 4-bromo-3-methylbenzonitrile (2.0 g, 5.1 mmol), trifluoroacetic acid (4.0 mL) and sulfuric acid (1.0 mL) were combined and heated to 65° C. for 18 h. The reaction was poured into ice water and the product precipitated and was filtered. The resulting material was dried under vacuum overnight to afford the title compound as a white solid (2.12 g, 97%). MS (ESI) m/z 215.1 [M+1]$^+$.

B. (Z)-4-Bromo-N-((dimethylamino)methylene)-3-methylbenzamide. A solution of 4-bromo-3-methylbenzamide (2.12 g, 9.88 mmol) and 1,1-dimethoxy-N,N-dimethylmethanamine (10.0 mL) was heated to 85° C. for 3 h. The reaction was concentrated under reduced pressure and used in the next step without further purification (1.93 g). MS (ESI) m/z 270 [M+1]$^+$.

C. 3-(4-Bromo-3-methylphenyl)-1H-1,2,4-triazole. (Z)-4-Bromo-N-((dimethylamino) methylene)-3-methylbenzamide (1.93 g, 7.17 mmol) was added to acetic acid (20.0 mL) and cooled to 0° C. Hydrazine (6.0 mL, 201 mmol) was added dropwise and the reaction was allowed to warm to room temperature with stirring for 2 h. Reaction was concentrated and diluted with water (20 mL). Product precipitated and was filtered and dried under high vacuum and used in the next step without further purification (1.88 g). MS (ESI) m/z 239 [M+1]$^+$.

D. 3-(4-Bromo-3-Methylphenyl)-1-(tetrahydro-2H-pyran-2-yl)-1H-1,2,4-triazole. 3-(4-Bromo-3-methylphenyl)-1H-1,2,4-triazole (1.88 g, 7.90 mmol) was added to tetrahydrofuran (15.0 mL) followed by the addition of 3,4-dihydro-2H-pyran (1.33 g, 15.8 mmol) and 4-methylbenzenesulfonic acid (0.300 g, 1.60 mmol). The reaction was heated to 75° C. for 2 h. The reaction was concentrated under reduced pressure and purified using Biotage column chromatography (0-80% hexanes in ethyl acetate) provided clean product (0.377 g, 15%). MS (ESI) m/z 322.2 [M+1]$^+$.

E. 3-(3-Methyl-4-(4,4,5,5-Tetramethyl-1,3,2-Dioxaborolan-2-yl)phenyl)-1-(tetrahydro-2H-pyran-2-yl)-1H-1,2,4-triazole. 3-(4-Bromo-3-methylphenyl)-1-(tetrahydro-2H-pyran-2-yl)-1H-1,2,4-triazole (0.377 g, 1.17 mmol), 4,4,4',4',5, 5,5',5'-octamethyl-2,2'-bi(1,3,2-dioxaborolane) (0.327 g, 1.29 mmol), [1,1'-Bis(diphenylphosphino)ferrocene]dichloropalladium(II) complex with dichloromethane (1:1) (0.086 g, 0.12 mmol), potassium acetate (0.345 g, 3.51 mmol) and dimethylsulfoxide (2.0 mL) were combined in a sealed tube and heated at 90° C. for 2 h. The solution was condensed under reduced pressure and purified using Biotage column chromatography (0-80% hexanes in ethyl acetate) to give semi pure product (0.232 g), which was used in the next step without further purification. MS (ESI) m/z 370.3 [M+1]$^+$.

F. 6-(3-Methyl-4-(1-(tetrahydro-2H-pyran-2-yl)-1H-1,2, 4-triazol-3-yl)phenyl)-1-((tetrahydro-2H-pyran-4-yl)methyl)-1H-imidazo[4,5-B]pyrazin-2(3H)-one. 3-(3-Methyl-4-(4,4,5,5-tetramethyl-1,3,2-dioxaborolan-2-yl)phenyl)-1-(tetrahydro-2H-pyran-2-yl)-1H-1,2,4-triazole (0.232 g, 0.628 mmol), 6-bromo-1-(2-(tetrahydro-2H-pyran-4-yl) ethyl)-1H-imidazo[4,5-b]pyrazin-2(3H)-one (See Example 108.B) (0.171 g, 0.523 mmol), [1,1'-bis(diphenyl-phosphino) ferrocene]dichloropalladium(II) complex with dichloromethane (1:1) (0.043 g, 0.05 mmol), potassium phosphate (0.444 g, 2.09 mmol), dimethylformamide (5.0 mL) and water (2.0 mL) were combined in a sealed tube and heated at 90° C. for 2 h. The solution was condensed under reduced pressure and purified using reverse-phase semi-preparatory HPLC (20-70% acetonitrile+0.1% TFA in H$_2$O+0.1% TFA, over 30 min) to give semi pure product (0.283 g), which was used in the next step without further purification. MS (ESI) m/z 476.5 [M+1]$^+$.

G. 6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one. 6-(3-Methyl-4-(1-(tetrahydro-2H-pyran-2-yl)-1H-1,2,4-triazol-3-yl)phenyl)-1-((tetrahydro-2H-pyran-4-yl)ethyl)-1H-imidazo[4,5-B]pyrazin-2(3H)-one (0.283 g, 0.578 mmol) was added to 6.0 M hydrogen chloride in dioxane (4.0 mL) and stirred at 25° C. for 2 h. The solution was condensed under reduced pressure and purified using reverse-phase semi-preparatory HPLC (20-70% acetonitrile+0.1% TFA in H$_2$O+0.1% TFA, over 30 min). Clean fractions were combined, neutralized with ammonium hydroxide, concentrated, diluted with water (20 mL). The desired product was collected by filtration to afford the title compound as an off white solid, 99.5% pure, (0.061 g, 26%). $^1$H NMR (400 MHz, CD$_3$OD-d$_4$) δ 8.40 (br. s., 1H), 8.07 (s, 1H), 8.00 (s, 1H), 7.94 (d, J=8.20, 1H), 7.55 (d, J=8.20, 1H), 4.04 (t, J=7.22, 2H), 3.90 (dd, J=11.32, 3.51, 2H), 3.34-3.42 (m, 3H), 2.49 (s, 3H), 1.70-1.87 (m, 4H), 1.58 (dddd, J=10.93, 7.32, 4.10, 3.81, 1H), 1.50-1.66 (m, 1H), 1.22-1.40 (m, 2H); MS (ESI) m/z 408.5 [M+1]$^+$; mp 258-260° C.

5.1.202 Example 202

SYNTHESIS OF 1-(CYCLOHEXYLMETHYL)-6-(6-(2-HYDROXYPROPAN-2-YL)PYRIDIN-3-YL)-1H-IMIDAZO[4,5-B]PYRAZIN-2(3H)-ONE

A. 2-(5-Bromopyridin-2-yl)propan-2-ol. 2,5-Dibromopyridine (1.04 g, 4.39 mmol) was dissolved in toluene (22 ml) in a 100 mL round-bottomed flask. The mixture was cooled to −78° C. n-Butyllithium (3.02 ml, 4.83 mmol) was added dropwise. The mixture was stirred 30 min, followed by the addition of acetone (2 mL). The mixture was stirred 40 min and then let warm to rt. The mixture was washed with 5% ammonium chloride (aq, 50 mL), water (50 mL), and then brine (50 mL). The organic was dried over sodium sulfate, filtered, and concentrated. The residue was purified by Biotage (5:1 hexanes:ethyl acetate). Concentration of the desired fractions afforded the product (0.82 g, 86%). $^1$H NMR (300 MHz, CDCl$_3$) δ 8.57 (dd, J=5.4, 0.6, 1H), 7.81 (dd, J=8.4, 2.4, 1H), 7.30 (dd, J=8.4, 0.6, 1H), 4.43 (s, 1H), 1.54 (s, 6H).

B. 2-(5-(Trimethylstannyl)pyridin-2-yl)propan-2-ol. 2-(5-Bromopyridin-2-yl)propan-2-ol (0.34 g, 1.574 mmol), 1,1,1,2,2,2-hexamethyldistannane (0.361 ml, 1.652 mmol), and tetrakis(triphenylphosphine)palladium(0) (0.182 g, 0.157 mmol) were combined in toluene (5 mL) in a 50 mL resealable flask. The reaction was stirred at 115° C. for 1.5 h. The mixture was then concentrated to about a 2 mL volume. The residue was purified via Biotage (5:1 hexanes:ethyl acetate). Concentration of the desired fractions afforded the title compound (0.33 g, 70%). $^1$H NMR (300 MHz, CDCl$_3$) δ 8.57 (dd, J=5.4, 0.6, 1H), 7.81 (dd, J=8.4, 2.4, 1H), 7.30 (dd, J=8.4, 0.6, 1H), 5.18 (br s, 1H), 1.54 (s, 6H), 0.35 (s, 9H).

C. 1-(Cyclohexylmethyl)-6-(6-(2-hydroxypropan-2-yl) pyridin-3-yl)-1H-imidazo[4,5-b]pyrazin-2(3H)-one. In a 20 mL microwave flask was added 6-bromo-1-(cyclohexylmethyl)-1H-imidazo[4,5-b]pyrazin-2(3H)-one (See Example 55.B) (0.17 g, 0.546 mmol), 2-(5-(trimethylstannyl)pyridin-2-yl)propan-2-ol (0.164 g, 0.546 mmol), and [1,1'-bis(diphenyl-phosphino)ferrocene]dichloropalladium(II) complex with dichloromethane (1:1) (0.089 g, 0.109 mmol) in DMF (3 mL). The mixture was then purged with nitrogen (g) for 1 min and then stirred in a microwave reactor at 140° C. for 15 min. The mixture was concentrated and the residue was subjected to semi-preparatory HPLC (10-70% acetonitrile+0.1% TFA in H$_2$O+0.1% TFA, over 30 min). Fractions containing the desired product were passed through a Phenomenex Strata-X-C ion exchange column to remove TFA. The column was washed successively with water, methanol, and then 7N ammonia in methanol (10 mL). The product eluted with the ammonia in methanol. Concentration of the eluant afforded the product (11 mg, 5%, 96.9% pure by HPLC). $^1$H NMR (400 MHz, DMSO-d$_6$) δ 9.10 (dd, J=2.4, 0.8, 1H), 8.52 (s, 1H), 8.32 (dd, J=7.6, 2.4, 1H), 7.75 (dd, J=8.0, 0.4, 1H), 5.29 (s, 1H), 3.73 (d, J=7.2, 2H), 1.91 (m, 1H), 1.64 (m, 5H), 1.47 (s, 6H), 1.16 (m, 3H), 1.02 (m, 2H); MS (ESI) m/z 368.4 [M+1]$^+$; mp >250° C.

5.1.203 Example 203

SYNTHESIS OF 6-(6-(2-HYDROXYPROPAN-2-YL)PYRIDIN-3-YL)-1-((TETRAHYDRO-2H-PYRAN-4-YL)METHYL)-1H-IMIDAZO[4,5-B] PYRAZIN-2(3H)-ONE

A. 6-(6-(2-Hydroxypropan-2-yl)pyridin-3-yl)-1-((tetrahydro-2H-pyran-4-yl)methyl)-1H-imidazo[4,5-b]pyrazin-2 (3H)-one. In a 20 mL microwave flask was added 6-bromo-1-((tetrahydro-2H-pyran-4-yl)methyl)-1H-imidazo[4,5-b] pyrazin-2(3H)-one (See Example 101.B) (0.33 g, 1.054 mmol), 2-(5-(trimethylstannyl)pyridin-2-yl)propan-2-ol (See Example 202.B) (0.316 g, 1.054 mmol), and [1,1'-bis (diphenyl-phosphino)ferrocene]dichloropalladium(II) complex with dichloromethane (1:1) (0.172 g, 0.211 mmol) in DMF (4 mL). The mixture was stirred in a microwave reactor at 140° C. for 15 min. The mixture was concentrated and the residue was subjected to semipreparatory HPLC (10-70% acetonitrile+0.1% TFA in H$_2$O+0.1% TFA, over 30 min). Fractions containing the desired product were passed through a Phenomenex Strata-X-C ion exchange column to remove TFA. The column was washed successively with water, methanol, and then 7N ammonia in methanol (10 mL). The product eluted with the ammonia in methanol. Concentration of the eluant afforded the product (84 mg, 21%, 99.3% pure by HPLC). $^1$H NMR (400 MHz, CD$_3$OD) δ 9.08 (dd, J=2.4, 0.8, 1H), 8.44 (s, 1H), 8.36 (dd, J=10.8, 2.8, 1H), 7.79 (dd, J=10.4, 1.6, 1H), 3.98 (s, 1H), 3.93 (d, J=9.6, 2H), 3.37 (m, 3H), 2.26 (m, 1H), 1.67 (m, 2H), 1.60 (s, 6H), 1.46 (m, 2H); MS (ESI) m/z 370.1 [M+1]$^+$; mp 207-209° C.

5.1.204 Example 204

SYNTHESIS OF 6-(6-(2-HYDROXYPROPAN-2-YL)PYRIDIN-3-YL)-1-(2-(TETRAHYDRO-2H-PYRAN-4-YL)ETHYL)-1H-IMIDAZO[4,5-B]PYRAZIN-2(3H)-ONE

A. 6-(6-(2-Hydroxypropan-2-yl)pyridin-3-yl)-1-(2-(tetrahydro-2H-pyran-4-yl)ethyl)-1H-imidazo[4,5-b]pyrazin-2(3H)-one. In a 20 mL microwave flask was added 6-bromo-1-(2-(tetrahydro-2H-pyran-4-yl)ethyl)-1H-imidazo[4,5-b]pyrazin-2(3H)-one (See Example 108.B) (0.17 g, 0.520 mmol), 2-(5-(trimethylstannyl)pyridin-2-yl)propan-2-ol (See Example 202.B) (0.156 g, 0.520 mmol), and [1,1'-bis(diphenyl-phosphino)ferrocene]dichloropalladium(II) complex with dichloromethane (1:1) (0.085 g, 0.104 mmol) in DMF (3 mL). The mixture was stirred in a microwave reactor at 140° C. for 15 min. The mixture was concentrated and the residue was subjected to semipreparatory HPLC (10-70% acetonitrile+0.1% TFA in H$_2$O+0.1% TFA, over 30 min). Fractions containing the desired product were passed through a Phenomenex Strata-X-C ion exchange column to remove TFA. The column was washed successively with water, methanol, and then 7N ammonia in methanol (10 mL). The product eluted with the ammonia in methanol. Concentration of the eluant afforded the product (40 mg, 20%, 95.9% pure by HPLC). $^1$H NMR (400 MHz, CD$_3$OD) δ 9.03 (d, J=2.0, 1H), 8.39 (s, 1H), 8.30 (d, J=2.4, 1H), 7.74 (d, J=8.1, 1H), 3.99 (t, J=7.2, 2H), 3.87 (dd, J=11.2, 3.2, 2H), 3.31 (m, 1H), 1.76 (m, 4H), 1.55 (s, 6H), 1.53 (m, 2H), 1.27 (m, 2H); MS (ESI) m/z 384.3 [M+1]$^+$; mp 132-133° C.

5.1.205 Example 205

SYNTHESIS OF 6-(4-(4H-1,2,4-TRIAZOL-3-YL)PHENYL)-1-(2-MORPHOLINO-2-OXOETHYL)-1H-IMIDAZO[4,5-B]PYRAZIN-2(3H)-ONE

A. Ethyl 2-(3-(3,5-dibromopyrazin-2-yl)ureido)acetate. 3,5-Dibromopyrazin-2-amine (5.00 g, 19.8 mmol), 1,1'-carbonyldiimidazole (3.37 g, 20.8 mmol), diisopropylethylamine (10.3 mL, 7.67 mmol), 1,4-dioxane (7.5 mL), and N,N-dimethylformamide (15 mL) were combined in a 100 mL round-bottom flask with a stirbar, stirred, and heated at 50° C. under a reflux condenser under nitrogen for 4.5 h. More 1,1'-carbonyldiimidazole (0.34 g, 2.08 mmol) was added and the reaction heated at 50° C. for an additional 3.5 h. The resulting reaction mixture was cooled to room temperature and glycine ethyl ester hydrochloride (2.90 g, 20.8 mmol) was added. The resulting reaction mixture was stirred at room temperature for 13 h at which time water was added with vigorous stirring to cause precipitation of solids. The solids were collected by vacuum filtration, washed twice with water and twice with hexane, and dried under vacuum at 45° C. to give the desired product (5.17 g, 68%) as a light orange solid which was contaminated with a small amount of ethyl 2-(3-(5-bromo-3-(1H-imidazol-1-yl)pyrazin-2-yl)ureido)acetate. $^1$H NMR (400 MHz, DMSO-d$_6$) δ 8.89 (s, 1H) 8.53 (s, 1H) 8.08 (t, J=5.66, 1H) 4.12 (q, J=7.29, 2H) 3.96 (d, J=5.86, 2H) 1.21 (t, J=7.03, 3H); MS (ESI) m/z 383 [M+1]$^+$.

B. Ethyl 2-(6-bromo-2-oxo-2,3-dihydro-1H-imidazo[4,5-b]pyrazin-1-yl)acetate and isopropyl 2-(6-bromo-2-oxo-2,3-dihydro-1H-imidazo[4,5-b]pyrazin-1-yl)acetate. Ethyl 2-(3-(3,5-dibromopyrazin-2-yl)ureido)acetate (1.00 g, 2.62 mmol), palladium (II) acetate (0.059 g, 0.26 mmol), Xantphos (0.454 g, 0.79 mmol), sodium bicarbonate (0.660 g, 7.85 mmol), and wet isopropanol (15 mL) were combined in a sealable vessel with a stirbar. The mixture was purged with nitrogen for 1 min and then sealed, stirred vigorously, and heated at 120° C. for 26 h. The resulting mixture was cooled to room temperature, diluted with ethyl acetate, and filtered through Celite. The filter cake was washed thoroughly the ethyl acetate and the filtrate concentrated on a rotary evaporator with silica gel. Flash chromatography through a short silica gel column (20-60% ethyl acetate in hexane) provided partial purification. After the eluent was concentrated on a rotary evaporator the resulting residue was purified using reverse-phase preparatory HPLC (20-60% acetonitrile+0.1% TFA in H$_2$O+0.1% TFA, over 30 min and then 60-80% acetonitrile+0.1% TFA in H$_2$O+0.1% TFA, from 30 to 35 min). Vials containing product were combined and all of the solvent removed on a rotary evaporator. The residue was dried under vacuum to give a mixture of the desired products (188 mg, 24%) as a light yellow solid. MS (ESI) m/z 301 and 315 [M+1]$^+$.

C. 2-(6-Bromo-2-oxo-2,3-dihydro-1H-imidazo[4,5-b]pyrazin-1-yl)acetic acid. A mixture of ethyl 2-(6-bromo-2-oxo-2,3-dihydro-1H-imidazo[4,5-b]pyrazin-1-yl)acetate and isopropyl 2-(6-bromo-2-oxo-2,3-dihydro-1H-imidazo[4,5-b]pyrazin-1-yl)acetate (170 mg, 0.565 mmol), lithium hydroxide (41 mg, 1.69 mmol), water (3 mL), and tetrahydrofuran (15 mL) were combined in a round-bottom flask with a stirbar, stirred vigorously, and heated at 65° C. under a reflux condenser under nitrogen for 45 min. All of the solvent was removed on a rotary evaporator. The resulting residue was dissolved in a mixture of methanol (4 mL) and 6 N hydrochloric acid in water (0.38 mL, 2.28 mmol), filtered, and purified using reverse-phase preparatory HPLC (5-50% acetonitrile+0.1% TFA in H$_2$O+0.1% TFA, over 30 min). Vials containing product were combined and all of the solvent removed on a rotary evaporator. The residue was dried under vacuum at 45° C. to give the desired product (140 mg, 91%) as a slightly yellow foam-solid. $^1$H NMR (400 MHz, DMSO-d$_6$) δ 13.40 (br. s., 1H), 12.42 (s, 1H), 8.11 (s, 1H), 4.54 (s, 2H); MS (ESI) m/z 273 [M+1]$^+$.

D. 6-Bromo-1-(2-morpholino-2-oxoethyl)-1H-imidazo[4,5-b]pyrazin-2(3H)-one-2,2,2-trifluoroacetate. 2-(6-Bromo-2-oxo-2,3-dihydro-1H-imidazo[4,5-b]pyrazin-1-yl)acetic acid (141 mg, 0.516 mmol) and 1,1'-carbonyldiimidazole (256 mg, 1.58 mmol) were combined in a round-bottom flask with a stirbar. Methylene chloride (6 mL) was added and the resulting mixture stirred at room temperature under nitrogen. DMF (2 mL) was added. All of the solids dissolved. The resulting clear reaction mixture was stirred at room temperature under nitrogen for 2.5 h at which time morpholine (0.34 mL, 3.90 mmol) was added. The resulting mixture was stirred at room temperature for 1 h. The methylene chloride was removed on a rotary evaporator. The resulting mixture was diluted with methanol, filtered, and purified using reverse-phase preparatory HPLC (5-50% acetonitrile+0.1% TFA in H$_2$O+0.1% TFA, over 30 min). Vials containing product were combined and all of the solvent removed on a rotary evaporator. The residue was dried under vacuum to give the desired product (209 mg, 89%) as a slightly yellow foam-solid. $^1$H NMR (400 MHz, DMSO-d$_6$) δ 12.36 (s, 1H), 8.09 (s, 1H), 4.78 (s, 2H), 3.63-3.69 (m, 2H), 3.55-3.62 (m, 4H), 3.43 (t, J=4.88, 2H); MS (ESI) m/z 342[M+1]$^+$.

E. 6-(4-(4H-1,2,4-Triazol-3-yl)phenyl)-1-(2-morpholino-2-oxoethyl)-1H-imidazo[4,5-b]pyrazin-2(3H)-one.

6-Bromo-1-(2-morpholino-2-oxoethyl)-1H-imidazo[4,5-b]pyrazin-2(3H)-one 2,2,2-trifluoroacetate (205 mg, 0.449 mmol), 4-(1H-1,2,4-triazol-5-yl)phenylboronic acid hydrochloride (See Example 159.D) (152 mg, 0.674 mmol), dichloro[1,1'-bis(diphenylphosphino)ferrocene]palladium (II) dichloromethane (33 mg, 0.045 mmol), 1 M sodium carbonate in water (2.25 mL, 2.25 mmol), 1,4-dioxane (1.5 mL), and isopropanol (0.5 mL) were combined in a sealable tube with a stirbar. The mixture was purged with nitrogen for 1 min to remove air. The resulting mixture was sealed, stirred vigorously, and heated at 120° C. overnight. The resulting mixture was cooled to room temperature, diluted with methanol, and all the solvent removed on a rotary evaporator. Methanol was added to the residue and the resulting mixture filtered. The filtrate was purified using reverse-phase preparatory HPLC (5-60% acetonitrile+0.1% TFA in $H_2O$+0.1% TFA, over 30 min). Vials containing product were combined and almost all the solvent removed on a rotary evaporator. Acetonitrile was added and the resulting mixture loaded on a Strata-XC ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator. The residue was dissolved in 20% methanol in dichloromethane and concentrated on a rotary evaporator with silica gel. Flash chromatography (5-12-15% methanol in dichloromethane) gave the desired product (43 mg, 24%) as a white solid. $R_f$=0.16 (10% methanol in dichloromethane). $^1$H NMR (400 MHz, DMSO-$d_6$) δ 12.21 (br. s., 1H), 8.60 (s, 1H), 8.09-8.17 (m, 4H), 4.86 (s, 2H), 3.63-0.72 (m, 4H), 3.60 (t, J=4.88, 2H), 3.45 (t, J=4.69, 2H); MS (ESI) m/z 407 [M+1]$^+$.

5.1.206 Example 206

SYNTHESIS OF (R)-6-(4-(4H-1,2,4-TRIAZOL-3-YL)PHENYL)-3-(CYCLOHEXYLMETHYL)-3,4-DIHYDROPYRAZINO[2,3-B]PYRAZIN-2(1H)-ONE

A. (R)-tert-Butyl 3-cyclohexyl-1-(3,5-dibromopyrazin-2-ylamino)-1-oxopropan-2-ylcarbamate. (R)-2-(tert-Butoxycarbonylamino)-3-cyclohexylpropanoic acid (1.00 g, 3.69 mmol), 1,1'-carbonyldiimidazole (896 mg, 5.53 mmol), dichloromethane (3 mL), and DMF (1 mL) were combined in a scintillation vial and stirred 3.75 h at room temperature under nitrogen. 3,5-Dibromopyrazin-2-amine (1.86 g, 7.37 mmol) was added and the resulting mixture sealed and heated 21 h at 40° C., then 22.5 h at 50° C. Diisopropylethylamine (1.3 mL, 7.37 mmol) was added and the resulting mixture sealed and heated at 45° C. with stirring overnight. The dichloromethane was removed on a rotary evaporator. The resulting mixture was diluted with ethyl acetate and water and shaken in a separatory funnel. The resulting suspension was filtered through Celite and the filter cake washed thoroughly with ethyl acetate. Brine was added to the filtrate and the resulting two layers separated in a separatory funnel. The organics were washed with water, then brine, and concentrated on a rotary evaporator. The residue was dissolved in methanol, filtered, and purified using reverse-phase preparatory HPLC (20-100% acetonitrile+0.1% TFA in $H_2O$+0.1% TFA, over 30 min). Vials containing product were combined and neutralized with saturated aqueous sodium bicarbonate. Acetonitrile was removed on a rotary evaporator and the resulting aqueous mixture extracted with ethyl acetate. The organics were washed with brine, dried over magnesium sulfate, filtered, concentrated on a rotary evaporator, and dried under vacuum to give the desired product (616 mg, 33%) as an off-white solid. $^1$H NMR (400 MHz, DMSO-$d_6$) δ 10.54 (s, 1H), 8.77 (s, 1H), 7.14 (d, J=8.20, 1H), 4.26 (q, J=7.81, 1H), 1.77 (d, J=12.49, 1H), 1.58-1.72 (m, 5H), 1.51-1.57 (m, 2H), 1.38 (s, 9H), 1.07-1.25 (m, 3H), 0.80-0.98 (m, 2H); MS (ESI) m/z 507 [M+1]$^+$.

B. (R)-6-Bromo-3-(cyclohexylmethyl)-3,4-dihydropyrazino[2,3-b]pyrazin-2(1H)-one. (R)-tert-Butyl 3-cyclohexyl-1-(3,5-dibromopyrazin-2-ylamino)-1-oxopropan-2-ylcarbamate (726 mg, 1.43 mmol) was dissolved in dichloromethane (20 mL) with stirring under nitrogen. Trifluoroacetic acid (2 mL) was added and the resulting clear yellow solution stirred 50 min at room temperature. More trifluoroacetic acid (1 mL) was added and the resulting mixture stirred another 5.5 h at room temperature. All solvent was removed on a rotary evaporator and the resulting residue dried under vacuum overnight. Sodium bicarbonate (1.21 g, 14.4 mmol), Xantphos (249 mg, 0.43 mmol), palladium (II) acetate (32 mg, 0.143 mmol), and wet isopropanol (21 mL) were added and the resulting mixture sparged with nitrogen for 1 min to remove air. The resulting mixture was stirred vigorously and heated at 80° C. under a reflux condenser under nitrogen for 8 h 20 min and then cooled to room temperature overnight. The resulting mixture was diluted with ethyl acetate and filtered through Celite. The filter cake was washed thoroughly with ethyl acetate and the filtrate concentrated on a rotary evaporator. Methanol was added and the resulting solids collected by vacuum filtration. The solids were washed twice with methanol, twice with ethyl ether, and dried under vacuum to give the desired product (241 mg, 53%) as a yellow-tan solid. $^1$H NMR (400 MHz, DMSO-$d_6$) δ 11.21 (s, 1H), 8.05 (d, J=2.34, 1H), 7.50 (s, 1H), 4.16 (td, J=6.15, 2.15, 1H), 1.73 (d, J=11.32, 1H), 1.50-1.68 (m, 8H), 1.07-1.27 (m, 3H), 0.77-0.94 (m, 1H); MS (ESI) m/z 325 [M+1]$^+$.

C. (R)-di-tert-Butyl 6-bromo-3-(cyclohexylmethyl)-2-oxo-2,3-dihydropyrazino[2,3-b]pyrazine-1,4-dicarboxylate (R)-6-Bromo-3-(cyclohexylmethyl)-3,4-dihydropyrazino[2,3-b]pyrazin-2(1H)-one (167 mg, 0.514 mmol), di-tert-butyl dicarbonate (280 mg, 1.28 mmol), 4-(dimethylamino)pyridine (6 mg, 0.051 mmol), and acetonitrile (4 mL) were combined in a scintillation vial, stirred, and heated at 60° C. under nitrogen for 1 h. The resulting mixture was cooled to room temperature. Water was added with vigorous stirring and the resulting solids were collected by vacuum filtration. The solids were washed with water and dried under vacuum at 45° C. to give the desired product (241 mg, 89%) as a light orange powder. $^1$H NMR (400 MHz, DMSO-$d_6$) δ 8.45 (s, 1H), 4.94 (dd, J=9.18, 6.44, 1H), 1.84 (d, J=12.49, 1H), 1.57-1.70 (m, 4H), 1.53 (s, 9H), 1.49 (s, 9H), 1.34-1.42 (m, 2H), 1.23-1.30 (m, 1H), 1.09-1.18 (m, 3H), 0.82-0.94 (m, 2H); MS (ESI) m/z 525[M+1]$^+$.

D. (R)-6-(4-(4H-1,2,4-Triazol-3-yl)phenyl)-3-(cyclohexylmethyl)-3,4-dihydropyrazino[2,3-b]pyrazin-2(1H)-one (R)-di-tert-Butyl 6-bromo-3-(cyclohexylmethyl)-2-oxo-2,3-dihydropyrazino[2,3-b]pyrazine-1,4-dicarboxylate (237 mg, 0.451 mmol), 4-(1H-1,2,4-triazol-5-yl)phenylboronic acid hydrochloride (See Example J59.D) (153 mg, 0.677 mmol), dichloro[1,1'-bis(diphenylphosphino)ferrocene]palladium (II) dichloromethane (33 mg, 0.045 mmol), 1 M sodium carbonate in water (1.80 mL, 1.80 mmol), 1,4-dioxane (1.5 mL), and isopropanol (0.5 mL) were combined in a sealable tube with a stirbar. The mixture was purged with nitrogen for 1 min to remove air. The resulting mixture was sealed, stirred vigorously, and heated at 120° C. overnight.

The resulting mixture was cooled to room temperature, diluted with methanol, and all the solvent removed on a rotary evaporator. Methanol (5 mL) and 6 N hydrochloric acid in water (0.35 mL, 2.1 mmol) were added to the residue. The resulting mixture was heated briefly with a heat gun and then filtered. The filtrate was purified using reverse-phase preparatory HPLC (20-70% acetonitrile+0.1% TFA in H$_2$O+0.1% TFA, over 30 min). Vials containing product were combined and almost all the solvent removed on a rotary evaporator. Acetonitrile was added and the resulting mixture loaded on a Strata ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and then dried under vacuum at 45° C. to give the desired product (7 mg, 4%) as a yellow solid. $^1$H NMR (400 MHz, DMSO-d$_6$) δ 11.21 (br. s., 1H), 8.46 (br. s., 1H) 8.03-8.14 (m, 5H), 7.68 (d, J=1.56, 1H), 4.14-4.20 (m, 1H), 1.77 (d, J=12.10, 1H), 1.53-1.71 (m, 7H), 1.07-1.30 (m, 3H), 0.79-0.97 (m, 2H); MS (ESI) m/z 390 [M+1]$^+$.

5.1.207 Example 207

SYNTHESIS OF (R)-6-(4-(1H-1,2,4-TRIAZOL-3-YL)PHENYL)-1-(1-PHENYLETHYL)-1H-IMIDAZO[4,5-B]PYRAZIN-2(3H)-ONE

A. ((1R)-1-Phenylethyl)(3-amino-6-bromopyrazin-2-yl)amine. A solution of (R)-α-methylbenzylamine (2.28 mL, 17.93 mmol) and 2-amino-3,5-dibromo-pyrazine (3.00 g, 11.96 mmol) in n-butanol (30 mL) as described in General Procedure A. The crude molecule was purified via silica gel chromatography (20-30% ethyl acetate in hexanes). Clean fraction were combined and condensed, and subsequently triturated from methanol with water while sonicating to afford (1.92 g, 6.54 mmol, 55%) of ((1R)-1-phenylethyl)(3-amino-6-bromopyrazin-2-yl)amine. MS (ESI) m/z 294.0 [M+1]$^+$.

B. 1-((1R)-1-Phenylethyl)-6-bromo-4-imidazolino[4,5-b]pyrazin-2-one. The title compound was prepared using ((1R)-1-phenylethyl)(3-amino-6-bromopyrazin-2-yl)amine (0.50 g, 1.71 mmol, 1.0 eq.), 1,1'-carbonyldiimidazole (0.35 g, 2.13 mmol, 1.25 eq.), and tetrahydrofuran (7 mL) as described in General Procedure D1. The crude material was dissolved in methanol (5 mL), and the product was triturated with water while sonicating. The precipitate was filtered and dried in a vacuum oven overnight to afford 0.27 g (0.83 mmol, 49%) of 1-((1S)-1-phenylethyl)-6-bromo-4-imidazolino[4,5-b]pyrazin-2-one. MS (ESI) m/z 319.3 [M+1]$^+$.

C. (R)-4-(2-Oxo-3-(1-phenylethyl)-2,3-dihydro-1H-imidazo[4,5-b]pyrazin-5-yl)benzonitrile. 1-((1R)-1-Phenylethyl)-6-bromo-4-imidazolino[4,5-b]pyrazin-2-one (0.500 g, 1.57 mmol), 4-cyanophenylboronic acid (0.276 g, 1.88 mmol), [1,1'-bis(diphenylphosphino)ferrocene]dichloropalladium(II) complex with dichloromethane (1:1) (0.128 g, 0.10 mmol), potassium phosphate (1.33 g, 6.27 mmol), dimethylformamide (5.0 mL) and water (2.0 mL) were combined in a sealed tube and heated together at 90° C. for 2 h. The solution was condensed under reduced pressure and purified using reverse-phase semi-preparatory HPLC (20-70% acetonitrile+0.1% TFA in H$_2$O+0.1% TFA, over 30 min) to give pure product (0.462 g, 86%). MS (ESI) m/z 476.5 [M+1]$^+$. D. (R)-Ethyl 4-(2-oxo-3-(1-phenylethyl)-2,3-dihydro-1H-imidazo[4,5-b]pyrazin-5-yl)benzimidate. A solution of (R)-4-(2-oxo-3-(1-phenylethyl)-2,3-dihydro-1H-imidazo[4,5-b]pyrazin-5-yl)benzonitrile (0.462 g, 1.35 mmol) and ethanol (100 mL) was cooled to 0° C. and hydrogen chloride gas was bubbled through the solution for 10 min. The reaction was allowed to stir and warm to 25° C. over 18 h. The reaction was concentrated under reduced pressure and used in the next step without further purification as the hydrochloride salt (0.281 g, 57%). MS (ESI) m/z 388.4 [M+1]$^+$.

E. (R)-6-(4-(1H-1,2,4-Triazol-3-yl)phenyl)-1-(1-phenylethyl)-1H-imidazo[4,5-B]pyrazin-2(3H)-one. (R)-Ethyl 4-(2-oxo-3-(1-phenylethyl)-2,3-dihydro-1H-imidazo[4,5-b]pyrazin-5-yl)benzimidate (0.281 g, 0.725 mmol), formohydrazide (0.174 g, 2.90 mmol), triethylamine (0.734 g, 7.25 mmol) and methanol (4.0 mL) are combined in a sealed tube and heated to 100° C. for 4 h. The solution was condensed under reduced pressure and purified using reverse-phase semi-preparatory HPLC (20-70% acetonitrile+0.1% TFA in H$_2$O+0.1% TFA, over 30 min). Clean fractions were combined, neutralized with ammonium hydroxide, concentrated, diluted with water (20 mL) and the desired product was collected by filtration to afford the title compound as an off white solid, 96.7% pure, (0.039 g, 14%). $^1$H NMR (400 MHz, CD$_3$OD) δ 8.48-8.51 (m, 1H), 8.49 (s, 2H), 8.41 (br. s., 1H), 8.12 (s, 4H), 7.60 (d, J=7.03, 2H), 7.31-7.39 (m, 2H), 7.23-7.30 (m, 1H), 5.85 (q, J=7.29, 1H), 2.12 (d, J=7.42, 3H); MS (ESI) m/z 384.4 [M+1]$^+$; mp 258-260° C.

5.1.208 Example 208

SYNTHESIS OF (S)-6-(4-(4H-1,2,4-TRIAZOL-3-YL)PHENYL)-1-(1-PHENYLETHYL)-1H-IMIDAZO[4,5-B]PYRAZIN-2(3H)-ONE

A. (S)-6-(4-(4H-1,2,4-Triazol-3-yl)phenyl)-1-(1-phenylethyl)-1H-imidazo[4,5-b]pyrazin-2(3H)-one. In a sealed tube, to a solution of 4-(1H-1,2,4-triazol-5-yl)phenylboronic acid hydrochloride (See Example 159.D) (0.239 g, 1.265 mmol), (S)-6-(4-bromophenyl)-1-(1-phenylethyl)-1H-imidazo[4,5-b]pyrazin-2(3H)-one (0.5 g, 1.265 mmol), [1,1'-bis(diphenyl-phosphino)ferrocene]dichloropalladium(II) complex with dichloromethane (1:1) (1.033 g, 1.265 mmol) in DMF (30 mL) was added potassium phosphate (0.281 g, 1.265 mmol) in water (10 mL). The resulting reaction mixture was degassed, and brought to 120° C. for 2 h. The volatiles were removed under reduced pressure, the crude product was filtered through celite, rinsed with methanol. After concentration, the crude product was purified by reverse-phase semi-preparatory HPLC (10-80% acetonitrile+0.1% TFA in H$_2$O+ 0.1% TFA, over 30 min). The desired fractions were pooled, concentrated to a minimum of solvent and neutralized with ammonium hydroxide. The free base obtained was filtered, rinsed with water, and dried in vacuum oven to provide the title compound (0.008 g, 0.021 mmol, 1.649% yield). $^1$H NMR (400 MHz, DMSO-d$_6$) δ 9.24 (s, 1H), 8.53 (s, 1H), 8.22 (d, J=8.8, 2H), 8.10 (d, J=8.8, 2H), 7.58 (d, J=7.6, 2H), 7.32 (d, J=7.6, 2H), 7.26 (d, J=8.8, 1H), 5.84 (q, J=7.2, 1H), 2.10 (d, J=7.2, 2H); MS (ESI) m/z 384.1 [M+1]$^+$.

5.1.209 Example 209

SYNTHESIS OF (1R,4R)-4-(6-(4-(2-HYDROXYPROPAN-2-YL)PHENYL)-2-OXO-2,3-DIHYDRO-1H-IMIDAZO[4,5-B]PYRAZIN-1-YL)CYCLOHEXANECARBOXAMIDE

A. tert-Butyl (1r,4r)-4-carbamoylcyclohexylcarbamate. (1r,4r)-4-(tert-Butoxycarbonyl-amino)cyclohexanecarboxylic acid (1.7 g, 6.99 mmol), ammonium chloride (560 mg, 10.5 mmol), O-(benzotriazol-1-yl)-N,N,N'N'-tetramethyluronium hexafluorophosphate (2.66 g, 6.99 mmol), triethylamine (2.92 ml, 20.96 mmol), and acetonitrile (20 ml) were stirred at room temperature for 1 h. The reaction was filtered and rinsed with fresh acetonitrile. The solid was vacuum dried to give the desired product (1.57 g 93% yield) as a white solid. MS (ESI) m/z 242.9 [M+1]$^+$ B. (1r,4r)-4-(6-Bromo-2-oxo-2,3-dihydro-1H-imidazo[4,5-b]pyrazin-1-yl)cyclohexane carboxamide. tert-Butyl (1r,4r)-4-carbamoylcyclohexylcarbamate (0.5 g, 2.063 mmol) was treated with 4N hydrochloric acid in dioxane for 2 h at room temperature. The reaction was concentrated to give a white solid. The solid was added with 3,5-dibromopyrazin-2-amine (0.522 g, 2.063 mmol), diisopropylethylamine (0.721 ml, 4.13 mmol), and methyl sulfoxide (4 ml) and heated in a Biotage Emrys Optimizer microwave reactor for 2 h at 150° C. The reaction mixture was subjected to silica gel chromatography (0-100% (5% methanol in ethyl acetate) in hexanes) to isolate the diamine. The diamine was added with 1,1'-carbonyldiimidazole (0.669 g, 4.13 mmol) and dioxane (4 mL) and the mixture was heated in a Biotage Emrys Optimizer microwave reactor for 10 min at 100° C. The reaction was purified on silica gel (0-100% (5% methanol in ethyl acetate) in hexanes). The isolated fractions were concentrated and triturated with ether to give a white solid, (85 mg, 12% yield over 3-steps). MS (ESI) m/z 340.0 [M]$^+$, 342.0 [M+2]$^+$.

C. 2-(4-Bromophenyl)propan-2-ol. 1-(4-Bromophenyl)ethanone (9.25 g, 46.5 mmol) was dissolved in tetrahydrofuran (200 ml). The solution was cooled in a −50° C. bath. Methylmagnesium bromide (3M in ether, 46.5 ml, 139 mmol) was added over a 15 min period. The reaction was allowed to warm to room temperature and then stirred for 20 h. The reaction was quenched with saturated ammonium chloride and then extracted with ethyl acetate. The organic layer was dried over magnesium sulfate, filtered, and concentrated to give an oil. The oil was purified on a silica gel column (0-20% ethyl acetate in hexanes) to give the product a colorless oil (9.1 g, 91% yield). MS (ESI) m/z 197.1 [M]$^+$, 199.1 [M+2]$^+$.

D. 2-(4-(4,4,5,5-Tetramethyl-1,3,2-dioxaborolan-2-yl)phenyl)propan-2-ol. 2-(4-Bromophenyl)propan-2-ol (4.7 g, 21.85 mmol), bis(pinacolato)diboron (6.66 g, 26.2 mmol), potassium acetate (6.43 g, 65.6 mmol), and dimethylsulfoxide (50 ml) were stirred together and degassed under vacuum for 10 min. [1,1'-Bis(diphenyl-phosphino)ferrocene]dichloropalladium(II) complex with dichloromethane (1:1) (0.892 g, 1.093 mmol) was added and the reaction was degassed for another 5 min. The reaction was then heated to 80° C. under nitrogen for 2 h. The reaction was cooled to room temperature, and then extract with 1:1 ether:ethyl acetate and water. A black emulsion was filtered through a pad of celite. The organic layer was dried over magnesium sulfate, filtered, and then purified on silica gel column (0-25% ethyl acetate in hexanes). The product fractions were concentrated and then triturated in hexanes to give a white solid, (4 g, 70% yield). MS (ESI) m/z 263.3 [M+1]$^+$.

E. (1r,4r)-4-(6-(4-(2-Hydroxypropan-2-yl)phenyl)-2-oxo-2,3-dihydro-1H-imidazo[4,5-b]pyrazin-1-yl)cyclohexanecarboxamide. (1r,4r)-4-(6-Bromo-2-oxo-2,3-dihydro-1H-imidazo[4,5-b]pyrazin-1-yl)cyclohexanecarboxamide (100 mg, 0.29 mmol), 2-(4-(4,4,5,5-tetramethyl-1,3,2-dioxaborolan-2-yl)phenyl)propan-2-ol (53 mg, 0.29 mmol), dichloro[1,1'-bis(diphenylphosphino)ferrocene]palladium(II) dichloromethane adduct (12 mg, 0.015 mmol), 1M sodium carbonate (0.88 mL, 0.88 mmol), and dioxane (2 mL) were heated in a Biotage Emrys Optimizer microwave reactor at 130° C. for 20 min. The reaction was purified by reverse-phase semi-preparatory HPLC (10-70% acetonitrile+0.1% TFA in H$_2$O+0.1% TFA, over 30 min). The product fractions were neutralized by addition of potassium carbonate. The solution was concentrated and dried. The solid was purified on silica gel column (0-100% (5% methanol in ethyl acetate) in hexanes) to give a white solid, (50 mg, 43% yield). $^1$H NMR (400 MHz, DMSO-d$_6$) δ 12.01 (s, 1H), 8.44 (s, 1H), 7.93 (d, J=8.6, 2H), 7.57 (d, J=8.2, 2H), 7.30 (s, 1H), 6.77 (s, 1H), 5.08 (s, 1H), 4.24 (t, J=12.5, 1H), 2.40 (m, 2H), 2.22 (t, J=12.3, 1H), 1.92 (d, J=10.9, 2H), 1.85 (d, J=9.0, 2H), 1.53 (m, 2H), 1.46 (s, 6H); MS (ESI) m/z 396.0 [M+1]$^+$; mp 280-282° C.

5.1.210 Example 210

SYNTHESIS OF 6-(4-(5-METHYL-1H-1,2,4-TRIAZOL-3-YL)PHENYL)-1-(2-(TETRAHYDRO-2H-PYRAN-4-YL)ETHYL)-1H-IMIDAZO[4,5-B]PYRAZIN-2(3H)-ONE

A. 4-(2-Oxo-3-(2-(tetrahydro-2H-pyran-4-yl)ethyl)-2,3-dihydro-1H-imidazo[4,5-b]pyrazin-5-yl)benzonitrile. 6-Bromo-1-(2-(tetrahydro-2H-pyran-4-yl)ethyl)-1H-imidazo[4,5-b]pyrazin-2(3H)-one (See Example 108.B) (2.5 g, 7.60 mmol), 4-cyanophenylboronic acid (1.69 g, 11.5 mmol) and dichloro[1,1'-bis(diphenylphosphino)ferrocene]palladium (II) dichloromethane (0.62 g, 0.70 mmol) were combined in dioxane (10 mL). Sodium carbonate (0.91 g, 15.2 mmol) in water (10 mL) was added and the reaction stirred at 100° C. overnight. The cooled reaction solution was filtered through Celite and the filter cake was washed with ethyl acetate. Filtrate and ethyl acetate wash were combined and solvent removed under reduced pressure. The resulting material was purified using reverse-phase preparatory HPLC (20-80% acetonitrile+0.1% TFA in H$_2$O+0.1% TFA, over 30 min). Fractions containing clean product were passed through a Phenomenex Strata-X-C ion exchange column to remove TFA. The column was washed successively with water, methanol, and then 5% ammonium hydroxide in methanol. The product was released with the 5% ammonium hydroxide in methanol eluent and was concentrated on a rotary evaporator. The residue was triturated with ethyl ether in hexane to give a fine powder and dried under vacuum at 50° C. to give the desired product (1.2 g, 46%) as a white solid. MS (ESI) m/z 350.0 [M+1]$^+$.

B. Ethyl 4-(2-oxo-3-(2-(tetrahydro-2H-pyran-4-yl)ethyl)-2,3-dihydro-1H-imidazo[4,5-b]pyrazin-5-yl)benzimidate. HCl gas was bubbled in a suspension of 4-(2-Oxo-3-(2-(tetrahydro-2H-pyran-4-yl)ethyl)-2,3-dihydro-1H-imidazo[4,5-b]pyrazin-5-yl)benzonitrile (1.2 g, 3.43 mmol) in anhydrous ethanol (30 mL) at 0° C. The flask was capped, and the reaction mixture was stirred overnight at room temperature. Upon complete conversion to product (monitored by LCMS), the volatiles were removed under reduced pressure, and the resulting white solid was dried in a vacuum oven to give the desired product (1.2 g, 88%). The material was used in the next step without further purification. MS (ESI) m/z 396.0 [M+1]$^+$.

C. 6-(4-(5-Methyl-1H-1,2,4-triazol-3-yl)phenyl)-1-(2-(tetrahydro-2H-pyran-4-yl)ethyl)-1H-imidazo[4,5-b]pyrazin-2(3H)-one. Ethyl 4-(2-oxo-3-(2-(tetrahydro-2H-pyran-4-yl)ethyl)-2,3-dihydro-1H-imidazo[4,5-b]pyrazin-5-yl)benzimidate (0.250 g, 0.63 mmol) in ethanol (20 mL) was treated with acetohydrazide (0.23 g, 3.16 mmol) and triethylamine (3.23 mL, 2.32 mmol), and the resulting reaction mixture was stirred at 110° C. for 3 h. The cooled reaction solvent removed under reduced pressure. The resulting material was purified using reverse-phase semi-preparatory HPLC (20-50% acetonitrile+0.1% TFA in H$_2$O+0.1% TFA, over 30 min). Fractions containing clean product were passed through a Phenomenex Strata-X-C ion exchange column to remove TFA. The column was washed successively with water, methanol, and then 5% ammonium hydroxide in methanol. The product came off with the 5% ammonium hydroxide in methanol eluent and was concentrated on a rotary evaporator. The residue was triturated with ethyl ether in hexane to make a fine powder and dried under vacuum at 50° C. to give the desired product (0.185 g, 72%) as a white solid. $^1$H NMR (400 MHz, DMSO-d$_6$) δ 13.73 (br. s., 1H), 12.07 (br. s., 1H), 8.56 (s, 1H), 8.09 (m, 4H), 3.93 (d, 2H), 3.83 (d, J=14.1, 2H), 3.22 (m, 2H), 2.42 (br. s., 3H), 1.73 (m, 4H), 1.52 (m, 1H), 1.21 (m, 2H); MS (ESI) m/z 406.2[M+1]$^+$; mp 290-292° C.

5.2 Biological Examples

5.2.1 MG63 pS6 MesoScale Assay

The following is an example of an assay that can be used to determine the anticancer activity of a test compound.

MG63 human osteosarcoma cells (ATCC: CRL-1427) (passage 7-15) are used in this assay. Cells are maintained using DMEM (high glucose with L-glutamine), 10% FBS and Pen/Strep. The following buffers are used: Complete Tris Lysis Buffer (for 10 ml use: 100 μl phosphatase inhibitor I (100× stock), 100 μl phosphatase inhibitor II (100× stock), 1 tablet Complete Mini (EDTA-free), 40 μl PMSF, all mixed thoroughly for 5 minutes at room temperature); 1× Tris wash Buffer (for 250 ml use: 25 ml 10× Tris wash buffer, 225 ml deionized water, store at room temperature); MSD blocking solution-A (for 20 ml use: 20 ml 1× tris wash buffer and 600 mg MSD blocker A, store on ice); Antibody dilution buffer (for 3 ml use: 1 ml blocking solution-A, 1.82 ml 1× tris wash buffer, 150 μl 2% MSD blocker D-M, 30 μl 10% MSD blocker D-R, store on ice).

On day one in the afternoon, cells are plated in 96-well flat bottom cell culture plates at 5000 cells/well in 100 μl of volume. On day 2 in the morning, test compounds are diluted to the desired concentration and added to the cells. Cells are treated with compound for 16-24 hours at 37° C., 0.5% CO$_2$.

Plates are blocked about 5 minutes before compound treatment is complete by adding 150 μl of MSD blocking solution-A to the plate and incubating with vigorous shaking at room temperature for 1 hour.

Cells are harvested and lysates are prepared by removing the medium with a multi-channel pipette, washing 1× with ice-cold PBS (Ca-free, Mg-free), adding 50 μl/well of Complete Tris Lysis Buffer and incubating with shaking at 4° C. for 1 hour.

Lysate samples are added to an MSD multi-spot plate by pipetting cell lysates up and down about 4-5 times, transferring 25 μl/well to an MSD multi-spot plate (R$_A$ for negative control and R$_B$ for positive control) (lysis buffer is only added to background wells) and incubating with vigorous shaking at room temperature for 2 hours.

Detection antibody is added by diluting anti-pS6 antibody (SULFO-TAG labeled, light sensitive) in 3 ml of cold antibody dilution buffer to a final concentration of 10 nM, adding 25 μl/well of 10 nM detection antibody to MSD plate, incubating with vigorous shaking at room temperature in the dark for 1 hour and washing the plate 4 times with 1× tris wash buffer.

The plate is read by adding 150 μl/well of 1× read buffer T (with surfactant) and using, for example, an MSD SECTOR plate reader and an appropriate program for data analysis.

5.2.2 mTOR HTR-FRET Assay

The following is an example of an assay that can be used to determine the mTOR inhibitory activity of a test compound. Reagents are prepared as follows:

"Simple TOR buffer" (used to dilute high glycerol TOR fraction): 10 mM Tris pH 7.4, 100 mM NaCl, 0.1% Tween-20, 1 mM DTT (from 1M stock frozen at −20° C. just prior to use). For convenience a large quantity of "Simple TOR buffer" w/o DTT can be stored at 4° C. It can be brought to room temperature and DTT added just prior to dilution of TOR fraction.

5×KB/5×Mn/5×ATP solution (used to dilute substrate GST-p70S6kin 81 a.a. just prior to use) (40 ml screen quantity shown):

| | |
|---|---|
| 0.075 mM ATP | 30 μL 0.1M ATP (made fresh from powder) |
| 12.5 mM MnCl$_2$ | 500 μL 1M MnCl$_2$ |
| 50 mM Hepes, pH 7.4 | 2 ml 1M Hepes, pH7.4 |
| 50 mM β-GOP | 2 ml 1M β-GOP |
| 250 nM Microcystin LR | 500 μL 20 μM Microcystin LR (in DMSO) |
| 0.25 mM EDTA | 20 μL 0.5M EDTA |
| 5 mM DTT | 200 μL 1M DTT |
| ddH$_2$0 | 34.752 ml |

Enzyme solution: Dilute TOR fraction 1:14 in "Simple TOR Buffer". For current lot that is 640 μg/ml TOR fraction diluted 14× to yield 45.7 μg/ml TOR in buffer (i.e. 7.85 ml TOR pooled fraction+102.1 ml Simple TOR buffer=110 ml 14× diluted TOR fraction). Each Enzyme Lot must be QC'd prior to assay.

Substrate solution: This may be prepared just prior to assay if preferred. Dilute 5.3 mg/ml GST-p70S6kinase fragment stock to 3.5 μg/ml (97 nM) working stock in 5×KB/5×Mn/5× ATP solution (i.e. 26.41 μL (5.3 mg/ml) GST-p70S6+40 ml 5×KB/5×Mn/5×ATP=40 ml 3.5 μg/ml (97 nM)).

Assay Buffer (for dilution of Antibodies used in Antibody Detection Reagent):

| | |
|---|---|
| 50 mM Hepes, pH 7.4 | 12.5 ml 1M Hepes, pH7.4 |
| 1 mM DTT | 250 μL 1M DTT |
| 0.01% Triton X-100 | 250 μL 10% Triton X-100 |
| 0.01% BSA | 25 mg BSA |
| 0.1 mM EDTA | 50 uL 0.5M EDTA |
| ddH$_2$O | 236.5 ml |

Antibody Detection Reagent (this reagent should be made just prior to addition to Assay Plates):

| | |
|---|---|
| 3.056 ml | 1000 μg/ml Cy5-αGST Amersham Cat#PA92002V |
| 0.07661 ml | 1000 μg/ml α-phospho p70S6(Thr389) Cell Signalling Mouse Monoclonal #9206L |
| 0.223 ml | 690 μg/ml α-mouse Lance Eu Perkin Elmer Cat#AD0077 |
| 236.64 ml | Assay Buffer |

Using PlateTrak program (Screen) or Matrix Pipettor (SAR), 19.5 μL of diluted TOR fraction is added to assay plate in all test, reference or positive control wells. 19.5 μL of "Simple TOR buffer" is added to all negative control wells. If treating multiple plates with the same compounds, can increase volume of enzyme to multiples of 19.5 μL in a tall 384 well polypropylene plate.

Using EP3, 0.5 µl of test, reference or control DMSO is added to each well with mixing. Plates are incubated for 30 minutes at room temperature.

Using PlateTrak program (Screen) or Matrix Pipettor (SAR) 5 µL of 5×KB/5×Mn/5×ATP/5× substrate solution is added to each well of the assay plate to start the reaction. The solutions are mixed well and incubated for 2 hours at room temperature.

Using PlateTrak program (Screen) or Matrix Pipettor (SAR) 5 µL of 60 mM EDTA is added to stop the reaction. The solutions are mixed well and allowed to sit for 15-20 minutes before the next step.

Using PlateTrak program (Screen) or Matrix Pipettor (SAR) 10 µl of Antibody Detection Reagent is added. The solutions are mixes well and incubated for 5 hours to O/N to allow antibodies to form complexes with phosphorylated substrate.

Plates are read on AnalystHT using protocol Multi-Method protocol.

5.2.3 PKCθ IMAP Assay

The following is an example of an assay that can be used to determine the PKCθ inhibitory activity of a test compound. Reagents are prepared as follows:

Assay Buffer: 50 mM HEPES (pH 7.6), 10 mM MgCl, 0.1 mM EDTA, 5 mM MBP, 0.01% Triton, 1 mM DTT, 0.05 mg/ml phosphatidyl serine, 0.05 mg/ml diacylglycerol.

The final concentration of PKCθ (Invitrogen) is 0.5 nM. The final concentration of substrate (FAM-AKRRRLSS-LRA) (Molecular Devices) is 100 nM. The final concentration of ATP in the reaction is 35 µM. The final concentration of DMSO in the reaction is 2.5%.

Enzyme is kept in 5 µl aliquots and stored at −80° C. prior to use. Test compound is allowed to pre-incubate with enzyme for 45 minutes before the reactions is initiated.

The reaction mixture consists of: 5 µl of test compound in 10% DMSO, 5 µl of 400 nM substrate (FAM-AKRRRLSS-LRA), 5 µl of 40 nM PKCθ, and 5 µl of 140 µM ATP (ATP is added to the reaction mixture last to initiate the reaction) per well.

The reaction is allowed to proceed for 60 minutes and is terminated by adding 30 µl per well of 90% Progressive A buffer/10% Progressive B buffer and a 1:400 dilution of binding beads (Molecular Devices).

The reaction is given a binding incubation time of at least 30 minutes prior to reading the fluorescence polarization signal on an Analyst reader (the following detector settings are used: fluorescein excitation-485 nm, fluorescein emission-530 nm, fluorescein dichroic-505 nm).

5.2.4 Tyk2 HTRF Assay Protocol (with ATP Shift Option)

The following is an example of an assay that can be used to determine the Tyk2 inhibitory activity of a test compound.

25 µl/well DMSO is added to Columns 2 and 14 (except 28.5 µl is added to well P14 of Greiner 384-well polypropylene plate). 20 µl/well DMSO is added to all remaining wells.

5 mM compound solutions are added by addition of 5 µl of 30 mM compound to 25 µl DMSO in Columns 2 and 14 of plate. 1.5 mM reference control is prepared by addition of 1.5 µl of 30 mM JAK3 Inhibitor VI to 28.5 µl DMSO in Well P14.

Serial dilution is then performed by the following steps: (i) Compounds in Column 2 are mixed by pipetting 20 µl up and down 6×; (ii) 10 µl/well compounds in DMSO are transferred from one column to the next column for Columns 2-11; (iii) wells are mixed by pipetting 20 µl up and down 6×; (iv) tips are washed 3×25 µl DMSO, 2×25 µl next DMSO; (v) steps i-iv repeated for Columns 14-23.

The following buffers are prepared:
Assay Buffer: 50 mM HEPES pH 7.6; 1 mM DTT; 10 mM MgCl₂; 0.01% Triton X100; 0.01% BSA; and 0.1 mM EDTA.

Kinase in Assay Buffer: 450 ng/ml TYK2 KD (Carna Biosciences 08-147 Lot 06CBS-3022D).

Substrate/Detection Mixture (1×ATP) in Assay Buffer: 188 nM DyLight 647-Streptavidin (Pierce 21824); 5 µM Biotin-EQEDEPEGDYFEWLE (Lyn Substrate Peptide); 750 ng/ml Eu-anti-phospho-Tyrosine (PerkinElmer AD0069); 62.5 µM ATP; 80 nM Substrate Peptide (American Peptide Company 332722).

Substrate/Detection Mixture (20×ATP) in Assay Buffer: 188 nM DyLight 647-Streptavidin; 5 µM Biotin-EQEDE-PEGDYFEWLE; 750 ng/ml Eu-anti-phospho-Tyrosine; 1250 µM ATP; 80 nM Substrate Peptide.

14.5 µl/well Enzyme Mix or Dilution Buffer (Background Controls) is added to Costar 384 well black plates.

Compound addition and mixture is performed by the following steps: (i) 0.5 µl/well DMSO/compounds in DMSO is transferred from Greiner 384-well polypropylene plate to a plate containing 14.5 µl/well Enzyme Mix and Dilution Buffer; (ii) mixed by pipetting 10 µl up and down 4×; (iii) tips are washed 4×10 µl in DMSO, 2×20 µl in other DMSO; (iv) steps i-iii are repeated until all plates are completed.

10 µl/well Substrate/Detection Mixtures is added and incubated at room temperature 2 hours (on shaker for first 2+ minutes).

10 µl/well 50 mM EDTA/0.01% Triton X100 is added and incubated >15 minutes at room temperature (on shaker for first 2+ minutes).

Plates are read at 665 nm and 620 nm emission on Analyst GT protocol HTRF_SP_A (Counts=665/620×10000).

5.2.5 Syk HTRF Assay Protocol

5 µl/well DMSO is added to Column 2 Wells A-O and 29.5 µl to well P2 of Greiner 384-well polypropylene plate. 20 µl/well DMSO is added to Columns 1 and 3-12.

25 mM compound solutions are prepared by the addition of 25 µl of 30 mM compound to Column 2 and 0.5 µl 30 mM reference control to well P2.

Serial dilution is then performed by the following steps: (i) compounds in Column 2 are mixed by pipetting 20 µl up and down 6×; (ii) 10 µl/well compounds in DMSO are transferred from one column to the next column for Columns 2-11; (iii) wells are mixed by pipetting 20 µl up and down 6×; (iv) tips washed 3×25 µl DMSO, 2×25 µl next DMSO.

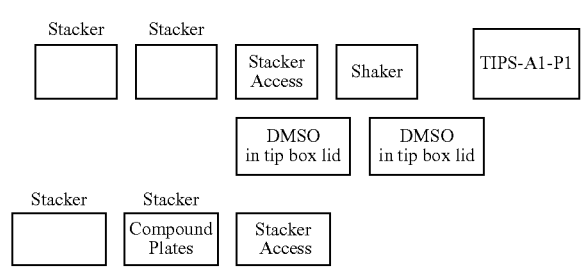

The following buffers are prepared:
Dilution Buffer: 50 mM HEPES pH 7.6; 1 mM DTT; 10 mM MgCl$_2$; 0.01% Triton X100; 0.01% BSA; 0.1 mM EDTA.
Enzyme Mix in Dilution Buffer: 8.621 ng/ml Syk (Carna Biosciences 08-176).
Start Mix in Dilution Buffer: 87.5 µM ATP; 80 nM Substrate Peptide (American Peptide Company 332722).

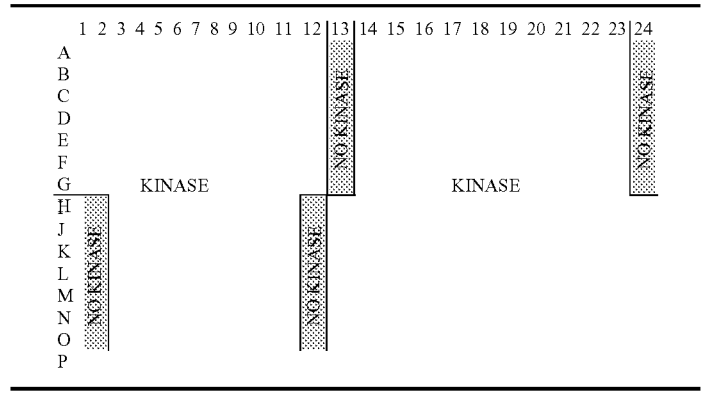

14.5 µl/well Enzyme Mix or Dilution Buffer (Background Controls) is added to Costar 384-well black plates.

Compound addition and mixture is performed by the following steps: (i) 0.5 µl/well DMSO/compounds in DMSO transferred from Greiner 384-well polypropylene plate to left half of assay plate containing 14.5 µl/well Enzyme Mix and Dilution Buffer; (ii) Mix by pipetting 10 µl up and down 4×; (iii) tips are washed 4×10 µl in DMSO, 2×20 µl in other DMSO; (iv) steps i-iii are repeated with transfer to right half of assay plate; (v) steps i-iv are repeated with each compound/assay plate until all plates are completed.

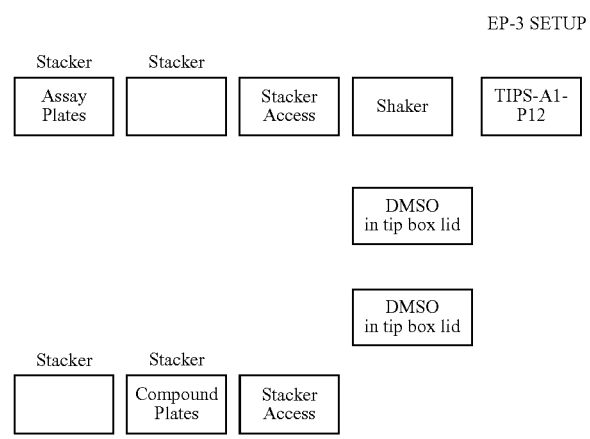

EP-3 SETUP

10 µl/well Start Mix is added and incubated at room temperature on shaker for 2 minutes (1 hour total reaction time).

The following buffers are prepared:
Stop Solution in Dilution Buffer: 120 mM EDTA
Antibody Mix in Dilution Buffer: 4.86 µg/ml DyLight 647 Streptavidin (Pierce 21824); 1 µg/ml Lance Eu-Anti-Phosphotyrosine (PerkinElmer AD0069).

5 µl/well/in Dilution Buffer is added and incubated at room temperature on shaker for 2 minutes.
10 ml/well Antibody Mix is added and Incubated at room temperature on shaker for 2 minutes (4 hours to overnight total time).
Plates are read at 665 nm and 620 nm emission on Analyst GT protocol HTRF_SP_A or EnVision protocol Steve's TR-FRET.

5.2.6 Syk Functional Assay Protocol (CD69 Expression in Anti-IgM Stimulated Primary B-Cells)

Cells: Primary B-cells are purified from Buffy coat cell preparations obtained from healthy human donors at San Diego Blood Bank (SDBB). Cells are maintained in RPIM/10% FBS.

Reagents: AffiniPure F(ab') fragment goat anti-human IgM (Jackson, cat. 109-006-129, 1.3 mg/ml); PE labeled anti-human CD69 (BD Pharmingen, cat. 555531, 2 mls); 7AAD (BD Pharmingen, cat. 559925, 2 mls); RosetteSep B-cell enrichment Reagent (Stem Cell Technologies, cat. 15064, 10 mls); Ficoll-Paque Plus (Amersham, cat. 17-440-02); FBS Stain Buffer (BD Pharmingen).

Protocol: (i) Buffy coat cell preparation is ordered in advance from SDBB (two are typically ordered in case difficulty is encountered with one of them); (ii) B-cells are purified using the RosetteSep negative selection procedure, as follows:

a. 2.0 mL of RosetteSep reagent is added to 40 mL of buffy coat. Each buffy coat is typically 80-100 mL. The mixture is gently mixed and allowed to sit at room temperature for 20 minutes (some settling may occur).

b. In a tissue culture flask, 40 ml buffy coat is mixed with an equal volume of sterile filtered 2% FBS in PBS (no calcium/magnesium).

c. 35 mL of this diluted buffy coat is added to each of five 50 mL polypropylene conical tubes. 14 mL of Ficoll Paque is slowly added under buffy coat and bottom of each tube (being careful not to mix with buffy coat).

d. Tubes are spun at 2200 rpm for 20 minutes in Sorvall tabletop centrifuge with brake off.

e. After spin, cells should be visible at serum/Ficoll interface. The serum is gently aspirated off to a point near the interface. With a Pasteur pipette and pipetteman, cell layer is removed from the interface taking care to remove as little Ficoll as possible.

f. Recovered cells are diluted (approx. 10 mls) in 100 mL 2% FBS in PBS, spun at 1200 rpm from 5 minutes and the cell pellet is resuspend in 5-10 mL RPMI growth media, depending on anticipated cells recovery.

Cells are counted and cell density is adjusted to 1 mln/ml in RPMI growth media. Compound pretreatment plate in 96 well round-bottom format is prepared with enough cell volume to cover the desired number of wells, assuming 50 µl cells/well in the treatment plate. In a separate 96 well plate, compounds are diluted 1:50 into RPMI growth media. 22 µL of diluted compound is added to 200 µL cells in compound pretreatment plate. The mixture is placed in tissue culture incubator for 30-60 minutes.

20 µg/ml anti-IgM solution in RPMI growth media is prepared. 50 µL of anti-IgM solution per well is added into a new 96 well round bottom plate (cell stimulation plate). Controls spent culture media only are included. 50 µL of compound pretreated cells are added to the anti-IgM containing plate using a multichannel pipettor. The mixture is placed back in tissue culture incubator for 12-14 hours.

Plate is spun at 1200 rpm for 5 minutes. Media is dumped and the plate is gently blotted dry. Enough antibody solution to cover plate is prepared, assuming 100 µL Stain Buffer containing 5 µL of CD69 antibody/well. 100 µL of antibody solution per well is added, plate is gently tapped to mix, plate is covered with aluminum foil and placed in drawer at room temperature for 30 minutes.

Plate is spun, dumped and blotted. Plate is washed once with 250 µL Stain buffer, spun, dumped, and blotted. Final cell pellet is resuspended in 100 µL Stain buffer and read on cytometer.

5.2.7 Syk Functional Assay S.O.P. (IgE-Dependent Beta-Hexosaminidase Secretion from the LAD2 Human Mast Cell Line)

Overview: LAD2 cells are plated into 96 well format, sensitized through FcepsilonR with NP-IgE, and degranulated by crosslinking with $NP_{16}$-BSA. The supernatants are collected and secretory granule components including beta-hexosaminidase measured in various colorimetric assays.

Cells: LAD2 cells are provided by Metcalf lab at NIH. For detailed description of the derivation, characteristics, and growth/storage of these cells refer to original publication (Kirshenbaum, et al., *Leukemia Research* 27:677-682, 2003). The cells grow quite slowly, doubling every 10-14 days, and so need to feed by hemidepletion every week and split infrequently. Growth media: StemPro-34 plus serum supplement (Invitrogen) with 100 ng/ml recombinant human SCF (BioSource). The cells can be maintained in culture for approximately 15 passages before morphology and functionality changes.

Reagents: chimeric human nitrophenyl-IgE (Serotec, MCA333S, 20 ug/ml stock solution); $NP_{16}$-BSA (Biosearch Technologies, N5050-10 mg, 10 mg/ml stock solution); PNAG substrate (p-Nitrophenyl N-acetyl-β-D-Glucosaminide; Sigma N-9376) 0.004 M=1.37 mg/ml; prepare 1.37 mg/mL1 in citrate/phosphate buffer, 150 µL/sample (will take 30-60 min at 37° C. with frequent vortexing)); Citrate/Phosphate Buffer (0.04 M Anhydrous Citric acid (FW 192 g/mol); 2 mL of 1M Citric Acid (Hampton Research); 0.02 M $Na_2HPO_4$; 2 mL of 0.5 M $Na_2HPO_4$ (SIGMA), use 5N NaOH to pH to 4.6 (approx 1 mL) per 50 mls soln); Modified Tyrode's Buffer (Tyrode's Buffer Powder (SIGMA, T2145) one vial into 1 L distilled water; allow powder to dissolve and then add the following: 1 M HEPES buffer pH 7.8 to 20 mM final (1:50), 0.5M NA2HPO4 to 0.5 mM final (1:1000), 0.04% BSA (400 mg/L), pH should be 7.4); Glycine Stop Solution (0.32 M glycine, 2.4 g/100 ml; 0.2 M Sodium Carbonate (FW 106 g/mol), 2.5 g/100 ml).

Protocol: LAD2 is gently dislodged from culture flask, collected, and spun down at 1200 rpm for 5 minutes. Spent culture media is removed and saved. Cells are resuspended at 0.8-1 million/ml in spent culture media. 100 µL of 0.5 ug/ml NP-IgE is plated in spent culture media into a round bottom 96 well plate. Note: IgE solution needs to be clarified to remove aggregates by spinning at >10000 rpm for 10 minutes at 4° C. 100 µL cells is added to plate and placed back in tissue culture incubator for 12-14 hours to sensitize cells and load FcepsilonR receptors. Cold Modified Tyrode's Buffer is allowed to warm to room temp overnight.

The next morning, plate is spun at 1200 rpm for 5 minutes. Media is removed with multichannel pipetor. Cell pellets are resuspended in 100 ul Modified Tyrode's buffer with GENTLE trituration (5 strokes). Cells are allowed to rest for 3.5 hours in tissue culture incubator. Note: During this time, it will be necessary to warm the Citrate/Phosphate buffer to 37° C. and then resuspend the PNAG substrate to 1.3 mg/ml with periodic vortexing. Compound series are diluted 1:50 in Modified Tyrode's buffer and then 11 µL of compound, without further mixing, is added to each well (giving a 0.2% dmso final concentration). Compound is pre-incubated for 30-60 minutes in tissue culture incubator.

12 µL of 1.0 µg/ml $NP_{16}$-BSA diluted in Modified Tyrode's is added. Total volume is now 123 µL. Ionomycin at 100 nM final can be added instead of NP-BSA as a Syk-independent control for stimulation. Incubated in tissue culture incubator for 90 minutes.

Plate is spun at 1200 rpm for 5 minutes, 75 µL of supernatant (SN) is transferred to empty 96 well plate for storage. Remaining SN is removed from cell plate and discarded. 125 µL 0.1% triton X-100 in Modified Tyrode's buffer is added to cell pellet, pipetted up/down to lyse cells and mixture is Incubated on ice for 15 min.

30 µL supernatant from storage plate or 5 µL cell pellet lysate plus 25 µL 0.1% Triton solution is added to a new 96 well flat-bottom plates in identical layout for the final plate read. 150 µL PNAG substrate is added to all wells. Plate is incubated in 37° C. bacterial incubator for 1 hour.

50 µL stop solution is added to each well. Wells with most activity will be brightest yellow. The plate is read immediately at 405 nm.

% release per well is calculated (after subtracting background from all wells)=100×(SN/(SN+6×cell lysate)). Net % release=100×(SN stim−SN PBS)/(SN stim+cell lysate stim−SN PBS).]

Assay Quality Control criteria: 3 primary parameters of assay performance: 1) Percent release values should be between 10-20% in IgE- and DMSO-treated wells (40% release with 100 nM Ionomycin); 2) $IC_{50}$ values with Syk tool compounds should be in the range of 50-200 nM; 3) Z' for assay should be >0.55.

5.2.8 Syk Biomarker Assay Protocol (phosphoBLNK Measurement by PhosFlow in Anti-IgM Stimulated Ramos)

Cells: Ramos B-cell lymphoma (clone RA1, CRL1596) from ATCC grow rapidly and need to be split 1:20 every 3-4 days for maintenance. The cells grow in RPMI/10% FBS.

Reagents: AffiniPure F(ab') fragment goat anti-human IgM (Jackson, cat. 109-006-129, 1.3 mg/ml); PE mouse anti-phosphoBLNK (pY84, BD Pharmingen, cat. 558442); CytoFix Reagent (BD Pharmingen, cat. 554655); Perm/Wash Buffer I (BD Pharmingen, cat. 557885, 10× solution); BSA Stain Buffer (BD Pharmingen, cat 554657)

Protocol: Ramos cells are split 1:1 with fresh growth media the day before experiment. On the day of the experiment, cells are spun down at 1200 rpm for 5 minutes. All spent culture media is saved. Cells are resuspended at 1 mln/ml in spent culture media. Compound pretreatment plate is prepared in 96 well round-bottom format with enough cell volume to cover the desired number of wells, assuming 50 μL cells/well in the treatment plate, e.g. for 4 wells 200 μL cells is added. In a separate 96 well plate, compounds are diluted 1:50 into spent culture media. 22 μL of diluted compound is added to 200 μL cells in compound pretreatment plate. Plated is placed back in tissue culture incubator for 30-60 minutes. CytoFix reagent is pre-warmed in 37° C. waterbath prior to stimulating cells.

40 μg/ml anti-IgM solution in spent culture media is prepared. 50 μL of anti-IgM solution per well is added into a new 96 well round bottom plate (cell stimulation plate). Controls of spent culture media only are included. Using a multichannel pipettor, 50 μL of compound pretreated cells are quickly added to the anti-IgM containing plate, and the plate is placed back in tissue culture incubator for 10 minutes.

An equal volume (100 μL) of prewarmed CytoFix reagent is added to all wells of cell stimulation plate. Plate is placed back into tissue culture incubator for 10 minutes, spun at 1200 rpm for 5 minutes, and media is gently dumped out and the plate is blotted dry.

100 μL of Perm/Wash Buffer I is added to all wells. Plate is left at room temperature for 10 minutes, spun at 1200 rpm for 5 minutes, and media is gently dumped out and plate is blotted dry. Cells are washed three times with 200 μL BSA Stain Buffer. Plate is spun plate, dumped, and blotted.

Enough antibody solution to cover plate is prepared, assuming 100 μL Stain Buffer containing 5 μL of pBLNK antibody/well. 100 μL of antibody solution per well is added, plate is gently tapped to mix, and covered with aluminum foil and placed in drawer at room temperature for 30 minutes.

Plate is spun plate, dumped, and blotted. Plate is washed once with 200 μL Stain buffer. Plate is spun plate, dumped, and blotted. Final cell pellet is resuspended in 100 μL Stain buffer and read on cytometer.

The compounds of Table 1 were found to have the following values in the PKCθ, mTOR and Syk screening assays.

| Compound | mTOR (μM) | PKCθ IC$_{50}$ (μM) | Syk IC$_{50}$ (μM) |
|---|---|---|---|
| 1 | ND | * | * |
| 2 | ***** | * | ND |
| 3 | ND | * | ND |
| 4 | ***** | * | ND |
| 5 | **** | * | ND |
| 6 | ***** | ND | ND |
| 7 | ND | * | ND |
| 8 | ND | ***** | ***** |
| 9 | ND | * | ND |
| 10 | *** | ***** | ND |
| 11 | * | ** | * |
| 12 | ND | * | ND |
| 13 | ND | *** | **** |
| 14 | ***** | * | ND |
| 15 | ***** | * | ND |
| 16 | ND | * | ND |
| 17 | ND | * | ND |
| 18 | ND | **** | ND |
| 19 | ND | * | ND |
| 20 | ND | * | ND |
| 21 | ND | * | ND |
| 22 | ND | * | ND |
| 23 | ND | * | ND |
| 24 | * | * | ND |
| 25 | * | * | ND |
| 26 | * | **** | ND |
| 27 | * | **** | ND |
| 28 | ND | ***** | ***** |
| 29 | ND | * | ND |
| 30 | ND | ** | ***** |
| 31 | ND | * | ND |
| 32 | ND | *** | ND |
| 33 | ND | * | ND |
| 34 | ND | * | ND |
| 35 | ND | * | ND |
| 36 | ND | * | ND |
| 37 | ND | * | ND |
| 38 | ND | * | ND |
| 39 | ND | * | ND |
| 40 | *** | *** | ND |
| 41 | **** | ***** | ND |
| 42 | ND | ***** | ND |
| 43 | ND | * | ND |
| 44 | ND | * | ND |
| 45 | * | ***** | ND |
| 46 | ND | *** | ND |
| 47 | ***** | * | ND |
| 48 | ND | * | ND |
| 49 | ND | * | ND |
| 50 | ***** | *** | ND |
| 51 | **** | **** | ND |
| 52 | **** | ***** | ND |
| 53 | **** | * | ND |
| 54 | **** | ***** | ND |
| 55 | **** | ***** | ND |
| 56 | * | ***** | ND |
| 57 | * | * | ND |
| 58 | *** | * | ND |
| 59 | *** | *** | ND |
| 60 | * | ** | ND |
| 61 | **** | *** | ND |
| 62 | ND | * | ND |
| 63 | ND | * | ND |
| 64 | **** | ** | ND |
| 65 | **** | ***** | ND |
| 66 | ND | * | ND |
| 67 | ND | ** | ND |
| 68 | * | * | ND |
| 69 | * | **** | ND |
| 70 | ND | ND | ND |
| 71 | ND | ND | ND |
| 72 | ND | ND | ND |
| 73 | **** | * | ND |
| 74 | ND | * | ND |
| 75 | ND | *** | ND |
| 76 | ND | **** | ND |
| 77 | ND | ** | ND |
| 78 | ND | * | ND |
| 79 | ND | ND | ND |
| 80 | **** | ND | ND |
| 81 | * | ND | ND |
| 82 | ND | ND | ND |
| 83 | ND | * | ND |
| 84 | ***** | *** | ND |
| 85 | **** | * | ND |
| 86 | * | ND | ND |
| 87 | ***** | ND | ND |
| 88 | ***** | ND | ND |
| 89 | ***** | ND | ND |
| 90 | ***** | ND | ND |
| 91 | ***** | ND | ND |

In the table set forth above, the following system is used:
***** = 0.1-5 μM,
**** = 5.1-10 μM,
*** = 10.1-20 μM,
** = 20.1-30 μM,
* = >30 μM.
"ND" means that the compound was not tested against that particular enzyme.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A compound having the following formula:

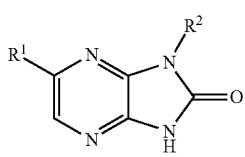

or a pharmaceutically acceptable salt thereof, wherein:
$R^1$ is substituted or unsubstituted heteroaryl; and
$R^2$ is H; unsubstituted $C_{3-4}$ alkyl; $C_{1-4}$ alkyl substituted with substituted or unsubstituted cycloalkyl or substituted or unsubstituted heterocycloalkyl; substituted or unsubstituted cycloalkyl; or substituted or unsubstituted heterocycloalkyl.

2. A compound of claim 1, wherein $R^1$ is substituted or unsubstituted quinoline, substituted or unsubstituted pyridine, substituted or unsubstituted pyrimidine, substituted or unsubstituted indole, or substituted or unsubstituted thiophene.

3. A compound having the following formula:

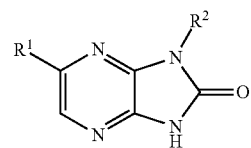

or a pharmaceutically acceptable salt thereof, wherein:
$R^1$ is substituted or unsubstituted aryl or substituted or unsubstituted heteroaryl; and
$R^2$ is $C_{1-4}$ alkyl substituted with substituted or unsubstituted cycloalkyl or substituted or unsubstituted heterocycloalkyl.

4. A compound or a pharmaceutically acceptable salt thereof, wherein the compound is:

| | |
|---|---|
| (S)-1-(1-hydroxy-3-methylbutan-2-yl)-6-phenyl-1H-imidazo[4,5-b]pyrazin-2(3H)-one; | 1-((tetrahydro-2H-pyran-4-yl)methyl)-6-(3,4,5-trimethoxyphenyl)-1H-imidazo[4,5-b]pyrazin-2(3H)-one; |
| | 6-(4-hydroxyphenyl)-1-((tetrahydro-2H-pyran-4-yl)methyl)-1H-imidazo[4,5-b]pyrazin-2(3H)-one; |
| | (S)-1-(1-hydroxy-3-methylbutan-2-yl)-6-(5-isopropyl-2-methoxyphenyl)-1H-imidazo[4,5-b]pyrazin-2(3H)-one; |
| (R)-1-(1-hydroxy-3-methylbutan-2-yl)-6-phenyl-1H-imidazo[4,5-b]pyrazin-2(3H)-one; | |
| (S)-1-(1-hydroxy-3-methylbutan-2-yl)-6-(quinolin-5-yl)-1H-imidazo[4,5-b]pyrazin-2(3H)-one; | (R)-1-(1-hydroxy-3-methylbutan-2-yl)-6-(quinolin-5-yl)-1H-imidazo[4,5-b]pyrazin-2(3H)-one; |
| (R)-1-(1-hydroxy-3-methylbutan-2-yl)-6-(5-isopropyl-2-methoxyphenyl)-1H-imidazo[4,5-b]pyrazin-2(3H)-one; | |
| | (R)-1-(1-phenylethyl)-1H-imidazo[4,5-b]pyrazin-2(3H)-one; |
| (S)-1-(1-phenylethyl)-1H-imidazo[4,5-b]pyrazin-2(3H)-one; | 1-isopropyl-6-(5-isopropyl-2-methoxyphenyl)-1H-imidazo[4,5-b]pyrazin-2(3H)-one; |
| 1-cyclohexyl-6-(5-isopropyl-2-methoxyphenyl)-1H-imidazo[4,5-b]pyrazin-2(3H)-one; | 5-(quinolin-5-yl)-1H-imidazo[4,5-b]pyrazin-2(3H)-one; |
| 1-isobutyl-6-(5-isopropyl-2-methoxyphenyl)-1H-imidazo[4,5-b]pyrazin-2(3H)-one; | 1-(2-hydroxyethyl)-6-(5-isopropyl-2-methoxyphenyl)-1H-imidazo[4,5-b]pyrazin-2(3H)-one; |
| 6-(5-isopropyl-2-methoxyphenyl)-1-(tetrahydro-2H-pyran-4-yl)-1H-imidazo[4,5-b]pyrazin-2(3H)-one; | |
| | (R)-6-(5-isopropyl-2-methoxyphenyl)-1-(3-methylbutan-2-yl)-1H-imidazo[4,5-b]pyrazin-2(3H)-one; |
| (S)-6-(5-isopropyl-2-methoxyphenyl)-1-(tetrahydrofuran-3-yl)-1H-imidazo[4,5-b]pyrazin-2(3H)-one; | (S)-6-(5-isopropyl-2-methoxyphenyl)-1-(3-methylbutan-2-yl)-1H-imidazo[4,5-b]pyrazin-2(3H)-one; |
| 1-cyclopentyl-6-(5-isopropyl-2-methoxyphenyl)-1H-imidazo[4,5-b]pyrazin-2(3H)-one; | (R)-6-(5-isopropyl-2-methoxyphenyl)-1-(tetrahydrofuran-3-yl)-1H-imidazo[4,5-b]pyrazin-2(3H)-one; |
| 1-(cyclopropylmethyl)-6-(5-isopropyl-2-methoxyphenyl)-1H-imidazo[4,5-b]pyrazin-2(3H)-one; | 1-(cyclopentylmethyl)-6-(5-isopropyl-2-methoxyphenyl)-1H-imidazo[4,5-b]pyrazin-2(3H)-one; |
| 1-(cyclohexylmethyl)-6-(5-isopropyl-2-methoxyphenyl)-1H-imidazo[4,5-b]pyrazin-2(3H)-one; | 6-(5-isopropyl-2-methoxyphenyl)-1-neopentyl-1H-imidazo[4,5-b]pyrazin-2(3H)-one; |

-continued 1-isopropyl-6-(3-isopropylphenyl)-1H-imidazo[4,5-b]pyrazin-2(3H)-one;

1-cyclopentyl-6-(quinolin-5-yl)-1H-imidazo[4,5-b]pyrazin-2(3H)-one;
6-(quinolin-5-yl)-1-(tetrahydro-2H-pyran-4-yl)-1H-imidazo[4,5-b]pyrazin-2(3H)-one;

1-((1s,4s)-4-hydroxycyclohexyl)-6-(quinolin-5-yl)-1H-imidazo[4,5-b]pyrazin-2(3H)-one;

1-((1s,4s)-4-(hydroxymethyl)cyclohexyl)-6-(quinolin-5-yl)-1H-imidazo[4,5-b]pyrazin-2(3H)-one;
1-(cyclopentylmethyl)-6-(4-hydroxyphenyl)-1H-imidazo[4,5-b]pyrazin-2(3H)-one;
6-(4-hydroxyphenyl)-1-isobutyl-1H-imidazo[4,5-b]pyrazin-2(3H)-one;

1-(cyclohexylmethyl)-6-(4-hydroxyphenyl)-1H-imidazo[4,5-b]pyrazin-2(3H)-one;

1-Cyclohexyl-6-(4-hydroxyphenyl)-1H-imidazo[4,5-b]pyrazin-2(3H)-one;

Methyl 4-(3-(cyclohexylmethyl)-2-oxo-2,3-dihydro-1H-imidazo[4,5-b]pyrazin-5-yl)benzoate;
4-(3-(Cyclohexylmethyl)-2-oxo-2,3-dihydro-1H-imidazo[4,5-b]pyrazin-5-yl)-N-methylbenzamide;
1-(Cyclohexylmethyl)-6-(pyridin-3-yl)-1H-imidazo[4,5-b]pyrazin-2(3H)-one;

1-(Cyclohexylmethyl)-6-(1H-indol-5-yl)-1H-imidazo[4,5-b]pyrazin-2(3H)-one;

1-(2-Hydroxyethyl)-6-(4-hydroxyphenyl)-1H-imidazo[4,5-b]pyrazin-2(3H)-one;
3-(3-(Cyclohexylmethyl)-2-oxo-2,3-dihydro-1H-imidazo[4,5-b]pyrazin-5-yl)benzamide;

6-(4-Hydroxyphenyl)-1-((1-methylpiperidin-4-yl)methyl)-1H-imidazo[4,5-b]pyrazin-2(3H)-one;
1-((1s,4s)-4-Hydroxycyclohexyl)-6-(4-hydroxyphenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-ethylbenzamide;
1-(Cyclohexylmethyl)-6-(4-hydroxy-2-methylphenyl)-1H-imidazo[4,5-b]pyrazin-2(3H)-one;
6-(4-Hydroxyphenyl)-1-(2-methoxyethyl)-1H-imidazo[4,5-b]pyrazin-2(3H)-one;

6-(4-(1H-1,2,4-Triazol-3-yl)phenyl)-1-(cyclohexylmethyl)-1H-imidazo[4,5-b]pyrazin-2(3H)-one;
1-(Cyclohexylmethyl)-6-(1H-pyrazol-5-yl)-1H-imidazo[4,5-b]pyrazin-2(3H)-one;

1-isopropyl-6-(2-methoxyphenyl)-1H-imidazo[4,5-b]pyrazin-2(3H)-one;
6-(5-isopropyl-2-methoxyphenyl)-1-(tetrahydro-2H-pyran-3-yl)-1H-imidazo[4,5-b]pyrazin-2(3H)-on;
1-(cyclopentylmethyl)-6-(quinolin-5-yl)-1H-imidazo[4,5-b]pyrazin-2(3H)-one;

6-(quinolin-5-yl)-1-(tetrahydro-2H-pyran-3-yl)-1H-imidazo[4,5-b]pyrazin-2(3H)-one;
1-((1r,4Ω-4-hydroxycyclohexyl)-6-(quinolin-5-yl)-1H-imidazo[4,5-b]pyrazin-2(3H)-one;
1-isopropyl-6-(quinolin-5-yl)-1H-imidazo[4,5-b]pyrazin-2(3H)-on;
1-(piperidin-4-ylmethyl)-6-(quinolin-5-yl)-1H-imidazo[4,5-b]pyrazin-2(3H)-one;

6-(4-hydroxyphenyl)-1-isopropyl-1H-imidazo[4,5-b]pyrazin-2(3H)-one;
6-(4-hydroxyphenyl)-1-((tetrahydro-2H-pyran-3-yl)methyl)-1H-imidazo[4,5-b]pyrazin-2(3H)-one;

1-Cyclopentyl-6-(4-hydroxyphenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzamid;
1-(Cyclohexylmethyl)-6-(pyridin-4-yl)-1H-imidazo[4,5-b]pyrazin-2(3H)-one;

1-(Cyclohexylmethyl)-6-(4-(hydroxymethyl)phenyl)-1H-imidazo[4,5-b]pyrazin-2(3H)-one;
3-(Cyclohexylmethyl)-2-oxo-2,3-dihydro-1H-imidazo[4,5-b]pyrazin-5-yl)benzonitrile;
4-(3-(Cyclohexylmethyl)-2-oxo-2,3-dihydro-1H-imidazo[4,5-b]pyrazin-5-yl)-N-isopropylbenzamide;
1-(Cyclohexylmethyl)-6-(1H-indol-6-yl)-1H-imidazo[4,5-b]pyrazin-2(3H)-one;
6-(4-(Aminomethyl)phenyl)-1-(cyclohexylmethyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzonitrile;
1-(Cyclohexylmethyl)-6-(pyridin-2-yl)-1H-imidazo[4,5-b]pyrazin-2(3H)-one;

1-(Cyclohexylmethyl)-6-(4-(2-hydroxypropan-2-yl)phenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzoic acid;
6-(4-Hydroxyphenyl)-1-(3-methoxypropyl)-1H-imidazo[4,5-b]pyrazin-2(3H)-one;
6-(4-Hydroxyphenyl)-1-(2-(tetrahydro-2H-pyran-4-yl)ethyl)-1H-imidazo[4,5-b]pyrazin-2(3H)-one;
1-((1r,4Ω-4-Hydroxycyclohexyl)-6-(4-hydroxyphenyl)-1H-imidazo[4,5-b]pyrazin-2(3H)-one;
1-(Cyclohexylmethyl)-6-phenyl-1H-imidazo[4,5-b]pyrazin-2(3H)-one;

1-(Cyclohexylmethyl)-6-(1H-pyrazol-4-yl)-1H-imidazo[4,5-b]pyrazin-2(3H)-one;

1-(Cyclohexylmethyl)-6-(1-oxoisoindolin-5-yl)-1H-imidazo[4,5-b]pyrazin-2(3H)-one;

1-(Cyclohexylmethyl)-6-(2-oxoindolin-5-yl)-1H-imidazo[4,5-b]pyrazin-2(3H)-one;

1-(Cyclohexylmethyl)-6-(6-methoxypyridin-3-yl)-1H-imidazo[4,5-b]pyrazin-2(3H)-one;

6-(4-Hydroxyphenyl)-1-(piperidin-4-ylmethyl)-1H-imidazo[4,5-b]pyrazin-2(3H)-one;

1-(Cyclohexylmethyl)-6-(6-hydroxypyridin-3-yl)-1H-imidazo[4,5-b]pyrazin-2(3H)-one;

4-(3-((1r,40-4-Hydroxycyclohexyl)-2-oxo-2,3-dihydro-1H-imidazo[4,5-b]pyrazin-5-yl)benzamide;

2-(4-(3-(Cyclohexylmethyl)-2-oxo-2,3-dihydro-1H-imidazo[4,5-b]pyrazin-5-yl)phenyl) acetamide;

4-(3-(Cyclohexylmethyl)-2-oxo-2,3-dihydro-1H-imidazo[4,5-b]pyrazin-5-yl)-3-methyl benzoic acid;

4-(2-oxo-3-((Tetrahydro-2H-pyran-4-yl)methyl)-2,3-dihydro-1H-imidazo[4,5-b]pyrazin-5-yl)benzamide;

6-(4-(2-Hydroxypropan-2-yl)phenyl)-1-((tetrahydro-2H-pyran-4-yl)methyl)-1H-imidazo[4,5-b]pyrazin-2(3H)-one;

6-(4-(4H-1,2,4-Triazol-3-yl)phenyl)-1-((tetrahydro-2H-pyran-4-yl)methyl)-1H-imidazo[4,5-b]pyrazin-2(3H)-one;

4-(2-oxo-3-(2-(Tetrahydro-2H-pyran-4-yl(ethyl)-2,3-dihydro-1H-imidazo[4,5-b]pyrazin-5-yl)benzamide;

6-(4-(1H-Imidazol-1-yl)phenyl)-1-(cyclohexylmethyl)-1H-imidazo[4,5-b]pyrazin-2(3H)-one;

6-(4-(2H-tetrazol-5-yl)phenyl)-1-(cyclohexylmethyl)-1H-imidazo[4,5-b]pyrazin-2(3H)-one;

6-(4-(1H-1,2,4-Triazol-3-yl)phenyl)-1-(2-(tetrahydro-2H-pyran-4-yl)ethyl)-1H-imidazo[4,5-b]pyrazin-2(3H)-one;

6-(4-(1H-1,2,3-Triazol-1-yl)phenyl)-1-(cyclohexylmethyl)-1H-imidazo[4,5-b]pyrazin-2(3H)-one;

1-(Cyclohexylmethyl)-6-(4-(5-methyl-1H-1,2,4-triazol-3-yl)phenyl)-1H-imidazo[4,5-b]pyrazin-2(3H)-one;

6-(4-(1H-Pyrazol-4-yl)phenyl)-1-(cyclohexylmethyl)-1H-imidazo[4,5-b]pyrazin-2(3H)-one;

1-(Cyclohexylmethyl)-6-(4-(5-(trifluoromethyl)-1H-1,2,4-triazol-3-yl)phenyl)-1H-imidazo[4,5-b]pyrazin-2(3H)-one;

6-(4-Hydroxyphenyl)-1-((tetrahydrofuran-2-yl)methyl)-1H-imidazo[4,5-b]pyrazin-2(3H)-one;

1-((1r,4r)-4-(Hydroxymethyl)cyclohexyl)-6-(4-hydroxyphenyl)-1H-imidazo[4,5-b]pyrazin-2(3H)-one;

6-(4-Hydroxyphenyl)-1-((1r,4r)-4-(methoxymethyl)cyclohexyl)-1H-imidazo[4,5-b]pyrazin-2(3H)-one;

1-(((1r,4r-4-Hydroxycyclohexyl)methyl)-6-(4-hydroxyphenyl)-1H-imidazo[4,5-b]pyrazin-2(3H)-one;

1-(((1s,4s)-4-Hydroxycyclohexyl)methyl)-6-(4-hydroxyphenyl)-1H-imidazo[4,5-b]pyrazin-2(3H)-one;

6-(4-(5-(Morpholinomethyl)-1H-1,2,4-triazol-3-yl)phenyl)-1-((tetrahydro-2H-pyran-4-yl)methyl)-1H-imidazo[4,5-b]pyrazin-2(3H)-one;

6-(3-(1H-Tetrazol-5-yl)phenyl)-1-(cyclohexylmethyl)-1H-imidazo[4,5-b]pyrazin-2(3H)-one;

1-(Cyclohexylmethyl)-6-(1H-indazol-5-yl)-1H-imidazo[4,5-b]pyrazin-2(3H)-one;

6-(4-Hydroxyphenyl)-1-(tetrahydro-2H-pyran-4-yl)-1H-imidazo[4,5-b]pyrazin-2(3H)-one;

1-(((1r,4r)-4-Aminocyclohexyl)methyl)-6-(4-hydroxyphenyl)-1H-imidazo[4,5-b]pyrazin-2(3H)-one;

1-(Cyclohexylmethyl)-6-(2-methoxypyridin-4-yl)-1H-imidazo[4,5-b]pyrazin-2(3H)-one;

2-(4-(3-(Cyclohexylmethyl)-2-oxo-2,3-dihydro-1H-imidazo[4,5-b]pyrazin-5-yl)phenyl) acetic acid;

1-(Cyclohexylmethyl)-6-(2-oxoindolin-6-yl)-1H-imidazo[4,5-b]pyrazin-2(3H)-one;

N-Methyl-4-(2-oxo-3-((tetrahydro-2H-pyran-4-yl)methyl)-2,3-dihydro-1H-imidazo[4,5-b]pyrazin-5-yl)benzamide;

6-(1H-Indol-5-yl)-1-((tetrahydro-2H-pyran-4-yl)methyl)-1H-imidazo[4,5-b]pyrazin-2(3H)-one;

6-(1H-Benzo[d]imidazol-5-yl)-1-(cyclohexylmethyl)-1H-imidazo[4,5-b]pyrazin-2(3H)-one;

6-(3-(2H-1,2,3-Triazol-4-yl)phenyl)-1-(cyclohexylmethyl)-1H-imidazo[4,5-b]pyrazin-2(3H)-one;

6-(4-(1H-1,2,4-Triazol-3-yl)phenyl)-1-((1r,4r-4-hydroxycyclohexyl)-1H-imidazo[4,5-b]pyrazin-2(3H)-one;

1-(Cyclohexylmethyl)-6-(2-hydroxypyridin-4-yl)-1H-imidazo[4,5-b]pyrazin-2(3H)-one;

6-(4-(1H-Imidazol-2-yl)phenyl)-1-(cyclohexylmethyl)-1H-imidazo[4,5-b]pyrazin-2(3H)-one;

6-(4-(2-Hydroxypropan-2-yl)phenyl)-1-(2-(tetrahydro-2H-pyran-4-yl)ethyl)-1H-imidazo[4,5-b]pyrazin-2(3H)-one;

6-(4-(1H-Pyrazol-3-yl)phenyl)-1-(cyclohexylmethyl)-1H-imidazo[4,5-b]pyrazin-2(3H)-one;

6-(4-(5-(Aminomethyl)-1H-1,2,4-triazol-3-yl)phenyl)-1-(cyclohexylmethyl)-1H-imidazo[4,5-b]pyrazin-2(3H)-one hydrochloride;

6-(4-Hydroxyphenyl)-1-((1r,4r-4-methoxycyclohexyl)-1H-imidazo[4,5-b]pyrazin-2(3H)-one;

6-(3-(1H-1,2,4-Triazol-3-yl)phenyl)-1-(cyclohexylmethyl)-1H-imidazo[4,5-b]pyrazin-2(3H)-one;

6-(4-Hydroxyphenyl)-1-((1s,4s)-4-methoxycyclohexyl)-1H-imidazo[4,5-b]pyrazin-2(3H)-one;

6-(1-Methyl-1H-pyrazol-4-yl)-1-((tetrahydro-2H-pyran-4-yl)methyl)-1H-imidazo[4,5-b]pyrazin-2(3H)-one;

6-(4-Hydroxyphenyl)-1-((tetrahydrofuran-3-yl)methyl)-1H-imidazo[4,5-b]pyrazin-2(3H)-one;

6-(1H-Benzo[d]imidazol-5-yl)-1-((tetrahydro-2H-pyran-4-yl)methyl)-1H-imidazo[4,5-b]pyrazin-2(3H)-one hydrochloride;

6-(4-Hydroxyphenyl)-1-(3-(2-oxopyrrolidin-1-yl)propyl)-1H-imidazo[4,5-b]pyrazin-2(3H)-one;

6-(4-Hydroxyphenyl)-1-(2-morpholinoethyl)-1H-imidazo[4,5-b]pyrazin-2(3H)-one hydrochloride;
6-(2-Methyl-1H-benzo[d]imidazol-5-yl)-1-((tetrahydro-2H-pyran-4-yl)methyl)-1H-imidazo[4,5-b]pyrazin-2(3H)-one hydrocholoride;
1-((1s,4s)-4-(Hydroxymethyl)cyclohexyl)-6-(4-hydroxyphenyl)-1H-imidazo[4,5-b]pyrazin-2(3H)-one;
6-(1H-Pyrazol-4-yl)-1-((tetrahydro-2H-pyran-4-yl)methyl)-1H-imidazo[4,5-b]pyrazin-2(3H)-one;

6-(4-(5-(2-Hydroxypropan-2-yl)-1H-1,2,4-triazol-3-yl)phenyl)-1-((tetrahydro-2H-pyran-4-yl)methyl)-1H-imidazo[4,5-b]pyrazin-2(3H)-one;
6-(4-Hydroxyphenyl)-1-((1s,4s)-4-(methoxymethyl)cyclohexyl)-1H-imidazo[4,5-b]pyrazin-2(3H)-one;
1-(2-(2,2-Dimethyltetrahydro-2H-pyran-4-yl)ethyl)-6-(4-hydroxyphenyl)-1H-imidazo[4,5-b]pyrazin-2(3H)-one;
6-(4-(4H-1,2,4-Triazol-3-yl)phenyl)-1-(2-morpholinoethyl)-1H-imidazo[4,5-b]pyrazin-2(3H)-one;

6-(4-(1H-Imidazol-2-yl)phenyl)-1-((tetrahydro-2H-pyran-4-yl)methyl)-1H-imidazo[4,5-b]pyrazin-2(3H)-one hydrochloride;
6-(4-(1H-Imidazol-5-yl)phenyl)-1-((tetrahydro-2H-pyran-4-yl)methyl)-1H-imidazo[4,5-b]pyrazin-2(3H)-one hydrochloride;
6-(4-(4,5-Dimethyl-1H-imidazol-2-yl)phenyl)-1-((tetrahydro-2H-pyran-4-yl)methyl)-1H-imidazo[4,5-b]pyrazin-2(3H)-one;
6-(4-(1H-1,2,4-Triazol-5-yl)phenyl)-1-(((1r,4r-4-methoxycyclohexyl)methyl)-1H-imidazo[4,5-b]pyrazin-2(3H)-one;

6-(4-(1H-1,2,4-Triazol-3-yl)phenyl)-1-(2-(2-oxopyrrolidin-1-yl)ethyl)-1H-imidazo[4,5-b]pyrazin-2(3H)-one;

6-(4-Hydroxyphenyl)-1-(pyrrolidin-2-ylmethyl)-1H-imidazo[4,5-b]pyrazin-2(3H)-one hydrochloride;
6-(2-(Dimethylamino)-1H-benzo[d]imidazol-5-yl)-1-((tetrahydro-2H-pyran-4-yl)methyl)-1H-imidazo[4,5-b]pyrazin-2(3H)-one;
6-(4-(4H-1,2,4-triazol-3-yl)phenyl)-1-(2-(piperidin-1-yl)ethyl)-1H-imidazo[4,5-b]pyrazin-2(3H)-one hydrochloride;
6-(3-methyl-4-(1H-1,2,4-triazol-3-yl)phenyl)-1-((tetrahydro-2H-pyran-4-yl)methyl)-1H-imidazo[4,5-b]pyrazin-2(3H)-one;
6-(4-(5-((methylamino)methyl)-1H-1,2,4-triazol-3-yl)phenyl)-1-((tetrahydro-2H-pyran-4-yl)methyl)-1H-imidazo[4,5-b]pyrazin-2(3H)-one;
6-(4-(5-methyl-1H-1,2,4-triazol-3-yl)phenyl)-1-(2-(tetrahydro-2H-pyran-4-yl)ethyl)-1H-imidazo[4,5-b]pyrazin-2(3H)-one;
6-(4-(4H-1,2,4-triazol-3-yl)phenyl)-1-(2-methyl-2-morpholinopropyl)-1H-imidazo[4,5-b]pyrazin-2(3H)-one;
6-(4-(Pyrrolidin-2-yl)phenyl)-1-(2-(tetrahydro-2H-pyran-4-yl)ethyl)-1H-imidazo[4,5-b]pyrazin-2(3H)-one;

6-(5-(Hydroxymethyl)thiophen-2-yl)-1-((tetrahydro-2H-pyran-4-yl)methyl)-1H-imidazo[4,5-b]pyrazin-2(3H)-one;

1-(Cyclohexylmethyl)-6-(4-(oxazol-5-yl)phenyl)-1H-imidazo[4,5-b]pyrazin-2(3H)-one;
6-(4-(5-(Methoxymethyl)-1H-1,2,4-triazol-3-yl)phenyl)-1-((tetrahydro-2H-pyran-4-yl)methyl)-1H-imidazo[4,5-b]pyrazin-2(3H)-one;
6-(3-Methyl-1H-pyrazol-4-yl)-1-((tetrahydro-2H-pyran-4-yl)methyl)-1H-imidazo[4,5-b]pyrazin-2(3H)-one;
6-(2-Amino-1H-benzo[d]imidazol-5-yl)-1-((tetrahydro-2H-pyran-4-yl)methyl)-1H-imidazo[4,5-b]pyrazin-2(3H)-one di hydrochloride;
6-(4-(5-Isopropyl-1H-1,2,4-triazol-3-yl)phenyl)-1-((tetrahydro-2H-pyran-4-yl)methyl)-1H-imidazo[4,5-b]pyrazin-2(3H)-one;
6-(3H-imidazo[4,5-b]pyridin-6-yl)-1-((tetrahydro-2H-pyran-4-yl)methyl)-1H-imidazo[4,5-b]pyrazin-2(3H)-one;
6-(4-(1H-Pyrazol-1-yl)phenyl)-1-((tetrahydro-2H-pyran-4-yl)methyl)-1H-imidazo[4,5-b]pyrazin-2(3H)-one;
6-(4-(1H-Benzo[d]imidazol-2-yl)phenyl)-1-((tetrahydro-2H-pyran-4-yl)methyl)-1H-imidazo[4,5-b]pyrazin-2(3H)-one;
6-(4-(5-(Hydroxymethyl)-1H-1,2,4-triazol-3-yl)phenyl)-1-((tetrahydro-2H-pyran-4-yl)methyl)-1H-imidazo[4,5-b]pyrazin-2(3H)-one;
6-(4-Hydroxyphenyl)-1-((5-oxopyrrolidin-2-yl)methyl)-1H-imidazo[4,5-b]pyrazin-2(3H)-one;

6-(4-(1H-1,2,4-Triazol-5-yl)phenyl)-1-(((1s,4s)-4-methoxycyclohexyl)methyl)-1H-imidazo[4,5-b]pyrazin-2(3H)-one;

6-(6-(1H-1,2,4-Triazol-3-yl)pyridin-3-yl)-1-((tetrahydro-2H-pyran-4-yl)methyl)-1H-imidazo[4,5-b]pyrazin-2(3H)-one;
6-(4-(5-((dimethylamino)methyl)-1H-1,2,4-triazol-3-yl)phenyl)-1-((tetrahydro-2H-pyran-4-yl)methyl)-1H-imidazo[4,5-b]pyrazin-2(3H)-one;
6-(2-Aminobenzimidazol-5-yl)-1-(cyclohexylmethyl)-4-imidazolino[4,5-b]pyrazin-2-one dihydrochloride;
6-(4-Hydroxyphenyl)-1-(piperidin-3-ylmethyl)-1H-imidazo[4,5-b]pyrazin-2(3H)-one;

1-(Cyclohexylmethyl)-6-(2-(methylamino)pyrimidin-5-yl)-1H-imidazo[4,5-b]pyrazin-2(3H)-one;
1-(Cyclohexylmethyl)-6-(2-(2-methoxyethylamino)pyrimidin-5-yl)-1H-imidazo[4,5-b]pyrazin-2(3H)-one;

6-(4-(5-Oxopyrrolidin-2-yl)phenyl)-1-(2-(tetrahydro-2H-pyran-4-yl)ethyl)-1H-imidazo[4,5-b]pyrazin-2(3H)-one;

6-(4-(1H-imidazol-2-yl)phenyl)-1-(2-(tetrahydro-2H-pyran-4-yl)ethyl)-1H-imidazo[4,5-b]pyrazin-2(3H)-one;

6-(4-(4H-1,2,4-Triazol-3-yl)phenyl)-1-(1-morpholinopropan-2-yl)-1H-imidazo[4,5-b]pyrazin-2(3H)-one;
6-(4-(5-(aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one;
(1r,4r-4-(6-(4-Hydroxyphenyl)-2-oxo-2,3-dihydro-1H-imidazo[4,5-b]pyrazin-1-yl)cyclo-hexanecarboxamide;

-continued (1s,4s)-4-(6-(4-Hydroxyphenyl)-2-oxo-2,3-dihydro-1H-imidazo[4,5-b]pyrazin-1-yl)cyclohexanecarboxamide;
6-(4-(5-Oxopyrrolidin-3-yl)phenyl)-1-(2-(tetrahydro-2H-pyran-4-yl)ethyl)-1H-imidazo[4,5-b]pyrazin-2(3H)-one;
6-(1H-benzo[d]imidazol-5-yl)-1-(2-(tetrahydro-2H-pyran-4-yl)ethyl)-1H-imidazo[4,5-b]pyrazin-2(3H)-one;
6-(5-(2-Hydroxyethyl)thiophen-2-yl)-1-((tetrahydro-2H-pyran-4-yl)methyl)-1H-imidazo[4,5-b]pyrazin-2(3H)-one;
6-(6-Fluoropyridin-3-yl)-1-((tetrahydro-2H-pyran-4-yl)methyl)-1H-imidazo[4,5-b]pyrazin-2(3H)-one;
6-(4-(5-methyl-1H-imidazol-2-yl)phenyl)-1-((tetrahydro-2H-pyran-4-yl)methyl)-1H-imidazo[4,5-b]pyrazin-2(3H)-one;

6-(6-(Methylamino)pyridin-3-yl)-1-((tetrahydro-2H-pyran-4-yl)methyl)-1H-imidazo[4,5-b]pyrazin-2(3H)-one;
6-(4-(2-hydroxypropan-2-yl)phenyl)-1-(((1r,4r-4-methoxycyclohexyl)methyl)-1H-imidazo[4,5-b]pyrazin-2(3H)-one;
6-(2-methyl-4-(1H-1,2,4-triazol-3-yl)phenyl)-1-(2-(tetrahydro-2H-pyran-4-yl)ethyl)-1H-imidazo[4,5-b]pyrazin-2(3H)-one;
6-(4-(hydroxymethyl)thiophen-2-yl)-1-((tetrahydro-2H-pyran-4-yl)methyl)-1H-imidazo[4,5-b]pyrazin-2(3H)-one;
6-(4-(4,5-dimethyl-1H-imidazol-2-yl)phenyl)-1-(2-morpholinoethyl)-1H-imidazo[4,5-b]pyrazin-2(3H)-one;

6-(6-(2-hydroxypropan-2-yl)pyridin-3-yl)-1-(2-(tetrahydro-2H-pyran-4-yl)ethyl)-1H-imidazo[4,5-b]pyrazin-2(3H)-one;
(1r,4r)-4-(6-(4-(2-hydroxypropan-2-yl)phenyl)-2-oxo-2,3-dihydro-1H-imidazo[4,5-b]pyrazin-1-yl)cyclohexanecarboxamide;
6-(4-(1H-imidazol-2-yl)phenyl)-1-(2-(tetrahydro-2H-pyran-4-yl)ethyl)-1H-imidazo[4,5-b]pyrazin-2(3H)-one;

6-(1H-benzo[d]imidazol-5-yl)-1-(2-(tetrahydro-2H-pyran-4-yl)ethyl)-1H-imidazo[4,5-b]pyrazin-2(3H)-one;
6-(4-Hydroxyphenyl)-1-((1-methylpiperidin-2-yl)methyl)-1H-imidazo[4,5-b]pyrazin-2(3H)-one hydrochloride;

1-(Cyclohexylmethyl)-6-(6-(2-hydroxypropan-2-yl)-1H-imidazo[4,5-b]pyrazin-2(3H)-one;

6-(6-(2-Hydroxypropan-2-yl)pyridin-3-yl)-1-(2-(tetrahydro-2H-pyran-4-yl)ethyl)-1H-imidazo[4,5-b]pyrazin-2(3H)-one;

6-(4-(5-Methyl-1H-1,2,4-triazol-3-yl)phenyl)-1-(2-(tetrahydro-2H-pyran-4-yl)ethyl)-1H-imidazo[4,5-b]pyrazin-2(3H)-one.

6-(4-(5-methyl-1H-1,2,4-triazol-3-yl)phenyl)-1-(2-morpholinoethyl)-1H-imidazo[4,5-b]pyrazin-2(3H)-one;
6-(4-(Pyrrolidin-3-yl)phenyl)-1-(2-(tetrahydro-2H-pyran-4-yl)ethyl)-1H-imidazo[4,5-b]pyrazin-2(3H)-one;
6-(3-(Hydroxymethyl)thiophen-2-yl)-1-((tetrahydro-2H-pyran-4-yl)methyl)-1H-imidazo[4,5-b]pyrazin-2(3H)-one;
1-(Cyclohexylmethyl)-6-(pyrimidin-5-yl)-1H-imidazo[4,5-b]pyrazin-2(3H)-one;
6-(6-Aminopyridin-3-yl)-1-((tetrahydro-2H-pyran-4-yl)methyl)-1H-imidazo[4,5-b]pyrazin-2(3H)-one;
6-(4-(5-Methyl-1H-1,2,4-triazol-3-yl)phenyl)-1-(2-(2-oxopyrrolidin-1-yl)ethyl)-1H-imidazo[4,5-b]pyrazin-2(3H)-one;
6-(2-aminopyrimidin-5-yl)-1-(cyclohexylmethyl)-1H-imidazo[4,5-b]pyrazin-2(3H)-one;
6-(4-hydroxyphenyl)-1-((1-methylpiperidin-3-yl)methyl)-1H-imidazo[4,5-b]pyrazin-2(3H)-one;
1-(cyclohexylmethyl)-6-(6-(2-hydroxypropan-2-yl)pyridin-3-yl)-1H-imidazo[4,5-b]pyrazin-2(3H)-one;

6-(1H-benzo[d]imidazol-6-yl)-1-(((1r,4r-4-methoxycyclohexyl)methyl)-1H-imidazo[4,5-b]pyrazin-2(3H)-one;
6-(6-(2-hydroxypropan-2-yl)pyridin-3-yl)-1-((tetrahydro-2H-pyran-4-yl)methyl)-1H-imidazo[4,5-b]pyrazin-2(3H)-one;

6-(4-(4H-1,2,4-triazol-3-yl)phenyl)-1-(2-morpholino-2-oxoethyl)-1H-imidazo[4,5-b]pyrazin-2(3H)-one;
6-(3-methyl-4-(1H-1,2,4-triazol-3-yl)phenyl)-1-((tetrahydro-2H-pyran-4-yl)methyl)-1H-imidazo[4,5-b]pyrazin-2(3H)-one;
6-(4-(5-(Aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one;
6-(2-Aminopyrimidin-5-yl)-1-(cyclohexylmethyl)-1H-imidazo[4,5-b]pyrazin-2(3H)-one;
6-(3-methyl-4-(1H-1,2,4-triazol-3-yl)phenyl)-1-((tetrahydro-2H-pyran-4-yl)methyl)-1H-imidazo[4,5-b]pyrazin-2(3H)-one;
6-(6-(2-Hydroxypropan-2-yl)pyridin-3-yl)-1-((tetrahydro-2H-pyran-4-yl)methyl)-1H-imidazo[4,5-b]pyrazin-2(3H)-one;
6-(4-(4H-1,2,4-Triazol-3-yl)phenyl)-1-(2-morpholino-2-oxoethyl)-1H-imidazo[4,5-b]pyrazin-2(3H)-one;
(1r,4r-4-(6-(4-(2-Hydroxypropan-2-yl)phenyl)-2-oxo-2,3-dihydro-1H-imidazo[4,5-b]pyrazin-1-yl)cyclohexanecarboxamide; or

5. A pharmaceutical composition comprising an effective amount of a compound of claim 1, or a pharmaceutically acceptable salt thereof, and a pharmaceutically acceptable carrier, excipient or vehicle.

6. The pharmaceutical composition of claim 5, suitable for oral, parenteral, mucosal, transdermal or topical administration.

7. A pharmaceutical composition comprising an effective amount of a compound of claim 3, or a pharmaceutically acceptable salt thereof, and a pharmaceutically acceptable carrier, excipient or vehicle.

8. The pharmaceutical composition of claim 7, suitable for oral, parenteral, mucosal, transdermal or topical administration.

9. A pharmaceutical composition comprising an effective amount of a compound of claim 4, or a pharmaceutically acceptable salt thereof, and a pharmaceutically acceptable carrier, excipient or vehicle.

10. The pharmaceutical composition of claim 9, suitable for oral, parenteral, mucosal, transdermal or topical administration.

* * * * *